United States Patent
Guo et al.

(10) Patent No.: US 11,932,694 B2
(45) Date of Patent: Mar. 19, 2024

(54) ANTI-VTCN1 ANTIBODIES AND ANTIBODY DRUG CONJUGATES

(71) Applicant: Bluefin BioMedicine, Inc., Beverly, MA (US)

(72) Inventors: Ailan Guo, Lexington, MA (US); Svetlana Popova, Andover, MA (US); Scott Michael Lonning, Westford, MA (US); Jason G. Beaudet, Beverly, MA (US)

(73) Assignee: Bluefin BioMedicine, Inc., Beverly, MA (US)

( * ) Notice: Subject to any disclaimer, the term of this patent is extended or adjusted under 35 U.S.C. 154(b) by 1112 days.

(21) Appl. No.: 16/606,246

(22) PCT Filed: Apr. 19, 2018

(86) PCT No.: PCT/US2018/028347
§ 371 (c)(1),
(2) Date: Oct. 18, 2019

(87) PCT Pub. No.: WO2018/195302
PCT Pub. Date: Oct. 25, 2018

(65) Prior Publication Data
US 2023/0069760 A1 Mar. 2, 2023

Related U.S. Application Data

(60) Provisional application No. 62/487,424, filed on Apr. 19, 2017.

(51) Int. Cl.
*C07K 16/28* (2006.01)
*A61K 39/00* (2006.01)
(Continued)

(52) U.S. Cl.
CPC .......... *C07K 16/2827* (2013.01); *A61K 45/06* (2013.01); *A61K 47/6851* (2017.08); *A61P 35/00* (2018.01); *A61K 2039/505* (2013.01)

(58) Field of Classification Search
CPC ............ C07K 16/2827; C07K 16/2818; C07K 2317/21; C07K 2317/24; C07K 2317/33;
(Continued)

(56) References Cited

U.S. PATENT DOCUMENTS

| 2011/0085970 A1 | 4/2011 | Terrett et al. |
| 2014/0255407 A1 | 9/2014 | Koenig |

(Continued)

FOREIGN PATENT DOCUMENTS

| WO | WO-2013052772 A2 * | 4/2013 | ............ C07K 16/18 |
| WO | 2014/100483 A1 | 6/2014 | |

(Continued)

OTHER PUBLICATIONS

Chailyan, A., et al (2011) The association of heavy and light chain variable domains in antibodies: implications for antigen specificity FEBS Journal 278; 2858-2866 (Year: 2011).*

(Continued)

*Primary Examiner* — Scarlett Y Goon
*Assistant Examiner* — Audrey L Buttice
(74) *Attorney, Agent, or Firm* — McCarter & English, LLP; Marcie B. Clarke

(57) ABSTRACT

Disclosed herein are anti-V-set domain containing T cell activation inhibitor 1 (VTCN1) antibodies and antibody drug conjugates (ADCs), including compositions and methods of using said antibodies and ADCs.

14 Claims, 14 Drawing Sheets

Specification includes a Sequence Listing.

(51) Int. Cl.
*A61K 45/06* (2006.01)
*A61K 47/68* (2017.01)
*A61P 35/00* (2006.01)

(58) Field of Classification Search
CPC .......... C07K 2317/73; C07K 2317/732; C07K 2317/76; C07K 2317/92; A61K 45/06; A61K 47/6851; A61K 47/6849; A61K 47/6803; A61K 2039/505; A61K 2039/507; A61K 39/3955; A61K 31/7068; A61P 35/00
See application file for complete search history.

(56) References Cited

U.S. PATENT DOCUMENTS

2014/0294834 A1 10/2014 Harms et al.
2014/0322129 A1 10/2014 Leong et al.

FOREIGN PATENT DOCUMENTS

WO 2016/073747 A1 5/2016
WO WO-2016164637 A1 * 10/2016 ......... A61K 31/7088

OTHER PUBLICATIONS

Rabia, L., et al (2018) Understanding and overcoming trade-offs between antibody affinity, specificity, stability, and solubility Biochem Eng. J. 15(137); 365-374 (Year: 2018).*
Hummer, A.M., et al (2022) Advances in computational structure-based antibody design Current Opinion in Structural Biology 74( 102379); 1-7 (Year: 2022).*
Leong et al., An anti-B7-H4 antibody-drug conjugate for the treatment of breast cancer. Mol Pharm. Jun. 1, 2015;12 (6):1717-29.
International Search Report and Written Opinion for Application No. PCT/US2018/028347, dated Aug. 30, 2018, 13 pages.
International Preliminary Report on Patentability for Application No. PCT/US2018/028347, dated Oct. 31, 2019, 8 pages.

* cited by examiner

SEQUENCE LISTING

<160> NUMBER OF SEQ ID NOS: 308

<210> SEQ ID NO 1
<211> LENGTH: 119
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 1

Gln Met Gln Leu Lys Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val Gln Trp Val Arg Gln Phe Ser Gly Lys Gly Leu Glu Trp Leu
        35                  40                  45

Gly Val Ile Trp Ser Ser Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Pro Asp Asp Thr Ala Met Tyr Tyr Cys Ala
                85                  90                  95

Arg Asp Ile Thr Thr Ile Val Glu Gly Phe Ala Tyr Trp Gly Gln Gly
            100                 105                 110

Thr Leu Val Thr Val Ser Ala
        115

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Ser Leu Thr Ser Tyr Gly Val Gln
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ile Trp Ser Ser Gly Ser Thr Asp Tyr Asn Ala Ala Phe Ile Ser
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Thr Thr Ile Val Glu Gly Phe Ala Tyr
1               5                   10

<210> SEQ ID NO 5
<211> LENGTH: 108
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 5

Ile Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys Arg
            100                 105

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Ala Ser Glu Asn Val Gly Thr Tyr Val Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ala Ser Asn Arg Tyr Thr
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gln Ser Tyr Ser Tyr Pro Phe Thr
1               5

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Ile Gln Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Thr Thr
            20                  25                  30

Gly Met Gln Trp Val Gln Lys Met Pro Gly Lys Gly Phe Lys Trp Ile
        35                  40                  45

Gly Trp Ile Asn Thr His Ser Gly Glu Pro Lys Tyr Ala Asp Asp Phe
50                  55                  60

Lys Gly Arg Phe Ala Phe Ser Leu Glu Thr Ser Ala Ser Thr Ala His
65                  70                  75                  80

Leu Gln Ile Ser Asn Leu Lys Asn Glu Asp Thr Ala Thr Tyr Phe Cys
                85                  90                  95

Ala Arg Thr Ser Tyr Trp Tyr Leu Asp Val Trp Gly Ala Gly Thr Thr
            100                 105                 110

Val Thr Val Ser Ser
        115

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Tyr Thr Phe Thr Thr Thr Gly Met Gln
1               5                   10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ile Asn Thr His Ser Gly Glu Pro Lys Tyr Ala Asp Asp Phe Lys
1               5                   10                  15

Gly

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Tyr Trp Tyr Leu Asp Val
1               5

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Ile Val Gly Thr Asn
            20                  25                  30

Ile Ala Trp Tyr Gln Gln Lys Pro Gly Gln Ser Pro Lys Ala Leu Ile
        35                  40                  45

Tyr Ser Ala Ser Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys
            100                 105
```

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Lys Ala Ser Gln Ile Val Gly Thr Asn Ile Ala
1               5                   10
```

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

```
Ser Ala Ser Tyr Arg Asn Ser
1               5
```

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gln Gln Tyr Asn Ser Tyr Pro Leu Thr
1               5
```

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gln Ile Gln Leu Lys Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30
```

```
Gly Val His Trp Val Arg Gln Ser Pro Gly Lys Gly Leu Glu Trp Leu
            35                  40                  45

Gly Val Ile Trp Ser Gly Gly Tyr Thr Asp Tyr Asn Ser Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asp Ile Thr Thr Ile Val Glu Gly Phe Ala Tyr Trp Gly Gln Gly
            100                 105                 110

Thr Leu Val Thr Val Ser Ala
        115

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Phe Ser Leu Thr Ser Tyr Gly Val His
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Ile Trp Ser Gly Gly Tyr Thr Asp Tyr Asn Ser Ala Phe Ile Ser
1               5                   10                  15

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Thr Thr Ile Val Glu Gly Phe Ala Tyr
1               5                   10

<210> SEQ ID NO 21
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ile Ile Val Met Thr Gln Ser Pro Lys Ser Met Ser Met Ser Val Gly
1               5                   10                  15

Glu Arg Ile Thr Leu Asn Cys Lys Ala Ser Glu Asn Val Gly Thr Tyr
            20                  25                  30

Val Ser Trp Tyr Gln Gln Lys Pro Glu Gln Ser Pro Lys Leu Leu Ile
```

```
            35                  40                  45
Tyr Gly Ala Ser Asn Arg Tyr Thr Gly Val Pro Asp His Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Thr Tyr Ser Tyr Pro Phe
                85                  90                  95

Thr Phe Gly Ser Gly Thr Lys Leu Glu Ile Lys
            100                 105

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Ala Ser Glu Asn Val Gly Thr Tyr Val Ser
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Ala Ser Asn Arg Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gln Thr Tyr Ser Tyr Pro Phe Thr
1               5

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Ser Gly Ser Thr Asp Tyr Asn Ala Ala Phe Ile
    50                  55                  60
```

```
Ser Arg Leu Ser Ile Ser Lys Asp Asn Ser Lys Ser Gln Val Phe Phe
 65                  70                  75                  80

Lys Ile His Ser Leu Gln Ala Asp Thr Ala Ile Tyr Tyr Cys Ala
                 85                  90                  95

Arg Asp Ile Thr Thr Ile Val Glu Gly Phe Ala Tyr Trp Ala Gln Gly
            100                 105                 110

Thr Leu Val Thr Val Ser Ala
        115

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Phe Ser Leu Thr Ser Tyr Gly Val His
1               5                   10

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Ile Trp Ser Ser Gly Ser Thr Asp Tyr Asn Ala Ala Phe Ile Ser
1               5                   10                  15

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Thr Thr Ile Val Glu Gly Phe Ala Tyr
1               5                   10

<210> SEQ ID NO 29
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asn Ile Val Met Thr Gln Ser Pro Lys Ser Met Ser Met Ser Val Gly
1               5                   10                  15

Glu Arg Val Thr Leu Ile Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80
```

Glu Asp Leu Ala Asp Tyr His Cys Gly Gln Thr Tyr Ser Tyr Pro Phe
                85                  90                  95

Thr Phe Gly Ser Gly Thr Lys Leu Glu Ile Lys
            100                 105

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Ala Ser Glu Asn Val Gly Thr Tyr Val Ser
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ala Ser Asn Arg Tyr Thr
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Gln Thr Tyr Ser Tyr Pro Phe Thr
1               5

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Ile Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val Gln Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asp Ile Ser Thr Ile Val Glu Gly Phe Ala His Trp Gly Gln Gly

```
                        100                 105                 110
Thr Leu Val Thr Val Ser Ser
        115

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Phe Ser Leu Thr Ser Tyr Gly Val Gln
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Ile Trp Ser Gly Gly Ser Thr Asp Tyr Asn Ala Ala Phe Ile Ser
1               5                   10                  15

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Ser Thr Ile Val Glu Gly Phe Ala His
1               5                   10

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asn Ile Val Met Thr Gln Ser Pro Lys Ser Met Ser Met Ser Val Gly
1               5                   10                  15

Glu Arg Val Thr Leu Ser Cys Lys Ala Ser Glu Lys Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Arg Tyr Pro Phe
                85                  90                  95

Thr Phe Gly Ser Gly Thr Lys Leu Glu Ile Lys
            100                 105
```

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Ala Ser Glu Lys Val Gly Thr Tyr Val Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Ala Ser Asn Arg Tyr Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gln Ser Tyr Arg Tyr Pro Phe Thr
1               5

<210> SEQ ID NO 41
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Met Lys Glu Ser Gly Pro Glu Leu Lys Lys Pro Gly Glu
1               5                   10                  15

Thr Val Lys Ile Ser Cys Lys Ala Ser Gly Tyr Thr Phe Thr Thr Thr
            20                  25                  30

Gly Met Gln Trp Val Gln Lys Met Pro Gly Lys Gly Phe Lys Trp Ile
        35                  40                  45

Gly Trp Ile Asn Thr His Ser Gly Glu Pro Lys Tyr Ala Asp Asp Phe
    50                  55                  60

Lys Gly Arg Phe Ala Phe Ser Leu Glu Thr Ser Ala Ser Thr Ala His
65                  70                  75                  80

Leu Gln Ile Ser Asn Leu Lys Asn Glu Asp Thr Ala Thr Tyr Phe Cys
                85                  90                  95

Ala Arg Thr Ser Tyr Trp Tyr Leu Asp Val Trp Gly Ala Gly Thr Thr
            100                 105                 110

Val Thr Val Ser Ser
        115

<210> SEQ ID NO 42

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Tyr Thr Phe Thr Thr Thr Gly Met Gln
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Ile Asn Thr His Ser Gly Glu Pro Lys Tyr Ala Asp Asp Phe Lys
1               5                   10                  15

Gly

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Tyr Trp Tyr Leu Asp Val
1               5

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Val Met Thr Gln Ser Gln Lys Phe Met Ser Thr Ser Val Gly
1               5                   10                  15

Asp Arg Val Ser Val Thr Cys Lys Ala Ser Gln Ile Val Gly Thr Asn
            20                  25                  30

Ile Ala Trp Tyr Gln Gln Lys Pro Gly Gln Ser Pro Lys Ala Leu Ile
        35                  40                  45

Tyr Ser Ala Ser Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys
            100                 105

<210> SEQ ID NO 46
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 46

Lys Ala Ser Gln Ile Val Gly Thr Asn Ile Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Ala Ser Tyr Arg Asn Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Tyr Asn Ser Tyr Pro Leu Thr
1               5

<210> SEQ ID NO 49
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Ile Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Ser Gly Ser Thr Asp Tyr Asn Ala Ala Phe Ile
    50                  55                  60

Ser Arg Leu Ser Ile Ser Lys Asp Asn Ser Arg Ser Gln Val Phe Phe
65                  70                  75                  80

Lys Met Asn Ser Leu Gln Pro Asp Asp Thr Ala Ile Tyr Tyr Cys Ala
                85                  90                  95

Arg Asp Ile Thr Thr Ile Val Glu Gly Phe Ala Tyr Trp Ala Gln Gly
            100                 105                 110

Thr Leu Val Thr Val Ser Ala
        115

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 50

Gly Phe Ser Leu Thr Ser Tyr Gly Val His
1               5                   10

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ile Trp Ser Ser Gly Ser Thr Asp Tyr Asn Ala Ala Phe Ile Ser
1               5                   10                  15

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Thr Thr Ile Val Glu Gly Phe Ala Tyr
1               5                   10

<210> SEQ ID NO 53
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asn Val Val Met Thr Gln Ser Pro Lys Ser Met Ser Met Ser Val Gly
1               5                   10                  15

Glu Arg Val Thr Leu Ile Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Thr Tyr Ser Tyr Pro Phe
                85                  90                  95

Ala Phe Gly Ser Gly Thr Lys Leu Glu Ile Lys
            100                 105

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Ala Ser Glu Asn Val Gly Thr Tyr Val Ser

-continued

```
<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ala Ser Asn Arg Tyr Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Gln Thr Tyr Ser Tyr Pro Phe Ala
1               5

<210> SEQ ID NO 57
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Gln Glu Ser Gly Pro Glu Leu Val Lys Pro Gly Ala
1               5                   10                  15

Ser Val Lys Leu Ser Cys Lys Ala Ser Gly Tyr Ile Phe Thr Asp Tyr
                20                  25                  30

Thr Ile His Trp Leu Lys Gln Ser Pro Gly Gln Gly Leu Glu Trp Ile
            35                  40                  45

Gly Trp Ile Tyr Pro Gly Ser Gly His Thr His Tyr Asn Asp Lys Phe
        50                  55                  60

Lys Gly Lys Ala Thr Met Thr Ala Asp Lys Ser Ser Thr Thr Ala Tyr
65                  70                  75                  80

Met Gln Leu Ser Ser Leu Thr Ser Glu Asp Ser Ala Val Phe Phe Cys
                85                  90                  95

Ala Arg Gly Gly Glu Ser Ile Thr Thr Val Phe Pro Leu Ala Tyr Trp
                100                 105                 110

Gly Gln Gly Thr Leu Val Thr Val Ser Ala
            115                 120

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Tyr Ile Phe Thr Asp Tyr Thr Ile His
1               5                   10
```

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Ile Tyr Pro Gly Ser Gly His Thr His Tyr Asn Asp Lys Phe Lys
1               5                   10                  15

Gly

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Glu Ser Ile Thr Thr Val Phe Pro Leu Ala Tyr
1               5                   10

<210> SEQ ID NO 61
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asp Gln Lys Asn Tyr Leu Ala Trp Tyr Gln Gln Lys Pro Gly Gln
        35                  40                  45

Ser Pro Lys Leu Leu Ile Tyr Trp Ala Ser Thr Trp Glu Ser Gly Val
    50                  55                  60

Pro Asp Arg Phe Ile Gly Ser Gly Ser Gly Thr Asp Phe Thr Leu Thr
65                  70                  75                  80

Val Ser Ser Val Lys Ala Glu Asp Leu Ala Val Tyr Tyr Cys His Gln
                85                  90                  95

Tyr Tyr Ser Tyr Pro Pro Thr Phe Gly Ala Gly Thr Lys Leu Glu Ile
            100                 105                 110

Lys

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Ser Ser Gln Ser Leu Leu Tyr Ser Ser Asp Gln Lys Asn Tyr Leu
1               5                   10                  15

Ala

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Trp Ala Ser Thr Trp Glu Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Gln Tyr Tyr Ser Tyr Pro Pro Thr
1               5

<210> SEQ ID NO 65
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asp Ile Thr Thr Ile Val Glu Gly Phe Ala Tyr Trp Gly Gln Gly
            100                 105                 110

Thr Leu Val Thr Val Ser Ala
        115

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Phe Ser Leu Thr Ser Tyr Gly Val His
1               5                   10

```
<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Ile Trp Ser Gly Gly Ser Thr Asp Tyr Asn Ala Ala Phe Ile Ser
1               5                   10                  15

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Thr Thr Ile Val Glu Gly Phe Ala Tyr
1               5                   10

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Val Thr Asp Tyr His Cys Gly Gln Thr Tyr Ser Tyr Pro Phe
                85                  90                  95

Thr Phe Gly Ser Gly Thr Lys Leu Glu Ile Lys
            100                 105

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Ala Ser Glu Asn Val Gly Thr Tyr Val Ser
1               5                   10

<210> SEQ ID NO 71
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 71

Gly Ala Ser Asn Arg Tyr Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gln Thr Tyr Ser Tyr Pro Phe Thr
1               5

<210> SEQ ID NO 73
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Ile Gln Leu Gln Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val Gln Trp Val Arg Gln Ser Pro Gly Lys Gly Leu Glu Trp Leu
        35                  40                  45

Gly Val Ile Trp Ser Ser Gly Asn Thr Asp Tyr Asn Ala Ala Phe Ile
    50                  55                  60

Ser Arg Leu Thr Ile Thr Lys Asp Asn Ser Lys Ser Gln Ile Phe Phe
65                  70                  75                  80

Lys Met Asn Ser Leu Gln Ala Asp Asp Thr Ala Ile Tyr Tyr Cys Ala
                85                  90                  95

Arg Asp Ile Thr Thr Ile Val Glu Gly Phe Ala Tyr Trp Gly Gln Gly
            100                 105                 110

Thr Leu Val Thr Val Ser Ala
        115

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Phe Ser Leu Thr Ser Tyr Gly Val Gln
1               5                   10

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 75

Val Ile Trp Ser Ser Gly Asn Thr Asp Tyr Asn Ala Ala Phe Ile Ser
1               5                   10                  15

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Thr Thr Ile Val Glu Gly Phe Ala Tyr
1               5                   10

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Thr Tyr Ser Tyr Pro Phe
                85                  90                  95

Thr Phe Gly Ser Gly Thr Lys Leu Glu Ile Lys
            100                 105

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Ala Ser Glu Asn Val Gly Thr Tyr Val Ser
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ala Ser Asn Arg Tyr Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Gln Thr Tyr Ser Tyr Pro Phe Thr
1               5

<210> SEQ ID NO 81
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Ile Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Ala
            20                  25                  30

Gly Met Gln Trp Val Gln Lys Met Pro Gly Lys Gly Phe Lys Trp Leu
        35                  40                  45

Gly Trp Ile Asn Thr His Ser Gly Glu Pro Lys Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr His Cys
                85                  90                  95

Ala Arg Thr Ser Tyr Trp Tyr Leu Asp Ile Trp Gly Ala Gly Thr Thr
            100                 105                 110

Val Thr Val Ser Ser
        115

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Tyr Thr Phe Thr Thr Ala Gly Met Gln
1               5                   10

<210> SEQ ID NO 83
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Trp Ile Asn Thr His Ser Gly Glu Pro Lys Tyr Ala Asp Asp Phe Lys
1               5                   10                  15

Gly

```
<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Tyr Trp Tyr Leu Asp Ile
1               5

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Cys Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Ile Lys
            100                 105

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Lys Ala Ser Gln Asn Val Gly Thr Asn Val Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Ala Ser Tyr Arg Cys Ser
1               5

<210> SEQ ID NO 88
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 88

Gln Gln Tyr Asn Ser Tyr Pro Leu Thr
1               5

<210> SEQ ID NO 89
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Thr Ser Tyr
            20                  25                  30

Trp Met Asn Trp Val Lys Gln Arg Pro Gly Arg Gly Leu Glu Trp Ile
        35                  40                  45

Gly Arg Ile His Pro Ser Asp Ser Glu Thr His Tyr Asn Gln Asn Phe
    50                  55                  60

Lys Ser Lys Ala Thr Leu Thr Val Asp Lys Ser Ser Ser Thr Ala Tyr
65                  70                  75                  80

Ile Gln Leu Asn Ser Leu Thr Ser Glu Asp Ser Ala Val Tyr Tyr Cys
                85                  90                  95

Ala Arg Pro Tyr Tyr Phe Tyr Gly Ser Ser Pro Tyr Ala Met Asp Tyr
            100                 105                 110

Trp Gly Gln Gly Ala Ser Val Thr Val Ser Ser
        115                 120

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Tyr Ser Phe Thr Ser Tyr Trp Met Asn
1               5                   10

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Ile His Pro Ser Asp Ser Glu Thr His Tyr Asn Gln Asn Phe Lys
1               5                   10                  15

Ser

<210> SEQ ID NO 92
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 92

Tyr Tyr Phe Tyr Gly Ser Ser Pro Tyr Ala Met Asp Tyr
1               5                   10

<210> SEQ ID NO 93
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Phe Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 94
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Ser Ser Gln Ser Ile Val His Ser Asn Gly Asn Thr Tyr Leu Glu
1               5                   10                  15

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Lys Val Ser Asn Arg Phe Ser
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 96

Phe Gln Gly Ser His Val Pro Tyr Thr
1               5

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Met Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Ile Trp Ser Ser Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ser Asp Asp Thr Ala Ile His Tyr Cys Ala
                85                  90                  95

Arg Asp Ile Thr Thr Ile Ala Glu Gly Phe Ala Tyr Trp Gly Gln Gly
            100                 105                 110

Thr Leu Val Thr Val Ser Ser
        115

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Phe Ser Leu Thr Ser Tyr Gly Ile His
1               5                   10

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Val Ile Trp Ser Ser Gly Ser Thr Asp Tyr Asn Ala Ala Phe Ile Ser
1               5                   10                  15

<210> SEQ ID NO 100
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Thr Thr Ile Ala Glu Gly Phe Ala Tyr
1               5                   10

<210> SEQ ID NO 101
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Lys Ala Ser Glu Asn Val Gly Thr Tyr Val Ser
1               5                   10

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Ala Ser Asn Arg Tyr Thr
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gln Ser Tyr Ser Tyr Pro Phe Thr
1               5

<210> SEQ ID NO 105

<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Val Gln Leu Gln Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val Gln Trp Val Arg Gln Ser Pro Gly Lys Gly Leu Glu Trp Leu
        35                  40                  45

Gly Val Ile Trp Ser Ser Gly Ser Thr Asp Tyr Asn Ala Ala Phe Ile
    50                  55                  60

Ser Arg Leu Ser Ile Asn Lys Asp Asn Ser Lys Ser Gln Val Phe Phe
65                  70                  75                  80

Lys Met Asn Ser Leu Gln Pro Asp Asp Thr Ala Ile Tyr Tyr Cys Ala
                85                  90                  95

Arg Asp Ile Thr Thr Ile Val Glu Gly Phe Ala Tyr Trp Gly Gln Gly
            100                 105                 110

Thr Leu Val Thr Val Ser Ala
        115

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Phe Ser Leu Thr Ser Tyr Gly Val Gln
1               5                   10

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Val Ile Trp Ser Ser Gly Ser Thr Asp Tyr Asn Ala Ala Phe Ile Ser
1               5                   10                  15

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Thr Thr Ile Val Glu Gly Phe Ala Tyr
1               5                   10

<210> SEQ ID NO 109
<211> LENGTH: 107
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 109

Ile Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Lys Ala Ser Glu Asn Val Gly Thr Tyr Val Ser
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Ala Ser Asn Arg Tyr Thr
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gly Gln Ser Tyr Ser Tyr Pro Phe Thr
1               5

<210> SEQ ID NO 113
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 113

Gln Ile Gln Leu Gln Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val Gln Trp Ile Arg Gln Ser Pro Gly Lys Gly Leu Glu Trp Leu
        35                  40                  45

Gly Val Ile Trp Ser Ser Gly Ser Thr Asp Tyr Asn Ala Ala Phe Leu
    50                  55                  60

Ser Arg Leu Ser Phe Ser Lys Asp Asn Ser Lys Ser Gln Val Phe Phe
65                  70                  75                  80

Gln Met Asn Ser Leu Gln Ala Asp Asp Ser Ala Ile Tyr Tyr Cys Ala
                85                  90                  95

Arg Asp Val Thr Thr Ile Val Glu Gly Phe Ala His Trp Gly Gln Gly
            100                 105                 110

Thr Leu Val Thr Val Ser Ala
        115

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Gly Phe Ser Leu Thr Ser Tyr Gly Val Gln
1               5                   10

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Val Ile Trp Ser Ser Gly Ser Thr Asp Tyr Asn Ala Ala Phe Leu Ser
1               5                   10                  15

<210> SEQ ID NO 116
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Val Thr Thr Ile Val Glu Gly Phe Ala His
1               5                   10

<210> SEQ ID NO 117
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117
```

```
Asn Ile Val Met Thr Gln Ser Pro Lys Ser Met Ser Met Ser Val Gly
1               5                   10                  15

Glu Arg Val Thr Leu Ser Cys Lys Ala Ser Glu Lys Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Val
65                  70                  75                  80

Glu Asp Leu Ala Asp Tyr His Cys Gly Gln Thr Tyr Ser Tyr Pro Phe
                85                  90                  95

Thr Phe Gly Ser Gly Thr Lys Leu Glu Ile Lys
            100                 105

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Lys Ala Ser Glu Lys Val Gly Thr Tyr Val Ser
1               5                   10

<210> SEQ ID NO 119
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Ala Ser Asn Arg Tyr Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gln Thr Tyr Ser Tyr Pro Phe Thr
1               5

<210> SEQ ID NO 121
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Ile Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30
```

```
Gly Val Gln Trp Val Arg Gln Ser Pro Gly Lys Gly Leu Glu Trp Leu
            35                  40                  45

Gly Val Ile Trp Ser Ser Gly Ser Thr Asp Tyr Asn Ala Ala Phe Ile
        50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asp Ile Thr Thr Ile Val Glu Gly Phe Ala Tyr Trp Gly Gln Gly
            100                 105                 110

Thr Leu Val Thr Val Ser Ala
        115

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Phe Ser Leu Thr Ser Tyr Gly Val Gln
1               5                   10

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Val Ile Trp Ser Ser Gly Ser Thr Asp Tyr Asn Ala Ala Phe Ile Ser
1               5                   10                  15

<210> SEQ ID NO 124
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ile Thr Thr Ile Val Glu Gly Phe Ala Tyr
1               5                   10

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Asn Ile Val Met Thr Gln Ser Pro Lys Ser Met Ser Met Ser Val Gly
1               5                   10                  15

Glu Arg Val Thr Leu Arg Cys Lys Ala Ser Glu Asn Val Asn Thr Tyr
            20                  25                  30

Val Ser Trp Tyr Gln Gln Lys Pro Glu Gln Ser Pro Lys Leu Leu Ile
```

```
                    35                  40                  45
Tyr Gly Ala Ser Asn Arg Tyr Thr Gly Val Pro Asp Arg Phe Thr Gly
            50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Lys Ala Ser Glu Asn Val Asn Thr Tyr Val Ser
1               5                   10

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Ala Ser Asn Arg Tyr Thr
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Gln Ser Tyr Ser Tyr Pro Phe Thr
1               5

<210> SEQ ID NO 129
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Ile Gln Leu Lys Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
                20                  25                  30

Gly Val Gln Trp Val Arg Gln Ser Pro Gly Lys Gly Leu Glu Trp Leu
            35                  40                  45

Gly Val Ile Trp Ser Gly Gly Ser Thr Asp Tyr Asn Ala Ala Phe Ile
        50                  55                  60
```

```
Ser Arg Leu Ser Ile Ser Lys Asp Asn Ser Lys Ser Gln Val Phe Phe
 65                  70                  75                  80

Lys Met Asn Ser Leu Gln Ala Asp Asp Thr Ala Ile Tyr Tyr Cys Ala
                 85                  90                  95

Arg Asp Ile Thr Thr Ile Val Glu Gly Phe Ala Tyr Trp Ala Gln Gly
            100                 105                 110

Thr Leu Val Thr Val Ser Ala
        115
```

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
Gly Phe Ser Leu Thr Ser Tyr Gly Val Gln
1               5                   10
```

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Val Ile Trp Ser Gly Gly Ser Thr Asp Tyr Asn Ala Ala Phe Ile Ser
1               5                   10                  15
```

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

```
Ile Thr Thr Ile Val Glu Gly Phe Ala Tyr
1               5                   10
```

<210> SEQ ID NO 133
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

```
Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80
```

```
Glu Asp Leu Ala Asp Tyr His Cys Gly Gln Thr Tyr Ser Tyr Pro Phe
                85                  90                  95

Thr Phe Gly Ser Gly Thr Lys Leu Glu Ile Lys
            100                 105

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Lys Ala Ser Glu Asn Val Gly Thr Tyr Val Ser
1               5                   10

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Ala Ser Asn Arg Tyr Thr
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Gln Thr Tyr Ser Tyr Pro Phe Thr
1               5

<210> SEQ ID NO 137
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Gln Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Ile Trp Ser Ser Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ser Asp Asp Thr Ala Ile His Tyr Cys Ala
                85                  90                  95

Arg Asp Ile Thr Thr Ile Ala Glu Gly Phe Ala Tyr Trp Gly Gln Gly
```

Thr Leu Val Thr Val Ser Ala
        115

<210> SEQ ID NO 138
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Phe Ser Leu Thr Ser Tyr Gly Ile His
1               5                   10

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Val Ile Trp Ser Ser Gly Ser Thr Asp Tyr Asn Ala Ala Phe Ile Ser
1               5                   10                  15

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Thr Thr Ile Ala Glu Gly Phe Ala Tyr
1               5                   10

<210> SEQ ID NO 141
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Lys Ala Ser Glu Asn Val Gly Thr Tyr Val Ser
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Ala Ser Asn Arg Tyr Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Gln Ser Tyr Ser Tyr Pro Phe Thr
1               5

<210> SEQ ID NO 145
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Met Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val Gln Trp Val Arg Gln Ser Pro Gly Lys Gly Leu Gln Trp Leu
        35                  40                  45

Gly Val Ile Trp Ser Ser Gly Ser Thr Asp Tyr Asn Ala Ala Val Ile
    50                  55                  60

Ser Arg Leu Ser Ile Ser Lys Asp Thr Ser Lys Ser Gln Val Phe Phe
65                  70                  75                  80

Lys Met Asn Ser Leu Gln Pro Asp Asp Thr Ala Ile Tyr Tyr Cys Ala
                85                  90                  95

Arg Asp Ile Thr Thr Ile Val Glu Gly Phe Ala Tyr Trp Gly Gln Gly
            100                 105                 110

Thr Leu Val Thr Val Ser Ser
        115

<210> SEQ ID NO 146

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Phe Ser Leu Thr Ser Tyr Gly Val Gln
1               5                   10

<210> SEQ ID NO 147
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Val Ile Trp Ser Ser Gly Ser Thr Asp Tyr Asn Ala Ala Val Ile Ser
1               5                   10                  15

<210> SEQ ID NO 148
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ile Thr Thr Ile Val Glu Gly Phe Ala Tyr
1               5                   10

<210> SEQ ID NO 149
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ile Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 150

Lys Ala Ser Glu Asn Val Gly Thr Tyr Val Ser
1               5                   10

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Ala Ser Asn Arg Tyr Thr
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Gln Ser Tyr Ser Tyr Pro Phe Thr
1               5

<210> SEQ ID NO 153
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gln Ile Gln Leu Gln Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Ile Trp Ser Ser Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ser Asp Asp Thr Ala Ile His Tyr Cys Ala
                85                  90                  95

Arg Asp Ile Thr Thr Ile Ala Glu Gly Phe Ala Tyr Trp Gly Gln Gly
            100                 105                 110

Thr Leu Val Thr Val Ser Ala
        115

<210> SEQ ID NO 154
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 154

Gly Phe Ser Leu Thr Ser Tyr Gly Ile His
1               5                   10

<210> SEQ ID NO 155
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Val Ile Trp Ser Ser Gly Ser Thr Asp Tyr Asn Ala Ala Phe Ile Ser
1               5                   10                  15

<210> SEQ ID NO 156
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile Thr Thr Ile Ala Glu Gly Phe Ala Tyr
1               5                   10

<210> SEQ ID NO 157
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Lys Ala Ser Glu Asn Val Gly Thr Tyr Val Ser
1               5                   10
```

```
<210> SEQ ID NO 159
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Ala Ser Asn Arg Tyr Thr
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gly Gln Ser Tyr Ser Tyr Pro Phe Thr
1               5

<210> SEQ ID NO 161
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Ile His Trp Val Arg Gln Ser Pro Gly Lys Gly Leu Glu Trp Leu
        35                  40                  45

Gly Val Ile Trp Ser Ser Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ser Asp Asp Thr Ala Ile His Tyr Cys Ala
                85                  90                  95

Arg Asp Ile Thr Thr Ile Ala Glu Gly Phe Ala Tyr Trp Gly Gln Gly
            100                 105                 110

Thr Leu Val Thr Val Ser Ala
        115

<210> SEQ ID NO 162
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Phe Ser Leu Thr Ser Tyr Gly Ile His
1               5                   10

<210> SEQ ID NO 163
```

<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Val Ile Trp Ser Ser Gly Ser Thr Asp Tyr Asn Ala Ala Phe Ile Ser
1               5                   10                  15

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Thr Thr Ile Ala Glu Gly Phe Ala Tyr
1               5                   10

<210> SEQ ID NO 165
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 166
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Lys Ala Ser Glu Asn Val Gly Thr Tyr Val Ser
1               5                   10

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Gly Ala Ser Asn Arg Tyr Thr
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Gln Ser Tyr Ser Tyr Pro Phe Thr
1               5

<210> SEQ ID NO 169
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Ile Gln Leu Gln Glu Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val Gln Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asp Ile Thr Thr Ile Val Glu Gly Phe Ala His Trp Gly Gln Gly
            100                 105                 110

Thr Leu Val Thr Val Ser Ala
        115

<210> SEQ ID NO 170
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Gly Phe Ser Leu Thr Ser Tyr Gly Val Gln
1               5                   10

<210> SEQ ID NO 171
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Val Ile Trp Ser Gly Gly Ser Thr Asp Tyr Asn Ala Ala Phe Ile Ser
1               5                   10                  15

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ile Thr Thr Ile Val Glu Gly Phe Ala His
1               5                   10

<210> SEQ ID NO 173
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asn Ile Val Met Thr Gln Ser Pro Lys Ser Met Ser Met Ser Val Gly
1               5                   10                  15

Glu Arg Val Thr Leu Ser Cys Lys Ala Ser Glu Lys Val Gly Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Phe
                85                  90                  95

Thr Phe Gly Ser Gly Thr Lys Leu Glu Ile Lys
            100                 105

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Lys Ala Ser Glu Lys Val Gly Thr Tyr Val Ser
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gly Ala Ser Asn Arg Tyr Thr
1               5

```
<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Gln Ser Tyr Ser Tyr Pro Phe Thr
1               5

<210> SEQ ID NO 177
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Gln Glu Ser Gly Pro Glu Leu Val Lys Pro Gly Ala
1               5                   10                  15

Ser Val Lys Leu Ser Cys Lys Ala Ser Gly Tyr Ser Phe Thr Asp Tyr
            20                  25                  30

Thr Met His Trp Val Lys Gln Ser Pro Gly Gln Gly Leu Glu Trp Ile
        35                  40                  45

Gly Trp Ile Tyr Pro Gly Ser Gly Asn Thr Met Tyr Asn Asp Lys Phe
    50                  55                  60

Lys Gly Glu Ala Thr Met Thr Ala Asp Lys Ser Ser Thr Thr Tyr
65                  70                  75                  80

Met Gln Leu Ser Ser Leu Thr Ser Glu Asp Ser Ala Val Tyr Phe Cys
                85                  90                  95

Ala Arg Gly Gly Asp Ser Ile Ile Thr Val Phe Pro Phe Thr Tyr Trp
            100                 105                 110

Gly Gln Gly Thr Leu Val Thr Val Ser Ala
        115                 120

<210> SEQ ID NO 178
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Tyr Ser Phe Thr Asp Tyr Thr Met His
1               5                   10

<210> SEQ ID NO 179
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Trp Ile Tyr Pro Gly Ser Gly Asn Thr Met Tyr Asn Asp Lys Phe Lys
1               5                   10                  15

Gly Glu Ala Thr Met Thr Ala Asp
            20
```

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gly Asp Ser Ile Ile Thr Val Phe Pro Phe Thr Tyr
1               5                   10

<210> SEQ ID NO 181
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Glu Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Pro Thr Phe Gly Ala Gly Thr Lys Leu Glu Ile
            100                 105                 110

Lys

<210> SEQ ID NO 182
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Lys Ser Ser Gln Ser Leu Leu Tyr Ser Ser Asn Gln Lys Asn Tyr Leu
1               5                   10                  15

Ala

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Trp Ala Ser Thr Arg Glu Ser
1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln Gln Tyr Tyr Ser Tyr Pro Pro Thr
1               5

<210> SEQ ID NO 185
<211> LENGTH: 282
<212> TYPE: PRT
<213> ORGANISM: Homo sapiens

<400> SEQUENCE: 185

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
                20                  25                  30

Gly Arg His Ser Ile Thr Val Thr Thr Val Ala Ser Ala Gly Asn Ile
            35                  40                  45

Gly Glu Asp Gly Ile Leu Ser Cys Thr Phe Glu Pro Asp Ile Lys Leu
        50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
130                 135                 140

Tyr Lys Thr Gly Ala Phe Ser Met Pro Glu Val Asn Val Asp Tyr Asn
                150                 155                 160
145

Ala Ser Ser Glu Thr Leu Arg Cys Glu Ala Pro Arg Trp Phe Pro Gln
            165                 170                 175

Pro Thr Val Val Trp Ala Ser Gln Val Asp Gln Gly Ala Asn Phe Ser
        180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280

<210> SEQ ID NO 186
<211> LENGTH: 40

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 186
atagctcttc agggaccatg aarcayctgt ggttcttcct                         40

<210> SEQ ID NO 187
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 187
atagctcttc agggaccatg gacatacttt gttccacgc                          39

<210> SEQ ID NO 188
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 188
atagctcttc agggaccatg gacacacttt gctacacac                          39

<210> SEQ ID NO 189
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 189
atagctcttc agggaccatg tctgtctcct tcctcatct                          39

<210> SEQ ID NO 190
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 190
atagctcttc agggaccatg gactggacct ggagvatc                           38

<210> SEQ ID NO 191
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 191
atagctcttc agggaccatg gactggattt ggaggrtc                           38

<210> SEQ ID NO 192
<211> LENGTH: 38
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 192
atagctcttc agggaccatg gactgcacct ggaggatc                38

<210> SEQ ID NO 193
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
atagctcttc agggaccatg gactggacct ggaggktc                38

<210> SEQ ID NO 194
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 194
atagctcttc agggaccatg gagttkggrc tgagctgg                38

<210> SEQ ID NO 195
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
atagctcttc agggaccatg gagtttkggc tkagctgg                38

<210> SEQ ID NO 196
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
atagctcttc agggaccatg gaactggggc tccgctgg                38

<210> SEQ ID NO 197
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
atagctcttc agggaccatg garttggggc tgwgctgg                38

<210> SEQ ID NO 198
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 198
atagctcttc agggaccatg gggtcaaccg ccatcctc                        38

<210> SEQ ID NO 199
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
atagctcttc agggaccatg gacatgaggg tsccygctca gctc                 44

<210> SEQ ID NO 200
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
atagctcttc agggaccatg gacatgagrg tcctcgctca gctc                 44

<210> SEQ ID NO 201
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
atagctcttc agggaccatg gaagccccag cdcagcttct c                    41

<210> SEQ ID NO 202
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
atagctcttc agggaccatg gaaaccccag cgcagcttct c                    41

<210> SEQ ID NO 203
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
atagctcttc agggaccatg gtgttgcaga cccaggtctt c                    41

<210> SEQ ID NO 204
<211> LENGTH: 41
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 204
atagctcttc agggaccatg gggtcccagg ttcacctcct c                          41

<210> SEQ ID NO 205
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 205
atagctcttc agggaccatg aggctccytg ctcagctcct g                          41

<210> SEQ ID NO 206
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
atagctcttc ttcgtttgat ctccascttg gtc                                   33

<210> SEQ ID NO 207
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
atagctcttc ttcgtttaat ctccagtcgt gtc                                   33

<210> SEQ ID NO 208
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
atagctcttc tggctgagga gacggtgacc                                       30

<210> SEQ ID NO 209
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
atagctcttc atgtgacgct gttgtgactc agga                                  34

<210> SEQ ID NO 210
<211> LENGTH: 34
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 210
atagctcttc atgtgaccyt gtgctcactc agtc                    34

<210> SEQ ID NO 211
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 211
gatgctcttc tgggctggcc taggacagtc amcytgg                 37

<210> SEQ ID NO 212
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Thr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Asn Ser Val Thr Ala Ala Asp Thr Ala Val Tyr Tyr Cys
                85                  90                  95

Ala Thr Tyr Ser Ser Gly Trp Tyr Phe Tyr Phe Asp Tyr Trp Gly Gln
            100                 105                 110

Gly Thr Leu Val Thr Val Ser Ser
        115                 120

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Gly Tyr Ser Ile Ser Ser Gly Tyr Tyr Trp Gly
1               5                   10

<210> SEQ ID NO 214
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

```
Ser Ile Tyr His Ser Gly Thr Thr Tyr Tyr Asn Pro Ser Leu Lys Ser
1               5                   10                  15
```

<210> SEQ ID NO 215
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Tyr Ser Ser Gly Trp Tyr Phe Tyr Phe Asp Tyr
1               5                   10
```

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Val Ala Ser Thr Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Ile
                85                  90                  95

Thr Phe Gly Gln Gly Thr Arg Leu Glu Ile Lys
            100                 105
```

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

```
Arg Ala Ser Gln Gly Ile Ser Ser Tyr Leu Ala
1               5                   10
```

<210> SEQ ID NO 218
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

```
Val Ala Ser Thr Leu Gln Ser
1               5
```

<210> SEQ ID NO 219

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Gln Leu Asn Ser Tyr Pro Ile Thr
1               5

<210> SEQ ID NO 220
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Ser Tyr
            20                  25                  30

Gly Val Gln Trp Val Arg Gln Ala Pro Gly Lys Gly Leu Glu Trp Leu
        35                  40                  45

Gly Val Ile Trp Ser Ser Gly Ser Thr Asp Tyr Asn Ala Ala Phe Leu
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Arg Asp Val Thr Thr Ile Val Glu Gly Phe Ala His Trp Gly Gln Gly
            100                 105                 110

Thr Leu Val Thr Val Ser Ser
        115

<210> SEQ ID NO 221
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Phe Ser Leu Thr Ser Tyr Gly Val Gln
1               5                   10

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Val Ile Trp Ser Ser Gly Ser Thr Asp Tyr Asn Ala Ala Phe Leu Ser
1               5                   10                  15

<210> SEQ ID NO 223
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 223

Asp Val Thr Thr Ile Val Glu Gly Phe Ala His
1               5                   10

<210> SEQ ID NO 224
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Lys Val Gly Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gly Gln Thr Tyr Ser Tyr Pro Phe
                85                  90                  95

Thr Phe Gly Gln Gly Thr Lys Leu Glu Ile Lys
            100                 105

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Lys Ala Ser Glu Lys Val Gly Thr Tyr Val Ser
1               5                   10

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Gly Ala Ser Asn Arg Tyr Thr
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 227

Gly Gln Thr Tyr Ser Tyr Pro Phe Thr
1               5

<210> SEQ ID NO 228
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Val Gln Leu Val Glu Ser Gly Pro Gly Val Val Gln Pro Gly Arg
1               5                   10                  15

Ser Leu Arg Leu Ser Cys Ala Val Ser Gly Phe Ser Leu Thr Ser Tyr
            20                  25                  30

Gly Val Gln Trp Val Arg Gln Ala Pro Gly Lys Gly Leu Glu Trp Leu
        35                  40                  45

Ala Val Ile Trp Ser Ser Gly Ser Thr Asp Tyr Asn Ala Ala Phe Leu
    50                  55                  60

Ser Arg Leu Thr Ile Ser Lys Asp Asn Ser Lys Ser Thr Val Tyr Phe
65                  70                  75                  80

Gln Met Asn Ser Leu Arg Ala Glu Asp Thr Ala Val Tyr Tyr Cys Ala
                85                  90                  95

Arg Asp Val Thr Thr Ile Val Glu Gly Phe Ala His Trp Gly Gln Gly
            100                 105                 110

Thr Leu Val Thr Val Ser Ser
        115

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Gly Phe Ser Leu Thr Ser Tyr Gly Val Gln
1               5                   10

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Val Ile Trp Ser Ser Gly Ser Thr Asp Tyr Asn Ala Ala Phe Leu Ser
1               5                   10                  15

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

```
Asp Val Thr Thr Ile Val Glu Gly Phe Ala His
1               5                   10
```

<210> SEQ ID NO 232
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

```
Gln Val Gln Leu Val Glu Ser Gly Gly Gly Val Val Gln Pro Gly Arg
1               5                   10                  15

Ser Leu Arg Leu Ser Cys Ala Val Ser Gly Phe Ser Leu Thr Ser Tyr
            20                  25                  30

Gly Val Gln Trp Val Arg Gln Ala Pro Gly Lys Gly Leu Glu Trp Leu
        35                  40                  45

Ala Val Ile Trp Ser Ser Gly Ser Thr Asp Tyr Asn Ala Ala Phe Leu
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Arg Asp Val Thr Thr Ile Val Glu Gly Phe Ala His Trp Gly Gln Gly
            100                 105                 110

Thr Leu Val Thr Val Ser Ser
        115
```

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

```
Gly Phe Ser Leu Thr Ser Tyr Gly Val Gln
1               5                   10
```

<210> SEQ ID NO 234
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

```
Val Ile Trp Ser Ser Gly Ser Thr Asp Tyr Asn Ala Ala Phe Leu Ser
1               5                   10                  15
```

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

```
Asp Val Thr Thr Ile Val Glu Gly Phe Ala His
1               5                   10
```

```
<210> SEQ ID NO 236
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Ser Tyr
            20                  25                  30

Gly Val Gln Trp Val Arg Gln Ala Pro Gly Lys Gly Leu Glu Trp Leu
        35                  40                  45

Gly Val Ile Trp Ser Ser Gly Ser Thr Asp Tyr Asn Ala Ala Phe Leu
    50                  55                  60

Ser Arg Leu Thr Ile Ser Lys Asp Asn Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Arg Asp Val Thr Thr Ile Val Glu Gly Phe Ala His Trp Gly Gln Gly
            100                 105                 110

Thr Leu Val Thr Val Ser Ser
        115

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Gly Phe Thr Phe Ser Ser Tyr Gly Val Gln
1               5                   10

<210> SEQ ID NO 238
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Val Ile Trp Ser Ser Gly Ser Thr Asp Tyr Asn Ala Ala Phe Leu Ser
1               5                   10                  15

<210> SEQ ID NO 239
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Asp Val Thr Thr Ile Val Glu Gly Phe Ala His
1               5                   10
```

```
<210> SEQ ID NO 240
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Glu Val Gln Leu Val Glu Ser Gly Gly Leu Val Gln Pro Gly Gly
1               5                   10                  15

Ser Leu Arg Leu Ser Cys Ala Val Ser Gly Phe Ser Leu Thr Ser Tyr
            20                  25                  30

Gly Val Gln Trp Val Arg Gln Ala Pro Gly Lys Gly Leu Glu Trp Leu
        35                  40                  45

Gly Val Ile Trp Ser Ser Gly Ser Thr Asp Tyr Asn Ala Ala Phe Leu
    50                  55                  60

Ser Arg Leu Thr Ile Ser Lys Asp Thr Ser Lys Asn Thr Val Tyr Phe
65                  70                  75                  80

Gln Met Asn Ser Leu Arg Ala Glu Asp Thr Ala Val Tyr Tyr Cys Ala
                85                  90                  95

Arg Asp Val Thr Thr Ile Val Glu Gly Phe Ala His Trp Gly Gln Gly
            100                 105                 110

Thr Leu Val Thr Val Ser Ser
        115

<210> SEQ ID NO 241
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gly Phe Ser Leu Thr Ser Tyr Gly Val Gln
1               5                   10

<210> SEQ ID NO 242
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Val Ile Trp Ser Ser Gly Ser Thr Asp Tyr Asn Ala Ala Phe Leu Ser
1               5                   10                  15

<210> SEQ ID NO 243
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asp Val Thr Thr Ile Val Glu Gly Phe Ala His
1               5                   10

<210> SEQ ID NO 244
<211> LENGTH: 107
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Asp Ile Gln Met Thr Gln Ser Pro Ser Ser Leu Ser Ala Ser Val Gly
1               5                   10                  15

Asp Arg Val Thr Ile Thr Cys Lys Ala Ser Glu Lys Val Gly Thr Tyr
            20                  25                  30

Val Ser Trp Tyr Gln Gln Lys Pro Gly Lys Ala Pro Lys Leu Leu Ile
        35                  40                  45

Tyr Gly Ala Ser Asn Arg Tyr Thr Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gly Gln Thr Tyr Ser Tyr Pro Phe
                85                  90                  95

Thr Phe Gly Gln Gly Thr Lys Val Glu Ile Lys
            100                 105

<210> SEQ ID NO 245
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Lys Ala Ser Glu Lys Val Gly Thr Tyr Val Ser
1               5                   10

<210> SEQ ID NO 246
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Ala Ser Asn Arg Tyr Thr
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gly Gln Thr Tyr Ser Tyr Pro Phe Thr
1               5

<210> SEQ ID NO 248
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 248

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Ala
        35                  40                  45

Ile Gly Glu Ile Tyr His Ser Gly Asn Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Ile Tyr Tyr Cys
                85                  90                  95

Ala Arg Asp Gly Tyr Ser Ser Gly Trp Tyr Trp Gly Tyr Phe Asp Tyr
            100                 105                 110

Trp Gly Gln Gly Thr Leu Val Thr Val Ser Ser
        115                 120

<210> SEQ ID NO 249
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Gly Ser Ile Ser Ser Ser Asn Trp Trp Ser
1               5                   10

<210> SEQ ID NO 250
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Glu Ile Tyr His Ser Gly Asn Thr Asn Tyr Asn Pro Ser Leu Lys Ser
1               5                   10                  15

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asp Gly Tyr Ser Ser Gly Trp Tyr
1               5

<210> SEQ ID NO 252
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Lys Pro Gly Gln Ala Pro Trp Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65              70                  75                  80

Glu Asp Phe Ala Val Tyr Tyr Cys Gln Gln Tyr Asn His Trp Pro Tyr
                85                  90                  95

Thr Phe Gly Gln Gly Thr Lys Leu Glu Ile Lys
            100                 105
```

<210> SEQ ID NO 253
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

```
Arg Ala Ser Gln Ser Val Asn Ser Asn Leu Ala
1               5                   10
```

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

```
Gly Ala Ser Thr Arg Ala Thr
1               5
```

<210> SEQ ID NO 255
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

```
Gln Gln Tyr Asn His Trp Pro Tyr Thr
1               5
```

<210> SEQ ID NO 256
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser His Tyr
```

```
                    20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Pro Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Thr Tyr Tyr Tyr Gly Ser Gly Ser Phe Pro Asp Ala Phe Asp Ile
            100                 105                 110

Trp Gly Gln Gly Thr Met Val Thr Val Ser Ser
        115                 120

<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Gly Ser Ile Ser His Tyr Tyr Trp Ser
1               5                   10

<210> SEQ ID NO 258
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Tyr Ile Tyr Tyr Ser Gly Pro Thr Asn Tyr Asn Pro Ser Leu Lys Ser
1               5                   10                  15

<210> SEQ ID NO 259
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Thr Tyr Tyr Tyr Gly Ser Gly Ser Phe Pro Asp Ala Phe Asp Ile
1               5                   10                  15

<210> SEQ ID NO 260
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Lys Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

```
Leu Ala Trp Tyr Gln Gln Thr Pro Gly Gln Ala Pro Arg Leu Leu Ile
            35                  40                  45

Tyr Asp Ala Ser Asn Arg Ala Thr Gly Ile Pro Ala Arg Phe Ser Val
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Ser Trp Pro Leu
                 85                  90                  95

Thr Phe Gly Gly Gly Thr Lys Leu Glu Ile Lys
            100                 105
```

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

```
Arg Ala Ser Gln Ser Val Ser Ser Tyr Leu Ala
 1               5                  10
```

<210> SEQ ID NO 262
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

```
Asp Ala Ser Asn Arg Ala Thr
 1               5
```

<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

```
Gln Gln Arg Ser Ser Trp Pro Leu Thr
 1               5
```

<210> SEQ ID NO 264
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

```
Gln Val Gln Leu Val Gln Ser Gly Ala Glu Val Lys Lys Pro Gly Ser
 1               5                  10                  15

Ser Met Lys Val Ser Cys Lys Ala Ser Gly Asp Thr Phe Ser Ser Tyr
                 20                  25                  30

Ala Ile Ser Trp Val Arg Gln Ala Pro Gly Gln Gly Leu Glu Trp Met
             35                  40                  45

Ala Gly Ile Ile Pro Val Phe Gly Thr Ala His Asn Ala Gln Lys Phe
         50                  55                  60
```

```
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Thr Arg Gly Gly Pro Tyr Phe Asp Tyr Trp Gly Gln Gly Thr Leu Val
            100                 105                 110

Thr Val Ser Ser
        115

<210> SEQ ID NO 265
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Asp Thr Phe Ser Ser Tyr Ala Ile Ser
1               5                   10

<210> SEQ ID NO 266
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Gly Ile Ile Pro Val Phe Gly Thr Ala His Asn Ala Gln Lys Phe Gln
1               5                   10                  15

Gly

<210> SEQ ID NO 267
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Gly Gly Pro Tyr Phe Asp Tyr
1               5

<210> SEQ ID NO 268
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Glu Ile Val Met Thr Gln Ser Pro Ala Thr Leu Ser Val Ser Pro Gly
1               5                   10                  15

Glu Arg Ala Ala Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Val Ser Thr Arg Ala Thr Gly Ile Pro Asp Arg Phe Asn Gly
        50                  55                  60
```

```
Ser Gly Ser Gly Thr Glu Phe Thr Leu Thr Ile Ser Ser Leu Gln Ser
 65                  70                  75                  80

Glu Asp Phe Gly Ala Tyr Tyr Cys Gln Gln Tyr Lys Lys Trp Pro Phe
                 85                  90                  95

Ile Phe Gly Pro Gly Thr Lys Leu Glu Ile Lys
            100                 105
```

<210> SEQ ID NO 269
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

```
Arg Ala Ser Gln Ser Val Ser Ser Asn Leu Ala
1               5                   10
```

<210> SEQ ID NO 270
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

```
Gly Val Ser Thr Arg Ala Thr
1               5
```

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

```
Gln Gln Tyr Lys Lys Trp Pro Phe Ile
1               5
```

<210> SEQ ID NO 272
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Asn Pro Ser Leu Lys
        50                  55                  60

Ser Arg Val Thr Ile Ser Val Asp Thr Ser Lys Asn Gln Phe Ser Leu
 65                 70                  75                  80

Lys Leu Ile Ser Val Thr Ala Ala Asp Thr Ala Val Tyr Tyr Cys Ala
```

```
                    85                  90                  95

Arg Val Tyr Asn Asn Tyr Asp Trp Gly Phe Asp Tyr Trp Gln Gly
            100                 105                 110

Thr Leu Val Thr Val Ser Ser
        115

<210> SEQ ID NO 273
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Gly Gly Ser Ile Ser Ser Tyr Tyr Trp Ser
1               5                   10

<210> SEQ ID NO 274
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Tyr Ile Tyr Tyr Ser Gly Ser Thr Asn Asn Pro Ser Leu Lys Ser
1               5                   10                  15

<210> SEQ ID NO 275
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Val Tyr Asn Asn Tyr Asp Trp Gly Phe Asp Tyr
1               5                   10

<210> SEQ ID NO 276
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Arg Ser Leu Gln Ser
65                  70                  75                  80

Glu Asp Phe Ala Val Tyr Tyr Cys Gln Gln Tyr His Asn Trp Pro Leu
                85                  90                  95
```

Thr Phe Gly Gly Gly Thr Lys Leu Glu Ile Lys
            100                 105

<210> SEQ ID NO 277
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Gln Gln Tyr His Asn Trp Pro Leu Thr
1               5

<210> SEQ ID NO 278
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

Gln Val Gln Leu Val His Ser Gly Ala Glu Val Lys Arg Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Ile Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Pro Tyr Phe Asp Tyr Trp Gly Gln Gly Ile Leu Val
            100                 105                 110

Thr Val Ser Ser
        115

<210> SEQ ID NO 279
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Gly Gly Thr Phe Ser Ser Tyr Ala Ile Ser
1               5                   10

<210> SEQ ID NO 280
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Gly Ile Ile Pro Ile Phe Gly Ile Ala Asn Tyr Ala Gln Lys Phe Gln
1               5                   10                  15

Gly

<210> SEQ ID NO 281
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Lys Trp Pro Phe
                85                  90                  95

Thr Phe Gly Pro Gly Thr Lys Val Asp Ile Lys
            100                 105

<210> SEQ ID NO 282
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gln Gln Tyr Asn Lys Trp Pro Phe Thr
1               5

<210> SEQ ID NO 283
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Gln Val Gln Val Val Gln Ser Gly Ala Glu Val Lys Lys Pro Gly Ser
1               5                   10                  15

Ser Val Lys Val Ser Cys Lys Ala Ser Gly Asp Thr Phe Ser Asn Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Ile Thr Asn Tyr Ala Gln Lys Phe
50                  55                  60

Gln Gly Arg Val Thr Ile Ile Ala Asp Lys Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ser Arg Gly Gly Pro Tyr Phe Asp Tyr Trp Gly Gln Gly Ile Leu Val

```
                100             105             110

Thr Val Ser Ser
        115

<210> SEQ ID NO 284
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gly Asp Thr Phe Ser Asn Tyr Ala Ile Ser
1               5                   10

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gly Ile Ile Pro Ile Phe Gly Ile Thr Asn Tyr Ala Gln Lys Phe Gln
1               5                   10                  15

Gly

<210> SEQ ID NO 286
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 286

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Lys Trp Pro Phe
                85                  90                  95

Thr Phe Gly Pro Gly Thr Lys Val Asp Ile Lys
            100                 105

<210> SEQ ID NO 287
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Gln Gln Tyr Lys Lys Trp Pro Phe Thr
```

<210> SEQ ID NO 288
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 288
caggtgcagc tgcaggagtc gggcccagga ctggtgaagc cttcggagac cctgtccctc      60
acctgcgctg tctctggtta ctccatcagt agtggttatt actggggctg gatccggcag     120
cccccaggaa aggggctgga gtggattggg agtatctatc atagtgggac cacctactac     180
aatccgtccc tcaagagtcg agtcaccata tcagtggaca cgtccaagaa ccagttctcc     240
ctgaagctga actctgtgac cgccgcagac acggccgtgt attactgtgc gacctatagc     300
agtggctggt acttctactt tgactactgg ggccagggaa ccctggtcac cgtctcctca     360

<210> SEQ ID NO 289
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 289
gacatccagt tgacccagtc tccatccttc ctgtctgcat ctgtaggaga cagagtcacc      60
atcacttgcc gggccagtca gggcattagc agttatttag cctggtatca gcaaaaacca     120
gggaaagccc ctaagctcct gatctatgtt gcatccactt tgcaaagtgg ggtcccatca     180
aggttcagcg gcagtggatc tgggacagaa ttcactctca caatcagcag cctgcagcct     240
gaagattttg caacttatta ctgtcaacag cttaatagtt acccgatcac cttcggccaa     300
gggacacgac tggagattaa a                                                321

<210> SEQ ID NO 290
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290
caagttcaac tcgtggaatc cggtggcggg gtagtacaac ctggtcgcag cctccggctt      60
tcatgcgctg ttagtggttt ctctctcaca tcttacggtg tgcaatgggt acggcaagcc     120
cccggcaagg gtttggaatg gctcggagtg atctggagta gcgggtctac cgactataac     180
gctgcgtttc ttagcaggct gactatttct aaagataatt ccaaaaatac ggtttatttc     240
caaatgaact ccctgcgggc tgaagacact gccgtttatt actgtgctcg ggatgttaca     300
acgattgtag aaggcttcgc ccattggggc caagggacat tggtcacagt atcctca        357

<210> SEQ ID NO 291
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 291

```
gacattcaga tgacccaatc acctagttca ctctcagcaa gtgtaggtga cagagtaaca      60
attacatgca aggccagcga aaaagttggc acctacgtga gttggtacca gcaaaaaccg     120
ggcaaagctc cgaaattgct tatttacggt gcttcaaatc gctatactgg agtgcccagt     180
cgatttagtg ggtctggctc aggtaccgac tttacactca ccatctctag cctgcagcca     240
gaggactttg cgacgtatta ttgcggccag acgtatagtt atccgttcac ctttggacaa     300
ggtaccaagt tggaaataaa g                                              321
```

<210> SEQ ID NO 292
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 292

```
caagtccagt tggttgagag cggtcctggg gtcgtgcagc ctgggcggtc tctgaggctg      60
agttgtgcag tgtcaggttt cagccttaca tcatacgggg ttcaatgggt aaggcaagca    120
cctgggaaag gtctggaatg gcttgcggta atttggtcta gcggtagcac tgactacaat    180
gcggcgtttc tgagtaggct cacgattcct aaagacaatt caaaaagcac ggtttatttt    240
caaatgaaca gtcttcgagc agaagatact gctgtttact attgtgctcg cgacgtgacg    300
acaatcgtgg agggattcgc ccattggggt cagggcaccc tcgttactgt aagttct      357
```

<210> SEQ ID NO 293
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 293

```
caggttcaac ttgtagagtc tggtggtgga gttgtgcaac cgggtaggtc cctccgcctc      60
tcatgcgcag tgtctgggtt ctccttgact agctacgggg ttcagtgggt ccggcaagcc    120
ccaggaaagg gtcttgaatg gttggcagta atttggtcca gcggaagtac cgattataac    180
gcagccttcc tgtcccggtt gaccataagt aaggataatt caaaaaacac cgtttacttt    240
cagatgaata gtctgcgagc ggaggacaca gcggtttact actgcgctag agacgttacc    300
accattgtgg aagggtttgc tcattgggt caagggacac ttgtgacggt ttctagc       357
```

<210> SEQ ID NO 294
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 294

```
caagttcaac ttgttgagtc aggggggagga gttgtgcaac cgggccgctc cctgcgactt      60
tcatgtgcag tatcaggctt tacctttcca tcctacgggg tccaatgggt taggcaggct    120
ccaggtaaag gactggaatg gcttggtgta atatggagca gcggcagtac ggattacaat    180
gctgcattct tgagtcggct cactatatca aaggacaact ctaagaatac cgtctatttt    240
```

<210> SEQ ID NO 295
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 295

```
caaatgaact cactgcgcgc cgaagacacc gcagtttact attgcgcccg agatgtcact      300
acaatagtgg agggttttgc acattggggc caaggaaccc tcgtaactgt gtcctca        357
```

<210> SEQ ID NO 295
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 295

```
gaggttcaac tcgtggaatc tggaggaggt ttggttcagc caggcggttc tctccgactg      60
tcttgcgctg taagtggatt tagtctgacg tcctatggag tacagtgggt gcgccaagct     120
cctgggaagg gcttggaatg gttggggtg atctggtctt ccggttctac agattacaat      180
gcagcattcc tctcacgcct gactataagt aaagatactt ctaaaaatac cgtctacttt     240
cagatgaaca gtcttagggc tgaggatact gcggtctact attgtgcgag gatgtcacg      300
acgattgtag aaggattcgc tcactggggc cagggcactt tggtaacagt ctcctca         357
```

<210> SEQ ID NO 296
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 296

```
gacattcaga tgactcaatc tccttcatcc cttagcgcat ccgtaggaga tcgagtgacc      60
ataacatgca aggcctctga gaagtaggg acttacgtga gctggtatca gcaaaagccg      120
gggaaagcac cgaagttgct catttatggg gcgtctaata ggtacacggg agtcccgagc     180
agattttccg gctctcggag tggaaccgac tttacccctta caattagtag tctccaacct    240
gaggattttg ccacgtacta ctgtggccag acttactctt atccatttac attcggccaa     300
ggtacgaagg ttgaaattaa a                                               321
```

<210> SEQ ID NO 297
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 297

```
caggtgcagc tgcaggagtc gggcccagga ctggtgaagc cttcggggac cctgtccctc      60
acctgcgctg tctctggtgg ctccatcagc agtagtaact ggtggagttg ggtccgccag     120
cccccaggga aggggctgga ggccattggg gaaatctatc atagtggaaa caccaactac     180
aacccgtccc tcaagagtcg agtcaccata tcagtagaca gtccaagaa ccagttctcc      240
ctgaagctga gctctgtgac cgccgcggac acggccattt attactgtgc gagagatggg     300
tatagcagtg gctggtactg gggctacttt gactactggg gccagggaac cctggtcacc     360
gtctcctca                                                              369
```

<210> SEQ ID NO 298
<211> LENGTH: 321

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 298
gaaatagtga tgacgcagtc tccagccacc ctgtctgtgt ctccagggga aagagccacc    60
ctctcctgca gggccagtca gagtgttaac agcaacttag cctggtacca gcagaaacct   120
ggccaggctc cctggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataatcact ggccgtacac ttttggccag   300
gggaccaagc tggagatcaa a                                              321

<210> SEQ ID NO 299
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 299
caggtgcagc tgcaggagtc gggccccgga ctggtgaagc cttcggagac cctgtccctc    60
acctgcactg tctctggtgg ctccatcagt cattactact ggagctggat ccggcagccc   120
ccagggaagg gactggagtg gattgggtat atctattaca gtgggcccac caactacaac   180
ccctccctca gagtcgagt caccatatca gtagacacgt ccaagaacca gttctccctg    240
aagctgagct ctgtgaccgc tgcggacacg gccgtgtatt actgtgcgag gacgtattac   300
tatggttcgg ggagttttcc cgatgctttt gatatctggg gccaagggac aatggtcacc   360
gtctcctca                                                           369

<210> SEQ ID NO 300
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 300
aaaattgtgt tgacacagtc tccagccacc ctgtctttgt ctccaggtga aagagccacc    60
ctctcctgca gggccagtca gagtgttagc agctacttag cctggtacca acagacacct   120
ggccaggctc ccaggctcct catctatgat gcatccaaca gggccactgg catcccagcc   180
aggttcagtg tcagtgggtc tgggacagac ttcactctca ccatcagcag cctagagcct   240
gaagattttg cagtttatta ctgtcagcag cgtagcagct ggcctctcac tttcggcgga   300
gggaccaagc tggagatcaa a                                              321

<210> SEQ ID NO 301
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 301

```
caggtgcagc tggtgcagtc tggggctgag gtgaagaagc ctgggtcctc aatgaaggtc    60
tcctgcaagg cttctggaga caccttcagc agctatgcta tcagctgggt gcgacaggcc   120
cctggacaag ggcttgagtg gatggcaggg atcatccctg tctttggtac agcacacaac   180
gcacagaagt tccagggcag agtcacgatt accgcggaca atccacgag cacagcctac    240 atggagctga gcagcctgag atctgaggac acggccgtgt attactgtac gagaggggt    300 ccttactttg actactgggg ccagggaacc ctggtcaccg tctcctca                348
```

<210> SEQ ID NO 302
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 302

```
gaaatagtga tgacgcagtc tccagccacc ctgtctgtgt ctccagggga aagagccgcc    60
ctctcctgta gggccagtca gagtgttagc agcaacttag cctggtacca gcagaaacct   120
ggccaggctc ccaggctcct catctatggt gtttctacca gggccactgg tatcccagac   180
aggttcaatg gcagtgggtc tgggacagag ttcactctca ccatcagcag cctgcagtct   240
gaagattttg gagcttatta ctgtcagcag tataaaagt ggccattcat tttcggccct    300
gggaccaagc tggagatcaa a                                             321
```

<210> SEQ ID NO 303
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 303

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagtac caataacaac   180
ccctccctca agagtcgagt caccatatca gtagacacgt ccaagaacca gttctccctg   240
aagctgatct ctgtgaccgc tgcggacacg gccgtatact actgtgcgag gtctataat    300 aattacgatt ggggctttga ctactggggc cagggaaccc tggtcaccgt ctcctca      357
```

<210> SEQ ID NO 304
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 304

```
gaaatagtaa tgacgcagtc tccagccacc ctgtctgtgt ctccagggga gagagccacc    60
ctctcctgca gggccagtca gagtgttagc agcaacttag cctggtacca gcagaaacct   120
ggtcaggctc ccagactcct catctatggt gcatccacca gggccactgg tatcccagcc   180
aggttcagtg gcagtgggtc tgggacagag ttcactctca ccatccgcag cctgcagtct   240
gaagattttg cagtttatta ctgtcagcag tatcataact ggcctctcac tttcggcgga   300
```
gggaccaagc tggagatcaa a                                                  321

<210> SEQ ID NO 305
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 305
caggtgcagc tggttcattc tggggctgag gtgaagaggc ctgggtcctc ggtgaaggtc          60
tcctgcaagg cttctggagg caccttcagc agctatgcta tcagttgggt gcgacaggcc        120
cctggacaag gcttgagtg gatgggaggg atcatcccta tctttggtat agcaaactac         180
gcacagaagt tccagggcag agtcacgatt atcgcggaca atccacgag acagcctac          240 atggagctga gcagcctgag atctgaggac acggccgtgt attactgtgc gagagggggt        300
ccttactttg actactgggg ccagggaatc ctggtcaccg tctcctca                     348

<210> SEQ ID NO 306
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 306
gaaatagtga tgacgcagtc tccagccacc ctgtctgtgt ctccagggga aagagccacc          60
ctctcctgca gggccagtca gagtgttagc agcaacttag cctggtacca gcagaaacct        120
ggccaggctc ccaggctcct catctatggt gcatccacca gggccactgg tatcccagcc        180
aggttcagtg gcagtgggtc tgggacagag ttcactctca ccatcagcag cctgcagtct        240
gaagattttg cagtttatta ctgtcagcag tataataagt ggccattcac tttcggccct        300
gggaccaaag tggatatcaa a                                                  321

<210> SEQ ID NO 307
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 307
caggtgcagg tggtgcagtc tggggctgag gtgaagaagc ctgggtcctc ggtgaaggtc          60
tcctgcaagg cttctggaga caccttcagc aactatgcta tcagttgggt gcgacaggcc        120
cctggacaag gcttgagtg gatgggaggg atcatcccta tctttggtat aacaaactac         180
gcacaaaagt tccagggcag agtcacgatt atcgcggaca atccacgag acagcctac          240 atggagctga gcagcctgag atctgaggac acggccgtgt attactgttc gagagggggt        300
ccttactttg actactgggg ccagggaatc ctggtcaccg tctcctca                     348

<210> SEQ ID NO 308
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 308
gaaatagtga tgacgcagtc tccagccacc ctgtctgtgt ctccagggga aagagccacc        60
ctctcctgca gggccagtca gagtgtgagc agcaacttag cctggtacca gcagaaacct       120
ggccaggctc ccaggctcct catctatggt gcatccacca gggccactgg tatcccagcc       180
aggttcagtg gcagtgggtc tgggacagag ttcactctca ccatcagcag cctgcagtct       240
gaagattttg cagtttatta ctgtcagcag tataaaaagt ggccattcac tttcggccct       300
gggaccaaag tggatatcaa a                                                 321
```

ANTI-VTCN1 ANTIBODIES AND ANTIBODY DRUG CONJUGATES

RELATED APPLICATIONS

The instant application is a 35 U.S.C. § 371 national stage filing of International Application No. PCT/US2018/028347, filed on Apr. 19, 2018, which in turn claims priority to U.S. Provisional Application No. 62/487,424, filed on Apr. 19, 2017, the entire contents of each of which are expressly incorporated by reference herein in their entirety.

SEQUENCE LISTING

The instant application contains a Sequence Listing which has been filed electronically in ASCII format and is hereby incorporated by reference in its entirety. Said ASCII copy, created on Apr. 18, 2018, is named 127913-00320_SL.txt and is 144,067 bytes in size.

BACKGROUND

VTCN1, also known as "V-set domain containing T cell activation inhibitor 1," "Immune costimulatory protein B7-H4," "T-Cell Costimulatory Molecule B7x," "B7-H4," "B7h.5," and "B7H4," is a member of the B7 costimulatory protein family. Proteins in this family are present on the surface of antigen-presenting cells and interact with ligand bound to receptors on the surface of T cells. Studies have shown that high levels of the encoded protein has been correlated with tumor progression. VTCN1 was originally cloned in 2003 (Sica, G. L., et al. *Immunity* 18: 849-861, 2003; Prasad, D. V. R., et al. *Immunity* 18: 863-873, 2003; and Zang, X., et al. *Proc. Nat. Acad. Sci.* 100: 10388-10392, 2003).

VTCN1 negatively regulates T-cell-mediated immune response by inhibiting T-cell activation, proliferation, cytokine production and development of cytotoxicity. When VTCN1 is expressed on the cell surface of tumor macrophages, VTCN1 plays an important role, together with regulatory T-cells (Treg), in the suppression of tumor-associated antigen-specific T-cell immunity.

Antibody drug conjugates (ADC) represent a new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen.

Accordingly, there remains a need in the art for anti-VTCN1 antibodies and ADCs that can be used for therapeutic purposes in the treatment of cancer.

SUMMARY

In certain aspects, the present invention provides for anti-VTCN1 antibodies and antibody drug conjugates (ADCs). In certain embodiments of the invention, the antibodies, or antigen binding portions thereof, bind to VTCN1 (SEQ ID NO: 185) or the extracellular domain of VTCN1.

In one embodiment, it has been surprisingly found that the antibodies, and antigen-binding portions thereof, disclosed herein surprisingly reduce primary tumor size and/or inhibit primary tumor growth of VTCN1-expressing tumors (see Examples). Prior to the instant disclosure, anti-VTCN1 antibodies had only been shown to inhibit or prevent tumor metastasis, and it had not been demonstrated that any VTCN1 antibodies were capable of affecting primary tumor size or primary tumor growth. Thus, the novel antibodies, and antigen-binding portions thereof, disclosed herein provide a surprisingly effective new treatment for not only inhibiting tumor metastasis, but also for inhibition of primary tumors and reduction of primary tumor size.

In another embodiment, it has been shown that antibody-dependent cell-mediated cytotoxicity (ADCC) activity is not necessary for anti-VTCN1 antibodies to inhibit tumor growth. Accordingly, in one embodiment, an antibody, or antigen binding portion thereof, of the invention comprises an isotype lacking effector function (e.g., human IgG4).

In one embodiment, the antibodies, or antigen binding portions thereof, of the invention, bind to VTCN1 with a $K_d$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less.

In yet other embodiments of the invention, anti-VTCN1 antibody drug conjugates (ADCs) of the invention (e.g., the VTCN1 antibodies of the invention conjugated to a toxin) capable of being internalized. In another embodiment, the anti-VTCN1 antibody drug conjugates (ADCs) of the invention are capable of inducing cell death of cells endogenously expressing VTCN1.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 223 and a light chain variable region comprising a CDR3 having the amino acid sequence of SEQ ID NO: 227.

In some embodiments, the antibody, or antigen binding portion thereof, comprises a heavy chain variable region comprising a CDR2 having the amino acid sequence of SEQ ID NO: 222 and a light chain variable region comprising a CDR2 having the amino acid sequence of SEQ ID NO: 226. In other embodiments, the antibody, or antigen binding portion thereof, comprises a heavy chain variable region comprising a CDR1 having the amino acid sequence of SEQ ID NO: 221 and a light chain variable region comprising a CDR1 having the amino acid sequence of either SEQ ID NO: 225.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 231 and a light chain variable region comprising a CDR3 having the amino acid sequence of SEQ ID NO: 227.

In some embodiments, the antibody, or antigen binding portion thereof, comprises a heavy chain variable region comprising a CDR2 having the amino acid sequence of SEQ ID NO: 230 and a light chain variable region comprising a CDR2 having the amino acid sequence of SEQ ID NO: 226. In other embodiments, the antibody, or antigen binding portion thereof, comprises a heavy chain variable region comprising a CDR1 having the amino acid sequence of SEQ ID NO: 229 and a light chain variable region comprising a CDR1 having the amino acid sequence of either SEQ ID NO: 225.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 235 and a light chain variable region comprising a CDR3 having the amino acid sequence of SEQ ID NO: 227.

In some embodiments, the antibody, or antigen binding portion thereof, comprises a heavy chain variable region comprising a CDR2 having the amino acid sequence of SEQ ID NO: 234 and a light chain variable region comprising a CDR2 having the amino acid sequence of SEQ ID NO: 226. In other embodiments, the antibody, or antigen binding portion thereof, comprises a heavy chain variable region comprising a CDR1 having the amino acid sequence of SEQ ID NO: 233 and a light chain variable region comprising a CDR1 having the amino acid sequence of either SEQ ID NO: 225.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 239 and a light chain variable region comprising a CDR3 having the amino acid sequence of SEQ ID NO: 227.

In some embodiments, the antibody, or antigen binding portion thereof, comprises a heavy chain variable region comprising a CDR2 having the amino acid sequence of SEQ ID NO: 238 and a light chain variable region comprising a CDR2 having the amino acid sequence of SEQ ID NO: 226. In other embodiments, the antibody, or antigen binding portion thereof, comprises a heavy chain variable region comprising a CDR1 having the amino acid sequence of SEQ ID NO: 237 and a light chain variable region comprising a CDR1 having the amino acid sequence of either SEQ ID NO: 225.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 243 and a light chain variable region comprising a CDR3 having the amino acid sequence of SEQ ID NO: 247.

In some embodiments, the antibody, or antigen binding portion thereof, comprises a heavy chain variable region comprising a CDR2 having the amino acid sequence of SEQ ID NO: 242 and a light chain variable region comprising a CDR2 having the amino acid sequence of SEQ ID NO: 246. In other embodiments, the antibody, or antigen binding portion thereof, comprises a heavy chain variable region comprising a CDR1 having the amino acid sequence of SEQ ID NO: 241 and a light chain variable region comprising a CDR1 having the amino acid sequence of either SEQ ID NO: 245.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 251 and a light chain variable region comprising a CDR3 having the amino acid sequence of SEQ ID NO: 255.

In some embodiments, the antibody, or antigen binding portion thereof, comprises a heavy chain variable region comprising a CDR2 having the amino acid sequence of SEQ ID NO: 250 and a light chain variable region comprising a CDR2 having the amino acid sequence of SEQ ID NO: 254. In other embodiments, the antibody, or antigen binding portion thereof, comprises a heavy chain variable region comprising a CDR1 having the amino acid sequence of SEQ ID NO: 249 and a light chain variable region comprising a CDR1 having the amino acid sequence of either SEQ ID NO: 253.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 259 and a light chain variable region comprising a CDR3 having the amino acid sequence of SEQ ID NO: 263.

In some embodiments, the antibody, or antigen binding portion thereof, comprises a heavy chain variable region comprising a CDR2 having the amino acid sequence of SEQ ID NO: 258 and a light chain variable region comprising a CDR2 having the amino acid sequence of SEQ ID NO: 262. In other embodiments, the antibody, or antigen binding portion thereof, comprises a heavy chain variable region comprising a CDR1 having the amino acid sequence of SEQ ID NO: 257 and a light chain variable region comprising a CDR1 having the amino acid sequence of either SEQ ID NO: 261.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 267 and a light chain variable region comprising a CDR3 having the amino acid sequence of SEQ ID NO: 271.

In some embodiments, the antibody, or antigen binding portion thereof, comprises a heavy chain variable region comprising a CDR2 having the amino acid sequence of SEQ ID NO: 266 and a light chain variable region comprising a CDR2 having the amino acid sequence of SEQ ID NO: 270. In other embodiments, the antibody, or antigen binding portion thereof, comprises a heavy chain variable region comprising a CDR1 having the amino acid sequence of SEQ ID NO: 265 and a light chain variable region comprising a CDR1 having the amino acid sequence of either SEQ ID NO: 269.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 275 and a light chain variable region comprising a CDR3 having the amino acid sequence of SEQ ID NO: 277.

In some embodiments, the antibody, or antigen binding portion thereof, comprises a heavy chain variable region comprising a CDR2 having the amino acid sequence of SEQ ID NO: 274 and a light chain variable region comprising a CDR2 having the amino acid sequence of SEQ ID NO: 254. In other embodiments, the antibody, or antigen binding portion thereof, comprises a heavy chain variable region comprising a CDR1 having the amino acid sequence of SEQ ID NO: 273 and a light chain variable region comprising a CDR1 having the amino acid sequence of either SEQ ID NO: 269.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 267 and a light chain variable region comprising a CDR3 having the amino acid sequence of SEQ ID NO: 282.

In some embodiments, the antibody, or antigen binding portion thereof, comprises a heavy chain variable region comprising a CDR2 having the amino acid sequence of SEQ ID NO: 280 and a light chain variable region comprising a CDR2 having the amino acid sequence of SEQ ID NO: 254. In other embodiments, the antibody, or antigen binding portion thereof, comprises a heavy chain variable region comprising a CDR1 having the amino acid sequence of SEQ ID NO: 279 and a light chain variable region comprising a CDR1 having the amino acid sequence of either SEQ ID NO: 269.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 267 and a light chain variable region comprising a CDR3 having the amino acid sequence of SEQ ID NO: 287.

In some embodiments, the antibody, or antigen binding portion thereof, comprises a heavy chain variable region comprising a CDR2 having the amino acid sequence of SEQ ID NO: 285 and a light chain variable region comprising a CDR2 having the amino acid sequence of SEQ ID NO: 254. In other embodiments, the antibody, or antigen binding portion thereof, comprises a heavy chain variable region comprising a CDR1 having the amino acid sequence of SEQ ID NO: 284 and a light chain variable region comprising a CDR1 having the amino acid sequence of either SEQ ID NO: 269.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 215 and a light chain variable region comprising a CDR3 having the amino acid sequence of SEQ ID NO: 219.

In some embodiments, the antibody, or antigen binding portion thereof, comprises a heavy chain variable region comprising a CDR2 having the amino acid sequence of SEQ ID NO: 214 and a light chain variable region comprising a CDR2 having the amino acid sequence of SEQ ID NO: 218. In other embodiments, the antibody, or antigen binding portion thereof, comprises a heavy chain variable region comprising a CDR1 having the amino acid sequence of SEQ ID NO: 213 and a light chain variable region comprising a CDR1 having the amino acid sequence of either SEQ ID NO: 217.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 4 and a light chain variable region comprising a CDR3 having the amino acid sequence of SEQ ID NO: 8.

In some embodiments, the antibody, or antigen binding portion thereof, further comprises a heavy chain variable region comprising a CDR2 having the amino acid sequence of SEQ ID NO: 3 and a light chain variable region comprising a CDR2 having the amino acid sequence of SEQ ID NO: 7. In other embodiments, the antibody, or antigen binding portion thereof, comprises a heavy chain variable region comprising a CDR1 having the amino acid sequence of SEQ ID NO: 2 and a light chain variable region comprising a CDR1 having the amino acid sequence of either SEQ ID NO: 6.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 12 and a light chain variable region comprising a CDR3 having the amino acid sequence of SEQ ID NO: 16.

In some embodiments, the antibody, or antigen binding portion thereof, further comprises a heavy chain variable region comprising a CDR2 having the amino acid sequence of SEQ ID NO: 11 and a light chain variable region comprising a CDR2 having the amino acid sequence of SEQ ID NO: 15. In other embodiments, the antibody, or antigen binding portion thereof, comprises a heavy chain variable region comprising a CDR1 having the amino acid sequence of SEQ ID NO: 10 and a light chain variable region comprising a CDR1 having the amino acid sequence of either SEQ ID NO: 14.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 20 and a light chain variable region comprising a CDR3 having the amino acid sequence of SEQ ID NO: 24.

In some embodiments, the antibody, or antigen binding portion thereof, comprises a heavy chain variable region comprising a CDR2 having the amino acid sequence of SEQ ID NO: 19 and a light chain variable region comprising a CDR2 having the amino acid sequence of SEQ ID NO: 23. In other embodiments, the antibody, or antigen binding portion thereof, comprises a heavy chain variable region comprising a CDR1 having the amino acid sequence of SEQ ID NO: 18 and a light chain variable region comprising a CDR1 having the amino acid sequence of either SEQ ID NO: 22.

In yet another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 28 and a light chain variable region comprising a CDR3 having the amino acid sequence of SEQ ID NO: 32.

In some aspects, the antibody, or antigen binding portion thereof, comprises a heavy chain variable region comprising a CDR2 having the amino acid sequence of SEQ ID NO: 27 and a light chain variable region comprising a CDR2 having the amino acid sequence of SEQ ID NO: 31. In other embodiments, the antibody, or antigen binding portion thereof, comprises a heavy chain variable region comprising a CDR1 having the amino acid sequence of SEQ ID NO: 26 and a light chain variable region comprising a CDR1 having the amino acid sequence of either SEQ ID NO: 30.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 36 and a light chain variable region comprising a CDR3 having the amino acid sequence of SEQ ID NO: 40.

In some aspects, the antibody, or antigen binding portion thereof, comprises a heavy chain variable region comprising a CDR2 having the amino acid sequence of SEQ ID NO: 35 and a light chain variable region comprising a CDR2 having the amino acid sequence of SEQ ID NO: 39. In other embodiments, the antibody, or antigen binding portion thereof, comprises a heavy chain variable region comprising a CDR1 having the amino acid sequence of SEQ ID NO: 34 and a light chain variable region comprising a CDR1 having the amino acid sequence of either SEQ ID NO: 38.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 44 and a light chain variable region comprising a CDR3 having the amino acid sequence of SEQ ID NO: 48.

In some aspects, the antibody, or antigen binding portion thereof, comprises a heavy chain variable region comprising a CDR2 having the amino acid sequence of SEQ ID NO: 43 and a light chain variable region comprising a CDR2 having the amino acid sequence of SEQ ID NO: 47. In other embodiments, the antibody, or antigen binding portion thereof, comprises a heavy chain variable region comprising a CDR1 having the amino acid sequence of SEQ ID NO: 42 and a light chain variable region comprising a CDR1 having the amino acid sequence of either SEQ ID NO: 46.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 52 and a light chain variable region comprising a CDR3 having the amino acid sequence of SEQ ID NO: 56.

In some aspects, the antibody, or antigen binding portion thereof, comprises a heavy chain variable region comprising a CDR2 having the amino acid sequence of SEQ ID NO: 51 and a light chain variable region comprising a CDR2 having the amino acid sequence of SEQ ID NO: 55. In other embodiments, the antibody, or antigen binding portion thereof, comprises a heavy chain variable region comprising a CDR1 having the amino acid sequence of SEQ ID NO: 50 and a light chain variable region comprising a CDR1 having the amino acid sequence of either SEQ ID NO: 54.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 60 and a light chain variable region comprising a CDR3 having the amino acid sequence of SEQ ID NO: 64.

In some aspects, the antibody, or antigen binding portion thereof, comprises a heavy chain variable region comprising a CDR2 having the amino acid sequence of SEQ ID NO: 59 and a light chain variable region comprising a CDR2 having the amino acid sequence of SEQ ID NO: 63. In other embodiments, the antibody, or antigen binding portion thereof, comprises a heavy chain variable region comprising a CDR1 having the amino acid sequence of SEQ ID NO: 58 and a light chain variable region comprising a CDR1 having the amino acid sequence of either SEQ ID NO: 62.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 68 and a light chain variable region comprising a CDR3 having the amino acid sequence of SEQ ID NO: 72.

In some aspects, the antibody, or antigen binding portion thereof, comprises a heavy chain variable region comprising a CDR2 having the amino acid sequence of SEQ ID NO: 67 and a light chain variable region comprising a CDR2 having the amino acid sequence of SEQ ID NO: 71. In other embodiments, the antibody, or antigen binding portion thereof, comprises a heavy chain variable region comprising a CDR1 having the amino acid sequence of SEQ ID NO: 66 and a light chain variable region comprising a CDR1 having the amino acid sequence of either SEQ ID NO: 70.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 76 and a light chain variable region comprising a CDR3 having the amino acid sequence of SEQ ID NO: 80.

In some aspects, the antibody, or antigen binding portion thereof, comprises a heavy chain variable region comprising a CDR2 having the amino acid sequence of SEQ ID NO: 75 and a light chain variable region comprising a CDR2 having the amino acid sequence of SEQ ID NO: 79. In other embodiments, the antibody, or antigen binding portion thereof, comprises a heavy chain variable region comprising a CDR1 having the amino acid sequence of SEQ ID NO: 74 and a light chain variable region comprising a CDR1 having the amino acid sequence of either SEQ ID NO: 78.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 84 and a light chain variable region comprising a CDR3 having the amino acid sequence of SEQ ID NO: 88.

In some aspects, the antibody, or antigen binding portion thereof, comprises a heavy chain variable region comprising a CDR2 having the amino acid sequence of SEQ ID NO: 83 and a light chain variable region comprising a CDR2 having the amino acid sequence of SEQ ID NO: 87. In other embodiments, the antibody, or antigen binding portion thereof, comprises a heavy chain variable region comprising a CDR1 having the amino acid sequence of SEQ ID NO: 82 and a light chain variable region comprising a CDR1 having the amino acid sequence of either SEQ ID NO: 86. In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 92 and a light chain variable region comprising a CDR3 having the amino acid sequence of SEQ ID NO: 96.

In some aspects, the antibody, or antigen binding portion thereof, comprises a heavy chain variable region comprising a CDR2 having the amino acid sequence of SEQ ID NO: 91 and a light chain variable region comprising a CDR2 having the amino acid sequence of SEQ ID NO: 95. In other embodiments, the antibody, or antigen binding portion thereof, comprises a heavy chain variable region comprising a CDR1 having the amino acid sequence of SEQ ID NO: 90 and a light chain variable region comprising a CDR1 having the amino acid sequence of either SEQ ID NO: 94.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 100 and a light chain variable region comprising a CDR3 having the amino acid sequence of SEQ ID NO: 104.

In some aspects, the antibody, or antigen binding portion thereof, comprises a heavy chain variable region comprising a CDR2 having the amino acid sequence of SEQ ID NO: 99 and a light chain variable region comprising a CDR2 having the amino acid sequence of SEQ ID NO: 103. In other embodiments, the antibody, or antigen binding portion thereof, comprises a heavy chain variable region comprising a CDR1 having the amino acid sequence of SEQ ID NO: 98 and a light chain variable region comprising a CDR1 having the amino acid sequence of either SEQ ID NO: 102.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 108 and a light chain variable region comprising a CDR3 having the amino acid sequence of SEQ ID NO: 112.

In some aspects, the antibody, or antigen binding portion thereof, comprises a heavy chain variable region comprising a CDR2 having the amino acid sequence of SEQ ID NO: 107 and a light chain variable region comprising a CDR2 having the amino acid sequence of SEQ ID NO: 111. In other embodiments, the antibody, or antigen binding portion thereof, comprises a heavy chain variable region comprising a CDR1 having the amino acid sequence of SEQ ID NO: 106 and a light chain variable region comprising a CDR1 having the amino acid sequence of either SEQ ID NO: 110.

In yet other aspects of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 116 and a light chain variable region comprising a CDR3 having the amino acid sequence of SEQ ID NO: 120.

In some aspects, the antibody, or antigen binding portion thereof, comprises a heavy chain variable region comprising a CDR2 having the amino acid sequence of SEQ ID NO: 115 and a light chain variable region comprising a CDR2 having the amino acid sequence of SEQ ID NO: 119. In other embodiments, the antibody, or antigen binding portion thereof, comprises a heavy chain variable region comprising a CDR1 having the amino acid sequence of SEQ ID NO: 114 and a light chain variable region comprising a CDR1 having the amino acid sequence of either SEQ ID NO: 118.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 124 and a light chain variable region comprising a CDR3 having the amino acid sequence of SEQ ID NO: 128.

In some aspects, the antibody, or antigen binding portion thereof, comprises a heavy chain variable region comprising a CDR2 having the amino acid sequence of SEQ ID NO: 123 and a light chain variable region comprising a CDR2 having the amino acid sequence of SEQ ID NO: 127. In other embodiments, the antibody, or antigen binding portion thereof, comprises a heavy chain variable region comprising a CDR1 having the amino acid sequence of SEQ ID NO: 122 and a light chain variable region comprising a CDR1 having the amino acid sequence of either SEQ ID NO: 126.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 132 and a light chain variable region comprising a CDR3 having the amino acid sequence of SEQ ID NO: 136.

In some aspects, the antibody, or antigen binding portion thereof, comprises a heavy chain variable region comprising a CDR2 having the amino acid sequence of SEQ ID NO: 131 and a light chain variable region comprising a CDR2 having the amino acid sequence of SEQ ID NO: 135. In other embodiments, the antibody, or antigen binding portion thereof, comprises a heavy chain variable region comprising a CDR1 having the amino acid sequence of SEQ ID NO: 130 and a light chain variable region comprising a CDR1 having the amino acid sequence of either SEQ ID NO: 134.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 140 and a light chain variable region comprising a CDR3 having the amino acid sequence of SEQ ID NO: 144.

In some aspects, the antibody, or antigen binding portion thereof, comprises a heavy chain variable region comprising a CDR2 having the amino acid sequence of SEQ ID NO: 139 and a light chain variable region comprising a CDR2 having the amino acid sequence of SEQ ID NO: 143. In other embodiments, the antibody, or antigen binding portion thereof, comprises a heavy chain variable region comprising a CDR1 having the amino acid sequence of SEQ ID NO: 138 and a light chain variable region comprising a CDR1 having the amino acid sequence of either SEQ ID NO: 142.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 148 and a light chain variable region comprising a CDR3 having the amino acid sequence of SEQ ID NO: 152.

In some aspects, the antibody, or antigen binding portion thereof, comprises a heavy chain variable region comprising a CDR2 having the amino acid sequence of SEQ ID NO: 147 and a light chain variable region comprising a CDR2 having the amino acid sequence of SEQ ID NO: 151. In other embodiments, the antibody, or antigen binding portion thereof, comprises a heavy chain variable region comprising a CDR1 having the amino acid sequence of SEQ ID NO: 146 and a light chain variable region comprising a CDR1 having the amino acid sequence of either SEQ ID NO: 150.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 156 and a light chain variable region comprising a CDR3 having the amino acid sequence of SEQ ID NO: 160.

In some aspects, the antibody, or antigen binding portion thereof, comprises a heavy chain variable region comprising a CDR2 having the amino acid sequence of SEQ ID NO: 155 and a light chain variable region comprising a CDR2 having the amino acid sequence of SEQ ID NO: 159. In other embodiments, the antibody, or antigen binding portion thereof, comprises a heavy chain variable region comprising a CDR1 having the amino acid sequence of SEQ ID NO: 154 and a light chain variable region comprising a CDR1 having the amino acid sequence of either SEQ ID NO: 158.

In another aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 164 and a light chain variable region comprising a CDR3 having the amino acid sequence of SEQ ID NO: 168.

In some aspects, the antibody, or antigen binding portion thereof, comprises a heavy chain variable region comprising a CDR2 having the amino acid sequence of SEQ ID NO: 163 and a light chain variable region comprising a CDR2 having the amino acid sequence of SEQ ID NO: 167. In other embodiments, the antibody, or antigen binding portion thereof, comprises a heavy chain variable region comprising a CDR1 having the amino acid sequence of SEQ ID NO: 162 and a light chain variable region comprising a CDR1 having the amino acid sequence of either SEQ ID NO: 166.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 172 and a light chain variable region comprising a CDR3 having the amino acid sequence of SEQ ID NO: 176.

In some aspects, the antibody, or antigen binding portion thereof, comprises a heavy chain variable region comprising a CDR2 having the amino acid sequence of SEQ ID NO: 171 and a light chain variable region comprising a CDR2 having the amino acid sequence of SEQ ID NO: 175. In other embodiments, the antibody, or antigen binding portion thereof, comprises a heavy chain variable region comprising a CDR1 having the amino acid sequence of SEQ ID NO: 170 and a light chain variable region comprising a CDR1 having the amino acid sequence of either SEQ ID NO: 174.

In one aspect of the invention, the present disclosure provides an isolated antibody, or antigen binding portion thereof, that binds to human VTCN1, wherein the antibody, or antigen binding portion thereof, comprises a heavy chain variable region comprising a CDR3 having the amino acid sequence of SEQ ID NO: 180 and a light chain variable region comprising a CDR3 having the amino acid sequence of SEQ ID NO: 184.

In some aspects, the antibody, or antigen binding portion thereof, comprises a heavy chain variable region comprising a CDR2 having the amino acid sequence of SEQ ID NO: 179 and a light chain variable region comprising a CDR2 having the amino acid sequence of SEQ ID NO: 183. In other embodiments, the antibody, or antigen binding portion thereof, comprises a heavy chain variable region comprising a CDR1 having the amino acid sequence of SEQ ID NO: 178 and a light chain variable region comprising a CDR1 having the amino acid sequence of either SEQ ID NO: 182.

In some aspects, the antibody, or antigen binding portion thereof, is a human or humanized antibody. In one embodiments, the antibody or antigen binding portion thereof is an IgG isotype. In some embodiments, the antibody, or antigen binding portion thereof, is an $IgG_1$ isotype. In another embodiment, the antibody, or antigen-binding portion thereof, is an $IgG_4$ isotype. In another embodiment, the antibody, or antigen-binding portion thereof, is an IgG2 isotype. In another embodiment, the antibody, or antigen-binding portion thereof, is an IgG3 isotype.

In certain embodiments, the anti-VTCN1 antibody, or antigen binding portion thereof, is a multispecific antibody, e.g. a bispecific antibody.

In some aspects, the antibody, or antigen binding portion thereof, has a $K_D$ of 200 nM or less.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 223, a CDR2 domain comprising the amino acid sequence of SEQ ID NO: 222, and a CDR1 domain comprising the amino acid sequence of SEQ ID NO: 221, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 231, a CDR2 domain comprising the amino acid sequence of SEQ ID NO: 230, and a CDR1 domain comprising the amino acid sequence of SEQ ID NO: 229, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 235, a CDR2 domain comprising the amino acid sequence of SEQ ID NO: 234, and a CDR1 domain comprising the amino acid sequence of SEQ ID NO: 233, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 239, a CDR2 domain comprising the amino acid sequence of SEQ ID NO: 238, and a CDR1 domain comprising the amino acid sequence of SEQ ID NO: 237, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 243, a CDR2 domain comprising the amino acid sequence of SEQ ID NO: 242, and a CDR1 domain comprising the amino acid sequence of SEQ ID NO: 241, and a light chain variable region comprising a CDR3 domain comprising the amino acid sequence of SEQ ID NO: 247, a CDR2 domain comprising the amino acid sequence of SEQ ID NO: 246, and a CDR1 domain comprising the amino acid sequence of SEQ ID NO: 245.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 251, a CDR2 domain comprising the amino acid sequence of SEQ ID NO: 250, and a CDR1 domain comprising the amino acid sequence of SEQ ID NO: 249, and a light chain variable region comprising a CDR3 domain comprising the amino acid sequence of SEQ ID NO: 255, a CDR2 domain comprising the amino acid sequence of SEQ ID NO: 254, and a CDR1 domain comprising the amino acid sequence of SEQ ID NO: 253.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 259, a CDR2 domain comprising the amino acid sequence of SEQ ID NO: 258, and a CDR1 domain comprising the amino acid sequence of SEQ ID NO: 257, and a light chain variable region comprising a CDR3 domain comprising the amino acid sequence of SEQ ID NO: 263, a CDR2 domain comprising the amino acid sequence of SEQ ID NO: 262, and a CDR1 domain comprising the amino acid sequence of SEQ ID NO: 261.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 267, a CDR2 domain comprising the amino acid sequence of SEQ ID NO: 266, and a CDR1 domain comprising the amino acid sequence of SEQ ID NO: 265, and a light chain variable region comprising a CDR3 domain comprising the amino acid sequence of SEQ ID NO: 271, a CDR2 domain comprising the amino acid sequence of SEQ ID NO: 270, and a CDR1 domain comprising the amino acid sequence of SEQ ID NO: 269.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 275, a CDR2 domain comprising the amino acid sequence of SEQ ID NO: 274, and a CDR1 domain comprising the amino acid sequence of SEQ ID NO: 273, and a light chain variable region comprising a CDR3 domain comprising the amino acid sequence of SEQ ID NO: 277, a CDR2 domain comprising the amino acid sequence of SEQ ID NO: 254, and a CDR1 domain comprising the amino acid sequence of SEQ ID NO: 269.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 267, a CDR2 domain comprising the amino acid sequence of SEQ ID NO: 280, and a CDR1 domain comprising the amino acid sequence of SEQ ID NO: 279, and a light chain variable region comprising a CDR3 domain comprising the amino acid sequence of SEQ ID NO: 282, a CDR2 domain comprising the amino acid sequence of SEQ ID NO: 254, and a CDR1 domain comprising the amino acid sequence of SEQ ID NO: 269.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 267, a CDR2 domain comprising the amino acid sequence of SEQ ID NO: 285, and a CDR1 domain comprising the amino acid sequence of SEQ ID NO: 284, and a light chain variable region comprising a CDR3 domain comprising the amino acid sequence of SEQ ID NO: 287, a CDR2 domain comprising the amino acid sequence of SEQ ID NO: 254, and a CDR1 domain comprising the amino acid sequence of SEQ ID NO: 269.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 215, a CDR2 domain comprising the amino acid sequence of SEQ ID NO: 214, and a CDR1 domain comprising the amino acid sequence of SEQ ID NO: 213, and a light chain variable region comprising a CDR3 domain comprising the amino acid sequence of SEQ ID NO: 219, a CDR2 domain comprising the amino acid sequence of SEQ ID NO: 218, and a CDR1 domain comprising the amino acid sequence of SEQ ID NO: 217.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO:

18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 32, a CDR2 domain comprising the amino acid sequence of SEQ ID NO: 31, and a CDR1 domain comprising the amino acid sequence of SEQ ID NO: 30.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 36, a CDR2 domain comprising the amino acid sequence of SEQ ID NO: 35, and a CDR1 domain comprising the amino acid sequence of SEQ ID NO: 34, and a light chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 38.

In one aspect of the invention, the present disclosure provides an anti-VTCN1 antibody, or antigen-binding portion thereof, comprising a heavy chain variable region comprising a CDR3 domain comprising the amino acid sequence of SEQ ID NO: 44, a CDR2 domain comprising the amino acid sequence of SEQ ID NO: 43, and a CDR1 domain comprising the amino acid sequence of SEQ ID NO: 42, and a light chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50, and a light chain variable region comprising a CDR3 domain comprising the amino acid sequence of SEQ ID NO: 56, a CDR2 domain comprising the amino acid sequence of SEQ ID NO: 55, and a CDR1 domain comprising the amino acid sequence of SEQ ID NO: 54.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 60, a CDR2 domain comprising the amino acid sequence of SEQ ID NO: 59, and a CDR1 domain comprising the amino acid sequence of SEQ ID NO: 58, and a light chain variable region comprising a CDR3 domain comprising the amino acid sequence of SEQ ID NO: 64, a CDR2 domain comprising the amino acid sequence of SEQ ID NO: 63, and a CDR1 domain comprising the amino acid sequence of SEQ ID NO: 62.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 68, a CDR2 domain comprising the amino acid sequence of SEQ ID NO: 67, and a CDR1 domain comprising the amino acid sequence of SEQ ID NO: 66, and a light chain variable region comprising a CDR3 domain comprising the amino acid sequence of SEQ ID NO: 72, a CDR2 domain comprising the amino acid sequence of SEQ ID NO: 71, and a CDR1 domain comprising the amino acid sequence of SEQ ID NO: 70.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 76, a CDR2 domain comprising the amino acid sequence of SEQ ID NO: 75, and a CDR1 domain comprising the amino acid sequence of SEQ ID NO: 74, and a light chain variable region comprising a CDR3 domain comprising the amino acid sequence of SEQ ID NO: 80, a CDR2 domain comprising the amino acid sequence of SEQ ID NO: 79, and a CDR1 domain comprising the amino acid sequence of SEQ ID NO: 78.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 84, a CDR2 domain comprising the amino acid sequence of SEQ ID NO: 83, and a CDR1 domain comprising the amino acid sequence of SEQ ID NO: 82, and a light chain variable region comprising a CDR3 domain comprising the amino acid sequence of SEQ ID NO: 88, a CDR2 domain comprising the amino acid sequence of SEQ ID NO: 87, and a CDR1 domain comprising the amino acid sequence of SEQ ID NO: 86.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 90, and a light chain variable region comprising a CDR3 domain comprising the amino acid sequence of SEQ ID NO: 96, a CDR2 domain comprising the amino acid sequence of SEQ ID NO: 95, and a CDR1 domain comprising the amino acid sequence of SEQ ID NO: 94.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 100, a CDR2 domain comprising the amino acid sequence of SEQ ID NO: 99, and a CDR1 domain comprising the amino acid sequence of SEQ ID NO: 98, and a light chain variable region comprising a CDR3 domain comprising the amino acid sequence of SEQ ID NO: 104, a CDR2 domain comprising the amino acid sequence of SEQ ID NO: 103, and a CDR1 domain comprising the amino acid sequence of SEQ ID NO: 102.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 108, a CDR2 domain comprising the amino acid sequence of SEQ ID NO: 107, and a CDR1 domain comprising the amino acid sequence of SEQ ID NO: 106, and a light chain variable region comprising a CDR3 domain comprising the amino acid sequence of SEQ ID NO:

112, a CDR2 domain comprising the amino acid sequence of SEQ ID NO: 111, and a CDR1 domain comprising the amino acid sequence of SEQ ID NO: 110.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 116, a CDR2 domain comprising the amino acid sequence of SEQ ID NO: 115, and a CDR1 domain comprising the amino acid sequence of SEQ ID NO: 114, and a light chain variable region comprising a CDR3 domain comprising the amino acid sequence of SEQ ID NO: 120, a CDR2 domain comprising the amino acid sequence of SEQ ID NO: 119, and a CDR1 domain comprising the amino acid sequence of SEQ ID NO: 118.

In one aspect of the invention, the present disclosure provides an anti-VTCN1 antibody, or antigen-binding portion thereof, comprising a heavy chain variable region comprising a CDR3 domain comprising the amino acid sequence of SEQ ID NO: 124, a CDR2 domain comprising the amino acid sequence of SEQ ID NO: 123, and a CDR1 domain comprising the amino acid sequence of SEQ ID NO: 122, and a light chain variable region comprising a CDR3 domain comprising the amino acid sequence of SEQ ID NO: 128, a CDR2 domain comprising the amino acid sequence of SEQ ID NO: 127, and a CDR1 domain comprising the amino acid sequence of SEQ ID NO: 126.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 132, a CDR2 domain comprising the amino acid sequence of SEQ ID NO: 131, and a CDR1 domain comprising the amino acid sequence of SEQ ID NO: 130, and a light chain variable region comprising a CDR3 domain comprising the amino acid sequence of SEQ ID NO: 136, a CDR2 domain comprising the amino acid sequence of SEQ ID NO: 135, and a CDR1 domain comprising the amino acid sequence of SEQ ID NO: 134.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 140, a CDR2 domain comprising the amino acid sequence of SEQ ID NO: 139, and a CDR1 domain comprising the amino acid sequence of SEQ ID NO: 138, and a light chain variable region comprising a CDR3 domain comprising the amino acid sequence of SEQ ID NO: 144, a CDR2 domain comprising the amino acid sequence of SEQ ID NO: 143, and a CDR1 domain comprising the amino acid sequence of SEQ ID NO: 142.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 148, a CDR2 domain comprising the amino acid sequence of SEQ ID NO: 147, and a CDR1 domain comprising the amino acid sequence of SEQ ID NO: 146, and a light chain variable region comprising a CDR3 domain comprising the amino acid sequence of SEQ ID NO: 152, a CDR2 domain comprising the amino acid sequence of SEQ ID NO: 151, and a CDR1 domain comprising the amino acid sequence of SEQ ID NO: 150.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 156, a CDR2 domain comprising the amino acid sequence of SEQ ID NO: 155, and a CDR1 domain comprising the amino acid sequence of SEQ ID NO: 154, and a light chain variable region comprising a CDR3 domain comprising the amino acid sequence of SEQ ID NO: 160, a CDR2 domain comprising the amino acid sequence of SEQ ID NO: 159, and a CDR1 domain comprising the amino acid sequence of SEQ ID NO: 158.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 164, a CDR2 domain comprising the amino acid sequence of SEQ ID NO: 163, and a CDR1 domain comprising the amino acid sequence of SEQ ID NO: 162, and a light chain variable region comprising a CDR3 domain comprising the amino acid sequence of SEQ ID NO: 168, a CDR2 domain comprising the amino acid sequence of SEQ ID NO: 167, and a CDR1 domain comprising the amino acid sequence of SEQ ID NO: 166.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 172, a CDR2 domain comprising the amino acid sequence of SEQ ID NO: 171, and a CDR1 domain comprising the amino acid sequence of SEQ ID NO: 170, and a light chain variable region comprising a CDR3 domain comprising the amino acid sequence of SEQ ID NO: 176, a CDR2 domain comprising the amino acid sequence of SEQ ID NO: 175, and a CDR1 domain comprising the amino acid sequence of SEQ ID NO: 174.

In another aspect of the invention, the present disclosure provides an anti-VTCN1 antibody, or antigen-binding portion thereof, comprising a heavy chain variable region comprising a CDR3 domain comprising the amino acid sequence of SEQ ID NO: 180, a CDR2 domain comprising the amino acid sequence of SEQ ID NO: 179, and a CDR1 domain comprising the amino acid sequence of SEQ ID NO: 178, and a light chain variable region comprising a CDR3 domain comprising the amino acid sequence of SEQ ID NO: 184, a CDR2 domain comprising the amino acid sequence of SEQ ID NO: 183, and a CDR1 domain comprising the amino acid sequence of SEQ ID NO: 182.

In another aspect of the invention, the present disclosure provides an anti-VTCN1 antibody, or antigen-binding portion thereof, comprising a heavy chain variable domain comprising an amino acid sequence set forth in SEQ ID NO: 220 and a light chain variable domain comprising an amino acid sequence set forth in SEQ ID NO: 224.

In another aspect of the invention, the present disclosure provides an anti-VTCN1 antibody, or antigen-binding portion thereof, comprising a heavy chain comprising an amino acid sequence set forth in SEQ ID NO: 220, or a sequence having at least 90%, 95%, 96%, 97%, 98%, or 99% identity to SEQ ID NO: 220, and/or a light chain comprising an amino acid sequence set forth in SEQ ID NO: 224, or a sequence having at least 90%, 95%, 96%, 97%, 98%, or 99% identity to SEQ ID NO: 224.

In another aspect of the invention, the present disclosure provides an anti-VTCN1 antibody, or antigen-binding portion thereof, comprising a heavy chain variable domain comprising an amino acid sequence set forth in SEQ ID NO: 228 and a light chain variable domain comprising an amino acid sequence set forth in SEQ ID NO: 224.

In another aspect of the invention, the present disclosure provides an anti-VTCN1 antibody, or antigen-binding portion thereof, comprising a heavy chain comprising an amino acid sequence set forth in SEQ ID NO: 228, or a sequence having at least 90%, 95%, 96%, 97%, 98%, or 99% identity to SEQ ID NO: 228, and/or a light chain comprising an amino acid sequence set forth in SEQ ID NO: 224, or a sequence having at least 90%, 95%, 96%, 97%, 98%, or 99% identity to SEQ ID NO: 224.

In another aspect of the invention, the present disclosure provides an anti-VTCN1 antibody, or antigen-binding portion thereof, comprising a heavy chain variable domain comprising an amino acid sequence set forth in SEQ ID NO: 232 and a light chain variable domain comprising an amino acid sequence set forth in SEQ ID NO: 224.

In another aspect of the invention, the present disclosure provides an anti-VTCN1 antibody, or antigen-binding portion thereof, comprising a heavy chain comprising an amino acid sequence set forth in SEQ ID NO: 232, or a sequence having at least 90%, 95%, 96%, 97%, 98%, or 99% identity to SEQ ID NO: 232, and/or a light chain comprising an amino acid sequence set forth in SEQ ID NO: 224, or a sequence having at least 90%, 95%, 96%, 97%, 98%, or 99% identity to SEQ ID NO: 224.

In another aspect of the invention, the present disclosure provides an anti-VTCN1 antibody, or antigen-binding portion thereof, comprising a heavy chain variable domain comprising an amino acid sequence set forth in SEQ ID NO: 236 and a light chain variable domain comprising an amino acid sequence set forth in SEQ ID NO: 224.

In another aspect of the invention, the present disclosure provides an anti-VTCN1 antibody, or antigen-binding portion thereof, comprising a heavy chain comprising an amino acid sequence set forth in SEQ ID NO: 236, or a sequence having at least 90%, 95%, 96%, 97%, 98%, or 99% identity to SEQ ID NO: 236, and/or a light chain comprising an amino acid sequence set forth in SEQ ID NO: 224, or a sequence having at least 90%, 95%, 96%, 97%, 98%, or 99% identity to SEQ ID NO: 224.

In another aspect of the invention, the present disclosure provides an anti-VTCN1 antibody, or antigen-binding portion thereof, comprising a heavy chain variable domain comprising an amino acid sequence set forth in SEQ ID NO: 240 and a light chain variable domain comprising an amino acid sequence set forth in SEQ ID NO: 244.

In another aspect of the invention, the present disclosure provides an anti-VTCN1 antibody, or antigen-binding portion thereof, comprising a heavy chain comprising an amino acid sequence set forth in SEQ ID NO: 240, or a sequence having at least 90%, 95%, 96%, 97%, 98%, or 99% identity to SEQ ID NO: 240, and/or a light chain comprising an amino acid sequence set forth in SEQ ID NO: 244, or a sequence having at least 90%, 95%, 96%, 97%, 98%, or 99% identity to SEQ ID NO: 244.

In another aspect of the invention, the present disclosure provides an anti-VTCN1 antibody, or antigen-binding portion thereof, comprising a heavy chain variable domain comprising an amino acid sequence set forth in SEQ ID NO: 248 and a light chain variable domain comprising an amino acid sequence set forth in SEQ ID NO: 252.

In another aspect of the invention, the present disclosure provides an anti-VTCN1 antibody, or antigen-binding portion thereof, comprising a heavy chain comprising an amino acid sequence set forth in SEQ ID NO: 248, or a sequence having at least 90%, 95%, 96%, 97%, 98%, or 99% identity to SEQ ID NO: 248, and/or a light chain comprising an amino acid sequence set forth in SEQ ID NO: 252, or a sequence having at least 90%, 95%, 96%, 97%, 98%, or 99% identity to SEQ ID NO: 252.

In another aspect of the invention, the present disclosure provides an anti-VTCN1 antibody, or antigen-binding portion thereof, comprising a heavy chain variable domain comprising an amino acid sequence set forth in SEQ ID NO: 256 and a light chain variable domain comprising an amino acid sequence set forth in SEQ ID NO: 260.

In another aspect of the invention, the present disclosure provides an anti-VTCN1 antibody, or antigen-binding portion thereof, comprising a heavy chain comprising an amino acid sequence set forth in SEQ ID NO: 256, or a sequence having at least 90%, 95%, 96%, 97%, 98%, or 99% identity to SEQ ID NO: 256, and/or a light chain comprising an amino acid sequence set forth in SEQ ID NO: 260, or a sequence having at least 90%, 95%, 96%, 97%, 98%, or 99% identity to SEQ ID NO: 260.

In another aspect of the invention, the present disclosure provides an anti-VTCN1 antibody, or antigen-binding portion thereof, comprising a heavy chain variable domain comprising an amino acid sequence set forth in SEQ ID NO: 264 and a light chain variable domain comprising an amino acid sequence set forth in SEQ ID NO: 268.

In another aspect of the invention, the present disclosure provides an anti-VTCN1 antibody, or antigen-binding portion thereof, comprising a heavy chain comprising an amino acid sequence set forth in SEQ ID NO: 264, or a sequence having at least 90%, 95%, 96%, 97%, 98%, or 99% identity to SEQ ID NO: 264, and/or a light chain comprising an amino acid sequence set forth in SEQ ID NO: 268, or a sequence having at least 90%, 95%, 96%, 97%, 98%, or 99% identity to SEQ ID NO: 268.

In another aspect of the invention, the present disclosure provides an anti-VTCN1 antibody, or antigen-binding portion thereof, comprising a heavy chain variable domain comprising an amino acid sequence set forth in SEQ ID NO: 272 and a light chain variable domain comprising an amino acid sequence set forth in SEQ ID NO: 276.

In another aspect of the invention, the present disclosure provides an anti-VTCN1 antibody, or antigen-binding portion thereof, comprising a heavy chain comprising an amino acid sequence set forth in SEQ ID NO: 272, or a sequence having at least 90%, 95%, 96%, 97%, 98%, or 99% identity to SEQ ID NO: 272, and/or a light chain comprising an amino acid sequence set forth in SEQ ID NO: 276, or a sequence having at least 90%, 95%, 96%, 97%, 98%, or 99% identity to SEQ ID NO: 276.

In another aspect of the invention, the present disclosure provides an anti-VTCN1 antibody, or antigen-binding portion thereof, comprising a heavy chain variable domain comprising an amino acid sequence set forth in SEQ ID NO: 278 and a light chain variable domain comprising an amino acid sequence set forth in SEQ ID NO: 281.

In another aspect of the invention, the present disclosure provides an anti-VTCN1 antibody, or antigen-binding portion thereof, comprising a heavy chain comprising an amino acid sequence set forth in SEQ ID NO: 278, or a sequence having at least 90%, 95%, 96%, 97%, 98%, or 99% identity to SEQ ID NO: 278, and/or a light chain comprising an amino acid sequence set forth in SEQ ID NO: 281, or a sequence having at least 90%, 95%, 96%, 97%, 98%, or 99% identity to SEQ ID NO: 281.

In another aspect of the invention, the present disclosure provides an anti-VTCN1 antibody, or antigen-binding portion thereof, comprising a heavy chain variable domain comprising an amino acid sequence set forth in SEQ ID NO: 283 and a light chain variable domain comprising an amino acid sequence set forth in SEQ ID NO: 286.

In another aspect of the invention, the present disclosure provides an anti-VTCN1 antibody, or antigen-binding portion thereof, comprising a heavy chain comprising an amino acid sequence set forth in SEQ ID NO: 283, or a sequence having at least 90%, 95%, 96%, 97%, 98%, or 99% identity to SEQ ID NO: 283, and/or a light chain comprising an amino acid sequence set forth in SEQ ID NO: 286, or a sequence having at least 90%, 95%, 96%, 97%, 98%, or 99% identity to SEQ ID NO: 286.

In another aspect of the invention, the present disclosure provides an anti-VTCN1 antibody, or antigen-binding portion thereof, comprising a heavy chain variable domain comprising an amino acid sequence set forth in SEQ ID NO: 212 and a light chain variable domain comprising an amino acid sequence set forth in SEQ ID NO: 216.

In another aspect of the invention, the present disclosure provides an anti-VTCN1 antibody, or antigen-binding portion thereof, comprising a heavy chain comprising an amino acid sequence set forth in SEQ ID NO: 212, or a sequence having at least 90%, 95%, 96%, 97%, 98%, or 99% identity to SEQ ID NO: 212, and/or a light chain comprising an amino acid sequence set forth in SEQ ID NO: 216, or a sequence having at least 90%, 95%, 96%, 97%, 98%, or 99% identity to SEQ ID NO: 216.

In another aspect of the invention, the present disclosure provides an anti-VTCN1 antibody, or antigen-binding portion thereof, comprising a heavy chain variable domain comprising an amino acid sequence set forth in SEQ ID NO: 1 and a light chain variable domain comprising an amino acid sequence set forth in SEQ ID NO: 5.

In another aspect of the invention, the present disclosure provides an anti-VTCN1 antibody, or antigen-binding portion thereof, comprising a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In another aspect of the invention, the present disclosure provides an anti-VTCN1 antibody, or antigen-binding portion thereof, comprising a heavy chain variable region comprising the amino acid sequence of SEQ ID NO: 9 and a light chain variable region comprising the amino acid sequence of SEQ ID NO: 13.

In another aspect of the invention, the present disclosure provides an anti-VTCN1 antibody, or antigen-binding portion thereof, comprising a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In another aspect of the invention, the present disclosure provides an anti-VTCN1 antibody, or antigen-binding portion thereof, comprising a heavy chain variable region comprising the amino acid sequence of SEQ ID NO: 17 and a light chain variable region comprising the amino acid sequence of SEQ ID NO: 21.

In another aspect of the invention, the present disclosure provides an anti-VTCN1 antibody, or antigen-binding portion thereof, comprising a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 21, or a sequence having at least 90%, 95%, 96%, 97%, 98%, or 99% identity to SEQ ID NO: 21.

In another aspect of the invention, the present disclosure provides an anti-VTCN1 antibody, or antigen-binding portion thereof, comprising a heavy chain variable region comprising the amino acid sequence of SEQ ID NO: 25 and a light chain variable region comprising the amino acid sequence of SEQ ID NO: 29.

In another aspect of the invention, the present disclosure provides an anti-VTCN1 antibody, or antigen-binding portion thereof, comprising a heavy chain comprising an amino acid sequence set forth in SEQ ID NO: 25, or a sequence having at least 90%, 95%, 96%, 97%, 98%, or 99% identity to SEQ ID NO: 25, and/or a light chain comprising an amino acid sequence set forth in SEQ ID NO: 29, or a sequence having at least 90%, 95%, 96%, 97%, 98%, or 99% identity to SEQ ID NO: 29.

In another aspect of the invention, the present disclosure provides an anti-VTCN1 antibody, or antigen-binding portion thereof, comprising a heavy chain variable region comprising the amino acid sequence of SEQ ID NO: 33 and a light chain variable region comprising the amino acid sequence of SEQ ID NO: 37.

In another aspect of the invention, the present disclosure provides an anti-VTCN1 antibody, or antigen-binding portion thereof, comprising a heavy chain comprising an amino acid sequence set forth in SEQ ID NO: 33, or a sequence having at least 90%, 95%, 96%, 97%, 98%, or 99% identity to SEQ ID NO: 33, and/or a light chain comprising an amino acid sequence set forth in SEQ ID NO: 37, or a sequence having at least 90%, 95%, 96%, 97%, 98%, or 99% identity to SEQ ID NO: 37.

In another aspect of the invention, the present disclosure provides an anti-VTCN1 antibody, or antigen-binding portion thereof, comprising a heavy chain variable region comprising the amino acid sequence of SEQ ID NO: 41 and a light chain variable region comprising the amino acid sequence of SEQ ID NO: 45.

In another aspect of the invention, the present disclosure provides an anti-VTCN1 antibody, or antigen-binding portion thereof, comprising a heavy chain comprising an amino acid sequence set forth in SEQ ID NO: 41, or a sequence having at least 90%, 95%, 96%, 97%, 98%, or 99% identity to SEQ ID NO: 41, and/or a light chain comprising an amino acid sequence set forth in SEQ ID NO: 45, or a sequence having at least 90%, 95%, 96%, 97%, 98%, or 99% identity to SEQ ID NO: 45.

In another aspect of the invention, the present disclosure provides an anti-VTCN1 antibody, or antigen-binding portion thereof, comprising a heavy chain variable region comprising the amino acid sequence of SEQ ID NO: 49 and a light chain variable region comprising the amino acid sequence of SEQ ID NO: 53.

In another aspect of the invention, the present disclosure provides an anti-VTCN1 antibody, or antigen-binding portion thereof, comprising a heavy chain comprising an amino acid sequence set forth in SEQ ID NO: 49, or a sequence having at least 90%, 95%, 96%, 97%, 98%, or 99% identity to SEQ ID NO: 49, and/or a light chain comprising an amino acid sequence set forth in SEQ ID NO: 53, or a sequence having at least 90%, 95%, 96%, 97%, 98%, or 99% identity to SEQ ID NO: 53.

In another aspect of the invention, the present disclosure provides an anti-VTCN1 antibody, or antigen-binding portion thereof, comprising a heavy chain variable region comprising the amino acid sequence of SEQ ID NO: 57 and a light chain variable region comprising the amino acid sequence of SEQ ID NO: 61.

In another aspect of the invention, the present disclosure provides an anti-VTCN1 antibody, or antigen-binding portion thereof, comprising a heavy chain comprising an amino acid sequence set forth in SEQ ID NO: 57, or a sequence having at least 90%, 95%, 96%, 97%, 98%, or 99% identity to SEQ ID NO: 57, and/or a light chain comprising an amino acid sequence set forth in SEQ ID NO: 61, or a sequence having at least 90%, 95%, 96%, 97%, 98%, or 99% identity to SEQ ID NO: 61.

In another aspect of the invention, the present disclosure provides an anti-VTCN1 antibody, or antigen-binding portion thereof, comprising a heavy chain variable region comprising the amino acid sequence of SEQ ID NO: 65 and a light chain variable region comprising the amino acid sequence of SEQ ID NO: 69.

In another aspect of the invention, the present disclosure provides an anti-VTCN1 antibody, or antigen-binding portion thereof, comprising a heavy chain comprising an amino acid sequence set forth in SEQ ID NO: 65, or a sequence having at least 90%, 95%, 96%, 97%, 98%, or 99% identity to SEQ ID NO: 65, and/or a light chain comprising an amino acid sequence set forth in SEQ ID NO: 69, or a sequence having at least 90%, 95%, 96%, 97%, 98%, or 99% identity to SEQ ID NO: 69.

In another aspect of the invention, the present disclosure provides an anti-VTCN1 antibody, or antigen-binding portion thereof, comprising a heavy chain variable region comprising the amino acid sequence of SEQ ID NO: 73 and a light chain variable region comprising the amino acid sequence of SEQ ID NO: 77.

In another aspect of the invention, the present disclosure provides an anti-VTCN1 antibody, or antigen-binding portion thereof, comprising a heavy chain comprising an amino acid sequence set forth in SEQ ID NO: 73, or a sequence having at least 90%, 95%, 96%, 97%, 98%, or 99% identity to SEQ ID NO: 73, and/or a light chain comprising an amino acid sequence set forth in SEQ ID NO: 77, or a sequence having at least 90%, 95%, 96%, 97%, 98%, or 99% identity to SEQ ID NO: 77.

In another aspect of the invention, the present disclosure provides an anti-VTCN1 antibody, or antigen-binding portion thereof, comprising a heavy chain variable region comprising the amino acid sequence of SEQ ID NO: 81 and a light chain variable region comprising the amino acid sequence of SEQ ID NO: 85.

In another aspect of the invention, the present disclosure provides an anti-VTCN1 antibody, or antigen-binding portion thereof, comprising a heavy chain comprising an amino acid sequence set forth in SEQ ID NO: 81, or a sequence having at least 90%, 95%, 96%, 97%, 98%, or 99% identity to SEQ ID NO: 81, and/or a light chain comprising an amino acid sequence set forth in SEQ ID NO: 85, or a sequence having at least 90%, 95%, 96%, 97%, 98%, or 99% identity to SEQ ID NO: 85.

In another aspect of the invention, the present disclosure provides an anti-VTCN1 antibody, or antigen-binding portion thereof, comprising a heavy chain variable region comprising the amino acid sequence of SEQ ID NO: 89 and a light chain variable region comprising the amino acid sequence of SEQ ID NO: 93.

In another aspect of the invention, the present disclosure provides an anti-VTCN1 antibody, or antigen-binding portion thereof, comprising a heavy chain comprising an amino acid sequence set forth in SEQ ID NO: 89, or a sequence having at least 90%, 95%, 96%, 97%, 98%, or 99% identity to SEQ ID NO: 89, and/or a light chain comprising an amino acid sequence set forth in SEQ ID NO: 93, or a sequence having at least 90%, 95%, 96%, 97%, 98%, or 99% identity to SEQ ID NO: 93.

In another aspect of the invention, the present disclosure provides an anti-VTCN1 antibody, or antigen-binding portion thereof, comprising a heavy chain variable region comprising the amino acid sequence of SEQ ID NO: 97 and a light chain variable region comprising the amino acid sequence of SEQ ID NO: 101.

In another aspect of the invention, the present disclosure provides an anti-VTCN1 antibody, or antigen-binding portion thereof, comprising a heavy chain comprising an amino acid sequence set forth in SEQ ID NO: 97, or a sequence having at least 90%, 95%, 96%, 97%, 98%, or 99% identity to SEQ ID NO: 97, and/or a light chain comprising an amino acid sequence set forth in SEQ ID NO: 101, or a sequence having at least 90%, 95%, 96%, 97%, 98%, or 99% identity to SEQ ID NO: 101.

In another aspect of the invention, the present disclosure provides an anti-VTCN1 antibody, or antigen-binding portion thereof, comprising a heavy chain variable region comprising the amino acid sequence of SEQ ID NO: 105 and a light chain variable region comprising the amino acid sequence of SEQ ID NO: 109.

In another aspect of the invention, the present disclosure provides an anti-VTCN1 antibody, or antigen-binding portion thereof, comprising a heavy chain comprising an amino acid sequence set forth in SEQ ID NO: 105, or a sequence having at least 90%, 95%, 96%, 97%, 98%, or 99% identity to SEQ ID NO: 105, and/or a light chain comprising an amino acid sequence set forth in SEQ ID NO: 109, or a sequence having at least 90%, 95%, 96%, 97%, 98%, or 99% identity to SEQ ID NO: 109.

In another aspect of the invention, the present disclosure provides an anti-VTCN1 antibody, or antigen-binding portion thereof, comprising a heavy chain variable region comprising the amino acid sequence of SEQ ID NO: 113 and a light chain variable region comprising the amino acid sequence of SEQ ID NO: 117.

In another aspect of the invention, the present disclosure provides an anti-VTCN1 antibody, or antigen-binding portion thereof, comprising a heavy chain comprising an amino acid sequence set forth in SEQ ID NO: 113, or a sequence having at least 90%, 95%, 96%, 97%, 98%, or 99% identity to SEQ ID NO: 113, and/or a light chain comprising an amino acid sequence set forth in SEQ ID NO: 117, or a sequence having at least 90%, 95%, 96%, 97%, 98%, or 99% identity to SEQ ID NO: 117.

In another aspect of the invention, the present disclosure provides an anti-VTCN1 antibody, or antigen-binding portion thereof, comprising a heavy chain variable region comprising the amino acid sequence of SEQ ID NO: 121 and a light chain variable region comprising the amino acid sequence of SEQ ID NO: 125.

In another aspect of the invention, the present disclosure provides an anti-VTCN1 antibody, or antigen-binding portion thereof, comprising a heavy chain comprising an amino acid sequence set forth in SEQ ID NO: 121, or a sequence having at least 90%, 95%, 96%, 97%, 98%, or 99% identity to SEQ ID NO: 121, and/or a light chain comprising an amino acid sequence set forth in SEQ ID NO: 125, or a sequence having at least 90%, 95%, 96%, 97%, 98%, or 99% identity to SEQ ID NO: 125.

In another aspect of the invention, the present disclosure provides an anti-VTCN1 antibody, or antigen-binding portion thereof, comprising a heavy chain variable region comprising the amino acid sequence of SEQ ID NO: 129 and a light chain variable region comprising the amino acid sequence of SEQ ID NO: 133.

In another aspect of the invention, the present disclosure provides an anti-VTCN1 antibody, or antigen-binding portion thereof, comprising a heavy chain comprising an amino acid sequence set forth in SEQ ID NO: 129, or a sequence having at least 90%, 95%, 96%, 97%, 98%, or 99% identity to SEQ ID NO: 129, and/or a light chain comprising an amino acid sequence set forth in SEQ ID NO: 133, or a sequence having at least 90%, 95%, 96%, 97%, 98%, or 99% identity to SEQ ID NO: 133. In another aspect of the invention, the present disclosure provides an anti-VTCN1 antibody, or antigen-binding portion thereof, comprising a heavy chain variable region comprising the amino acid sequence of SEQ ID NO: 137 and a light chain variable region comprising the amino acid sequence of SEQ ID NO: 141.

In another aspect of the invention, the present disclosure provides an anti-VTCN1 antibody, or antigen-binding portion thereof, comprising a heavy chain comprising an amino acid sequence set forth in SEQ ID NO: 137, or a sequence having at least 90%, 95%, 96%, 97%, 98%, or 99% identity to SEQ ID NO: 137, and/or a light chain comprising an amino acid sequence set forth in SEQ ID NO: 141, or a sequence having at least 90%, 95%, 96%, 97%, 98%, or 99% identity to SEQ ID NO: 141.

In another aspect of the invention, the present disclosure provides an anti-VTCN1 antibody, or antigen-binding portion thereof, comprising a heavy chain variable region comprising the amino acid sequence of SEQ ID NO: 145 and a light chain variable region comprising the amino acid sequence of SEQ ID NO: 149.

In another aspect of the invention, the present disclosure provides an anti-VTCN1 antibody, or antigen-binding portion thereof, comprising a heavy chain comprising an amino acid sequence set forth in SEQ ID NO: 145, or a sequence having at least 90%, 95%, 96%, 97%, 98%, or 99% identity to SEQ ID NO: 145, and/or a light chain comprising an amino acid sequence set forth in SEQ ID NO: 149, or a sequence having at least 90%, 95%, 96%, 97%, 98%, or 99% identity to SEQ ID NO: 149.

In another aspect of the invention, the present disclosure provides an anti-VTCN1 antibody, or antigen-binding portion thereof, comprising a heavy chain variable region comprising the amino acid sequence of SEQ ID NO: 153 and a light chain variable region comprising the amino acid sequence of SEQ ID NO: 157.

In another aspect of the invention, the present disclosure provides an anti-VTCN1 antibody, or antigen-binding portion thereof, comprising a heavy chain comprising an amino acid sequence set forth in SEQ ID NO: 153, or a sequence having at least 90%, 95%, 96%, 97%, 98%, or 99% identity to SEQ ID NO: 153, and/or a light chain comprising an amino acid sequence set forth in SEQ ID NO: 157, or a sequence having at least 90%, 95%, 96%, 97%, 98%, or 99% identity to SEQ ID NO: 157.

In another aspect of the invention, the present disclosure provides an anti-VTCN1 antibody, or antigen-binding portion thereof, comprising a heavy chain variable region comprising the amino acid sequence of SEQ ID NO: 161 and a light chain variable region comprising the amino acid sequence of SEQ ID NO: 165.

In another aspect of the invention, the present disclosure provides an anti-VTCN1 antibody, or antigen-binding portion thereof, comprising a heavy chain comprising an amino acid sequence set forth in SEQ ID NO: 161, or a sequence having at least 90%, 95%, 96%, 97%, 98%, or 99% identity to SEQ ID NO: 161, and/or a light chain comprising an amino acid sequence set forth in SEQ ID NO: 165, or a sequence having at least 90%, 95%, 96%, 97%, 98%, or 99% identity to SEQ ID NO: 165.

In another aspect of the invention, the present disclosure provides an anti-VTCN1 antibody, or antigen-binding portion thereof, comprising a heavy chain variable region comprising the amino acid sequence of SEQ ID NO: 169 and a light chain variable region comprising the amino acid sequence of SEQ ID NO: 173.

In another aspect of the invention, the present disclosure provides an anti-VTCN1 antibody, or antigen-binding portion thereof, comprising a heavy chain comprising an amino acid sequence set forth in SEQ ID NO: 169, or a sequence having at least 90%, 95%, 96%, 97%, 98%, or 99% identity to SEQ ID NO: 169, and/or a light chain comprising an amino acid sequence set forth in SEQ ID NO: 173, or a sequence having at least 90%, 95%, 96%, 97%, 98%, or 99% identity to SEQ ID NO: 173.

In another aspect of the invention, the present disclosure provides an anti-VTCN1 antibody, or antigen-binding portion thereof, comprising a heavy chain variable region comprising the amino acid sequence of SEQ ID NO: 177 and a light chain variable region comprising the amino acid sequence of SEQ ID NO: 181.

In another aspect of the invention, the present disclosure provides an anti-VTCN1 antibody, or antigen-binding portion thereof, comprising a heavy chain comprising an amino acid sequence set forth in SEQ ID NO: 177, or a sequence having at least 90%, 95%, 96%, 97%, 98%, or 99% identity to SEQ ID NO: 177, and/or a light chain comprising an amino acid sequence set forth in SEQ ID NO: 181, or a sequence having at least 90%, 95%, 96%, 97%, 98%, or 99% identity to SEQ ID NO: 181.

In another aspect of the invention, the present disclosure provides an antibody, or antigen-binding portion thereof, that binds to the same epitope as an antibody, or antigen-binding portion thereof, as described herein. In another aspect of the invention, the present disclosure provides an antibody, or antigen-binding portion thereof, that competes with binding to VTCN1 of an antibody, or antigen-binding portion thereof, described herein. In certain embodiments, the anti-VTCN1 antibody, or antigen binding portion thereof, is a multispecific antibody, e.g. a bispecific antibody.

In one aspect, the antibody, or antibody binding portion thereof is a human or humanized antibody. In some embodiments, the antibody, or antigen binding portion thereof, is an IgG isotype. In some embodiments, the antibody, or antigen binding portion thereof, is an $IgG_1$ isotype. In another embodiment, the antibody, or antigen-binding portion thereof, is an $IgG_4$ isotype. In another embodiment, the antibody, or antigen-binding portion thereof, is an $IgG_2$ isotype. In another embodiment, the antibody, or antigen-binding portion thereof, is an IgG3 isotype.

In one embodiment, an antibody, or antigen binding portion thereof, of the invention lacks ADCC activity. In another embodiment, the antibody, or antigen binding portion thereof comprises an isotype lacking effector function (e.g., human IgG4).

In another aspect of the invention, the present disclosure provides an isolated nucleic acid encoding an antibody, or antigen binding portion thereof, as described herein.

In another aspect of the invention, the present disclosure provides a pharmaceutical composition comprising the antibody, or antigen binding portion thereof, as described herein, and a pharmaceutically acceptable carrier.

In another aspect of the invention, the present disclosure provides an antibody, or antigen binding portion thereof, as described herein, conjugated to at least one drug.

In some aspects, the at least one drug is selected from the group consisting of an anti-apoptotic agent, a mitotic inhibitor, an anti-tumor antibiotic, an immunomodulating agent, a nucleic acid for gene therapy, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In other embodiments, the at least one drug is conjugated to the antibody, or antigen-binding portion thereof, via a linker. In another embodiment, the linker is a cleavable linker. In yet other embodiments, the linker is a non-cleavable linker.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 223, a CDR2 domain comprising the amino acid sequence of SEQ ID NO: 222, and a CDR1 domain comprising the amino acid sequence of SEQ ID NO: 221, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 231, a CDR2 domain comprising the amino acid sequence of SEQ ID NO: 230, and a CDR1 domain comprising the amino acid sequence of SEQ ID NO: 229, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 235, a CDR2 domain comprising the amino acid sequence of SEQ ID NO: 234, and a CDR1 domain comprising the amino acid sequence of SEQ ID NO: 233, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 239, a CDR2 domain comprising the amino acid sequence of SEQ ID NO: 238, and a CDR1 domain comprising the amino acid sequence of SEQ ID NO: 237, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 243, a CDR2 domain comprising the amino acid sequence of SEQ ID NO: 242, and a CDR1 domain comprising the amino acid sequence of SEQ ID NO: 241, and a light chain variable region comprising a CDR3 domain comprising the amino acid sequence of SEQ ID NO: 247, a CDR2 domain comprising the amino acid sequence of SEQ ID NO: 246, and a CDR1 domain comprising the amino acid sequence of SEQ ID NO: 245.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 251, a CDR2 domain comprising the amino acid sequence of SEQ ID NO: 250, and a CDR1 domain comprising the amino acid sequence of SEQ ID NO: 249, and a light chain variable region comprising a CDR3 domain comprising the amino acid sequence of SEQ ID NO: 255, a CDR2 domain comprising the amino acid sequence of SEQ ID NO: 254, and a CDR1 domain comprising the amino acid sequence of SEQ ID NO: 253.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 259, a CDR2 domain comprising the amino acid sequence of SEQ ID NO: 258, and a CDR1 domain comprising the amino acid sequence of SEQ ID NO: 257, and a light chain variable region comprising a CDR3 domain comprising the amino acid sequence of SEQ ID NO: 263, a CDR2 domain comprising the amino acid sequence of SEQ ID NO: 262, and a CDR1 domain comprising the amino acid sequence of SEQ ID NO: 261.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 267, a CDR2 domain comprising the amino acid sequence of SEQ ID NO: 266, and a CDR1 domain comprising the amino acid sequence of SEQ ID NO: 265, and a light chain variable region comprising a CDR3 domain comprising the amino acid sequence of SEQ ID NO: 271, a CDR2 domain comprising the amino acid sequence of SEQ ID NO: 270, and a CDR1 domain comprising the amino acid sequence of SEQ ID NO: 269.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 275, a CDR2 domain comprising the amino acid sequence of SEQ ID NO: 274, and a CDR1 domain comprising the amino acid sequence of SEQ ID NO: 273, and a light chain variable region comprising a CDR3 domain comprising the amino acid sequence of SEQ ID NO: 277, a CDR2 domain comprising the amino acid sequence of SEQ ID NO: 254, and a CDR1 domain comprising the amino acid sequence of SEQ ID NO: 269.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 267, a CDR2 domain comprising the amino acid sequence of SEQ ID NO: 280, and a CDR1 domain comprising the amino acid sequence of SEQ ID NO: 279, and a light chain variable region comprising a CDR3 domain comprising the amino acid sequence of SEQ ID NO: 282, a CDR2 domain comprising the amino acid sequence of SEQ ID NO: 254, and a CDR1 domain comprising the amino acid sequence of SEQ ID NO: 269.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 267, a CDR2 domain comprising the amino acid sequence of SEQ ID NO: 285, and a CDR1 domain comprising the amino acid sequence of SEQ ID NO: 284, and a light chain variable region comprising a CDR3 domain comprising the amino acid sequence of SEQ ID NO: 287, a CDR2 domain comprising the amino acid sequence of SEQ ID NO: 254, and a CDR1 domain comprising the amino acid sequence of SEQ ID NO: 269.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 215, a CDR2 domain comprising the amino acid sequence of SEQ ID NO: 214, and a CDR1 domain comprising the amino acid sequence of SEQ ID NO: 213, and a light chain variable region comprising a CDR3 domain comprising the amino acid sequence of SEQ ID NO: 219, a CDR2 domain comprising the amino acid sequence of SEQ ID NO: 218, and a CDR1 domain comprising the amino acid sequence of SEQ ID NO: 217.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 32, a CDR2 domain comprising the amino acid sequence of SEQ ID NO: 31, and a CDR1 domain comprising the amino acid sequence of SEQ ID NO: 30.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 36, a CDR2 domain comprising the amino acid sequence of SEQ ID NO: 35, and a CDR1 domain comprising the amino acid sequence of SEQ ID NO: 34, and a light chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 38.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 44, a CDR2 domain comprising the amino acid sequence of SEQ ID NO: 43, and a CDR1 domain comprising the amino acid sequence of SEQ ID NO: 42, and a light chain variable region comprising a CDR3 domain comprising the amino acid sequence of SEQ ID NO:

48, a CDR2 domain comprising the amino acid sequence of SEQ ID NO: 47, and a CDR1 domain comprising the amino acid sequence of SEQ ID NO: 46.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50, and a light chain variable region comprising a CDR3 domain comprising the amino acid sequence of SEQ ID NO: 56, a CDR2 domain comprising the amino acid sequence of SEQ ID NO: 55, and a CDR1 domain comprising the amino acid sequence of SEQ ID NO: 54.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 60, a CDR2 domain comprising the amino acid sequence of SEQ ID NO: 59, and a CDR1 domain comprising the amino acid sequence of SEQ ID NO: 58, and a light chain variable region comprising a CDR3 domain comprising the amino acid sequence of SEQ ID NO: 64, a CDR2 domain comprising the amino acid sequence of SEQ ID NO: 63, and a CDR1 domain comprising the amino acid sequence of SEQ ID NO: 62.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 68, a CDR2 domain comprising the amino acid sequence of SEQ ID NO: 67, and a CDR1 domain comprising the amino acid sequence of SEQ ID NO: 66, and a light chain variable region comprising a CDR3 domain comprising the amino acid sequence of SEQ ID NO: 72, a CDR2 domain comprising the amino acid sequence of SEQ ID NO: 71, and a CDR1 domain comprising the amino acid sequence of SEQ ID NO: 70.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 76, a CDR2 domain comprising the amino acid sequence of SEQ ID NO: 75, and a CDR1 domain comprising the amino acid sequence of SEQ ID NO: 74, and a light chain variable region comprising a CDR3 domain comprising the amino acid sequence of SEQ ID NO: 80, a CDR2 domain comprising the amino acid sequence of SEQ ID NO: 79, and a CDR1 domain comprising the amino acid sequence of SEQ ID NO: 78.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 84, a CDR2 domain comprising the amino acid sequence of SEQ ID NO: 83, and a CDR1 domain comprising the amino acid sequence of SEQ ID NO: 82, and a light chain variable region comprising a CDR3 domain comprising the amino acid sequence of SEQ ID NO: 88, a CDR2 domain comprising the amino acid sequence of SEQ ID NO: 87, and a CDR1 domain comprising the amino acid sequence of SEQ ID NO: 86.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 90, and a light chain variable region comprising a CDR3 domain comprising the amino acid sequence of SEQ ID NO: 96, a CDR2 domain comprising the amino acid sequence of SEQ ID NO: 95, and a CDR1 domain comprising the amino acid sequence of SEQ ID NO: 94.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 100, a CDR2 domain comprising the amino acid sequence of SEQ ID NO: 99, and a CDR1 domain comprising the amino acid sequence of SEQ ID NO: 98, and a light chain variable region comprising a CDR3 domain comprising the amino acid sequence of SEQ ID NO: 104, a CDR2 domain comprising the amino acid sequence of SEQ ID NO: 103, and a CDR1 domain comprising the amino acid sequence of SEQ ID NO: 102.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 108, a CDR2 domain comprising the amino acid sequence of SEQ ID NO: 107, and a CDR1 domain comprising the amino acid sequence of SEQ ID NO: 106, and a light chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 116, a CDR2 domain comprising the amino acid sequence of SEQ ID NO: 115, and a CDR1 domain comprising the amino acid sequence of SEQ ID NO: 114, and a light chain variable region comprising a CDR3 domain comprising the amino acid sequence of SEQ ID NO: 120, a CDR2 domain comprising the amino acid sequence of SEQ ID NO: 119, and a CDR1 domain comprising the amino acid sequence of SEQ ID NO: 118.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 124, a CDR2 domain comprising the amino acid sequence of SEQ ID NO: 123, and a CDR1 domain comprising the amino acid sequence of SEQ ID NO: 122, and a light chain variable region comprising a CDR3 domain comprising the amino acid sequence of SEQ ID NO: 128, a CDR2 domain comprising the amino acid sequence of SEQ ID NO: 127, and a CDR1 domain comprising the amino acid sequence of SEQ ID NO: 126.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 132, a CDR2 domain comprising the amino acid sequence of SEQ ID NO: 131, and a CDR1 domain comprising the amino acid sequence of SEQ ID NO: 130, and a light chain variable region comprising a CDR3 domain comprising the amino acid sequence of SEQ ID NO: 136, a CDR2 domain comprising the amino acid sequence of SEQ ID NO: 135, and a CDR1 domain comprising the amino acid sequence of SEQ ID NO: 134.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 140, a CDR2 domain comprising the amino acid sequence of SEQ ID NO: 139, and a CDR1 domain comprising the amino acid sequence of SEQ ID NO: 138, and a light chain variable region comprising a CDR3 domain comprising the amino acid sequence of SEQ ID NO: 144, a CDR2 domain comprising the amino acid sequence of SEQ ID NO: 143, and a CDR1 domain comprising the amino acid sequence of SEQ ID NO: 142.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 148, a CDR2 domain comprising the amino acid sequence of SEQ ID NO: 147, and a CDR1 domain comprising the amino acid sequence of SEQ ID NO: 146, and a light chain variable region comprising a CDR3 domain comprising the amino acid sequence of SEQ ID NO: 152, a CDR2 domain comprising the amino acid sequence of SEQ ID NO: 151, and a CDR1 domain comprising the amino acid sequence of SEQ ID NO: 150.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 156, a CDR2 domain comprising the amino acid sequence of SEQ ID NO: 155, and a CDR1 domain comprising the amino acid sequence of SEQ ID NO: 154, and a light chain variable region comprising a CDR3 domain comprising the amino acid sequence of SEQ ID NO: 160, a CDR2 domain comprising the amino acid sequence of SEQ ID NO: 159, and a CDR1 domain comprising the amino acid sequence of SEQ ID NO: 158.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 164, a CDR2 domain comprising the amino acid sequence of SEQ ID NO: 163, and a CDR1 domain comprising the amino acid sequence of SEQ ID NO: 162, and a light chain variable region comprising a CDR3 domain comprising the amino acid sequence of SEQ ID NO: 168, a CDR2 domain comprising the amino acid sequence of SEQ ID NO: 167, and a CDR1 domain comprising the amino acid sequence of SEQ ID NO: 166.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 172, a CDR2 domain comprising the amino acid sequence of SEQ ID NO: 171, and a CDR1 domain comprising the amino acid sequence of SEQ ID NO: 170, and a light chain variable region comprising a CDR3 domain comprising the amino acid sequence of SEQ ID NO: 176, a CDR2 domain comprising the amino acid sequence of SEQ ID NO: 175, and a CDR1 domain comprising the amino acid sequence of SEQ ID NO: 174.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 180, a CDR2 domain comprising the amino acid sequence of SEQ ID NO: 179, and a CDR1 domain comprising the amino acid sequence of SEQ ID NO: 178, and a light chain variable region comprising a CDR3 domain comprising the amino acid sequence of SEQ ID NO: 184, a CDR2 domain comprising the amino acid sequence of SEQ ID NO: 183, and a CDR1 domain comprising the amino acid sequence of SEQ ID NO: 182.

In some embodiments, the at least one drug is conjugated via a linker. In other embodiments, the linker is a cleavable linker. In yet other embodiments, the linker is a non-cleavable linker.

In some embodiments, the antibody, or antigen binding portion thereof, is an $IgG_1$ isotype. In other embodiment, the antibody, or antigen binding portion thereof, is an $IgG_4$ isotype. In another embodiment, the antibody, or antigen-binding portion thereof, is an $IgG_2$ isotype. In another embodiment, the antibody, or antigen-binding portion thereof, is an $IgG_3$ isotype. In another embodiment, the antibody, or antigen binding portion thereof, is a bispecific antibody.

In another aspect of the invention, the present disclosure provides a pharmaceutical composition comprising an ADC mixture comprising a plurality of the ADC as described herein, and a pharmaceutically acceptable carrier.

In some embodiments, the ADC mixture has an average drug to antibody ratio (DAR) of 0 to 8.

In another aspect of the invention, the present disclosure provides a method for treating cancer, comprising administering a therapeutically effective amount of an antibody or antigen binding portion thereof, as described herein, or an ADC as described herein, to a subject in need thereof.

In some embodiments, cancer is triple negative breast cancer (TNBC). In other embodiments, the cancer is selected from the groups consisting of renal cancer, ovarian cancer, NSCLC, endometrial cancer, and liver cancer. In yet other embodiments, the cancer is selected from the group consisting of breast cancer, renal cancer, ovarian cancer, gastric cancer, prostate cancer, uterine cancer, endometrial cancer, pancreatic cancer, liver cancer, colorectal cancer, or non-small cell lung cancer (NSCLC).

In some embodiments, the present disclosure provides a method for inhibiting or decreasing solid tumor growth, reducing primary tumor size and/or inhibiting primary tumor growth in a subject having a solid tumor, said method comprising administering an effective amount of the antibody or antigen binding portion thereof, as described herein, or the ADC, as described herein, to the subject having the solid tumor, such that the solid tumor growth is inhibited or decreased, the primary tumor size is reduced, and/or the primary tumor growth is inhibited.

In some embodiments, the cancer is triple negative breast cancer (TNBC). In other embodiments, the cancer is renal cancer or ovarian cancer. In yet other embodiments, the cancer is selected from the group consisting of breast cancer, renal cancer, ovarian cancer, gastric cancer, prostate cancer, uterine cancer, endometrial cancer, pancreatic cancer, liver cancer, colorectal cancer, or non-small cell lung cancer (NSCLC).

In some embodiments, the antibody or antigen binding portion thereof or the ADC is administered in combination with an additional agent or an additional therapy. In other embodiments, the additional agent is an immune checkpoint inhibitor. In yet another embodiment, the immune checkpoint inhibitor is an antibody. In another embodiment, the antibody is selected from the group consisting of an anti-PD1 antibody, an anti-PD-L1 antibody or an anti-CTLA-4 antibody. In other embodiments, the additional agent is a modulator, e.g., inhibitor, of activity or number of meyloid derived suppressor cells (MDSCs), such as, for example, gemcitabine. In other embodiments, the additional therapy is radiation. In yet another embodiment, the additional agent is one or more chemotherapeutic agent. In one embodiment, the one or more chemotherapeutic agent is pemetrexed and/or platinum chemotherapy, e.g., cisplatin or carboplatin.

In some embodiments, the antibody or antigen binding portion thereof or the ADC is administered in combination with IL-6 and/or interferon-gamma (IFN-γ). For example, IL-6 and/or IFN-γ can be administered prior to the antibody or antigen binding portion thereof or the ADC, to increase expression of VTCN1 in the subject.

In another embodiment, the antibody or antigen binding portion thereof or the ADC is administered in combination with a DNA alkylator (e.g., cisplatin) and/or a PARP inhibitor.

In one embodiment, the anti-VTCN1 antibodies or ADCs of the invention are administered in combination with one or more compound which is capable of decreasing T regulatory cells and/or increasing effector T cell:T regulatory cell ratio in a subject, e.g., gemcitabine.

In one aspect, the present invention provides a method for determining the therapeutic efficacy of an anti-VTCN1 antibody, antigen binding portion thereof, or an anti-VTCN1 antibody-drug conjugate (ADC), the method comprising administering the anti-VTCN1 antibody, antigen binding portion thereof, or ADC, to a syngeneic tumor animal model expressing VTCN1, and determining tumor size, wherein a decrease in tumor size or inhibition of tumor growth following administration of the anti-VTCN1 antibody, antigen binding portion thereof, or ADC indicates therapeutic efficacy of the anti-VTCN1 antibody, antigen binding portion thereof, or ADC. In one embodiment, the syngenic tumor animal model is a KLN205 tumor model. In another embodiment, the syngenic tumor animal model is a Hepa 1-6 tumor model. In another embodiment, the syngenic tumor animal model is an ID-8 ovarian tumor model. In another embodiment, the antibody or antigen binding portion thereof or the ADC is administered in combination with an additional agent or an additional therapy In some embodiments, the cancer or tumor is characterized as having VTCN1 expression or overexpression. In some embodiments, the cancer or tumor is characterized as lacking VTCN1 expression or overexpression.

BRIEF DESCRIPTION OF THE DRAWINGS

FIG. 9A shows tumor volume over time in individual mice in each treatment group. FIG. 9B shows mean tumor volume+SEM of different groups over time.

FIG. 11A shows the mean tumor volume+SEM of each treatment group over time. FIG. 11B shows the percentage of mice survival to tumor end point 1500 mm$^3$ over time from each group.

FIG. 12A shows tumor volume over time in individual mice in different treatment groups. The gemcitabine and 6D9 combination group has three complete responses (CR) by the end of the study. FIG. 12B shows the profile of immune cells from three rechallenged mice and two naïve mice. The MDSC population (CD11b positive) was reduced in tumors harvested from rechallenged mice comparing to naïve mice. CD44+ memory T cells increased in LN (lymph nodes) of rechallenged mice compared to naïve mice.

FIG. 13A. Mean tumor volume+SEM in mIgG2a isotype control group vs 6D9 treatment group. FIG. 13B. Median tumor volume in the mIgG2a isotype control group vs 6D9 treatment group.

DETAILED DESCRIPTION

Figure 1:
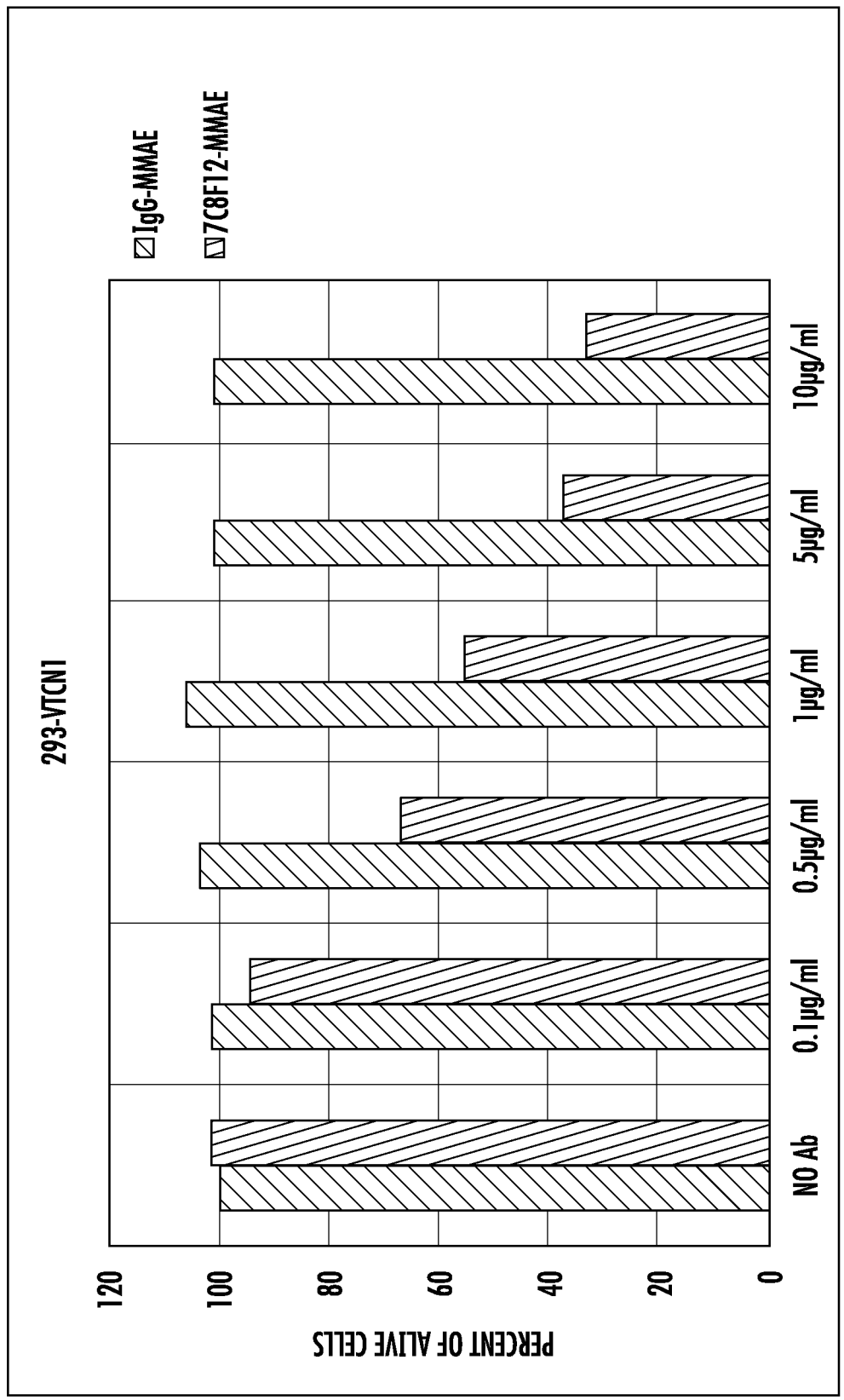
FIG. 1 shows the anti-VTCN1 antibody 7C8-MMAE inhibits 293-VTCN1 expressing cell growth. A dose response is evident in concentration of 0.1-10 µg/ml resulting in cytotoxicity ranging from ~5%-65% respectively. Increasing concentrations of 7C8-MMAE or the isotype control IgG-MMAE were added to 293-VTCN1 cells, the cells were incubated for 72 hours, and the cell viability was determined using CellTiter Glo™.

Various aspects of the disclosure relate to anti-VTCN1 antibodies and antibody fragments, anti-VTCN1 ADCs, and pharmaceutical compositions thereof, as well as nucleic acids, recombinant expression vectors and host cells for making such antibodies and fragments. Methods of using the antibodies and ADCs described herein to detect human VTCN1, to bind to and inhibit human VTCN1 on VTCN1 expressing cells, including T cells, to upmodulate an immune response in vivo, and/or to treat VTCN1-associated disorders, e.g., cancer, including, but not limited to, breast cancer (e.g., triple negative breast cancer (TNBC)), renal cancer, ovarian cancer, gastric cancer, prostate cancer, uterine cancer, endometrial cancer, pancreatic cancer, liver cancer, colorectal cancer, or non-small cell lung cancer (NSCLC). In one embodiment, the anti-VTCN1 antibodies or ADCs of the invention are capable of reducing primary tumor growth size and/or inhibiting primary tumor growth.

In one embodiment, the anti-VTCN1 antibody or ADC of the invention is administered in combination with one or more immune checkpoint inhibitors (e.g., antibody or small molecule immune checkpoint inhibitors) for the treatment of a cancer. In another embodiment, anti-VTCN1 antibody or ADC of the invention is administered in combination with one or more meyloid derived suppressor cell (MDSC) inhibitor, such as, for example, gemcitabine. In one embodiment, the anti-VTCN1 antibody or ADC of the invention is administered in combination with IL-6 or interferon-gamma (IFN-γ). In another embodiment, the anti-VTCN1 antibody or ADC of the invention is administered in combination with a DNA alkylator (e.g., cisplatin) and/or a PARP inhibitor.

In another embodiment of the invention, anti-VTCN1 antibody drug conjugates (ADCs) of the invention (e.g., the VTCN1 antibodies of the invention conjugated to a toxin) are internalized and induce cell death of cells endogenously expressing VTCN1.

I. Definitions

In order that the invention may be more readily understood, certain terms are first defined. In addition, it should be noted that whenever a value or range of values of a parameter are recited, it is intended that values and ranges intermediate to the recited values are also intended to be part of this invention.

The terms "V-set domain containing T cell activation inhibitor 1 antibody" or "anti-VTCN1 antibody", used interchangeably herein, refer to an antibody that specifically binds to VTCN1, e.g., human VTCN1. An antibody "which binds" an antigen of interest, i.e., VTCN1, is one capable of binding that antigen with sufficient affinity such that the antibody is useful in targeting a cell expressing the antigen. In a preferred embodiment, the antibody specifically binds to human VTCN1 (hVTCN1). Examples of anti-VTCN1 antibodies are disclosed in the Examples, below. Unless otherwise indicated, the term "anti-VTCN1 antibody" is meant to refer to an antibody which binds to wild type VTCN1, a variant, or an isoform of VTCN1.

Several different isoforms of VTCN1 have been identified. An exemplary amino acid sequence of wild type human VTCN1, which contains 282 amino acids, is provided below as SEQ ID NO: 185 (GenBank Accession No. NP_078902.2).

```
  1 maslgqilfw siisiiiila gaialiigfg isgrhsitvt tvasagnige dgilsctfep
 61 diklsdiviq wlkegvlglv hefkegkdel seqdemfrgr tavfadqviv gnaslrlknv
121 qltdagtykc yiitskgkgn anleyktgaf smpevnvdyn assetlrcea prwfpqptvv
181 wasqvdqgan fsevsntsfe insenvtmkv vsvlynvtin ntyscmiend iakatgdikv
241 teseikrrsh lqllnskasl cvssffaisw allplspylm lk
```

The terms "specific binding" or "specifically binding", as used herein, in reference to the interaction of a VTCN1 antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

In one embodiment, the phrase "specifically binds to hVTCN1" or "specific binding to hVTCN1", as used herein, refers to the ability of an anti-VTCN1 antibody or ADC to interact with VTCN1 (human or cynomolgus monkey VTCN1) with a dissociation constant ($K_D$) of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less. In another embodiment, the phrase "specifically binds to hVTCN1" or "specific binding to hVTCN1", as used herein, refers to the ability of an anti-VTCN1 antibody or ADC to interact with hVTCN1 with a dissociation constant ($K_D$) of between about 1 pM (0.001 nM) to 2,000 nM, between about 500 pM (0.5 nM) to 1,000 nM, between about 500 pM (0.5 nM) to 500 nM, between about 1 nM) to 200 nM, between about 1 nM to 100 nM, between about 1 nM to 50 nM, between about 1 nM to 20 nM, or between about 1 nM to 5 nM. In one embodiment, $K_D$ is determined by surface plasmon resonance. In another embodiment, $K_D$ is determined as described in Example 7, below.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4 Immunoglobulin molecules can be of any type (e.g., IgG, IgE, IgM, IgD, IgA and IgY) and class (e.g., IgG1, IgG2, IgG3, IgG4, IgA1 and IgA2) or subclass.

The term "antigen binding portion" of an antibody (or simply "antibody portion"), as used herein, refers to one or more fragments of an antibody that retain the ability to specifically bind to an antigen (e.g., hVTCN1). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding portion" of an antibody. In certain embodiments, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions disclosed herein linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) Proc. Natl. Acad. Sci. USA 90:6444-6448; Poljak, R. J., et al. (1994) Structure 2:1121-1123). An immunoglobulin constant domain refers to a heavy or light chain constant domain. Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds VTCN1 is substantially free of antibodies that specifically bind antigens other than VTCN1). An isolated antibody that specifically binds VTCN1 may, however, have cross-reactivity to other antigens, such as VTCN1 molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin In some embodiments, a humanized antibody contains both the light chain as well as at least the variable domain of a heavy chain. The antibody also may include the CH1, hinge, CH2, CH3, and CH4 regions of the heavy chain In some embodiments, a humanized antibody only contains a humanized light chain In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. In a preferred embodiment, the humanized antibody is IgG4 isotype. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest*, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In one embodiment, the disclosure includes an amino acid sequence having at least 80%, at least 85%, at least 90%, at least 95%, at least 96%, at least 97%, at least 98%, or at least 99% identity to an amino acid sequence set forth in any one of SEQ ID NOs: 1 to 36.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-VTCN1 DVD.

The term "activity" includes activities such as the binding specificity/affinity of an antibody or ADC for an antigen, for example, an anti-hVTCN1 antibody that binds to a VTCN1 antigen. In one embodiment, an anti-VTCN1 antibody or anti-VTCN1 ADC activity includes, but it not limited to, binding to VTCN1 in vitro; binding to VTCN1 on cells expressing VTCN1 in vivo (such as, for example, T cells); upmodulating immune response in vivo; increasing T cell activation in vivo; increasing CD8+ T cell expansion and effector functions that would result in anti-tumor response; inducing cell death in cells expressing VTCN1, including myeloid derived suppressor cells (MDSCs); inhibiting cancer cell invasion and metastasis; decreasing or inhibiting cancer, e.g., triple negative breast cancer (TNBC); decreasing or inhibiting tumor cellular proliferation or tumor growth in vivo, including decreasing or inhibiting primary tumor growth in vivo, and reducing primary tumor size in vivo. In some embodiments, the tumor can be a VTCN1 negative tumor or a VTCN1 positive tumor. In one embodiment, an anti-VTCN1 antibody is capable of being internalized into a cell expressing VTCN1. In one embodiment, an anti-VTCN1 antibody is lacks antibody dependent cellular cytotoxicity (ADCC) effector function. In another embodiment, an anti-VTCN1 antibody has ADCC function.

The term "epitope" refers to a region of an antigen that is bound by an antibody, antibody fragment, or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, NJ). For further descriptions, see Jönsson, U., et al. (1993) *Ann. Biol. Clin.* 51:19-26; Jönsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

The term "$k_{on}$" or "$k_a$", as used herein, is intended to refer to the on rate constant for association of an antibody to the antigen to form the antibody/antigen complex.

The term "$k_{off}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction. $K_D$ is calculated by $k_a/k_d$. In one embodiment, the antibodies of the invention have a $K_D$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods).

Examples of labels for polypeptides include, but are not limited to, the following: radioisotopes or radionuclides (e.g., $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The terms "V-set domain containing T cell activation inhibitor 1 antibody drug conjugate," "anti-VTCN1 antibody drug conjugate," or "anti-VTCN1 ADC", used interchangeably herein, refer to an ADC comprising an antibody that specifically binds to VTCN1, whereby the antibody is conjugated to one or more chemical agent(s) or payloads. In one embodiment, the chemical agent is linked to the antibody via a linker.

The term "drug-to-antibody ratio" or "DAR" refers to the number of drugs, e.g., IGN, auristatin, or maytansinoid, attached to the antibody of the ADC. The DAR of an ADC can range from 1 to 8, although higher loads, e.g., 10, are also possible depending on the number of linkage site on an antibody. The term DAR may be used in reference to the number of drugs loaded onto an individual antibody, or, alternatively, may be used in reference to the average or mean DAR of a group of ADCs.

The term "VTCN1 associated disorder," as used herein, includes any disorder or disease (including proliferative disorders, e.g., cancer) that is marked, diagnosed, detected or identified by a phenotypic or genotypic aberration of VTCN1 genetic components or expression during the course or etiology of the disease or disorder. In this regard a VTCN1 phenotypic aberration or determinant may, for example, comprise increased or decreased levels of VTCN1 protein expression on one cell population, e.g., a cancer cell population, or an immune cell population (such as a tumor infiltrating cell population), as compared to another cell population, e.g., a normal cell population, or increased or decreased VTCN1 protein expression on certain definable cell populations, or increased or decreased VTCN1 protein expression at an inappropriate phase or stage of a cell lifecycle. It will be appreciated that similar expression patterns of genotypic determinants (e.g., mRNA transcription levels) of VTCN1 may also be used to classify or detect VTCN1 associated disorders. An "VTCN1 associated disorder," as used herein, also includes a disorder characterized by infiltration of cells expressing VTCN1, e.g., tumor infiltrating immune cells or myeloid derived suppressor cells (MDSCs). In one embodiment, a VTCN1 associated disorder is breast cancer (e.g., triple negative breast cancer (TNBC)). In one embodiment, a VTCN1 associated disorder is renal cancer. In another embodiment, a VTCN1 associated disorder is ovarian cancer. In another embodiment, a VTCN1 associated disorder is gastric cancer. In another embodiment, a VTCN1 associated disorder is prostate cancer. In another embodiment, a VTCN1 associated disorder is uterine cancer. In another embodiment, a VTCN1 associated disorder is colorectal cancer. In another embodiment, a VTCN1 associated disorder is non small cell lung cancer (NSCLC). In yet another embodiments, a VTCN1 associated disorder is endometrial cancer. In one embodiment, a VTCN1 associated disorder is pancreatic cancer. In another embodiment, a VTCN1 associated disorder is liver cancer.

The term "cancer," as used herein, is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include, but are not limited to, breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. PVNS, acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, an anti-VTCN1 ADC of the present invention can be used to treat a cancer in a subject including, but not limited to Hodgkin's lymphoma, PVNS, acute myeloid leukemia, adrenocortico carcinoma, ladder urothelial carcinoma, breast cancer (Luminal A, TNBC, Ductal), cervical squamous cell carcinoma, endocervical adenocarcinoma, colorectal adenocarcinoma, diffuse large B cell lymphoma, non-hodgkin's lymphoma, glioblastoma multiforme, chronic lymphocytic leukemia, brain lower grade glioma, head and neck squamous cell carcinoma, hepatocellular carcinoma, lung adenocarcinoma, small cell lung cancer, large squamous cell carcinoma, cutaneous melanoma, ovarial serous cystadenocarcinoma, gastric cancer, soft tissue sarcoma, mesothelioma, pancreatic adenocarcinoma, testicular germ cell cancer, thymoma, thyroid carcinoma, uterine corpus endometrial carcinoma, uterine carcinosarcoma. kidney renal clear cell carcinoma, and kidney renal papillary cell carcinoma.

In one embodiment, the antibodies or ADCs of the invention are administered to a patient having a solid tumor, including an advanced solid tumor. In one embodiment, the tumor expresses VTCN1 or contains tumor infiltrating immune cells or myeloid derived suppressor cells (MDSCs) expressing VTCN1. In another embodiment, the tumor does not express VTCN1 and/or does not contain tumor infiltrating immune cells or MDSCs expressing VTCN1. In another embodiment, administration of the antibodies of the invention to a patient upregulates an immune response in the patient. In another embodiment, administration of ADCs of the invention induce cell death of VTCN1 expressing cells.

The term "VTCN1 expressing tumor," as used herein, refers to a tumor which expresses VTCN1 protein (including a tumor comprising tumor infiltrating cells that express VTCN1 protein), such as a triple negative breast cancer (TNBC) tumor. In one embodiment, VTCN1 expression in a tumor is determined using immunohistochemical staining of tumor cell membranes, where any immunohistochemical staining above background level in a tumor sample indicates that the tumor is a VTCN1 expressing tumor. In another embodiment, a VTCN1 expressing tumor, e.g., a TNBC tumor expressing VTCN1, is identified in a patient when greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a tumor sample are positive for VTCN1 expression. In one embodiment, the VTCN1 expressing cells in the sample are tumor infiltrating immune cells. In another embodiment, VTCN1 positive expression is determined based on membrane staining as determined by, e.g., immunohistochemistry (IHC) analysis.

A VTCN1 expressing tumor is identified as having an "elevated level of VTCN1" or "expressing VTCN1 at an elevated level" when the level of VTCN1 is higher than in tissue surrounding the cancer. In some embodiments, an "elevated level of VTCN1" is one in which 5% or more of the cells in a tumor sample have membrane staining In some embodiments a "high level" in regard to VTCN1 is 5% or more staining, for example, 5, 10, 20, 30, 40, 50, 60, 70, 80, 90, or 100% of the cells in the tumor sample are stained. In some embodiments, the protein expression levels can be measured by IHC analysis. In another embodiment, the VTCN1 expressing cells in the sample are tumor infiltrating immune cells.

A VTCN1 expressing tumor is identified as having a "low level of VTCN1" or "expressing VTCN1 at a low level" is one in which 5% or less of the cells in a tumor sample have membrane staining In some embodiments a "low level" in regard to VTCN1 is 5% or less staining, for example, 4.9, 4.5, 4, 3, 2, 1, 0.9, 0.8, 0.7, 0.6, 0.5, 0.4, 0.3, 0.2, 0.1% or less of the cells in the tumor sample are stained. In some embodiments, the protein expression levels can be measured by IHC analysis. In another embodiment, the VTCN1 expressing cells in the sample are tumor infiltrating immune cells.

A cell that expresses no VTCN1 can also be described as expressing a "low level of VTCN1". Thus, the phrase "expresses a low level of VTCN1" encompasses no VTCN1 expression. In some embodiments, a low level of VTCN1 is within the background staining levels. In some embodiments, a sample that is VTCN1 "negative" has no VTCN1 expression or a low level of VTCN1. In some embodiments, VTCN1 staining is negative when no or less than 5%, 4%, 3%, 2%, or 1% of the cells have membrane staining for VTCN1.

As used herein, the term TNBC "tumor sample" refers to a tumor tissue or cell sample obtained from a TNBC tumor. The sample can include both tumor cells and tumor infiltrating cells, e.g., tumor infiltrating immune cells.

As used herein, the term "non-cancer sample" or "normal sample" refers to a sample from a normal tissue (e.g., a breast tissue sample). In some embodiments, the non-cancer sample comes from the same subject, but is from a different part of the subject than that being tested. In some embodiments, the non-cancer sample is from a tissue area surrounding or adjacent to the cancer, e.g., TNBC. In some embodiments, the non-cancer sample is not from the subject being tested, but is a sample from a subject known to have, or not to have, a disorder in question (for example, a particular cancer such as TNBC or VTCN1 related disorder). In some embodiments, the non-cancer sample is from the same subject, but from a point in time before the subject developed cancer. In some embodiments, the reference sample is from a benign cancer sample (for example, benign breast cancer sample), from the same or a different subject.

Methods for detecting expression of VTCN1 in a tumor are known in the art. For example, immunohistochemistry (IHC) analysis was used by the inventors to show that VTCN1 is expressed in triple negative breast cancer (TNBC) tissue.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 5%, 10%, 20%, 30%, 40%, 50%, 60%, 70%, 80%, 90% or more in comparison to a normal cell or comparison cell. In certain embodiments, the anti-VTCN1 antibodies or ADCs are used to treat solid tumors likely to overexpress VTCN1.

The term "administering" as used herein is meant to refer to the delivery of a substance (e.g., an anti-VTCN1 antibody or ADC) to achieve a therapeutic objective (e.g., the treatment of an VTCN1-associated disorder or the inhibition or reduction of a tumor). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy", as used herein, refers to the administration of two or more therapeutic substances, e.g., an anti-VTCN1 antibody or ADC and an additional therapeutic agent. The additional therapeutic agent may be administered concomitant with, prior to, or following the administration of the anti-VTCN1 antibody or ADC. In one embodiment, the anti-VTCN1 antibodies or ADCs of the invention are administered in combination with one or more immune checkpoint inhibitors (e.g., one or more antibody or small molecule immune checkpoint inhibitors) for the treatment of a cancer.

In another embodiment, the anti-VTCN1 antibodies or ADCs of the invention are administered in combination with one or more MDSC inhibitors, such as, for example, an CSF-1R antibody, all-trans retinoic acid, gemcitabine, a COX2 inhibitor (e.g., SC58236), amino-biphosphonate, phosphodiesterase-5 inhibitor (e.g., sildenafil and tadalafil), a KIT-specific antibody, nitroaspirin, titerpenoid, 25-hydroxyvitamin D3, VEGF-trap, a VEGF-specific antibody (e.g., Avastin), doxorubicincyclophosphamide, an antagonist for CXCR2 (e.g., S-265610) or CXCR4 (e.g., AMD3100), a tyrosine kinase inhibitor (e.g., Sunitinib), or a PROK2-specific antibody, for the treatment of a cancer. In one embodiment, the anti-VTCN1 antibodies or ADCs of the invention are administered in combination with one or more compound which is capable of decreasing T regulatory cells and/or increasing effector T cell:T regulatory cell ratio in a subject (see, e.g., Eriksson et al. (2016) *Journal of Translational Medicine* 14:282). In one embodiment, the compound is, for example, gemcitabine.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

Various aspects of the invention are described in further detail in the following subsections.

II. Anti-VTCN1 Antibodies

One aspect disclosed herein provides humanized anti-VTCN1 antibodies, or antigen binding portions thereof. Another aspect disclosed herein provides human anti-VTCN1 antibodies, or antigen binding portions thereof. In one embodiment, the antibodies disclosed herein bind human VTCN1. In another embodiment, the antibodies disclosed herein bind cynomolgus monkey VTCN1. In another embodiment, the antibodies disclosed herein bind human VTCN1 expressed on T cells and/or APCs, e.g., dendritic cells (DCs), monocytes, and macrophages, B-cells, and natural killer (NK) cells. In another embodiment, the antibodies disclosed herein bind human VTCN1 expressed on tumor infiltrating immune cells, e.g., myeloid cells. In another embodiment, the antibodies disclosed herein bind human VTCN1 expressed on tumor cells.

Another aspect disclosed herein features antibody drug conjugates (ADCs) comprising an anti-VTCN1 antibody described herein and at least one drug(s). The antibodies or ADCs disclosed herein have characteristics including, but not limited to, binding to human VTCN1 in vitro, binding human VTCN1 expressed on T cells and/or APCs, e.g., dendritic cells (DCs), monocytes, and macrophages, B-cells, and natural killer (NK) cells, binding human VTCN1 expressed on tumor infiltrating immune cells, e.g., myeloid cells, binding human VTCN1 expressed on tumor cells, upregulating an immune response in vivo, increasing T cell activation in vivo; increasing CD8+ T cell expansion and effector functions that would result in anti-tumor response, inducing cell death in cells expressing VTCN1, including, but not limited to, myeloid derived suppressor cells (MDSCs) and tumor associated macrophages, and decreasing or inhibiting cancer, tumor cellular proliferation or tumor growth, or tumor invasion and metastasis. ADCs disclosed herein, in particular, have characteristics including, but not limited to, inducing cell death in cells expressing VTCN1, e.g., myeloid cells expressing VTCN1. In one embodiment, an anti-VTCN1 antibody or ADC disclosed herein is capable of being internalized into a cell expressing VTCN1.

In one embodiment, anti-VTCN1 antibodies are disclosed which have the ability to bind to VTCN1, as described in the Examples below. Collectively, the novel antibodies are referred to herein as "VTCN1 antibodies." The anti-VTCN1 antibodies, ADCs, or antigen binding fragments thereof, are able to inhibit or decrease tumor growth in vivo. The tumor can be a VTCN1 negative tumor or an VTCN1 expressing tumor. In various embodiments, anti-VTCN1 antibodies, ADCs, or antigen binding fragments thereof, are capable of modulating a biological function of VTCN1. In other embodiments of the foregoing aspects, the anti-VTCN1 antibodies, ADCs, or antigen binding fragments thereof, bind VTCN1 on cells expressing VTCN1. Thus, the disclosure includes anti-VTCN1 antibodies, ADCs, or antigen binding fragments thereof, that are effective at inhibiting or decreasing tumor growth.

In addition, the present inventors have shown that VTCN1 is expressed by tumor infiltrating cells in triple negative breast cancer (see Example 1). TNBC is notoriously biologically aggressive and difficult to treat (see, Wahba and El-Haddad (2015) *Cancer Biol. Med.* 12(2): 106-116). According, the anti-VTCN1 antibodies, ADCs, and antigen-binding portions thereof, can be used for the treatment of TNBC in a subject. In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a TNBC tumor sample are positive for VTCN1 expression. In another embodiment, a TNBC tumor sample has a high level of VTCN1 expression. For example, in one embodiment, at least 5% or more of the cells in a TNBC tumor sample have membrane staining In another embodiment, a TNBC tumor sample obtained from the subject displays a low level of expression of VTCN1. The expression level of VTCN1 can be determined by any method known in the art. For example, the expression level of VTCN1 can be determined via immunohistochemical analysis. In another embodiment, the TNBC has been previously treated with another anti-cancer agent or anti-cancer therapy, e.g., a chemotherapy. In one embodiment, the TNBC is resistant to chemotherapy.

Antibodies having combinations of any of the aforementioned characteristics are contemplated as aspects of the disclosure. ADCs, described in more detail below, may also have any of the foregoing characteristics.

One aspect of the disclosure features an anti-human VTCN1 (anti-hVTCN1) Antibody Drug Conjugate (ADC) comprising an anti-hVTCN1 antibody conjugated to a drug via a linker. Exemplary anti-VTCN1 antibodies (and sequences thereof) that can be used in the ADCs are described herein.

The anti-VTCN1 antibodies described herein provide the ADCs with the ability to bind to VTCN1 such that the cytotoxic molecule attached to the antibody may be delivered to the VTCN1-expressing cell, particularly a VTCN1 expressing cancer cell or a myeloid derived suppressor cell (MDSC).

While the term "antibody" is used throughout, it should be noted that antibody fragments (i.e., antigen-binding portions of an anti-VTCN1 antibody) are also included in the disclosure and may be included in the embodiments (methods and compositions) described throughout. For example, an anti-VTCN1 antibody fragment may be conjugated to the drugs, as described herein. In certain embodiments, an anti-VTCN1 antibody binding portion is a Fab, a Fab', a F(ab')2, a Fv, a disulfide linked Fv, an scFv, a single domain antibody, or a diabody.

Example 2 describes the generation of a fully human VTCN1 antibody against the extracellular domain of human VTCN1, identified herein as 7C8. The heavy and light chain variable region amino acid sequences for this human antibody are set forth in Table 2. The heavy and light chain variable region nucleic acid sequences for this human antibody are set forth in Table 3.

Example 11 describes the generation of an additional six fully human VTCN1 antibodies against the extracellular domain of human VTCN1, identified herein as 4C7_63A1, 7G7_44C6, 13H9_44 D2, 12B5_44B1, 14D6_60B5, and 16H12_60B4. The heavy and light chain variable region amino acid sequences for these human antibody are set forth in Table 10. The heavy and light chain variable region nucleic acid sequences for this human antibody are set forth in Table 11.

Thus, in one embodiment, the disclosure includes a fully human anti-hVTCN1 antibody, or antigen binding portion thereof, comprising a heavy chain variable region comprising an amino acid of SEQ ID NO: 212, and a light chain variable region comprising an amino acid sequence of SEQ ID NO: 216.

In one embodiment, the disclosure includes a human anti-hVTCN1 antibody, or antigen binding portion thereof, comprising an HC CDR set (CDR1, CDR2, and CDR3) of SEQ ID NOs: 213, 214, and 215; and an LC CDR set (CDR1, CDR2, and CDR3) of SEQ ID NOs: 217, 218, and 219.

In another embodiment, the disclosure includes human anti-hVTCN1 antibodies, or antigen binding portions thereof, comprising a heavy chain variable region comprising an amino acid sequence selected from the group consisting of SEQ ID NOs: 248, 256, 264, 272, 278, and 283; and a light chain variable region comprising an amino acid sequence selected from the group consisting of SEQ ID NOs: 252, 260, 268, 276, 281, and 286.

In one embodiment, the disclosure includes a human anti-hVTCN1 antibody, or antigen binding portion thereof, comprising an HC CDR set (CDR1, CDR2, and CDR3) selected from the group consisting of SEQ ID NOs: 249, 250, and 251; SEQ ID NOs: 257, 258, and 259; SEQ ID NOs: 265, 266, and 267; SEQ ID NOs: 273, 274, and 275; SEQ ID NOs: 279, 280, and 267; and SEQ ID NOs: 284, 285, and 267; and an LC CDR set (CDR1, CDR2, and CDR3) selected from the group consisting of SEQ ID NOs: 253, 254, and 255; SEQ ID NOs: 261, 262, and 263; SEQ ID NOs: 269, 270, and 271; SEQ ID NOs: 269, 254, and 277; SEQ ID NOs: 269, 254, and 282; SEQ ID NOs: 269, 254, and 287.

In one embodiment, an anti-VTCN1 antibody, or antigen binding portion thereof, is the human antibody 4C7_63 A1. The 4C7_63 A1 antibody comprises a heavy chain variable region comprising a CDR3 domain comprising the amino acid sequence of SEQ ID NO: 251, a CDR2 domain comprising the amino acid sequence of SEQ ID NO: 250, and a CDR1 domain comprising the amino acid sequence of SEQ ID NO: 249, and a light chain variable region comprising a CDR3 domain comprising the amino acid sequence of SEQ ID NO: 255, a CDR2 domain comprising the amino acid sequence of SEQ ID NO: 254, and a CDR1 domain comprising the amino acid sequence of SEQ ID NO: 253. In further embodiments, disclosed herein is an antibody having a heavy chain variable region comprising the amino acid sequence of SEQ ID NO: 248 and a light chain variable region comprising the amino acid sequence of SEQ ID NO: 252.

In some embodiments, an anti-VTCN1 antibody, or antigen-binding portion thereof, comprises a heavy chain comprising an amino acid sequence set forth in SEQ ID NO: 248, or a sequence having at least 90%, 95%, 96%, 97%, 98%, or 99% identity to SEQ ID NO: 248, and/or a light chain comprising an amino acid sequence set forth in SEQ ID NO: 252, or a sequence having at least 90%, 95%, 96%, 97%, 98%, or 99% identity to SEQ ID NO: 252.

In one embodiment, an anti-VTCN1 antibody, or antigen binding portion thereof, is the human antibody 7G7_44C6. The 7G7_44C6 antibody comprises a heavy chain variable region comprising a CDR3 domain comprising the amino acid sequence of SEQ ID NO: 259, a CDR2 domain comprising the amino acid sequence of SEQ ID NO: 258, and a CDR1 domain comprising the amino acid sequence of SEQ ID NO: 257, and a light chain variable region comprising a CDR3 domain comprising the amino acid sequence of SEQ ID NO: 263, a CDR2 domain comprising the amino acid sequence of SEQ ID NO: 262, and a CDR1 domain comprising the amino acid sequence of SEQ ID NO: 261. In further embodiments, disclosed herein is an antibody having a heavy chain variable region comprising the amino acid sequence of SEQ ID NO: 256 and a light chain variable region comprising the amino acid sequence of SEQ ID NO: 260.

In some embodiments, an anti-VTCN1 antibody, or antigen-binding portion thereof, comprises a heavy chain comprising an amino acid sequence set forth in SEQ ID NO: 256, or a sequence having at least 90%, 95%, 96%, 97%, 98%, or 99% identity to SEQ ID NO: 256, and/or a light chain comprising an amino acid sequence set forth in SEQ ID NO: 260, or a sequence having at least 90%, 95%, 96%, 97%, 98%, or 99% identity to SEQ ID NO: 260.

In one embodiment, an anti-VTCN1 antibody, or antigen binding portion thereof, is the human antibody 12B5_44B1. The 12B5_44B1 antibody comprises a heavy chain variable region comprising a CDR3 domain comprising the amino acid sequence of SEQ ID NO: 267, a CDR2 domain comprising the amino acid sequence of SEQ ID NO: 266, and a CDR1 domain comprising the amino acid sequence of SEQ ID NO: 265, and a light chain variable region comprising a CDR3 domain comprising the amino acid sequence of SEQ ID NO: 271, a CDR2 domain comprising the amino acid sequence of SEQ ID NO: 270, and a CDR1 domain comprising the amino acid sequence of SEQ ID NO: 269. In further embodiments, disclosed herein is an antibody having a heavy chain variable region comprising the amino acid sequence of SEQ ID NO: 264 and a light chain variable region comprising the amino acid sequence of SEQ ID NO: 268.

In some embodiments, an anti-VTCN1 antibody, or antigen-binding portion thereof, comprises a heavy chain comprising an amino acid sequence set forth in SEQ ID NO: 264, or a sequence having at least 90%, 95%, 96%, 97%, 98%, or 99% identity to SEQ ID NO: 264, and/or a light chain comprising an amino acid sequence set forth in SEQ ID NO: 268, or a sequence having at least 90%, 95%, 96%, 97%, 98%, or 99% identity to SEQ ID NO: 268.

In one embodiment, an anti-VTCN1 antibody, or antigen binding portion thereof, is the human antibody 13H9_44 D2. The 13H9_44 D2 antibody comprises a heavy chain variable region comprising a CDR3 domain comprising the amino acid sequence of SEQ ID NO: 275, a CDR2 domain comprising the amino acid sequence of SEQ ID NO: 274, and a CDR1 domain comprising the amino acid sequence of SEQ ID NO: 273, and a light chain variable region comprising a CDR3 domain comprising the amino acid sequence of SEQ ID NO: 277, a CDR2 domain comprising the amino acid sequence of SEQ ID NO: 254, and a CDR1 domain comprising the amino acid sequence of SEQ ID NO: 269. In further embodiments, disclosed herein is an antibody having a heavy chain variable region comprising the amino acid sequence of SEQ ID NO: 272 and a light chain variable region comprising the amino acid sequence of SEQ ID NO: 276.

In some embodiments, an anti-VTCN1 antibody, or antigen-binding portion thereof, comprises a heavy chain comprising an amino acid sequence set forth in SEQ ID NO: 272, or a sequence having at least 90%, 95%, 96%, 97%, 98%, or 99% identity to SEQ ID NO: 272, and/or a light chain comprising an amino acid sequence set forth in SEQ ID NO: 276, or a sequence having at least 90%, 95%, 96%, 97%, 98%, or 99% identity to SEQ ID NO: 276.

In one embodiment, an anti-VTCN1 antibody, or antigen binding portion thereof, is the human antibody 14D6_60B5. The 14D6_60B5 antibody comprises a heavy chain variable region comprising a CDR3 domain comprising the amino acid sequence of SEQ ID NO: 267, a CDR2 domain comprising the amino acid sequence of SEQ ID NO: 280, and a CDR1 domain comprising the amino acid sequence of SEQ ID NO: 279, and a light chain variable region comprising a CDR3 domain comprising the amino acid sequence of SEQ ID NO: 282, a CDR2 domain comprising the amino acid sequence of SEQ ID NO: 254, and a CDR1 domain comprising the amino acid sequence of SEQ ID NO: 269. In further embodiments, disclosed herein is an antibody having a heavy chain variable region comprising the amino acid sequence of SEQ ID NO: 278 and a light chain variable region comprising the amino acid sequence of SEQ ID NO: 281.

In some embodiments, an anti-VTCN1 antibody, or antigen-binding portion thereof, comprises a heavy chain comprising an amino acid sequence set forth in SEQ ID NO: 278, or a sequence having at least 90%, 95%, 96%, 97%, 98%, or 99% identity to SEQ ID NO: 278, and/or a light chain comprising an amino acid sequence set forth in SEQ ID NO: 281, or a sequence having at least 90%, 95%, 96%, 97%, 98%, or 99% identity to SEQ ID NO: 281.

In one embodiment, an anti-VTCN1 antibody, or antigen binding portion thereof, is the human antibody 16H12_60B4. The 16H12_60B4 antibody comprises a heavy chain variable region comprising a CDR3 domain comprising the amino acid sequence of SEQ ID NO: 267, a CDR2 domain comprising the amino acid sequence of SEQ ID NO: 285, and a CDR1 domain comprising the amino acid sequence of SEQ ID NO: 284, and a light chain variable region comprising a CDR3 domain comprising the amino acid sequence of SEQ ID NO: 287, a CDR2 domain comprising the amino acid sequence of SEQ ID NO: 254, and a CDR1 domain comprising the amino acid sequence of SEQ ID NO: 269. In further embodiments, disclosed herein is an antibody having a heavy chain variable region comprising the amino acid sequence of SEQ ID NO: 283 and a light chain variable region comprising the amino acid sequence of SEQ ID NO: 286.

In some embodiments, an anti-VTCN1 antibody, or antigen-binding portion thereof, comprises a heavy chain comprising an amino acid sequence set forth in SEQ ID NO: 283, or a sequence having at least 90%, 95%, 96%, 97%, 98%, or 99% identity to SEQ ID NO: 283, and/or a light chain comprising an amino acid sequence set forth in SEQ ID NO: 286, or a sequence having at least 90%, 95%, 96%, 97%, 98%, or 99% identity to SEQ ID NO: 286.

In one embodiment, an anti-VTCN1 antibody, or antigen binding portion thereof, is the human antibody 7C8. The 7C8 antibody comprises a heavy chain variable region comprising a CDR3 domain comprising the amino acid sequence of SEQ ID NO: 215, a CDR2 domain comprising the amino acid sequence of SEQ ID NO: 214, and a CDR1 domain comprising the amino acid sequence of SEQ ID NO: 213, and a light chain variable region comprising a CDR3 domain comprising the amino acid sequence of SEQ ID NO: 219, a CDR2 domain comprising the amino acid sequence of SEQ ID NO: 218, and a CDR1 domain comprising the amino acid sequence of SEQ ID NO: 217. In further embodiments, disclosed herein is an antibody having a heavy chain variable region comprising the amino acid sequence of SEQ ID NO: 212 and a light chain variable region comprising the amino acid sequence of SEQ ID NO: 216.

In some embodiments, an anti-VTCN1 antibody, or antigen-binding portion thereof, comprises a heavy chain comprising an amino acid sequence set forth in SEQ ID NO: 212, or a sequence having at least 90%, 95%, 96%, 97%, 98%, or 99% identity to SEQ ID NO: 212, and/or a light chain comprising an amino acid sequence set forth in SEQ ID NO: 216, or a sequence having at least 90%, 95%, 96%, 97%, 98%, or 99% identity to SEQ ID NO: 216.

Example 10 describes the generation of five humanized VTCN1 antibodies against the extracellular domain of human VTCN1, identified herein as hu6D9_57A3, hu6D9_57A4, hu6D9_57A5, hu6D9_66B1, and hu6D9_66C2. The heavy and light chain variable region amino acid sequences for these human antibody are set forth in Table 7. The heavy and light chain variable region nucleic acid sequences for this human antibody are set forth in Table 8.

Thus, in one embodiment, the disclosure includes humanized anti-hVTCN1 antibodies, or antigen binding portions thereof, comprising a heavy chain variable region comprising an amino acid sequence selected from the group consisting of SEQ ID NOs: 220, 228, 232, 236, and 240; and a light chain variable region comprising an amino acid sequence selected from the group consisting of SEQ ID NOs: 224 and 244.

In one embodiment, the disclosure includes a humanized anti-hVTCN1 antibody, or antigen binding portion thereof, comprising an HC CDR set (CDR1, CDR2, and CDR3) selected from the group consisting of SEQ ID NOs: 221, 222, and 223; SEQ ID NOs: 229, 230 and 231; SEQ ID NOs: 233, 234, and 235; SEQ ID NOs: 237, 238, and 239; and SEQ ID NOs: 241, 242, and 243; and an LC CDR set (CDR1, CDR2, and CDR3) selected from the group consisting of SEQ ID NOs: 225, 226, and 227; and SEQ ID NOs: 245, 246, and 247.

In one embodiment, an anti-VTCN1 antibody, or antigen binding portion thereof, is the humanized antibody hu6D9_57A3. The hu6D9_57A3 antibody comprises a heavy chain variable region comprising a CDR3 domain comprising the amino acid sequence of SEQ ID NO: 223, a CDR2 domain comprising the amino acid sequence of SEQ ID NO: 222, and a CDR1 domain comprising the amino acid sequence of SEQ ID NO: 221, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225. In further embodiments, disclosed herein is an antibody having a heavy chain variable region comprising the amino acid sequence of SEQ ID NO: 220 and a light chain variable region comprising the amino acid sequence of SEQ ID NO: 224.

In some embodiments, an anti-VTCN1 antibody, or antigen-binding portion thereof, comprises a heavy chain comprising an amino acid sequence set forth in SEQ ID NO: 220, or a sequence having at least 90%, 95%, 96%, 97%, 98%, or 99% identity to SEQ ID NO: 220, and/or a light chain comprising an amino acid sequence set forth in SEQ ID NO: 224, or a sequence having at least 90%, 95%, 96%, 97%, 98%, or 99% identity to SEQ ID NO: 224.

In one embodiment, an anti-VTCN1 antibody, or antigen binding portion thereof, is the humanized antibody hu6D9_57A4. The hu6D9_57A4 antibody comprises a heavy chain variable region comprising a CDR3 domain comprising the amino acid sequence of SEQ ID NO: 231, a CDR2 domain comprising the amino acid sequence of SEQ ID NO: 230, and a CDR1 domain comprising the amino acid sequence of SEQ ID NO: 229, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225. In further embodiments, disclosed herein is an antibody having a heavy chain variable region comprising the amino acid sequence of SEQ ID NO: 228 and a light chain variable region comprising the amino acid sequence of SEQ ID NO: 224.

In some embodiments, an anti-VTCN1 antibody, or antigen-binding portion thereof, comprises a heavy chain comprising an amino acid sequence set forth in SEQ ID NO: 228, or a sequence having at least 90%, 95%, 96%, 97%, 98%, or 99% identity to SEQ ID NO: 228, and/or a light chain comprising an amino acid sequence set forth in SEQ ID NO: 224, or a sequence having at least 90%, 95%, 96%, 97%, 98%, or 99% identity to SEQ ID NO: 224.

In one embodiment, an anti-VTCN1 antibody, or antigen binding portion thereof, is the humanized antibody hu6D9_57A5. The hu6D9_57A5 antibody comprises a heavy chain variable region comprising a CDR3 domain comprising the amino acid sequence of SEQ ID NO: 235, a CDR2 domain comprising the amino acid sequence of SEQ ID NO: 234, and a CDR1 domain comprising the amino acid sequence of SEQ ID NO: 233, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225. In further embodiments, disclosed herein is an antibody having a heavy chain variable region comprising the amino acid sequence of SEQ ID NO: 232 and a light chain variable region comprising the amino acid sequence of SEQ ID NO: 224.

In some embodiments, an anti-VTCN1 antibody, or antigen-binding portion thereof, comprises a heavy chain comprising an amino acid sequence set forth in SEQ ID NO: 232, or a sequence having at least 90%, 95%, 96%, 97%, 98%, or 99% identity to SEQ ID NO: 22, and/or a light chain comprising an amino acid sequence set forth in SEQ ID NO: 224, or a sequence having at least 90%, 95%, 96%, 97%, 98%, or 99% identity to SEQ ID NO: 224.

In one embodiment, an anti-VTCN1 antibody, or antigen binding portion thereof, is the humanized antibody hu6D9_66B1. The hu6D9_66B1 antibody comprises a heavy chain variable region comprising a CDR3 domain comprising the amino acid sequence of SEQ ID NO: 239, a CDR2 domain comprising the amino acid sequence of SEQ ID NO: 238, and a CDR1 domain comprising the amino acid sequence of SEQ ID NO: 237, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225. In further embodiments, disclosed herein is an antibody having a heavy chain variable region comprising the amino acid sequence of SEQ ID NO: 236 and a light chain variable region comprising the amino acid sequence of SEQ ID NO: 224.

In some embodiments, an anti-VTCN1 antibody, or antigen-binding portion thereof, comprises a heavy chain comprising an amino acid sequence set forth in SEQ ID NO: 236, or a sequence having at least 90%, 95%, 96%, 97%, 98%, or 99% identity to SEQ ID NO: 236, and/or a light chain comprising an amino acid sequence set forth in SEQ ID NO: 224, or a sequence having at least 90%, 95%, 96%, 97%, 98%, or 99% identity to SEQ ID NO: 224.

In one embodiment, an anti-VTCN1 antibody, or antigen binding portion thereof, is the humanized antibody hu6D9_66C2. The hu6D9_66C2 antibody comprises a heavy chain variable region comprising a CDR3 domain comprising the amino acid sequence of SEQ ID NO: 243, a CDR2 domain comprising the amino acid sequence of SEQ ID NO: 242, and a CDR1 domain comprising the amino acid sequence of SEQ ID NO: 241, and a light chain variable region comprising a CDR3 domain comprising the amino acid sequence of SEQ ID NO: 247, a CDR2 domain comprising the amino acid sequence of SEQ ID NO: 246, and a CDR1 domain comprising the amino acid sequence of SEQ ID NO: 245. In further embodiments, disclosed herein is an antibody having a heavy chain variable region comprising the amino acid sequence of SEQ ID NO: 240 and a light chain variable region comprising the amino acid sequence of SEQ ID NO: 244.

In some embodiments, an anti-VTCN1 antibody, or antigen-binding portion thereof, comprises a heavy chain comprising an amino acid sequence set forth in SEQ ID NO: 240, or a sequence having at least 90%, 95%, 96%, 97%, 98%, or 99% identity to SEQ ID NO: 240, and/or a light chain comprising an amino acid sequence set forth in SEQ ID NO: 244, or a sequence having at least 90%, 95%, 96%, 97%, 98%, or 99% identity to SEQ ID NO: 244.

Example 5 describes the generation of twenty-three mouse recombinant VTCN1 antibodies against the extracellular domain of human VTCN1, identified herein as 1F8, 3C6, 3G10, 4B9, 6E2, 7E12, 8G3, 10D1, 1A2, 1C3, 2C2, 3D11, 4C6, 5A12, 6D9, 7C9, 7D9, 7F10, 7G9, 9E7, 9F10, 9H12, and 9H7. The heavy and light chain variable region amino acid sequences for these mouse antibodies are set forth in Table 4.

Thus, in one embodiment, the disclosure includes mouse anti-hVTCN1 antibodies, or antigen binding portions thereof, comprising a heavy chain variable region comprising an amino acid sequence selected from the group consisting of SEQ ID NOs: 1, 9, 17, 25, 33, 41, 49, 57, 65, 73, 81, 89, 97, 105, 113, 121, 129, 137, 145, 153, 161, 169, and 177; and a light chain variable region comprising an amino acid sequence selected from the group consisting of SEQ ID NOs: 5, 13, 21, 29, 37, 45, 53, 61, 69, 77, 85, 93, 101, 109, 117, 125, 133, 141, 149, 157, 165, 173, and 181. In one embodiment, the disclosure includes a mouse anti-hVTCN1 antibody, or antigen binding portion thereof, comprising an HC CDR set (CDR1, CDR2, and CDR3) selected from the group consisting of SEQ ID NOs: 2, 3, and 4; SEQ ID NOs: 10, 11, and 12; SEQ ID NOs: 18, 19, and 20; SEQ ID NOs: 26, 27, and 28; SEQ ID NOs: 34, 35, and 36; SEQ ID NOs: 42, 43, and 44; SEQ ID NOs: 50, 51, and 52; SEQ ID NOs: 58, 59, and 60; SEQ ID NOs: 66, 67, and 68; SEQ ID NOs: 74, 75, and 76; SEQ ID NOs: 82, 83, and 84; SEQ ID NOs: 90, 91, and 92; SEQ ID NOs: 98, 99, and 100; SEQ ID NOs: 106, 107, and 108; SEQ ID NOs: 114, 115, and 116; SEQ ID NOs: 122, 123, and 124; SEQ ID NOs: 130, 131, and 132; SEQ ID NOs: 138, 139, and 140; SEQ ID NOs: 146, 147, and 148; SEQ ID NOs: 154, 155, and 156; SEQ ID NOs: 162, 163, and 164; SEQ ID NOs: 170, 171, and 172 and SEQ ID NOs: 178, 179, and 180; and an LC CDR set (CDR1, CDR2, and CDR3) selected from the group consisting of SEQ ID NOs: 6, 7, and 8; SEQ ID NOs: 14, 15, and 16; SEQ ID NOs: 22, 23, and 24; and SEQ ID NOs: 30, 31, and 32; SEQ ID NOs: 38, 39, and 40; SEQ ID NOs: 46, 47, and 48; SEQ ID NOs: 54, 55, and 56; SEQ ID NOs: 62, 63, and 64; SEQ ID NOs: 70, 71, and 72; SEQ ID NOs: 78, 79, and 80; SEQ ID NOs: 86, 87, and 88; SEQ ID NOs: 94, 95, and 96; SEQ ID NOs: 102, 103, and 104; SEQ ID NOs: 110, 111, and 112; SEQ ID NOs: 118, 119, and 120; SEQ ID NOs: 126, 127, and 128; SEQ ID NOs: 134, 135, and 136; SEQ ID NOs: 142, 143, and 144; SEQ ID NOs: 150, 151, and 152; SEQ ID NOs: 158, 159, and 160; SEQ ID NOs: 166, 167, and 168; SEQ ID NOs: 174, 175, and 176 and SEQ ID NOs: 182, 183, and 184.

In one embodiment, an anti-VTCN1 antibody, or antigen binding portion thereof, is the mouse antibody 1F8C6. The 1F8C6 antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 1 and a light chain variable region comprising the amino acid sequence of SEQ ID NO: 5.

In some embodiments, an anti-VTCN1 antibody, or antigen-binding portion thereof, comprises a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In one embodiment, the disclosure features an anti-VTCN1 antibody, or antigen binding portion thereof, which is the mouse antibody 3C6. The 3C6 antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 9 and a light chain variable region comprising the amino acid sequence of SEQ ID NO: 13.

In some embodiments, an anti-VTCN1 antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In one embodiment, the disclosure features an anti-VTCN1 antibody, or antigen binding portion thereof, which is the mouse antibody 3G10. The 3G10 antibody comprises a heavy chain variable region comprising a CDR3 domain comprising the amino acid sequence of SEQ ID NO: 20, a CDR2 domain comprising the amino acid sequence of SEQ ID NO: 19, and a CDR1 domain comprising the amino acid sequence of SEQ ID NO: 18, and a light chain variable region comprising a CDR3 domain comprising the amino acid sequence of SEQ ID NO: 24, a CDR2 domain comprising the amino acid sequence of SEQ ID NO: 23, and a CDR1 domain comprising the amino acid sequence of SEQ ID NO: 22. In further embodiments, the disclosure provides an antibody having a heavy chain variable region comprising the amino acid sequence of SEQ ID NO: 17 and a light chain variable region comprising the amino acid sequence of SEQ ID NO: 21.

In some embodiments, an anti-VTCN1 antibody, or antigen-binding portion thereof, comprises a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO:

21, or a sequence having at least 90%, 95%, 96%, 97%, 98%, or 99% identity to SEQ ID NO: 21.

In one embodiment, the disclosure features an anti-VTCN1 antibody, or antigen binding portion thereof, which is the mouse antibody 4B9. The 4B9 antibody comprises a heavy chain variable region comprising a CDR3 domain comprising the amino acid sequence of SEQ ID NO: 28, a CDR2 domain comprising the amino acid sequence of SEQ ID NO: 27, and a CDR1 domain comprising the amino acid sequence of SEQ ID NO: 26, and a light chain variable region comprising a CDR3 domain comprising the amino acid sequence of SEQ ID NO: 32, a CDR2 domain comprising the amino acid sequence of SEQ ID NO: 31, and a CDR1 domain comprising the amino acid sequence of SEQ ID NO: 30. In further embodiments, the disclosure provides an antibody having a heavy chain variable region comprising the amino acid sequence of SEQ ID NO: 25 and a light chain variable region comprising the amino acid sequence of SEQ ID NO: 29.

In some embodiments, an anti-VTCN1 antibody, or antigen-binding portion thereof, comprises a heavy chain comprising an amino acid sequence set forth in SEQ ID NO: 25, or a sequence having at least 90%, 95%, 96%, 97%, 98%, or 99% identity to SEQ ID NO: 25, and/or a light chain comprising an amino acid sequence set forth in SEQ ID NO: 29, or a sequence having at least 90%, 95%, 96%, 97%, 98%, or 99% identity to SEQ ID NO: 29.

In one embodiment, an anti-VTCN1 antibody, or antigen binding portion thereof, is the mouse antibody 6E2. The 6E2 antibody comprises a heavy chain variable region comprising a CDR3 domain comprising the amino acid sequence of SEQ ID NO: 36, a CDR2 domain comprising the amino acid sequence of SEQ ID NO: 35, and a CDR1 domain comprising the amino acid sequence of SEQ ID NO: 34, and a light chain variable region comprising a CDR3 domain comprising the amino acid sequence of SEQ ID NO: 40, a CDR2 domain comprising the amino acid sequence of SEQ ID NO: 39, and a CDR1 domain comprising the amino acid sequence of SEQ ID NO: 38. In further embodiments, disclosed herein is an antibody having a heavy chain variable region comprising the amino acid sequence of SEQ ID NO: 33 and a light chain variable region comprising the amino acid sequence of SEQ ID NO: 37.

In some embodiments, an anti-VTCN1 antibody, or antigen-binding portion thereof, comprises a heavy chain comprising an amino acid sequence set forth in SEQ ID NO: 33, or a sequence having at least 90%, 95%, 96%, 97%, 98%, or 99% identity to SEQ ID NO: 33, and/or a light chain comprising an amino acid sequence set forth in SEQ ID NO: 37, or a sequence having at least 90%, 95%, 96%, 97%, 98%, or 99% identity to SEQ ID NO: 37.

In one embodiment, an anti-VTCN1 antibody, or antigen binding portion thereof, is the mouse antibody 7E12. The 7E12 antibody comprises a heavy chain variable region comprising a CDR3 domain comprising the amino acid sequence of SEQ ID NO: 44, a CDR2 domain comprising the amino acid sequence of SEQ ID NO: 43, and a CDR1 domain comprising the amino acid sequence of SEQ ID NO: 42, and a light chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46. In further embodiments, disclosed herein is an antibody having a heavy chain variable region comprising the amino acid sequence of SEQ ID NO: 41 and a light chain variable region comprising the amino acid sequence of SEQ ID NO: 45.

In some embodiments, an anti-VTCN1 antibody, or antigen-binding portion thereof, comprises a heavy chain comprising an amino acid sequence set forth in SEQ ID NO: 41, or a sequence having at least 90%, 95%, 96%, 97%, 98%, or 99% identity to SEQ ID NO: 41, and/or a light chain comprising an amino acid sequence set forth in SEQ ID NO: 45, or a sequence having at least 90%, 95%, 96%, 97%, 98%, or 99% identity to SEQ ID NO: 45.

In one embodiment, an anti-VTCN1 antibody, or antigen binding portion thereof, is the mouse antibody 8G3. The 8G3 antibody comprises a heavy chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50, and a light chain variable region comprising a CDR3 domain comprising the amino acid sequence of SEQ ID NO: 56, a CDR2 domain comprising the amino acid sequence of SEQ ID NO: 55, and a CDR1 domain comprising the amino acid sequence of SEQ ID NO: 54. In further embodiments, disclosed herein is an antibody having a heavy chain variable region comprising the amino acid sequence of SEQ ID NO: 49 and a light chain variable region comprising the amino acid sequence of SEQ ID NO: 53.

In some embodiments, an anti-VTCN1 antibody, or antigen-binding portion thereof, comprises a heavy chain comprising an amino acid sequence set forth in SEQ ID NO: 49, or a sequence having at least 90%, 95%, 96%, 97%, 98%, or 99% identity to SEQ ID NO: 49, and/or a light chain comprising an amino acid sequence set forth in SEQ ID NO: 53, or a sequence having at least 90%, 95%, 96%, 97%, 98%, or 99% identity to SEQ ID NO: 53.

In one embodiment, an anti-VTCN1 antibody, or antigen binding portion thereof, is the mouse antibody 10D1. The 10D1 antibody comprises a heavy chain variable region comprising a CDR3 domain comprising the amino acid sequence of SEQ ID NO: 60, a CDR2 domain comprising the amino acid sequence of SEQ ID NO: 59, and a CDR1 domain comprising the amino acid sequence of SEQ ID NO: 58, and a light chain variable region comprising a CDR3 domain comprising the amino acid sequence of SEQ ID NO: 64, a CDR2 domain comprising the amino acid sequence of SEQ ID NO: 63, and a CDR1 domain comprising the amino acid sequence of SEQ ID NO: 62. In further embodiments, disclosed herein is an antibody having a heavy chain variable region comprising the amino acid sequence of SEQ ID NO: 57 and a light chain variable region comprising the amino acid sequence of SEQ ID NO: 61.

In some embodiments, an anti-VTCN1 antibody, or antigen-binding portion thereof, comprises a heavy chain comprising an amino acid sequence set forth in SEQ ID NO: 57, or a sequence having at least 90%, 95%, 96%, 97%, 98%, or 99% identity to SEQ ID NO: 57, and/or a light chain comprising an amino acid sequence set forth in SEQ ID NO: 61, or a sequence having at least 90%, 95%, 96%, 97%, 98%, or 99% identity to SEQ ID NO: 61.

In one embodiment, an anti-VTCN1 antibody, or antigen binding portion thereof, is the mouse antibody 1A2. The 1A2 antibody comprises a heavy chain variable region comprising a CDR3 domain comprising the amino acid sequence of SEQ ID NO: 68, a CDR2 domain comprising the amino acid sequence of SEQ ID NO: 67, and a CDR1 domain comprising the amino acid sequence of SEQ ID NO: 66, and a light chain variable region comprising a CDR3 domain comprising the amino acid sequence of SEQ ID NO: 72, a CDR2 domain comprising the amino acid sequence of SEQ ID NO: 71, and a CDR1 domain comprising the amino acid sequence of SEQ ID NO: 70. In further embodiments, disclosed herein is an antibody having a heavy chain variable region comprising the amino acid sequence of SEQ ID NO: 65 and a light chain variable region comprising the amino acid sequence of SEQ ID NO: 69.

In some embodiments, an anti-VTCN1 antibody, or antigen-binding portion thereof, comprises a heavy chain comprising an amino acid sequence set forth in SEQ ID NO: 65, or a sequence having at least 90%, 95%, 96%, 97%, 98%, or 99% identity to SEQ ID NO: 65, and/or a light chain comprising an amino acid sequence set forth in SEQ ID NO: 69, or a sequence having at least 90%, 95%, 96%, 97%, 98%, or 99% identity to SEQ ID NO: 69.

In one embodiment, an anti-VTCN1 antibody, or antigen binding portion thereof, is the mouse antibody 1C3. The 1C3 antibody comprises a heavy chain variable region comprising a CDR3 domain comprising the amino acid sequence of SEQ ID NO: 76, a CDR2 domain comprising the amino acid sequence of SEQ ID NO: 75, and a CDR1 domain comprising the amino acid sequence of SEQ ID NO: 74, and a light chain variable region comprising a CDR3 domain comprising the amino acid sequence of SEQ ID NO: 80, a CDR2 domain comprising the amino acid sequence of SEQ ID NO: 79, and a CDR1 domain comprising the amino acid sequence of SEQ ID NO: 78. In further embodiments, disclosed herein is an antibody having a heavy chain variable region comprising the amino acid sequence of SEQ ID NO: 73 and a light chain variable region comprising the amino acid sequence of SEQ ID NO: 77.

In some embodiments, an anti-VTCN1 antibody, or antigen-binding portion thereof, comprises a heavy chain comprising an amino acid sequence set forth in SEQ ID NO: 73, or a sequence having at least 90%, 95%, 96%, 97%, 98%, or 99% identity to SEQ ID NO: 73, and/or a light chain comprising an amino acid sequence set forth in SEQ ID NO: 77, or a sequence having at least 90%, 95%, 96%, 97%, 98%, or 99% identity to SEQ ID NO: 77.

In one embodiment, an anti-VTCN1 antibody, or antigen binding portion thereof, is the mouse antibody 2C2. The 2C2 antibody comprises a heavy chain variable region comprising a CDR3 domain comprising the amino acid sequence of SEQ ID NO: 84, a CDR2 domain comprising the amino acid sequence of SEQ ID NO: 83, and a CDR1 domain comprising the amino acid sequence of SEQ ID NO: 82, and a light chain variable region comprising a CDR3 domain comprising the amino acid sequence of SEQ ID NO: 88, a CDR2 domain comprising the amino acid sequence of SEQ ID NO: 87, and a CDR1 domain comprising the amino acid sequence of SEQ ID NO: 86. In further embodiments, disclosed herein is an antibody having a heavy chain variable region comprising the amino acid sequence of SEQ ID NO: 81 and a light chain variable region comprising the amino acid sequence of SEQ ID NO: 85.

In some embodiments, an anti-VTCN1 antibody, or antigen-binding portion thereof, comprises a heavy chain comprising an amino acid sequence set forth in SEQ ID NO: 81, or a sequence having at least 90%, 95%, 96%, 97%, 98%, or 99% identity to SEQ ID NO: 81, and/or a light chain comprising an amino acid sequence set forth in SEQ ID NO: 85, or a sequence having at least 90%, 95%, 96%, 97%, 98%, or 99% identity to SEQ ID NO: 85.

In one embodiment, an anti-VTCN1 antibody, or antigen binding portion thereof, is the mouse antibody 3D11. The 3D11 antibody comprises a heavy chain variable region comprising a CDR3 domain comprising the amino acid sequence of SEQ ID NO: 92, a CDR2 domain comprising the amino acid sequence of SEQ ID NO: 91, and a CDR1 domain comprising the amino acid sequence of SEQ ID NO: 90, and a light chain variable region comprising a CDR3 domain comprising the amino acid sequence of SEQ ID NO: 96, a CDR2 domain comprising the amino acid sequence of SEQ ID NO: 95, and a CDR1 domain comprising the amino acid sequence of SEQ ID NO: 94. In further embodiments, disclosed herein is an antibody having a heavy chain variable region comprising the amino acid sequence of SEQ ID NO: 89 and a light chain variable region comprising the amino acid sequence of SEQ ID NO: 93.

In some embodiments, an anti-VTCN1 antibody, or antigen-binding portion thereof, comprises a heavy chain comprising an amino acid sequence set forth in SEQ ID NO: 89, or a sequence having at least 90%, 95%, 96%, 97%, 98%, or 99% identity to SEQ ID NO: 89, and/or a light chain comprising an amino acid sequence set forth in SEQ ID NO: 93, or a sequence having at least 90%, 95%, 96%, 97%, 98%, or 99% identity to SEQ ID NO: 93.

In one embodiment, an anti-VTCN1 antibody, or antigen binding portion thereof, is the mouse antibody 4C6. The 4C6 antibody comprises a heavy chain variable region comprising a CDR3 domain comprising the amino acid sequence of SEQ ID NO: 100, a CDR2 domain comprising the amino acid sequence of SEQ ID NO: 99, and a CDR1 domain comprising the amino acid sequence of SEQ ID NO: 98, and a light chain variable region comprising a CDR3 domain comprising the amino acid sequence of SEQ ID NO: 104, a CDR2 domain comprising the amino acid sequence of SEQ ID NO: 103, and a CDR1 domain comprising the amino acid sequence of SEQ ID NO: 102. In further embodiments, disclosed herein is an antibody having a heavy chain variable region comprising the amino acid sequence of SEQ ID NO: 97 and a light chain variable region comprising the amino acid sequence of SEQ ID NO: 101.

In some embodiments, an anti-VTCN1 antibody, or antigen-binding portion thereof, comprises a heavy chain comprising an amino acid sequence set forth in SEQ ID NO: 97, or a sequence having at least 90%, 95%, 96%, 97%, 98%, or 99% identity to SEQ ID NO: 97, and/or a light chain comprising an amino acid sequence set forth in SEQ ID NO: 101, or a sequence having at least 90%, 95%, 96%, 97%, 98%, or 99% identity to SEQ ID NO: 101.

In one embodiment, an anti-VTCN1 antibody, or antigen binding portion thereof, is the mouse antibody 5A12. The 5A12 antibody comprises a heavy chain variable region comprising a CDR3 domain comprising the amino acid sequence of SEQ ID NO: 108, a CDR2 domain comprising the amino acid sequence of SEQ ID NO: 107, and a CDR1 domain comprising the amino acid sequence of SEQ ID NO: 106, and a light chain variable region comprising a CDR3 domain comprising the amino acid sequence of SEQ ID NO: 112, a CDR2 domain comprising the amino acid sequence of SEQ ID NO: 111, and a CDR1 domain comprising the amino acid sequence of SEQ ID NO: 110. In further embodiments, disclosed herein is an antibody having a heavy chain variable region comprising the amino acid sequence of SEQ ID NO: 105 and a light chain variable region comprising the amino acid sequence of SEQ ID NO: 109.

In some embodiments, an anti-VTCN1 antibody, or antigen-binding portion thereof, comprises a heavy chain comprising an amino acid sequence set forth in SEQ ID NO: 105, or a sequence having at least 90%, 95%, 96%, 97%, 98%, or 99% identity to SEQ ID NO: 105, and/or a light chain comprising an amino acid sequence set forth in SEQ ID NO: 109, or a sequence having at least 90%, 95%, 96%, 97%, 98%, or 99% identity to SEQ ID NO: 109.

In one embodiment, an anti-VTCN1 antibody, or antigen binding portion thereof, is the mouse antibody 6D9. The 6D9 antibody comprises a heavy chain variable region comprising a CDR3 domain comprising the amino acid sequence of SEQ ID NO: 116, a CDR2 domain comprising the amino acid sequence of SEQ ID NO: 115, and a CDR1 domain comprising the amino acid sequence of SEQ ID NO: 114, and a light chain variable region comprising a CDR3 domain comprising the amino acid sequence of SEQ ID NO: 120, a CDR2 domain comprising the amino acid sequence of SEQ ID NO: 119, and a CDR1 domain comprising the amino acid sequence of SEQ ID NO: 118. In further embodiments, disclosed herein is an antibody having a heavy chain variable region comprising the amino acid sequence of SEQ ID NO: 113 and a light chain variable region comprising the amino acid sequence of SEQ ID NO: 117.

In some embodiments, an anti-VTCN1 antibody, or antigen-binding portion thereof, comprises a heavy chain comprising an amino acid sequence set forth in SEQ ID NO: 113, or a sequence having at least 90%, 95%, 96%, 97%, 98%, or 99% identity to SEQ ID NO: 113, and/or a light chain comprising an amino acid sequence set forth in SEQ ID NO: 117, or a sequence having at least 90%, 95%, 96%, 97%, 98%, or 99% identity to SEQ ID NO: 117.

In one embodiment, an anti-VTCN1 antibody, or antigen binding portion thereof, is the mouse antibody 7C9. The 7C9 antibody comprises a heavy chain variable region comprising a CDR3 domain comprising the amino acid sequence of SEQ ID NO: 124, a CDR2 domain comprising the amino acid sequence of SEQ ID NO: 123, and a CDR1 domain comprising the amino acid sequence of SEQ ID NO: 122, and a light chain variable region comprising a CDR3 domain comprising the amino acid sequence of SEQ ID NO: 128, a CDR2 domain comprising the amino acid sequence of SEQ ID NO: 127, and a CDR1 domain comprising the amino acid sequence of SEQ ID NO: 126. In further embodiments, disclosed herein is an antibody having a heavy chain variable region comprising the amino acid sequence of SEQ ID NO: 121 and a light chain variable region comprising the amino acid sequence of SEQ ID NO: 125.

In some embodiments, an anti-VTCN1 antibody, or antigen-binding portion thereof, comprises a heavy chain comprising an amino acid sequence set forth in SEQ ID NO: 121, or a sequence having at least 90%, 95%, 96%, 97%, 98%, or 99% identity to SEQ ID NO: 121, and/or a light chain comprising an amino acid sequence set forth in SEQ ID NO: 125, or a sequence having at least 90%, 95%, 96%, 97%, 98%, or 99% identity to SEQ ID NO: 125.

In one embodiment, an anti-VTCN1 antibody, or antigen binding portion thereof, is the mouse antibody 7D9. The 7D9 antibody comprises a heavy chain variable region comprising a CDR3 domain comprising the amino acid sequence of SEQ ID NO: 132, a CDR2 domain comprising the amino acid sequence of SEQ ID NO: 131, and a CDR1 domain comprising the amino acid sequence of SEQ ID NO: 130, and a light chain variable region comprising a CDR3 domain comprising the amino acid sequence of SEQ ID NO: 136, a CDR2 domain comprising the amino acid sequence of SEQ ID NO: 135, and a CDR1 domain comprising the amino acid sequence of SEQ ID NO: 134. In further embodiments, disclosed herein is an antibody having a heavy chain variable region comprising the amino acid sequence of SEQ ID NO: 129 and a light chain variable region comprising the amino acid sequence of SEQ ID NO: 133.

In some embodiments, an anti-VTCN1 antibody, or antigen-binding portion thereof, comprises a heavy chain comprising an amino acid sequence set forth in SEQ ID NO: 129, or a sequence having at least 90%, 95%, 96%, 97%, 98%, or 99% identity to SEQ ID NO: 129, and/or a light chain comprising an amino acid sequence set forth in SEQ ID NO: 133, or a sequence having at least 90%, 95%, 96%, 97%, 98%, or 99% identity to SEQ ID NO: 133.

In one embodiment, an anti-VTCN1 antibody, or antigen binding portion thereof, is the mouse antibody 7F10. The 7F10 antibody comprises a heavy chain variable region comprising a CDR3 domain comprising the amino acid sequence of SEQ ID NO: 140, a CDR2 domain comprising the amino acid sequence of SEQ ID NO: 139, and a CDR1 domain comprising the amino acid sequence of SEQ ID NO: 138, and a light chain variable region comprising a CDR3 domain comprising the amino acid sequence of SEQ ID NO: 144, a CDR2 domain comprising the amino acid sequence of SEQ ID NO: 143, and a CDR1 domain comprising the amino acid sequence of SEQ ID NO: 142. In further embodiments, disclosed herein is an antibody having a heavy chain variable region comprising the amino acid sequence of SEQ ID NO: 137 and a light chain variable region comprising the amino acid sequence of SEQ ID NO: 141.

In some embodiments, an anti-VTCN1 antibody, or antigen-binding portion thereof, comprises a heavy chain comprising an amino acid sequence set forth in SEQ ID NO: 137, or a sequence having at least 90%, 95%, 96%, 97%, 98%, or 99% identity to SEQ ID NO: 137, and/or a light chain comprising an amino acid sequence set forth in SEQ ID NO: 141, or a sequence having at least 90%, 95%, 96%, 97%, 98%, or 99% identity to SEQ ID NO: 141.

In one embodiment, an anti-VTCN1 antibody, or antigen binding portion thereof, is the mouse antibody 7G9. The 7G9 antibody comprises a heavy chain variable region comprising a CDR3 domain comprising the amino acid sequence of SEQ ID NO: 148, a CDR2 domain comprising the amino acid sequence of SEQ ID NO: 147, and a CDR1 domain comprising the amino acid sequence of SEQ ID NO: 146, and a light chain variable region comprising a CDR3 domain comprising the amino acid sequence of SEQ ID NO: 152, a CDR2 domain comprising the amino acid sequence of SEQ ID NO: 151, and a CDR1 domain comprising the amino acid sequence of SEQ ID NO: 150. In further embodiments, disclosed herein is an antibody having a heavy chain variable region comprising the amino acid sequence of SEQ ID NO: 145 and a light chain variable region comprising the amino acid sequence of SEQ ID NO: 149.

In some embodiments, an anti-VTCN1 antibody, or antigen-binding portion thereof, comprises a heavy chain comprising an amino acid sequence set forth in SEQ ID NO: 145, or a sequence having at least 90%, 95%, 96%, 97%, 98%, or 99% identity to SEQ ID NO: 145, and/or a light chain comprising an amino acid sequence set forth in SEQ ID NO: 149, or a sequence having at least 90%, 95%, 96%, 97%, 98%, or 99% identity to SEQ ID NO: 149.

In one embodiment, an anti-VTCN1 antibody, or antigen binding portion thereof, is the mouse antibody 9E7. The 9E7 antibody comprises a heavy chain variable region comprising a CDR3 domain comprising the amino acid sequence of SEQ ID NO: 156, a CDR2 domain comprising the amino acid sequence of SEQ ID NO: 155, and a CDR1 domain comprising the amino acid sequence of SEQ ID NO: 154, and a light chain variable region comprising a CDR3 domain comprising the amino acid sequence of SEQ ID NO: 160, a CDR2 domain comprising the amino acid sequence of SEQ ID NO: 159, and a CDR1 domain comprising the amino acid sequence of SEQ ID NO: 158. In further embodiments, disclosed herein is an antibody having a heavy chain variable region comprising the amino acid sequence of SEQ ID NO: 153 and a light chain variable region comprising the amino acid sequence of SEQ ID NO: 157.

In some embodiments, an anti-VTCN1 antibody, or antigen-binding portion thereof, comprises a heavy chain comprising an amino acid sequence set forth in SEQ ID NO: 153, or a sequence having at least 90%, 95%, 96%, 97%, 98%, or 99% identity to SEQ ID NO: 153, and/or a light chain comprising an amino acid sequence set forth in SEQ ID NO: 157, or a sequence having at least 90%, 95%, 96%, 97%, 98%, or 99% identity to SEQ ID NO: 157.

In one embodiment, an anti-VTCN1 antibody, or antigen binding portion thereof, is the mouse antibody 9F10. The 9F10 antibody comprises a heavy chain variable region comprising a CDR3 domain comprising the amino acid sequence of SEQ ID NO: 164, a CDR2 domain comprising the amino acid sequence of SEQ ID NO: 163, and a CDR1 domain comprising the amino acid sequence of SEQ ID NO: 162, and a light chain variable region comprising a CDR3 domain comprising the amino acid sequence of SEQ ID NO: 168, a CDR2 domain comprising the amino acid sequence of SEQ ID NO: 167, and a CDR1 domain comprising the amino acid sequence of SEQ ID NO: 166. In further embodiments, disclosed herein is an antibody having a heavy chain variable region comprising the amino acid sequence of SEQ ID NO: 161 and a light chain variable region comprising the amino acid sequence of SEQ ID NO: 165.

In some embodiments, an anti-VTCN1 antibody, or antigen-binding portion thereof, comprises a heavy chain comprising an amino acid sequence set forth in SEQ ID NO: 161, or a sequence having at least 90%, 95%, 96%, 97%, 98%, or 99% identity to SEQ ID NO: 161, and/or a light chain comprising an amino acid sequence set forth in SEQ ID NO: 165, or a sequence having at least 90%, 95%, 96%, 97%, 98%, or 99% identity to SEQ ID NO: 165.

In one embodiment, an anti-VTCN1 antibody, or antigen binding portion thereof, is the mouse antibody 9H12. The 9H12 antibody comprises a heavy chain variable region comprising a CDR3 domain comprising the amino acid sequence of SEQ ID NO: 172, a CDR2 domain comprising the amino acid sequence of SEQ ID NO: 171, and a CDR1 domain comprising the amino acid sequence of SEQ ID NO: 170, and a light chain variable region comprising a CDR3 domain comprising the amino acid sequence of SEQ ID NO: 176, a CDR2 domain comprising the amino acid sequence of SEQ ID NO: 175, and a CDR1 domain comprising the amino acid sequence of SEQ ID NO: 174. In further embodiments, disclosed herein is an antibody having a heavy chain variable region comprising the amino acid sequence of SEQ ID NO: 169 and a light chain variable region comprising the amino acid sequence of SEQ ID NO: 173.

In some embodiments, an anti-VTCN1 antibody, or antigen-binding portion thereof, comprises a heavy chain comprising an amino acid sequence set forth in SEQ ID NO: 169, or a sequence having at least 90%, 95%, 96%, 97%, 98%, or 99% identity to SEQ ID NO: 169, and/or a light chain comprising an amino acid sequence set forth in SEQ ID NO: 173, or a sequence having at least 90%, 95%, 96%, 97%, 98%, or 99% identity to SEQ ID NO: 173.

In one embodiment, an anti-VTCN1 antibody, or antigen binding portion thereof, is the mouse antibody 9H7. The 9H7 antibody comprises a heavy chain variable region comprising a CDR3 domain comprising the amino acid sequence of SEQ ID NO: 180, a CDR2 domain comprising the amino acid sequence of SEQ ID NO: 179, and a CDR1 domain comprising the amino acid sequence of SEQ ID NO: 178, and a light chain variable region comprising a CDR3 domain comprising the amino acid sequence of SEQ ID NO: 184, a CDR2 domain comprising the amino acid sequence of SEQ ID NO: 183, and a CDR1 domain comprising the amino acid sequence of SEQ ID NO: 182. In further embodiments, disclosed herein is an antibody having a heavy chain variable region comprising the amino acid sequence of SEQ ID NO: 177 and a light chain variable region comprising the amino acid sequence of SEQ ID NO: 181.

In some embodiments, an anti-VTCN1 antibody, or antigen-binding portion thereof, comprises a heavy chain comprising an amino acid sequence set forth in SEQ ID NO: 177, or a sequence having at least 90%, 95%, 96%, 97%, 98%, or 99% identity to SEQ ID NO: 177, and/or a light chain comprising an amino acid sequence set forth in SEQ ID NO: 181, or a sequence having at least 90%, 95%, 96%, 97%, 98%, or 99% identity to SEQ ID NO: 181.

The foregoing anti-VTCN1 antibody CDR sequences establish a novel family of VTCN1 binding proteins, isolated in accordance with this disclosure, and comprising antigen binding polypeptides that include the CDR sequences listed in Tables 2, 4, 7, and 10 as well as the Sequence Summary and Sequence Listing To generate and to select CDRs having preferred VTCN1 binding and/or neutralizing activity with respect to hVTCN1, standard methods known in the art for generating antibodies, or antigen binding portions thereof, and assessing the VTCN1 binding and/or neutralizing characteristics of those antibodies, or antigen binding portions thereof, may be used, including but not limited to those specifically described herein.

In certain embodiments, the antibody comprises a heavy chain constant region, such as an IgG1, IgG2, IgG3, IgG4, IgA, IgE, IgM, or IgD constant region. In certain embodiments, the anti-VTCN1 antibody, or antigen binding portion thereof, comprises a heavy chain immunoglobulin constant domain selected from the group consisting of a human IgG constant domain, a human IgM constant domain, a human IgE constant domain, and a human IgA constant domain. In further embodiments, the antibody, or antigen binding portion thereof, has an IgG1 heavy chain constant region, an IgG2 heavy chain constant region, an IgG3 constant region, or an IgG4 heavy chain constant region. Preferably, the heavy chain constant region is an IgG1 heavy chain constant region or an IgG4 heavy chain constant region. In one embodiment, the antibody, or antigen binding portion thereof, is an IgG4 isotype.

Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-VTCN1 antibody binding portion is a Fab, a Fab', a F(ab')2, a Fv, a disulfide linked Fv, an scFv, a single domain antibody, or a diabody.

In certain embodiments, the anti-VTCN1 antibody, or antigen binding portion thereof, is a multispecific antibody, e.g. a bispecific antibody.

In certain embodiments, the anti-VTCN1 antibody, or antigen binding portion thereof, comprises a heavy chain variable domain comprising an amino acid sequence set forth in SEQ ID NO: 220 and/or a light chain variable domain comprising an amino acid sequence set forth in SEQ ID NO: 224.

In certain embodiments, the anti-VTCN1 antibody, or antigen binding portion thereof, comprises a heavy chain variable domain comprising an amino acid sequence set forth in SEQ ID NO: 228 and/or a light chain variable domain comprising an amino acid sequence set forth in SEQ ID NO: 224.

In certain embodiments, the anti-VTCN1 antibody, or antigen binding portion thereof, comprises a heavy chain variable domain comprising an amino acid sequence set forth in SEQ ID NO: 232 and/or a light chain variable domain comprising an amino acid sequence set forth in SEQ ID NO: 224.

In certain embodiments, the anti-VTCN1 antibody, or antigen binding portion thereof, comprises a heavy chain variable domain comprising an amino acid sequence set forth in SEQ ID NO: 236 and/or a light chain variable domain comprising an amino acid sequence set forth in SEQ ID NO: 224.

In certain embodiments, the anti-VTCN1 antibody, or antigen binding portion thereof, comprises a heavy chain variable domain comprising an amino acid sequence set forth in SEQ ID NO: 240 and/or a light chain variable domain comprising an amino acid sequence set forth in SEQ ID NO: 244.

In certain embodiments, the anti-VTCN1 antibody, or antigen binding portion thereof, comprises a heavy chain variable domain comprising an amino acid sequence set forth in SEQ ID NO: 248 and/or a light chain variable domain comprising an amino acid sequence set forth in SEQ ID NO: 252.

In certain embodiments, the anti-VTCN1 antibody, or antigen binding portion thereof, comprises a heavy chain variable domain comprising an amino acid sequence set forth in SEQ ID NO: 256 and/or a light chain variable domain comprising an amino acid sequence set forth in SEQ ID NO: 260.

In certain embodiments, the anti-VTCN1 antibody, or antigen binding portion thereof, comprises a heavy chain variable domain comprising an amino acid sequence set forth in SEQ ID NO: 264 and/or a light chain variable domain comprising an amino acid sequence set forth in SEQ ID NO: 268.

In certain embodiments, the anti-VTCN1 antibody, or antigen binding portion thereof, comprises a heavy chain variable domain comprising an amino acid sequence set forth in SEQ ID NO: 272 and/or a light chain variable domain comprising an amino acid sequence set forth in SEQ ID NO: 276.

In certain embodiments, the anti-VTCN1 antibody, or antigen binding portion thereof, comprises a heavy chain variable domain comprising an amino acid sequence set forth in SEQ ID NO: 278 and/or a light chain variable domain comprising an amino acid sequence set forth in SEQ ID NO: 281.

In certain embodiments, the anti-VTCN1 antibody, or antigen binding portion thereof, comprises a heavy chain variable domain comprising an amino acid sequence set forth in SEQ ID NO: 283 and/or a light chain variable domain comprising an amino acid sequence set forth in SEQ ID NO: 286.

In certain embodiments, the anti-VTCN1 antibody, or antigen binding portion thereof, comprises a heavy chain constant region comprising the amino acid sequence set forth in SEQ ID NO: 1 and/or a light chain constant region comprising the amino acid sequence set forth in SEQ ID NO: 5.

In certain embodiments, the anti-VTCN1 antibody, or antigen binding portion thereof, comprises a heavy chain constant region comprising the amino acid sequence set forth in SEQ ID NO: 9 and/or a light chain constant region comprising the amino acid sequence set forth in SEQ ID NO: 13.

In certain embodiments, the anti-VTCN1 antibody, or antigen binding portion thereof, comprises a heavy chain constant region comprising the amino acid sequence set forth in SEQ ID NO: 17 and/or a light chain constant region comprising the amino acid sequence set forth in SEQ ID NO: 21.

In certain embodiments, the anti-VTCN1 antibody, or antigen binding portion thereof, comprises a heavy chain constant region comprising the amino acid sequence set forth in SEQ ID NO: 25 and/or a light chain constant region comprising the amino acid sequence set forth in SEQ ID NO: 29.

In certain embodiments, the anti-VTCN1 antibody, or antigen binding portion thereof, comprises a heavy chain constant region comprising the amino acid sequence set forth in SEQ ID NO: 33 and/or a light chain constant region comprising the amino acid sequence set forth in SEQ ID NO: 37.

In certain embodiments, the anti-VTCN1 antibody, or antigen binding portion thereof, comprises a heavy chain constant region comprising the amino acid sequence set forth in SEQ ID NO: 41 and/or a light chain constant region comprising the amino acid sequence set forth in SEQ ID NO: 45.

In certain embodiments, the anti-VTCN1 antibody, or antigen binding portion thereof, comprises a heavy chain constant region comprising the amino acid sequence set forth in SEQ ID NO: 49 and/or a light chain constant region comprising the amino acid sequence set forth in SEQ ID NO: 53.

In certain embodiments, the anti-VTCN1 antibody, or antigen binding portion thereof, comprises a heavy chain constant region comprising the amino acid sequence set forth in SEQ ID NO: 57 and/or a light chain constant region comprising the amino acid sequence set forth in SEQ ID NO: 61.

In certain embodiments, the anti-VTCN1 antibody, or antigen binding portion thereof, comprises a heavy chain constant region comprising the amino acid sequence set forth in SEQ ID NO: 65 and/or a light chain constant region comprising the amino acid sequence set forth in SEQ ID NO: 69.

In certain embodiments, the anti-VTCN1 antibody, or antigen binding portion thereof, comprises a heavy chain constant region comprising the amino acid sequence set forth in SEQ ID NO: 73 and/or a light chain constant region comprising the amino acid sequence set forth in SEQ ID NO: 77.

In certain embodiments, the anti-VTCN1 antibody, or antigen binding portion thereof, comprises a heavy chain constant region comprising the amino acid sequence set forth in SEQ ID NO: 81 and/or a light chain constant region comprising the amino acid sequence set forth in SEQ ID NO: 85.

In certain embodiments, the anti-VTCN1 antibody, or antigen binding portion thereof, comprises a heavy chain constant region comprising the amino acid sequence set forth in SEQ ID NO: 89 and/or a light chain constant region comprising the amino acid sequence set forth in SEQ ID NO: 93.

In certain embodiments, the anti-VTCN1 antibody, or antigen binding portion thereof, comprises a heavy chain constant region comprising the amino acid sequence set forth in SEQ ID NO: 97 and/or a light chain constant region comprising the amino acid sequence set forth in SEQ ID NO: 101.

In certain embodiments, the anti-VTCN1 antibody, or antigen binding portion thereof, comprises a heavy chain constant region comprising the amino acid sequence set forth in SEQ ID NO: 105 and/or a light chain constant region comprising the amino acid sequence set forth in SEQ ID NO: 109.

In certain embodiments, the anti-VTCN1 antibody, or antigen binding portion thereof, comprises a heavy chain constant region comprising the amino acid sequence set forth in SEQ ID NO: 113 and/or a light chain constant region comprising the amino acid sequence set forth in SEQ ID NO: 117.

In certain embodiments, the anti-VTCN1 antibody, or antigen binding portion thereof, comprises a heavy chain constant region comprising the amino acid sequence set forth in SEQ ID NO: 121 and/or a light chain constant region comprising the amino acid sequence set forth in SEQ ID NO: 125.

In certain embodiments, the anti-VTCN1 antibody, or antigen binding portion thereof, comprises a heavy chain constant region comprising the amino acid sequence set forth in SEQ ID NO: 129 and/or a light chain constant region comprising the amino acid sequence set forth in SEQ ID NO: 133.

In certain embodiments, the anti-VTCN1 antibody, or antigen binding portion thereof, comprises a heavy chain constant region comprising the amino acid sequence set forth in SEQ ID NO: 137 and/or a light chain constant region comprising the amino acid sequence set forth in SEQ ID NO: 141.

In certain embodiments, the anti-VTCN1 antibody, or antigen binding portion thereof, comprises a heavy chain constant region comprising the amino acid sequence set forth in SEQ ID NO: 145 and/or a light chain constant region comprising the amino acid sequence set forth in SEQ ID NO: 149.

In certain embodiments, the anti-VTCN1 antibody, or antigen binding portion thereof, comprises a heavy chain constant region comprising the amino acid sequence set forth in SEQ ID NO: 153 and/or a light chain constant region comprising the amino acid sequence set forth in SEQ ID NO: 157.

In certain embodiments, the anti-VTCN1 antibody, or antigen binding portion thereof, comprises a heavy chain constant region comprising the amino acid sequence set forth in SEQ ID NO: 161 and/or a light chain constant region comprising the amino acid sequence set forth in SEQ ID NO: 165.

In certain embodiments, the anti-VTCN1 antibody, or antigen binding portion thereof, comprises a heavy chain constant region comprising the amino acid sequence set forth in SEQ ID NO: 169 and/or a light chain constant region comprising the amino acid sequence set forth in SEQ ID NO: 173.

In certain embodiments, the anti-VTCN1 antibody, or antigen binding portion thereof, comprises a heavy chain constant region comprising the amino acid sequence set forth in SEQ ID NO: 177 and/or a light chain constant region comprising the amino acid sequence set forth in SEQ ID NO: 181.

In certain embodiments, the anti-VTCN1 antibody, or antigen binding portion thereof, comprises a heavy chain constant region comprising the amino acid sequence set forth in SEQ ID NO: 212 and/or a light chain constant region comprising the amino acid sequence set forth in SEQ ID NO: 216.

Replacements of amino acid residues in the Fc portion to alter antibody effector function are have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment includes a labeled anti-VTCN1 antibody, or antibody portion thereof, where the antibody is derivatized or linked to one or more functional molecule(s) (e.g., another peptide or protein). For example, a labeled antibody can be derived by functionally linking an antibody or antibody portion of the disclosure (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying VTCN1 positive tumors. In a certain embodiment, anti-VTCN1 antibodies (or ADCs) described herein are labeled with $^{111}$I via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the disclosure provides a glycosylated binding protein wherein the anti-VTCN1 antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the disclosure is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the disclosure.

In still another embodiment, the glycosylation of the anti-VTCN1 antibody or antigen binding portion is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-VTCN1 antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/5434280, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies disclosed herein include Chinese Hamster Ovary (CHO cells) (including dhfr– CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the disclosure. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure and the other heavy and light chain are specific for an antigen other than the antigens of interest by cross-linking an antibody of the disclosure to a second antibody by standard chemical crosslinking methods.

In a preferred system for recombinant expression of an antibody, or antigen binding portion thereof, a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the disclosure provides a method of synthesizing a recombinant antibody by culturing a host cell in a suitable culture medium until a recombinant antibody is synthesized. Recombinant antibodies may be produced using nucleic acid molecules corresponding to the amino acid sequences disclosed herein. In one embodiment, the nucleic acid molecules set forth in SEQ ID NOs: 29-36 are used in the production of a recombinant antibody. The method can further comprise isolating the recombinant antibody from the culture medium.

III. Anti-VTCN1 Antibody Drug Conjugates (ADCs)

Anti-VTCN1 antibodies described herein may be conjugated to a drug moiety to form an anti-VTCN1 Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues or cells, e.g., VTCN1 expressing tumors or VTCN1 expressing cells. Thus, in certain embodiments, the disclosure provides anti-VTCN1 ADCs for therapeutic use, e.g., treatment of cancer.

Anti-VTCN1 ADCs comprise an anti-VTCN1 antibody, i.e., an antibody that specifically binds to VTCN1, linked to one or more drug moieties. The specificity of the ADC is defined by the specificity of the antibody, i.e., anti-VTCN1. In one embodiment, an anti-VTCN1 antibody is linked to one or more cytotoxic drug(s) which is delivered internally to a cancer cell expressing VTCN1.

Examples of drugs that may be used in the anti-VTCN1 ADCs are provided below, as are linkers that may be used to conjugate the antibody and the one or more drug(s). The terms "drug," "agent," and "drug moiety" are used interchangeably herein. The terms "linked" and "conjugated" are also used interchangeably herein and indicate that the antibody and moiety are covalently linked.

In some embodiments, the ADC has the following formula (formula I):

$$Ab\text{-}(L\text{-}D)_n \quad (I)$$

wherein Ab an anti-VTCN1 antibody described herein, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing VTCN1; and n is an integer from 1 to 20. In some embodiments, n ranges from 1 to 8, 1 to 7, 1 to 6, 1 to 5, 1 to 4, 1 to 3, 1 to 2, or is 1. The DAR of an ADC is equivalent to the "n" referred to in Formula I.

Additional details regarding drugs (D of Formula I) and linkers (L of Formula I) that may be used in the ADCs, as well as alternative ADC structures, are described below.

A. Anti-VTCN1 ADCs: Exemplary Drugs for Conjugation

Anti-VTCN1 antibodies may be used in ADCs to target one or more drug(s) to a cell of interest, e.g., a cell expressing VTCN1. The anti-VTCN1 ADCs disclosed herein provide a targeted therapy that may, for example, reduce the side effects often seen with anti-cancer therapies, as the one or more drug(s) is delivered to a specific cell. In one embodiment, the drug used in an ADC is saporin. In another embodiment, the drug used in an ADC is dacarbazine. In another embodiment, the drug used in an ADC is carboplatin.

Examples of drugs that may be used in ADCs, i.e., drugs that may be conjugated to the anti-VTCN1 antibodies, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Mitotic Inhibitors

In one aspect, anti-VTCN1 antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by effecting microtubule polymerization (e.g., inhibiting microtubule polymerization) or microtubule depolymerization (e.g., stabilizing the microtubule cytoskeleton against depolymrization). Thus, in one embodiment, an anti-VTCN1 antibody of the invention is conjugated to one or more mitotic inhibitor(s) that disrupts microtubule formation by inhibiting tubulin polymerization. In another embodiment, an anti-VTCN1 antibody of the invention is conjugated to one or more mitotic inhibitor(s) that stabilizes the microtubule cytoskeleton from deploymerization. In one embodiment, the mitotic inhibitor used in the ADCs of the invention is Ixempra (ixabepilone). Examples of mitotic inhibitors that may be used in the anti-VTCN1 ADCs of the invention are provided below. Included in the genus of mitotic inhibitors are auristatins, described below.

a. Dolastatins

The anti-VTCN1 antibodies of the invention may be conjugated to at least one dolastatin to form an ADC. Dolastatins are short peptidic compounds isolated from the Indian Ocean sea hare *Dolabella auricularia* (see Pettit et al., J. Am. Chem. Soc., 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-VTCN1 ADC of the invention comprises an anti-VTCN1 antibody, as described herein, and at least one dolastatin. Auristatins are synthetic derivatives of dolastatin 10.

b. Auristatins

Anti-VTCN1 antibodies may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239, 104; 6,034,065; 5,780,588; 5,665,860; 5,663,149; 5,635, 483; 5,599,902; 5,554,725; 5,530,097; 5,521,284; 5,504, 191; 5,410,024; 5,138,036; 5,076,973; 4,986,988; 4,978, 744; 4,879,278; 4,816,444; and 4,486,414, each of which is incorporated by reference herein.

In one embodiment, anti-VTCN1 antibodies are conjugated to at least one MMAE (monomethyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-VTCN1 antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent antimitotic mechanism.

The structure of MMAE is provided below.

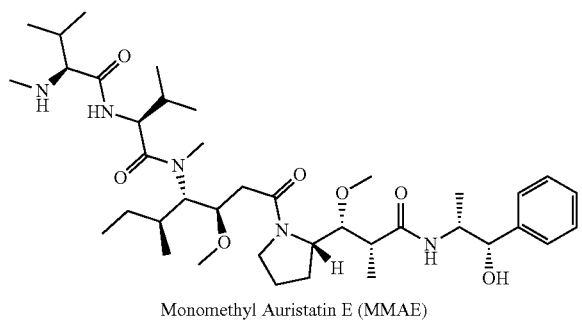 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

Monomethyl Auristatin E (MMAE)

In one embodiment, the antibody is coupled to a single drug and, therefore, has a DAR of 1. In certain embodiments, the ADC will have a DAR of 2 to 8, or, alternatively, 2 to 4.

c. Maytansinoids

The anti-VTCN1 antibodies of the invention may be conjugated to at least one maytansinoid to form an ADC. Maytansinoids are potent antitumor agents that were originally isolated from members of the higher plant families Celastraceae, Rhamnaceae, and Euphorbiaceae, as well as some species of mosses (Kupchan et al, J. Am. Chem. Soc. 94:1354-1356 [1972]; Wani et al, J. Chem. Soc. Chem. Commun. 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441, 163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate, and is described in more detail in the linker section below. The structure of an exemplary maytansinoid, mertansine (DM1), is provided below.

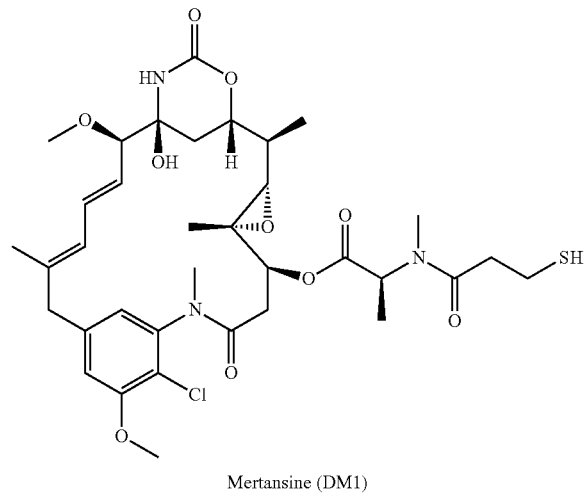

Mertansine (DM1)

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) *Cancer Res* 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine), and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

In one embodiment of the invention, an anti-VTCN1 antibody is conjugated to at least one DM1. In one embodiment, an anti-VTCN1 antibody is conjugated to at least one DM2. In one embodiment, an anti-VTCN1 antibody is conjugated to at least one DM3. In one embodiment, an anti-VTCN1 antibody is conjugated to at least one DM4.

2. Antitumor Antibiotics

Anti-VTCN1 antibodies may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-VTCN1 ADCs include, but are not limited to, actinomycines (e.g., pyrrolo[2,1-c][1,4]benzodiazepines), anthracyclines, calicheamicins, and duocarmycins. In addition to the foregoing, additional antitumor antibiotics that may be used in the anti-VTCN1 ADCs include bleomycin (Blenoxane, Bristol-Myers Squibb), mitomycin, and plicamycin (also known as mithramycin).

3. Immunomodulating Agents

In one aspect, anti-VTCN1 antibodies may be conjugated to at least one immunomodulating agent. As used herein, the term "immunomodulating agent" refers to an agent that can stimulate or modify an immune response. In one embodiment, an immunomodulating agent is an immunostimuator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, bacillus calmette-guerin (BCG) and levamisole (Ergamisol). Other examples of immunomodulating agents that may be used in the ADCs include, but are not limited to, cancer vaccines, and cytokines.

As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant disclosure, administering an ADC comprising an anti-VTCN1 antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-VTCN1 ADCs include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in one embodiment, the anti-VTCN1 antibody is conjugated to at least one cancer vaccine that is either an immunostimulator or is an immunosuppressant.

The anti-VTCN1 antibodies may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) *Cancers* 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the disclosure provides an ADC comprising an anti-VTCN1 antibody described herein and a cytokine.

The anti-VTCN1 antibodies may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-VTCN1 ADCs include, but are not limited to erythropoietin (Epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, an ADC may comprise an anti-VTCN1 antibody described herein and a CSF.

4. DNA Damaging Agents

In one embodiment, the antibodies and antigen-binding portions thereof described herein may be conjugated to one or more DNA damaging agents. The term "DNA damaging agent", as used herein, refers to an agent which is capable of damaging DNA and are well known to those of ordinary skill in the art (see, for example, Cheung-Ong et al., *Cell Chemical Biology*, 20(5): 648-659, 2013).

DNA damaging agents include DNA alkylating agents. DNA alkylating agents are a class of antineoplastic compounds that attaches an alkyl group ($C_nH_{2n+1}$) to DNA at a guanine base of DNA. Examples of DNA alkylating agents that may be used in the ADCs include, but are not limited to, alkyl sulfonates (e.g., busulfan), ethylenimimes (e.g., altretamine and thiotepa), methylamine derivatives, epoxides, nitrogen mustards (e.g., bendamustine, chlorambucil, cyclophosphamide, ifosfamide, mechlorethamine, melphalan), nitrosoureas (e.g., carmustine, lomustine, and streptozocin), triazines (e.g., dacarbazine and temozolomide), and hydrazines.

DNA damaging agents also include indolino-benzodiazepines (IGNs). IGNs represent a chemical class of cytotoxic molecules with high in vitro potency ($IC_{50}$ values in the low pmol/L range) toward cancer cells. Examples of IGN DNA alkylating agents that can be used as a cytotoxic payload in an ADC are described in Miller et al. (2016) *Molecular Cancer Therapeutics*, 15(8)). The IGN compounds described in Miller et al. bind to the minor groove of DNA followed by covalent reaction of guanine residues with the two imine functionalities in the molecule resulting in cross-linking of DNA. The structure of an exemplary IGN is provided below.

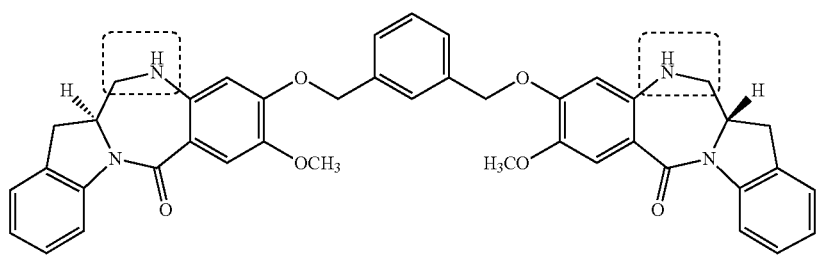

2

In one embodiment, a DNA damaging agent may also include a pyrrolobenzodiazepine (PBD) or pyridinobenzodiazepine (PDD) (see, e.g., N. Veillard et al. "Pyridinobenzodiazepines (PDDs): A new class of sequence-selective DNA mono-alkylating ADC payloads with low hydrophobicity" [abstract]. In: Proceedings of the 109th Annual Meeting of the American Association for Cancer Research; 2018 Apr. 14-18; Chicago, Illinois. Philadelphia (Pa.): AACR; 2018. Abstract no 736/3). In another embodiment, the DNA damaging agent is a PARP inhibitor, e.g., olaparib, rucaparib, niraparib, or iniparib. In one embodiment, the PARP inhibitor is olaparib. In one embodiment, the PARP inhibitor is rucaparib. In one embodiment, the PARP inhibitor is niraparib. In one embodiment, the PARP inhibitor is iniparib. In one embodiment, the agent is a saporin toxin.

5. Antiangiogenic Agents

In one aspect, the anti-VTCN1 antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

6. Antimetabolites

The anti-VTCN1 antibodies may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolies that may be used in the ADCs include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

7. Boron-Containing Agents

The anti-VTCN1 antibody may be conjugated to at least one boron containing agent. Boron-containing agents comprise a class of cancer therapeutic compounds which interfere with cell proliferation. Representative examples of boron containing agents include, but are not limited, to borophycin and bortezomib (Velcade, Millenium Pharmaceuticals).

8. Chemoprotective Agents

The anti-VTCN1 antibodies may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

9. Photoactive Therapeutic Agents

The anti-VTCN1 antibodies may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

10. Radionuclide Agents (Radioactive Isotopes)

The anti-VTCN1 antibodies may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{11}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rb, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

11. Radiosensitizers

The anti-VTCN1 antibodies may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin®, benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

12. Topoisomerase Inhibitors

The anti-VTCN1 antibodies may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

13. Tyrosine Kinase Inhibitors

The anti-VTCN1 antibodies may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

14. Other Agents

Examples of other agents that may be used in the ADCs include, but are not limited to, abrin (e.g. abrin A chain), alpha toxin, *Aleurites fordii* proteins, amatoxin, crotin, curcin, dianthin proteins, diptheria toxin (e.g., diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the anti-VTCN1 ADCs are not exclusive, in that certain examples of drugs may be found in more than one category, e.g., ansamitocins are both mitotic inhibitors and antitumor antibiotics.

All stereoisomers of the above drug moieties are contemplated for use herein, i.e. any combination of R and S configurations at the chiral carbons of D.

The above agents (i.e., naked agents not conjugated to an antibody) may also be used in combination therapies with the anti-VTCN1 antibodies described herein. In one embodiment, anti-VTCN1 antibodies or ADCs are used with any of the foregoing agents in a combination therapy to treat cancer, where the agent is administered prior to, at the same time as, or following administration of the anti-VTCN1 antibody or ADC to the subject.

B. Anti-VTCN1 ADCs: Exemplary Linkers

An anti-VTCN1 ADC comprises an anti-VTCN1 antibody and at least one drug(s), whereby the antibody and the at least one drug are conjugated by a linker. The term "linker," as used herein, refers to a chemical moiety that may be bifunctional or multifunctional, and is used to attach an antibody to a drug moiety. A linker may include one conjugating component or may include multiple components.

For example, the linker may include a spacer, which is a moiety that extends the drug linkage to avoid, for example, shielding the active site of the antibody or improving the solubility of the ADC. Other examples of components of linkers include a stretcher unit and an amino acid unit.

Two methods are commonly used for conjugating drugs to antibodies: alkylation of reduced interchain cysteine disulfides through an enzymatically non-cleavable maleimido or simple and cleavable disulfide linker, and acylation of lysines by cleavable linear amino acids.

In one aspect, a linker covalently attaches an antibody to a drug moiety. An ADC is prepared using a linker having reactive functionality for binding to the antibody and the drug. For example, a cysteine thiol, or an amine, e.g., N-terminus or amino acid side chain such as lysine, of the antibody may form a bond with a functional group of the linker.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

Suitable linkers include, for example, cleavable and non-cleavable linkers. A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker.

Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, Pharm. Therapeutics 83:67-123; Neville et al., 1989, Biol. Chem. 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in VTCN1-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-VTCN1 ADCs described herein is a non-cleavable linker that promotes cellular internalization.

In some embodiments, the ADC has the following formula (formula I):

Ab-(L-D)$_n$ (I)

or a pharmaceutically acceptable salt or solvate thereof; wherein Ab is the antibody, e.g., anti-VTCN1 antibody, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing VTCN1; and n is an integer from 1 to 20.

In some embodiments, n ranges from 1 to 8, 1 to 7, 1 to 6, 1 to 5, 1 to 4, 1 to 3, 1 to 2, or is 1.

In some embodiments, the –D moieties are the same. In yet another embodiment, the –D moieties are different.

In some embodiments, a linker component comprises an "amino acid unit." In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In one embodiment, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

Another approach for the generation of ADCs involves the use of heterobifunctional cross-linkers which link the anti-VTCN1 antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio) butyrate (SPDB), N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio) butyrate (SCPB) or N-sulfosuccinimidyl4-(5-N,N-dimethylcarboxamido-2-pyridyldithio) butyrate (SSCPB)). The antibodies may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC (see also U.S. Pat. No. 6,913,748, incorporated by reference herein).

In one embodiment, charged linkers (also referred to as pro-charged linkers) are used to conjugate anti-VTCN1 antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers that may be used include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly(lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfosuccinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the disclosure.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-VTCN1 antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

IV. Uses of Anti-VTCN1 Antibodies and Anti-VTCN1 ADCs

The antibodies and antibody portions (and ADCs) preferably are capable of neutralizing human VTCN1 activity both in vivo and in vitro. Accordingly, such antibodies and antibody portions can be used to inhibit hVTCN1 activity, e.g., in a cell culture containing hVTCN1, in human subjects or in other mammalian subjects having VTCN1 with which an antibody disclosed herein cross-reacts. In one embodiment, the disclosure provides a method for inhibiting hVTCN1 activity comprising contacting hVTCN1 with an antibody or antibody portion such that hVTCN1 activity is inhibited. For example, in a cell culture containing, or suspected of containing hVTCN1, an antibody or antibody portion can be added to the culture medium to inhibit hVTCN1 activity in the culture.

In another embodiment, disclosed herein is a method for reducing hVTCN1 activity in a subject, advantageously from a subject suffering from a VTCN1 associated disorder, e.g., cancer such as TNBC, or a disorder in which VTCN1 activity is detrimental. The disclosure provides methods for reducing VTCN1 activity in a subject suffering from such a disease or disorder, which method comprises administering to the subject an antibody or antibody portion of the disclosure such that VTCN1 activity in the subject is reduced. Surprisingly, the instant disclosure provides antibodies, antigen-binding portions thereof, and ADCs which are capable of not only inhibiting tumor metastasis, but also reducing primary tumor size and/or inhibiting primary tumor growth. Preferably, the VTCN1 is human VTCN1, and the subject is a human subject. Alternatively, the subject can be a mammal expressing a VTCN1 to which antibodies of the disclosure are capable of binding. Still further the subject can be a mammal into which VTCN1 has been introduced (e.g., by administration of VTCN1 or by expression of a VTCN1 transgene). Antibodies of the disclosure can be administered to a human subject for therapeutic purposes. Moreover, antibodies of the disclosure can be administered to a non-human mammal expressing a VTCN1 with which the antibody is capable of binding for veterinary purposes or as an animal model of human disease. Regarding the latter, such animal models may be useful for evaluating the therapeutic efficacy of antibodies and ADCs of the disclosure (e.g., testing of efficacy, dosages and time courses of administration). Examples of animal models useful for evaluating the therapeutic efficacy of the anti-VTNC1 antibodies and ADCs of the invention include, for example, syngeneic mouse tumor models expressing VTCN1, such as the KLN205 mouse tumor model or the Hepa 1-6 mouse tumor model, or the ID-8 ovarian tumor model. Syngeneic mouse models consist of tumor tissues from the same genetic background as the given immuno-competent mouse strain. The identification of natural tumor models expressing VTCN1 enables the evaluation of anti-VTCN1 antibodies in a model where carcinoma or sarcoma tumors are influenced by extracellular matrix components, immune effectors, vasculature and cytokines in a more "natural" state that mimics the human tumor setting (see, e.g., Example 12).

As used herein, the term "a disorder in which VTCN1 activity is detrimental" is intended to include diseases and other disorders in which the presence of VTCN1 in a subject suffering from the disorder has been shown to be or is suspected of being either responsible for the pathophysiology of the disorder or a factor that contributes to a worsening of the disorder. Accordingly, a disorder in which VTCN1 activity is detrimental is a disorder in which reduction of VTCN1 activity is expected to alleviate the symptoms and/or progression of the disorder. Such disorders may be evidenced, for example, by an increase in the concentration of VTCN1 in a biological cell, fluid or tissue of a subject suffering from the disorder (e.g., an increase in the concentration of VTCN1 in a tumor, serum, plasma, synovial fluid, etc. of the subject), which can be detected, for example, using an anti-VTCN1 antibody as described above.

Non-limiting examples of disorders that can be treated with the antibodies, or antigen binding fragments thereof, include those disorders discussed below. For example, suitable disorders include, but are not limited to, a variety of cancers including, but not limited to, breast cancer (e.g., triple negative breast cancer (TNBC)), renal cancer, ovarian cancer, gastric cancer, prostate cancer, uterine cancer, endometrial cancer, pancreatic cancer, liver cancer, colorectal cancer and non small cell lung cancer (NSCLC).

Other examples of cancers that may be treated using the compositions and methods disclosed herein include, but are not limited to carcinoma, lymphoma, blastoma, sarcoma, and leukemia or lymphoid malignancies. More particular examples of such cancers include but are not limited to breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. PVNS, acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, an anti-VTCN1 ADC of the present invention can be used to treat a cancer in a subject including, but not limited to Hodgkin's lymphoma, PVNS, acute myeloid leukemia, adrenocortico carcinoma, ladder urothelial carcinoma, breast cancer (Luminal A, TNBC, Ductal), cervical squamous cell carcinoma, endocervical adenocarcinoma, colorectal adenocarcinoma, diffuse large B cell lymphoma, non-hodgkin's lymphoma, glioblastoma multiforme, chronic lymphocytic leukemia, brain lower grade glioma, head and neck squamous cell carcinoma, hepatocellular carcinoma, lung adenocarcinoma, small cell lung cancer, large squamous cell carcinoma, cutaneous melanoma, ovarial serous cystadenocarcinoma, gastric cancer, soft tissue sarcoma, mesothelioma, pancreatic adenocarcinoma, testicular germ cell cancer, thymoma, thyroid carcinoma, uterine corpus endometrial carcinoma, uterine carcinosarcoma. kidney renal clear cell carcinoma, and kidney renal papillary cell carcinoma.

In one embodiment, the antibodies and ADCs disclosed herein are used to treat a solid tumor, e.g., inhibit growth of or decrease size of a solid tumor, e.g., a primary tumor, overexpressing VTCN1 or which is VTCN1 positive. In one embodiment, the antibodies and ADCs disclosed herein are used to treat breast cancer (e.g., triple negative breast cancer (TNBC)). Diseases and disorders described herein may be treated by anti-VTCN1 antibodies or ADCs, as well as pharmaceutical compositions comprising such anti-VTCN1 antibodies or ADCs.

In certain embodiments, the antibodies and ADCs disclosed herein are administered to a subject in need thereof in order to treat advanced solid tumor types likely to exhibit elevated levels of VTCN1.

In certain embodiments, the disclosure includes a method for inhibiting or decreasing solid tumor growth in a subject having a solid tumor, said method comprising administering an anti-VTCN1 antibody or ADC described herein, to the subject having the solid tumor, such that the solid tumor growth is inhibited or decreased. In certain embodiments, the solid tumor is a triple negative breast cancer (TNBC) tumor. In further embodiments, the solid tumor is a VTCN1 expressing solid tumor. In further embodiments, the solid tumor is a primary tumor. In certain embodiments the anti-VTCN1 antibodies or ADCs described herein are administered to a subject having triple negative breast cancer (TNBC), alone or in combination with an additional agent, e.g., radiation and/or chemotherapy, or an immune checkpoint inhibitor.

In certain embodiments, the disclosure includes a method for inhibiting or decreasing solid tumor growth in a subject having a solid tumor which was identified as a VTCN1 expressing or VTCN1 positive tumor, said method comprising administering an anti-VTCN1 antibody or ADC described herein, to the subject having the solid tumor, such that the solid tumor growth is inhibited or decreased. In further embodiments, the solid tumor is a primary tumor.

In certain embodiments, the disclosure includes a method for inhibiting or decreasing solid tumor growth in a subject having a solid tumor which was identified as not expressing VTCN1 or VTCN1 negative tumor, said method comprising administering an anti-VTCN1 antibody or ADC described herein, to the subject having the solid tumor, such that the solid tumor growth is inhibited or decreased. In further embodiments, the solid tumor is a primary tumor.

Methods for identifying VTCN1 expressing tumors are known in the art, and include FDA-approved tests and validation assays. For example, these assays may use primers that are specific for the VTCN1 gene and/or cDNA and result in the amplification of the VTCN1 gene/cDNA, or a portion thereof. The amplified PCR products may be subsequently analyzed, for example, by gel electrophoresis using standard methods known in the art to determine the size of the PCR products. Such tests may be used to identify tumors that may be treated with the methods and compositions described herein.

In another aspect, this application features a method of treating (e.g., curing, suppressing, ameliorating, delaying or preventing the onset of, or preventing recurrence or relapse of) or preventing a VTCN1-associated disorder, in a subject. The method includes: administering to the subject a VTCN1 binding agent (particularly an antagonist), e.g., an anti-VTCN1 antibody or fragment thereof as described herein, in an amount sufficient to treat or prevent the VTCN1-associated disorder. The VTCN1 antagonist, e.g., the anti-VTCN1 antibody or fragment thereof, can be administered to the subject, alone or in combination with other therapeutic modalities as described herein.

In some embodiments, the anti-VTCN1 antibody or fragment thereof used in the methods of the invention is a human or humanized anti-VTCN1 antibody or fragment thereof.

In another embodiment, antibody-dependent cell-mediated cytotoxicity (ADCC) activity is not necessary for anti-VTCN1 antibodies to inhibit tumor growth or reduce tumor size. Accordingly, in one embodiment, an antibody, or antigen binding portion thereof, of the invention comprises an isotype lacking effector function (e.g., human IgG4).

Antibodies or ADCs, or antigen binding portions thereof, can be used alone or in combination to treat such diseases. It should be understood that the antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody. The additional agent also can be an agent that imparts a beneficial attribute to the therapeutic composition, e.g., an agent which affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the disclosure and at least one additional agent selected from the lists below. The combination can also include more than one additional agent, e.g., two or three additional agents if the combination is such that the formed composition can perform its intended function.

The combination therapy can include one or more VTCN1 antagonists, e.g., anti-VTCN1 antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In a particular embodiment, the anti-VTCN1 antibodies disclosed herein are used in combination with an anti-cancer agent or an antineoplastic agent. The terms "anti-cancer agent" and "antineoplastic agent" refer to drugs used to treat malignancies, such as cancerous growths. In one embodiment, the anti-VTCN1 antibodies or ADCs of the invention are administered in combination with one or more immune checkpoint inhibitors (ICI) (e.g., antibody or small molecule immune checkpoint inhibitors) for the treatment of a cancer. In some embodiments, the immune checkpoint inhibitor is an inhibitor (e.g., an antibody) of Programmed Death-Ligand 1 (PD-L1, also known as B7-H1, CD274), Programmed Death 1 (PD-1), CTLA-4, PD-L2 (B7-DC, CD273), LAG3, TIM3, 2B4, 4-1BB, A2aR, B7H1, B7H3, BTLA, CD2, CD6, CD27, CD28, CD30, CD38, CD39, CD40, CD47, CD70, CD73, CD80, CD86, CD137, CD160, CD166, CD200, CD200R1, CD226, CD276, DR3, GAL9, GITR, HAVCR2, HVEM, IDO1, IDO2, ICOS (inducible T cell costimulator), KIR, LAG3, LAIR1, TREM2, LILRB1, LILRB2, LILRB3, LILRB4, LIGHT, MARCO (macrophage receptor with collageneous structure), PS (phosphatidylserine), OX-40, SLAM, SIRPA, CSF1R, CD47, SIRPA, TIGHT, TGFβ, VISTA, or any combinations thereof.

In some embodiments, the immune checkpoint inhibitor is an anti-CTLA-4, PD-L1, or PD-1 antibody therapy such as, but not limited to Yervoy® (ipilimumab; Bristol-Myers Squibb), Opdivo® (nivolumab; Bristol-Myers Squibb), Keytruda® (pembrolizumab; Merck), and Tecentriq® (atezolizumab; Roche).

In other embodiments, the immune checkpoint inhibitor is an anti-CD38 antibody therapy such as isatuximab (Sanofi), Darzalex® (daratumumab; Genmab A/S and Janssen Biotech), MOR202 (MorphoSys AG), and Tusk Therapeutics Ltd.'s anti-CD38 monoclonal antibody.

In some embodiments, the checkpoint inhibitor is an antibody or small molecule currently undergoing clinical testing, including, for example, an antibody against IDO (Epacadostat and Indoximod and BMS-986205), 4-1BB/CD137 (Utomilumab and Urelumab), KIR (Lirilulmab), CD40 (CP-870,893), CD27 (Varlilumab), LAG-3 (Relatilimab), MHCII (Eftilagimod Alpha).

In one embodiment, the anti-VTCN1 antibodies or ADCs of the invention are administered in combination with one checkpoint inhibitor, e.g., an anti-CTLA-4, CD38, PD-L1, or PD-1 antibody. In other embodiments, the anti-VTCN1 antibodies or ADCs of the invention are administered in combination with more than one checkpoint inhibitor, e.g., an anti-VTCN1 antibody or ADC of the invention in combination with an anti-CD38 antibody and an anti-PD-L1 antibody, or an anti-VTCN1 antibody or ADC of the invention in combination with an anti-CD38 antibody and an anti-PD-1 antibody.

Drug therapy may be used alone, or in combination with other treatments such as chemotherapy, surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone.

Provided herein are methods for treating cancer, e.g., breast cancer (e.g., triple negative breast cancer (TNBC)), renal cancer, ovarian cancer, gastric cancer, prostate cancer, uterine cancer, endometrial cancer, pancreatic cancer, liver cancer, colorectal cancer and non small cell lung cancer (NSCLC), or a disorder in which VTCN1 activity is detrimental, in a patient comprising administering to the patient an anti-VTCN1 antibody, or fragment thereof, or an ADC of the invention wherein the combination therapy exhibits synergy, e.g., therapeutic synergy, in the subject. As used herein, "synergy" or "therapeutic synergy" refers to a phenomenon where treatment of patients with a combination of therapeutic agents manifests a therapeutically superior outcome to the outcome achieved by each individual constituent of the combination used at its optimum dose (Corbett, T. H. et al., Cancer Treatment Reports, 66:1187 (1982)). For example, a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components.

In particular embodiments, the anti-VTCN1 antibodies or ADCs can be administered alone or with another anti-cancer agent which acts in conjunction with or synergistically with the antibody to treat the disease associated with VTCN1 activity. Such anti-cancer agents include, for example, one or more agents well known in the art (e.g., cytotoxins, chemotherapeutic agents, such as gemcitabine, carboplatin, and 5-Fu, small molecules and radiation) or one or more immune checkpoint inhibitor as set forth above. In one embodiment, the one or more chemotherapeutic agent is pemetrexed (Alimta) and/or platinum chemotherapy, e.g., cisplatin or carboplatin (see e.g., Gandhi et al. *New England Journal of Medicine* DOI: 10.1056/NEJMoa1801005, Apr. 16, 2018).

Other examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Examples of anti-cancer agents that can be administered in combination with an anti-VTCN1 antibody or ADC of the invention include any one or more of those agents described above in Section III (A) of this disclosure.

In one embodiment, the anti-VTCN1 antibodies or ADCs of the invention are administered in combination with one or more compound which is capable of decreasing T regulatory cells and/or increasing effector T cell:T regulatory cell ratio in a subject (see, e.g., Eriksson et al. (2016) *Journal of Translational Medicine* 14:282). In one embodiment, the compound is, for example, gemcitabine.

In another embodiment, the anti-VTCN1 antibodies or ADCs can be administered in combination with an anti-cancer agent that regulates the tumor micro-environment, including inhibiting the activity or population of MDSCs and macrophages, such as, for example, CSF-1R antibodies, all-trans retinoic acid, gemcitabine, COX2 inhibitor (SC58236), amino-biphosphonate, phosphodiesterase-5 inhibitor (sildenafil and tadalafil), KIT-specific antibody, nitroaspirin, titerpenoid, 25-hydroxyvitamin D3, VEGF-trap, VEGF-specific antibody (e.g., Avastin), doxorubicin-cyclophosphamide, antagonists for CXCR2 (e.g., S-265610) and CXCR4 (e.g., AMD3100), tyrosine kinase inhibitor (e.g., Sunitinib), and PROK2-specific antibody (see V. Bronte and D. Gabrilovich, Myeloid derived suppressor cells, *Nature Rev. Immunology* poster, available through www.Biolegend.com).

In another embodiment, the anti-VTCN1 antibodies or ADCs can be administered in combination with anti-cancer agents that modulate tumor agiogenesis such as, but not limited to angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

In some embodiments, the antibody or antigen binding portion thereof or the ADC is administered in combination with IL-6 and/or interferon-gamma (IFN-γ). For example, IL-6 and/or IFN-γ may be administered prior to the antibody or antigen binding portion thereof or the ADC. In one embodiment, administration of IL-6 and/or interferon-gamma (IFN-γ) increases expression of VTCN1 in the subject (see Example 8).

In another embodiment, the antibody or antigen binding portion thereof or the ADC is administered in combination with a DNA alkylator (e.g., cisplatin) and/or a PARP inhibitor.

Other anti-cancer agents include, but are not limited to, those disclosed in U.S. Pat. No. 7,598,028 and International Publication No. WO2008/100624, the contents of which are hereby incorporated by reference.

One or more anti-cancer agents may be administered either simultaneously or before or after administration of an antibody or antigen binding portion thereof.

In particular embodiments of the invention, the anti-VTCN1 antibodies or ADCs described herein can be used in a combination therapy with an inhibitor of NAMPT (see examples of inhibitors in US 2013/0303509; AbbVie, Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment, anti-VTCN1 antibodies and ADCs described herein are administered in combination with a NAMPT inhibitor for the treatment of cancer in a subject.

In particular embodiments, the anti-VTCN1 antibodies or ADCs described herein can be used in a combination therapy with SN-38, which is the active metabolite of the topoisomerase inhibitor irinotecan.

In particular embodiments, the anti-VTCN1 antibodies or ADCs described herein can be used in a combination therapy with the anti-cancer agent gemcitabine or other anti-cancer agents inhibiting myeloid derived suppressor cell activities.

The pharmaceutical compositions may include a "therapeutically effective amount" or a "prophylactically effective amount" of an antibody or antibody portion. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another aspect, this application provides a method for detecting the presence of VTCN1 in a sample in vitro (e.g., a biological sample, such as serum, plasma, tissue, biopsy). The subject method can be used to diagnose a disorder, e.g., a cancer. The method includes: (i) contacting the sample or a control sample with the anti-VTCN1 antibody or fragment thereof as described herein; and (ii) detecting formation of a complex between the anti-VTCN1 antibody or fragment thereof, and the sample or the control sample, wherein a statistically significant change in the formation of the complex in the sample relative to the control sample is indicative of the presence of VTCN1 in the sample.

Given their ability to bind to human VTCN1, the anti-human VTCN1 antibodies, or portions thereof, (as well as ADCs thereof) can be used to detect human VTCN1 (e.g., in a biological sample, such as serum or plasma), using a conventional immunoassay, such as an enzyme linked immunosorbent assays (ELISA), an radioimmunoassay (RIA) or tissue immunohistochemistry. In one aspect, the disclosure provides a method for detecting human VTCN1 in a biological sample comprising contacting a biological sample with an antibody, or antibody portion, and detecting either the antibody (or antibody portion) bound to human VTCN1 or unbound antibody (or antibody portion), to thereby detect human VTCN1 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

Alternative to labeling the antibody, human VTCN1 can be assayed in biological fluids by a competition immunoassay utilizing rhVTCN1 standards labeled with a detectable substance and an unlabeled anti-human VTCN1 antibody. In this assay, the biological sample, the labeled rhVTCN1 standards and the anti-human VTCN1 antibody are combined and the amount of labeled rhVTCN1 standard bound to the unlabeled antibody is determined. The amount of human VTCN1 in the biological sample is inversely proportional to the amount of labeled rhVTCN1 standard bound to the anti-VTCN1 antibody. Similarly, human VTCN1 can also be assayed in biological fluids by a competition immunoassay utilizing rhVTCN1 standards labeled with a detectable substance and an unlabeled anti-human VTCN1 antibody.

In yet another aspect, this application provides a method for detecting the presence of VTCN1 in vivo (e.g., in vivo imaging in a subject). The subject method can be used to diagnose a disorder, e.g., a VTCN1-associated disorder. The method includes: (i) administering the anti-VTCN1 antibody or fragment thereof as described herein to a subject or a control subject under conditions that allow binding of the antibody or fragment to VTCN1; and (ii) detecting formation of a complex between the antibody or fragment and VTCN1, wherein a statistically significant change in the formation of the complex in the subject relative to the control subject is indicative of the presence of VTCN1.

V. Pharmaceutical Compositions

The disclosure also provides pharmaceutical compositions comprising an antibody, or antigen binding portion thereof, or ADC and a pharmaceutically acceptable carrier. The pharmaceutical compositions comprising antibodies or ADCs are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies. In another embodiment, the pharmaceutical composition comprises one or more antibodies or ADCs and one or more prophylactic or therapeutic agents other than antibodies or ADCs for treating a disorder in which VTCN1 activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions or ADCs can be incorporated into pharmaceutical compositions suitable for administration to a subject. Typically, the pharmaceutical composition comprises an antibody or antibody portion and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

Various delivery systems are known and can be used to administer one or more antibodies or ADCs or the combination of one or more antibodies and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290, 540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody, combination therapy, or a composition is administered using Alkermes AIR® pulmonary drug delivery technology (Alkermes, Inc., Cambridge, Mass.). In a specific embodiment, prophylactic or therapeutic agents are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies antagonists is administered locally to the affected area to a subject to prevent, treat, manage, and/or ameliorate a disorder or a symptom thereof. In another embodiment, an effective amount of one or more antibodies is administered locally to the affected area in combination with an effective amount of one or more therapies (e.g., one or more prophylactic or therapeutic agents) other than an antibody of a subject to prevent, treat, manage, and/or ameliorate a disorder or one or more symptoms thereof.

A pharmaceutical composition is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the disclosure comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions is packaged in a hermetically sealed container such as an ampoule or sachette indicating the quantity of the agent. In one embodiment, one or more of the prophylactic or therapeutic agents, or pharmaceutical compositions is supplied as a dry sterilized lyophilized powder or water free concentrate in a hermetically sealed container and can be reconstituted (e.g., with water or saline) to the appropriate concentration for administration to a subject. The antibodies and antibody-portions or ADCs can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

Example 1: Analysis of VTCN1 Expression in Human Tumor Samples

Primary human tumor specimens were interrogated by proteomics and immunohistochemistry for VTCN1 expression. For proteomic detection, frozen tumor tissues were homogenized in urea lysis buffer to make protein lysate. The lysate was digested with trypsin, and peptides were subjected to analysis with mass spectrometry. Peptides from different samples were labeled with multiple tandem mass tags (TMT, Thermo Fisher Scientific) for quantitative comparison of the protein expression from different samples.

Immunohistochemical (IHC) analysis of VTCN1 expression was also performed on the same samples as well as specimens representative of additional tumors types. Tumor sample paraffin blocks were sectioned and mounted on microscope slides. The slides were stained with antibodies against VTCN1 (Cell Signaling Technology, Danvers, MA), using a standard IHC procedure. Briefly, paraffin embedded tissues were mounted on slides and paraffin was removed by incubating with xylene, 100% ethanol and 95% ethanol, followed by rehydration with deionized water. Antigen unmasking was achieved by heating slides in a microwave submersed in 1× citrate unmasking solution until boiling was initiated, followed by cooling at room temperature for 30 minutes. Sections were blocked in 1×TBST/5% normal goat serum for 1 hour and then subsequently incubated with the anti-VTCN1 primary antibody overnight at 4° C. A secondary reagent conjugated with horseradish peroxidase (HRP) recognizing rabbit immunoglobulins was used to visualize VTCN1 staining Counterstain using hematoxylin was done using manufacturer's instructions (Cell Signaling Technology, Danvers, MA).

Results from both proteomic and IHC analysis demonstrated that VTCN1 protein is highly expressed in multiple cancers including triple-negative breast cancer (TNBC), ovarian cancer, squamous NSCLC, and small cell lung cancer. Using similar proteomic and IHC detection methods, VTCN1 expression was found to be weak or absent in normal tissues.

Example 2. Generation of Fully Human Antibodies Against Human VTCN1

Experiments were performed to generate fully human antibodies against human VTCN1 using the following methods.

DNA Immunizations in Humanized Mice

Humanized mice were immunized using a standard DNA prime with recombinant protein and 293-VTCN1 cell boost method Human VTCN1 cDNA construct was purchased from Origene (Rockville, MD). Large scale DNA preparation of the VTCN1 construct was performed using standard plasmid expansion methods. Eight week old H2L2 mice were anesthetized and then received an intramuscular injection in the tibialis anterior muscle, containing 50 µg of VTCN1 plasmid DNA in a 50 µL volume Immediately following, the injected area was subjected to in vivo electroporation using a BTX 830 generator and a BTX 7 mm diameter tweezertrode electrode (BTX Harvard Apparatus, Holliston, MA) under the following conditions: 100 V/cm, 20 ms, 460 ms between pulses. Mice received a total of 3 DNA immunizations spaced by 1 week. Mice that showed anti-VTCN1 serum activity after the $3^{rd}$ DNA immunization were rested for one month and boosted once with 50 µg of VTCN1-Fc recombinant protein made in house intraperitoneal, and then boosted once with 1 million 293-VTCN1 cells intraperitoneal. 7 days after whole cell boost, spleens were taken immediately for fusions.

Cell Fusion

Cell fusion was done following a standard hybridoma procedure. Briefly, one week before the cell fusion, the fusion partner mouse myeloma cell line X63-Ag8.653 (#85011420, non-Ig-secreting; Sigma-Aldrich, St. Louis, MO) was cultured in complete RPMI 1640 medium (2 mM Glutamine and 20% Fetal Bovine Serum, FBS). Spleens from the immunized mice were mechanically processed and made into single-cell suspensions. The cell suspension was passed through a fine mesh 100 µm nylon filter and transferred to a sterile 50 mL conical tube full of serum-free RPMI 1640 medium. The splenocytes were pelleted by centrifuging for 5 min at 1500 rpm (500×g) at room temperature. Supernatant was discarded and the cell pellet was resuspended with 5 mL of ammonium chloride solution for 5 minutes at room temperature to lyse red blood cells (RBC). Cell suspension was washed twice with serum-free RPMI and then cell number and viability was determined using a hemocytometer. Concurrently, X63-Ag8.653 myeloma cells were harvested by transferring the cells from their culture vessels to a 50 mL conical tube and washed two times with serum free RPMI followed by cell count and viability assessment. The X63-Ag8.653 myeloma cells and the mouse splenocytes were mixed at a 1:10 ratio, respectively, in a 50 mL conical tube and then spun down for 5 min at 1500 rpm (500×g).

The cell fusion was performed by placing the tube containing the mixed cell pellet in a 37° C. water bath under sterile conditions. The mixed cell pellet received 1 mL of pre-warmed 50% PEG solution (Sigma-Aldrich, St. Louis, MO) in dropwise fashion over a 1-minute time period, with constant stirring after every drop. The cell mixture then received 1 mL of pre-warmed serum free RPMI, added dropwise for 1 minute, followed by 1 mL of complete RPMI added in a similar fashion. Cells were constantly stirred after every drop of serum free or complete RPMI media. In similar dropwise fashion, 7 mL of pre-warmed serum-free RPMI was added to the cells over a period of 3 minutes. The cells were then centrifuged for 5 min at 1500 rpm at room temperature and the cell pellet was thoroughly resuspended with 20 mL of pre-warmed complete RPMI. The cell suspension was then transferred to a sterile reservoir container and 200 μL of cell suspension was collected with a multichannel pipet and transferred to 96-well flat bottom plates until the entire cell suspension was plated (yielded about 10 plates). The fused cells were kept in a humidified incubator at 37° C. with 5% $CO_2$. On the second day, complete RPMI media was supplemented with 1×HAT (Sigma-Aldrich, St. Louis, MO) reagent and distributed to the 10 fusion plates. The fused cells were fed by removing 50% of the original culture media and replacing it with new HAT+ media on culture days 6, 7, and 10. After 12 days in culture, fusion supernatants were evaluated for anti-VTCN1 activity using high-throughput assays.

Immunofluorescence (IF) Based High Content Screening (HCS)

High content immunofluorescence was used to identify wells that contain immunoglobulin that preferentially bound VTCN1. Briefly, VTCN1 was ectopically expressed in the 293 Human Embryonic Kidney (HEK293) cell line, which were then used to identify wells containing anti-VTCN1 antibodies. Parental HEK293 cells, transfected with an empty DNA vector, were used to identify non-specific antibodies. These cells were seeded 24 hours before the assay and then were incubated for 45 minutes at 37° C. with hybridoma supernatant diluted 2-fold in DMEM+10% fetal bovine serum (FBS). After incubation, cells were fixed in 4% formaldehyde, washed with PBS, permeabilized with 0.3% Triton-X-100, and labeled with anti-rat Alexa 488 secondary antibodies for 1 hour at room temperature. Unbound secondary antibody was removed with PBS washes, and cells were stained with propidium iodide (PI) and Hoechst 33342 to identify cell nucleus.

Potential hits were initially identified via low-resolution, high-throughput screening using a TTP Labtech Acumen eX3 (TTP Labtech, Cambridge, MA), quantifying the fluorescence differential for each sample on both positive and negative cell lines. Those hits were subsequently verified and the subcellular localization of each sample was characterized using a Thermo ArrayScan VTi (Thermo Fisher Scientific, Waltham, MA) to obtain high-resolution images of both cell lines.

Flow Cytometry

Supernatant from hybridoma wells, containing VTCN1 specific antibodies, were re-tested on human breast cell lines SKBR3 and ZR-75-1. 70% confluent MX-1 cells in 10 cm dish were gently washed with 1× cold PBS once, 7 ml cold flow buffer (1×PBS, 0.5% BSA, 2 mM EDTA) was then added, the cells were gently scraped in to flow buffer using rubber cell lifter, pipet up down with 10 ml transfer pipets gently to resuspend the cells. The cells were pelleted by centrifuging them for 5 minutes at 1200 rpm at room temperature. The cell pellets were resuspended in cold flow buffer, the cells were counted and the concentration was adjusted to $1 \times 10^6$ cells per 1 mL. Using a multichannel pipette, 200 μL was collected and transferred to 96-V bottom polypropylene plates and spun at 1250 rpm for 5 min at 4° C. to pellet the cells. The cell pellets were resuspended with hybridoma supernatant diluted 2-fold with cold flow buffer and incubated at 4° C. for 30 min. After incubation, cells were washed 2× with flow buffer and then labeled with anti-rat Alexa 647 secondary antibodies for 30 min at 4° C. Unbound secondary antibodies were removed by washing the cells 2× with flow buffer. Cells were then resuspended in 200 μL of flow buffer containing PI to identify dead cells and remove from analysis. Cells were run on a MACSQuant Analyzer 10 flow cytometer (Miltenyi Biotec, Bergisch Gladbach, Germany) and analysis was performed with FlowJo software (FlowJo, Ashland, OR).

Cloning VH and VL Sequences from Hybridomas

For determination of CDR sequences, total RNA was isolated from hybridoma cells using an RNeasy® kit (Qiagen, Hilden, Germany). First and second-strand cDNA synthesis was performed using a OneTaq® One-Step RT-PCR kit (New England BioLabs, Ipswich, MA). Several primer sets were used (see Table 1). PCR products were separated by agarose electrophoresis and fragments were excised and purified by a QIAquick® gel extraction kit (Qiagen, Hilden, Germany). Fragments were cloned directly into expression vectors with BspQI (New England BioLabs, Ipswich, MA) by Golden Gate cloning techniques. Four colonies from each reaction were scaled up for miniprep-scale plasmid purification by SequeMid® DNA Purification Kit (Aline Biosciences, Woburn, MA).

TABLE 1

Oligonucleotide Sequences used to amplify human IgG genes

| SEQ ID NO | Oligonucleotide Sequence | Oligonucleotide Purpose |
|---|---|---|
| 186 | ATAGCTCTTCAGGGACCATGAARCAYCTGTGGTTCTTCCT | IGHV4 leader |
| 187 | ATAGCTCTTCAGGGACCATGGACATACTTTGTTCCACGC | IGHV2 leader |

TABLE 1-continued

Oligonucleotide Sequences used to amplify human IgG genes

| SEQ ID NO | Oligonucleotide Sequence | Oligonucleotide Purpose |
|---|---|---|
| 188 | ATAGCTCTTCAGGGaccATGGACACACTTTGCTACACAC | IGHV2-26 leader |
| 189 | ATAGCTCTTCAGGGaccATGTCTGTCTCCTTCCTCATCT | IGHV6 leader |
| 190 | ATAGCTCTTCAGGGaccATGGACTGGACCTGGAGVATC | IGHV1 leader |
| 191 | ATAGCTCTTCAGGGACCATGGACTGGATTTGGAGGRTC | IGHV1-58 leader |
| 192 | ATAGCTCTTCAGGGACCATGGACTGCACCTGGAGGATC | IGHV1-24 leader |
| 193 | ATAGCTCTTCAGGGACCATGGACTGGACCTGGAGGKTC | IGHV1-69/1-46/7-4-1 leader |
| 194 | ATAGCTCTTCAGGGACCATGGAGTTKGGRCTGAGCTGG | IGHV3 leader |
| 195 | ATAGCTCTTCAGGGACCATGGAGTTTKGGCTKAGCTGG | IGHV3-53/3-49 leader |
| 196 | ATAGCTCTTCAGGGACCATGGAACTGGGGCTCCGCTGG | IGHV3-21 leader |
| 197 | ATAGCTCTTCAGGGACCATGGARTTGGGGCTGWGCTGG | IGHV3-48/3-7 leader |
| 198 | ATAGCTCTTCAGGGACCATGGGGTCAACCGCCATCCTC | IGHV5 leader |
| 199 | ATAGCTCTTCAGGGACCATGGACATGAGGGTSCCYGCTCAGCTC | IgkV1a leader |
| 200 | ATAGCTCTTCAGGGACCATGGACATGAGRGTCCTCGCTCAGCTC | IgkV1b leader |
| 201 | ATAGCTCTTCAGGGACCATGGAAGCCCCAGCDCAGCTTCTC | IgkV3 leader |
| 202 | ATAGCTCTTCAGGGACCATGGAAACCCCAGCGCAGCTTCTC | IgkV3-20 leader |
| 203 | ATAGCTCTTCAGGGACCATGGTGTTGCAGACCCAGGTCTTC | IgkV4 leader |
| 204 | ATAGCTCTTCAGGGACCATGGGGTCCCAGGTTCACCTCCTC | IgkV5 leader |
| 205 | ATAGCTCTTCAGGGACCATGAGGCTCCYTGCTCAGCTCCTG | IgkV2 leader |
| 206 | ATAGCTCTTCTTCGTTTGATCTCCASCTTGGTC | Kappa FW4 |
| 207 | ATAGCTCTTCTTCGTTTAATCTCCAGTCGTGTC | Kappa FW4 |
| 208 | ATAGCTCTTCTGGCTGAGGAGACGGTGACC | Heavy FW4 |
| 209 | ATAGCTCTTCATGTGACGCTGTTGTGACTCAGGA | VL-FOR L1 |
| 210 | ATAGCTCTTCATGTGACCYTGTGCTCACTCAGTC | VL-FOR L2 |
| 211 | GATGCTCTTCTGGGCTGGCCTAGGACAGTCAMCYTGG | VL-REV L |

Identification of Functional, Recombinant VH and VL Sequences

For each hybridoma, four VH-containing plasmids and four VL-containing plasmids were sent for Sanger Sequencing. These plasmids were subjected to DNA sequence determination and analysis.

For each hybridoma, unique recombinant heavy chains were paired with unique recombinant light chains. These plasmid pairs were transfected into CHO cells in 24-well plates. Twelve days later conditioned medium from each pairing was subjected to concentration determination by OCTET™ and screened by Flow cytometric analysis for binding to 293-VTCN1 cells.

Transient Expression System

The VTCN1 recombinant proteins and anti-VTCN1 antibodies were expressed in Chinese hamster ovary (CHO) cells using recommended transfection and media components of the ExpiCHO system (Invitrogen, Carlsbad, CA). Cell culture supernatants were harvested 14 days post-transfection, centrifuged, and filtered (0.22 um).

Antibody Purification

Conditioned medium from CHO cell cultures was clarified, filtered, and purified by loading onto an AKTA pure system with a 5 mL MabSelect SuRe® column (GE Healthcare). Antibodies were eluted with 100 mM glycine, pH 3.5 and neutralized with 1 M Tris-Cl, pH 8.5.

Several fully human antibodies against the extracellular domain (ECD) of VTCN1 were generated using the methods as described above. One of the clones (i.e., 7C8) binds 293-VTCN1 cells, as well as MX-1 (TNBC cell line), and human breast cancer cell lines SKBR3, and ZR-75-1 cells. The VH and VL sequences of 7C8 were shown in Table 2.

TABLE 2

Variable Region Amino Acid Sequences of 7C8

| SEQ ID NO: | Protein Clone | Region | V Region |
|---|---|---|---|
| 212 | 7C8 | VH | MKHLWFFLLLVAAPRWVLPQVQLQESGPGLVKPSETLSLTCAVSGYSISSGYYWGWIRQPPGKGLEWIGSIYHSGTTYYNPSLKSRVTISVDTSKNQFSLKLNSVTAADTAVYYCATYSSGWYFYFDYWGQGTLVTVSSASTKGPS |
| 213 | 7C8 | CDR-H1 | SGYYWG |
| 214 | 7C8 | CDR-H2 | SIYHSGTTYYNPSLKS |
| 215 | 7C8 | CDR-H3 | YSSGWYFYFDY |
| 216 | 7C8 | VL | MRLPAQLLGLLLLWLPGARCDIQLTQSPSFLSASVGDRVTITCRASQGISSYLAWYQQKPGKAPKLLIYVASTLQSGVPSRFSGSGSGTEFTLTISSLQPEDFATYYCQQLNSYPITFGQGTRLEIKRTVAAPSVFIFPPSDEQLKSGTASV |
| 217 | 7C8 | CDR-L1 | RASQGISSYLA |
| 218 | 7C8 | CDR-L2 | VASTLQS |
| 219 | 7C8 | CDR-L3 | QQLNSYPIT |

TABLE 3

Variable Region Nucleic Acid Sequences of 7C8

| 288 | 7C8 VH | CAGGTGCAGCTGCAGGAGTCGGGCCCAGGACTGGTGAAGCCTTCGGAGACCCTGTCCCTCACCTGCGCTGTCTCTGGTTACTCCATCAGTAGTGGTTATTACTGGGGCTGGATCCGGCAGCCCCCAGGAAAGGGGCTGGAGTGGATTGGGAGTATCTATCATAGTGGGACCACCTACTACAATCCGTCCCTCAAGAGTCGAGTCACCATATCAGTGGACACGTCCAAGAACCAGTTCTCCCTGAAGCTGAACTCTGTGACCGCCGCAGACACGGCCGTGTATTACTGTGCGACCTATAGCAGTGGCTGGTACTTCTACTTTGACTACTGGGGCCAGGGAACCCTGGTCACCGTCTCCTCA |
| 289 | 7C8 VL | GACATCCAGTTGACCCAGTCTCCATCCTTCCTGTCTGCATCTGTAGGAGACAGAGTCACCATCACTTGCCGGGCAGTCAGGGCATTAGCAGTTATTTAGCCTGGTATCAGCAAAAACCAGGGAAAGCCCCTAAGCTCCTGATCTATGTTGCATCCACTTTGCAAAGTGGGGTCCCATCAAGGTTCAGCGGCAGTGGATCTGGGACAGAATTCACTCTCACAATCAGCAGCCTGCAGCCTGAAGATTTTGCAACTTATTACTGTCAACAGCTTAATAGTTACCCGATCACCTTCGGCCAAGGGACACGACTGGAGATTAAA |

Example 3. VTCN1 Antibody 7C8 Cross Reacts with Cynomolgus Monkey and Mouse VTCN1 Proteins, Binds to Full Length VTCN1 Protein, but not VTCN1 IgV or VTCN1 IgC Domains Only VTCN1 belongs to immunoglobulin superfamily of proteins, it has one IgV domain and IgC domain in its extracellular region. Experiments were performed to identify binding domain of VTCN1 by 7C8 clone.

Generate 293-VTCN1-IgV, 293-VTCN1-IgC, 293-VTCN1 (monkey), 293-VTCN1 (mouse) cell lines:

Two constructs were made, one with an IgV domain only and one with an IgC domain only. 293 cells were transfected with VTCN1-IgV and VTCN1-IgC constructs, and stable cell lines of 293 expressing VTCN1-IgV or VTCN1-IgC domains were made. Expression constructs also made to express VTCN1 (monkey, 99% identical to human VTCN1) and VTCN1 (mouse, 88% identical to human VTCN1), stable 293-VTCN1 (monkey), and 293-VTCN1 (mouse) cell lines made by transfecting these constructs.

Flow Cytometry to Test VTCN1 Domain Bound by 7C8.

Briefly, the 7C8 antibody was incubated with 293 cells, 293-VTCN1 (full length), 293-VTCN1-IgV domain, 293-VTCN1-IgC domain cell lines for 30 min at 4° C., unbound antibody was washed away, cells were then incubated with anti-human-Alexa488 conjugate, and analyzed by flow cytometry.

Flow cytometry analysis was also performed with 7C8 binding to 293-VTCN1 (monkey) and 293-VTCN1 (mouse).

Results: results from the flow cytometry analysis indicate that 7C8 cross reacts with both monkey and mouse VTCN1 proteins. In addition, 7C8 binds to full length VTCN1, but does not bind to the IgV domain only or the IgC domain only.

Example 4. VTCN1 Antibody 7C8 Inhibits 293-VTCN1 Cell Growth In Vitro in ADC Assay 7C8 was conjugated to vc-MMAE using methods generally known to one of ordinary skill in the art. 7C8-vc-MMAE was incubated with 293-VTCN1 cells in 96 well plate for 72 hours. At 72 hours, the CellTiter Glo reagent (Promega, Madison, WI) was thawed and equilibrated to room temperature as well as the plate for 10 min, 100 µL of prepared CellTiter Glo was added to each well, followed by a gentle shake with an orbital shaker. The plates were incubated for 30 minutes at room temperature and read with an EnSpire multimode plate luminometer (Perkin Elmer, Waltham, MA).

FIG. 1 shows that the 7C8-MMAE conjugated antibody causes death of 293-VTCN1 cells in a dose dependent manner.

Example 5: Generation of Surrogate Mouse VTCN1 Antibodies Against Human VTCN1

VTCN1 belongs to B7 family of immune check point proteins. It has been shown that VTCN1 inhibits T cell activation, proliferation and cytokine production. VTCN1 positive tumor cells escape immune system through VTCN1 inhibition of T cell function. Experiments were performed to generate mouse antibodies against human VTCN1 that can be used in syngeneic mouse tumor models to study VTCN1 antibody function in tumor.

Mouse Immunization and Hybridoma Fusion:

NZBW mice were immunized with human VTCN1-his protein (R&D systems, Minneapolis, MN) every two weeks. After 5 rounds of immunization, the mice were rested for 3-4 weeks, then the mice were given a final boost with 25 µg of VTCN1-his protein. Four days after the final boost, the spleens were taken from the mice, and cell fusion was performed using the same procedure as described in Example 2.

Immunofluorescence (IF) Based High Content Screening (HCS) for Potential Hits:

Using the same screening procedure as described in Example 2, hybridoma sup. was screened on 293 cells, 293-VTCN1 cells, SKBR3 and ZR-75-1 cells. The wells that are positive to both 293-VTCN1 cells and endogenous SKBR3 and ZR-75-1 cells were expanded, and subcloned. After one round of subclone, the positive wells that contain single colony of cells were harvested for molecular cloning of VTCN1 antibodies.

Molecular Cloning of Mouse VTCN1 Antibodies from Positive Hybridomas:

Using the same procedure as described in Example 2, VH and VL sequences were cloned from positive hybridomas. Paired heavy chain and light chain were transfected into Expi CHO cells, day 14 sup. was screened by flow cytometry using 293-VTCN1 cells to identify positive clones.

Twenty-three recombinant VTCN1 mouse antibodies were obtained. Sequences are shown in Table 4. These 23 mouse antibodies belong to 4 families based on sequence similarity. The recombinant antibodies were produced in CHO-Expi cells in 24 deep wells, CHO cell supernatant was used in FACS analysis to characterize the antibodies.

TABLE 4

Variable Region Sequences for Mouse Antibodies

| SEQ ID NO: | Antibody Name | Protein Domain | Amino Acid Sequence |
|---|---|---|---|
| 1 | 1F8 | VH | QMQLKESGPGLVQPSQSLSITCTVSGFSLTSYGVQWVRQFSGKGLEWLGVIWSSGSTDYNAAFISRLSISKDNSKSQVFFKMNSLQPDDTAMYYCARDITTIVEGFAYWGQGTLVTVSA |
| 2 | 1F8 | CDR-H1 | GFSLTSYGVQ |
| 3 | 1F8 | CDR-H2 | VIWSSGSTDYNAAFIS |
| 4 | 1F8 | CDR-H3 | ITTIVEGFAY |
| 5 | 1F8 | VL | IIVMTQSPKSMSMSVGERVTLSCKASENVGTYVSWYQQKPEQSPKLLIYGASNRYTGVPDRFTGSGSATDFTLTISSVQAEDLADYHCGQSYSYPFTFGSGTKLEIKR |
| 6 | 1F8 | CDR-L1 | KASENVGTYVS |
| 7 | 1F8 | CDR-L2 | GASNRYT |
| 8 | 1F8 | CDR-L3 | GQSYSYPFT |
| 9 | 3C6 | VH | QIQLQESGPELKKPGETVKISCKASGYTFTTTGMQWVQKMPGKGFKWIGWINTHSGEPKYADDFKGRFAFSLETSASTAHLQISNLKNEDTATYFCARTSYWYLDVWGAGTTVTVSS |
| 10 | 3C6 | CDR-H1 | GYTFTTTGMQ |
| 11 | 3C6 | CDR-H2 | WINTHSGEPKYADDFKG |
| 12 | 3C6 | CDR-H3 | SYWYLDV |
| 13 | 3C6 | VL | DIVMTQSQKFMSTSVGDRVSVTCKASQIVGTNIAWYQQKPGQSPKALIYSASYRNSGVPDRFTGSGSGTDFTLTITNVQSEDLAEYFCQQYNSYPLTFGAGTKLEIK |
| 14 | 3C6 | CDR-L1 | KASQIVGTNIA |
| 15 | 3C6 | CDR-L2 | SASYRNS |
| 16 | 3C6 | CDR-L3 | QQYNSYPLT |
| 17 | 3G10 | VH | QIQLKESGPGLVQPSQSLSITCTVSGFSLTSYGVHWVRQSPGKGLEWLGVIWSGGYTDYNSAFISRLSISKDNSKSQVFFKMNSLQADDTAIYYCARDITTIVEGFAYWGQGTLVTVSA |
| 18 | 3G10 | CDR-H1 | GFSLTSYGVH |
| 19 | 3G10 | CDR-H2 | VIWSGGYTDYNSAFIS |
| 20 | 3G10 | CDR-H3 | ITTIVEGFAY |
| 21 | 3G10 | VL | IIVMTQSPKSMSMSVGERITLNCKASENVGTYVSWYQQKPEQSPKLLIYGASNRYTGVPDHFTGSGSATDFTLTISSVQAEDLADYHCGQTYSYPFTFGSGTKLEIK |
| 22 | 3G10 | CDR-L1 | KASENVGTYVS |
| 23 | 3G10 | CDR-L2 | GASNRYT |
| 24 | 3G10 | CDR-L3 | GQTYSYPFT |

TABLE 4-continued

Variable Region Sequences for Mouse Antibodies

| SEQ ID NO: | Antibody Name | Protein Domain | Amino Acid Sequence |
|---|---|---|---|
| 25 | 4B9 | VH | EVQLQESGPGLVQPSQSLSITCTVSGFSLTSYGVHWVRQSPG KGLEWLGVIWSSGSTDYNAAFISRLSISKDNSKSQVFFKIHS LQADDTAIYYCARDITTIVEGFAYWAQGTLVTVSA |
| 26 | 4B9 | CDR-H1 | GFSLTSYGVH |
| 27 | 4B9 | CDR-H2 | VIWSSGSTDYNAAFIS |
| 28 | 4B9 | CDR-H3 | ITTIVEGFAY |
| 29 | 4B9 | VL | NIVMTQSPKSMSMSVGERVTLICKASENVGTYVSWYQQKPEQ SPKLLIYGASNRYTGVPDRFTGSGSATDFTLTISSVQAEDLA DYHCGQTYSYPFTFGSGTKLEIK |
| 30 | 4B9 | CDR-L1 | KASENVGTYVS |
| 31 | 4B9 | CDR-L2 | GASNRYT |
| 32 | 4B9 | CDR-L3 | GQTYSYPFT |
| 33 | 6E2 | VH | QIQLQESGPGLVQPSQSLSITCTVSGFSLTSYGVQWVRQSPG KGLEWLGVIWSGGSTDYNAAFISRLSISKDNSKSQVFFKMNS LQADDTAIYYCARDISTIVEGFAHWGQGTLVTVSS |
| 34 | 6E2 | CDR-H1 | GFSLTSYGVQ |
| 35 | 6E2 | CDR-H2 | VIWSGGSTDYNAAFIS |
| 36 | 6E2 | CDR-H3 | ISTIVEGFAH |
| 37 | 6E2 | VL | NIVMTQSPKSMSMSVGERVTLSCKASEKVGTYVSWYQQKPEQ SPKLLIYGASNRYTGVPDRFTGSGSATDFTLTISSVQAEDLA DYHCGQSYRYPFTFGSGTKLEIK |
| 38 | 6E2 | CDR-L1 | KASEKVGTYVS |
| 39 | 6E2 | CDR-L2 | GASNRYT |
| 40 | 6E2 | CDR-L3 | GQSYRYPFT |
| 41 | 7E12 | VH | QVQMKESGPELKKPGETVKISCKASGYTFTTTGMQWVQKMPG KGFKWIGWINTHSGEPKYADDFKGRFAFSLETSASTAHLQIS NLKNEDTATYFCARTSYWYLDVWGAGTTVTVSS |
| 42 | 7E12 | CDR-H1 | GYTFTTTGMQ |
| 43 | 7E12 | CDR-H2 | WINTHSGEPKYADDFKG |
| 44 | 7E12 | CDR-H3 | SYWYLDV |
| 45 | 7E12 | VL | DIVMTQSQKFMSTSVGDRVSVTCKASQIVGTNIAWYQQKPGQ SPKALIYSASYRNSGVPDRFTGSGSGTDFTLTITNVQSEDLA EYFCQQYNSYPLTFGAGTKLEIK |
| 46 | 7E12 | CDR-L1 | KASQIVGTNIA |
| 47 | 7E12 | CDR-L2 | SASYRNS |
| 48 | 7E12 | CDR-L3 | QQYNSYPLT |
| 49 | 8G3 | VH | QIQLQESGPGLVQPSQSLSITCTVSGFSLTSYGVHWVRQSPG KGLEWLGVIWSSGSTDYNAAFISRLSISKDNSRSQVFFKMNS LQPDDTAIYYCARDITTIVEGFAYWAQGTLVTVSA |
| 50 | 8G3 | CDR-H1 | GFSLTSYGVH |
| 51 | 8G3 | CDR-H2 | VIWSSGSTDYNAAFIS |
| 52 | 8G3 | CDR-H3 | ITTIVEGFAY |
| 53 | 8G3 | VL | NVVMTQSPKSMSMSVGERVTLICKASENVGTYVSWYQQKPEQ SPKLLIYGASNRYTGVPDRFTGSGSATDFTLTISSVQAEDLA DYHCGQTYSYPFAFGSGTKLEIK |

TABLE 4-continued

Variable Region Sequences for Mouse Antibodies

| SEQ ID NO: | Antibody Name | Protein Domain | Amino Acid Sequence |
|---|---|---|---|
| 54 | 8G3 | CDR-L1 | KASENVGTYVS |
| 55 | 8G3 | CDR-L2 | GASNRYT |
| 56 | 8G3 | CDR-L3 | GQTYSYPFA |
| 57 | 10D1 | VH | QVQLQESGPELVKPGASVKLSCKASGYIFTDYTIHWLKQSPG QGLEWIGWIYPGSGHTHYNDKFKGKATMTADKSSTTAYMQLS SLTSEDSAVFFCARGGESITTVFPLAYWGQGTLVTVSA |
| 58 | 10D1 | CDR-H1 | GYIFTDYTIH |
| 59 | 10D1 | CDR-H2 | WIYPGSGHTHYNDKFKG |
| 60 | 10D1 | CDR-H3 | GESITTVFPLAY |
| 61 | 10D1 | VL | DIVMSQSPSSLAVSVGEKVTMSCKSSQSLLYSSDQKNYLAWY QQKPGQSPKLLIYWASTWESGVPDRFIGSGSGTDFTLTVSSV KAEDLAVYYCHQYYSYPPTFGAGTKLEIK |
| 62 | 10D1 | CDR-L1 | KSSQSLLYSSDQKNYLA |
| 63 | 10D1 | CDR-L2 | WASTWES |
| 64 | 10D1 | CDR-L3 | HQYYSYPPT |
| 65 | 1A2 | VH | QVQLQQSGPGLVQPSQSLSITCTVSGFSLTSYGVHWVRQSPG KGLEWLGVIWSGGSTDYNAAFISRLSISKDNSKSQVFFKMNS LQADDTAIYYCARDITTIVEGFAYWGQGTLVTVSA |
| 66 | 1A2 | CDR-H1 | GFSLTSYGVH |
| 67 | 1A2 | CDR-H2 | VIWSGGSTDYNAAFIS |
| 68 | 1A2 | CDR-H3 | ITTIVEGFAY |
| 69 | 1A2 | VL | NIVMTQSPKSMSMSVGERVTLSCKASENVGTYVSWYQQKPEQ SPKLLIYGASNRYTGVPDRFTGSGSATDFTLTISSVQAEDVT DYHCGQTYSYPFTFGSGTKLEIK |
| 70 | 1A2 | CDR-L1 | KASENVGTYVS |
| 71 | 1A2 | CDR-L2 | GASNRYT |
| 72 | 1A2 | CDR-L3 | GQTYSYPFT |
| 73 | 1C3 | VH | QIQLQQSGPGLVQPSQSLSITCTVSGFSLTSYGVQWVRQSPG KGLEWLGVIWSSGNTDYNAAFISRLTITKDNSKSQIFFKMNS LQADDTAIYYCARDITTIVEGFAYWGQGTLVTVSA |
| 74 | 1C3 | CDR-H1 | GFSLTSYGVQ |
| 75 | 1C3 | CDR-H2 | VIWSSGNTDYNAAFIS |
| 76 | 1C3 | CDR-H3 | ITTIVEGFAY |
| 77 | 1C3 | VL | NIVMTQSPKSMSMSVGERVTLSCKASENVGTYVSWYQQKPEQ SPKLLIYGASNRYTGVPDRFTGSGSATDFTLTISSVQAEDLA DYHCGQTYSYPFTFGSGTKLEIK |
| 78 | 1C3 | CDR-L1 | KASENVGTYVS |
| 79 | 1C3 | CDR-L2 | GASNRYT |
| 80 | 1C3 | CDR-L3 | GQTYSYPFT |
| 81 | 2C2 | VH | QIQLQQSGPELKKPGETVKISCKASGYTFTTAGMQWVQKMPG KGFKWLGWINTHSGEPKYADDFKGRFAFSLETSASTAYLQIN NLKNEDTATYHCARTSYWYLDIWGAGTTVTVSS |
| 82 | 2C2 | CDR-H1 | GYTFTTAGMQ |
| 83 | 2C2 | CDR-H2 | WINTHSGEPKYADDFKG |
| 84 | 2C2 | CDR-H3 | SYWYLDI |

TABLE 4-continued

Variable Region Sequences for Mouse Antibodies

| SEQ ID NO: | Antibody Name | Protein Domain | Amino Acid Sequence |
|---|---|---|---|
| 85 | 2C2 | VL | DIVMTQSQKFMSTSVGDRVSVTCKASQNVGTNVAWYQQKPGQ SPKALIYSASYRCSGVPDRFTGSGSGTDFTLTISNVQSEDLA EYFCQQYNSYPLTFGAGTKLEIK |
| 86 | 2C2 | CDR-L1 | KASQNVGTNVA |
| 87 | 2C2 | CDR-L2 | SASYRCS |
| 88 | 2C2 | CDR-L3 | QQYNSYPLT |
| 89 | 3D11 | VH | QVQLQQPGAELVKPGASVKLSCKASGYSFTSYWMNWVKQRPG RGLEWIGRIHPSDSETHYNQNFKSKATLTVDKSSSTAYIQLN SLTSEDSAVYYCARPYYFYGSSPYAMDYWGQGASVTVSS |
| 90 | 3D11 | CDR-H1 | GYSFTSYWMN |
| 91 | 3D11 | CDR-H2 | RIHPSDSETHYNQNFKS |
| 92 | 3D11 | CDR-H3 | YYFYGSSPYAMDY |
| 93 | 3D11 | VL | DVVMTQTPLSLPVSLGDQASISCRSSQSIVHSNGNTYLEWYL QKPGQSPKLLIYKVSNRFSGVPDRFSGSGSGTDFTFKISRVE AEDLGVYYCFQGSHVPYTFGGGTKLEIK |
| 94 | 3D11 | CDR-L1 | RSSQSIVHSNGNTYLE |
| 95 | 3D11 | CDR-L2 | KVSNRFS |
| 96 | 3D11 | CDR-L3 | FQGSHVPYT |
| 97 | 4C6 | VH | QMQLQESGPGLVQPSQSLSITCTVSGFSLTSYGIHWVRQSPG KGLEWLGVIWSSGSTDYNAAFISRLSISKDNSKSQVFFKMNS LQSDDTAIHYCARDITTIAEGFAYWGQGTLVTVSS |
| 98 | 4C6 | CDR-H1 | GFSLTSYGIH |
| 99 | 4C6 | CDR-H2 | VIWSSGSTDYNAAFIS |
| 100 | 4C6 | CDR-H3 | ITTIAEGFAY |
| 101 | 4C6 | VL | NIVMTQSPKSMSMSVGERVTLSCKASENVGTYVSWYQQKPEQ SPKLLIYGASNRYTGVPDRFTGSGSATDFTLTISSVQAEDLA DYHCGQSYSYPFTFGSGTKLEIK |
| 102 | 4C6 | CDR-L1 | KASENVGTYVS |
| 103 | 4C6 | CDR-L2 | GASNRYT |
| 104 | 4C6 | CDR-L3 | GQSYSYPFT |
| 105 | 5A12 | VH | QVQLQQSGPGLVQPSQSLSITCTVSGFSLTSYGVQWVRQSPG KGLEWLGVIWSSGSTDYNAAFISRLSINKDNSKSQVFFKMNS LQPDDTAIYYCARDITTIVEGFAYWGQGTLVTVSA |
| 106 | 5A12 | CDR-H1 | GFSLTSYGVQ |
| 107 | 5A12 | CDR-H2 | VIWSSGSTDYNAAFIS |
| 108 | 5A12 | CDR-H3 | ITTIVEGFAY |
| 109 | 5A12 | VL | IIVMTQSPKSMSMSVGERVTLSCKASENVGTYVSWYQQKPEQ SPKLLIYGASNRYTGVPDRFTGSGSATDFTLTISSVQAEDLA DYHCGQSYSYPFTFGSGTKLEIK |
| 110 | 5A12 | CDR-L1 | KASENVGTYVS |
| 111 | 5A12 | CDR-L2 | GASNRYT |
| 112 | 5A12 | CDR-L3 | GQSYSYPFT |
| 113 | 6D9 | VH | QIQLQQSGPGLVQPSQSLSITCTVSGFSLTSYGVQWIRQSPG KGLEWLGVIWSSGSTDYNAAFLSRLSFSKDNSKSQVFFQMNS LQADDSAIYYCARDVTTIVEGFAHWGQGTLVTVSA |

TABLE 4-continued

Variable Region Sequences for Mouse Antibodies

| SEQ ID NO: | Antibody Name | Protein Domain | Amino Acid Sequence |
|---|---|---|---|
| 114 | 6D9 | CDR-H1 | GFSLTSYGVQ |
| 115 | 6D9 | CDR-H2 | VIWSSGSTDYNAAFLS |
| 116 | 6D9 | CDR-H3 | VTTIVEGFAH |
| 117 | 6D9 | VL | NIVMTQSPKSMSMSVGERVTLSCKASEKVGTYVSWYQQKPEQSPKLLIYGASNRYTGVPDRFTGSGSATDFTLTISSVQVEDLADYHCGQTYSYPFTFGSGTKLEIK |
| 118 | 6D9 | CDR-L1 | KASEKVGTYVS |
| 119 | 6D9 | CDR-L2 | GASNRYT |
| 120 | 6D9 | CDR-L3 | GQTYSYPFT |
| 121 | 7C9 | VH | QIQLQESGPGLVQPSQSLSITCTVSGFSLTSYGVQWVRQSPGKGLEWLGVIWSSGSTDYNAAFISRLSISKDNSKSQVFFKMNSLQADDTAIYYCARDITTIVEGFAYWGQGTLVTVSA |
| 122 | 7C9 | CDR-H1 | GFSLTSYGVQ |
| 123 | 7C9 | CDR-H2 | VIWSSGSTDYNAAFIS |
| 124 | 7C9 | CDR-H3 | ITTIVEGFAY |
| 125 | 7C9 | VL | NIVMTQSPKSMSMSVGERVTLRCKASENVNTYVSWYQQKPEQSPKLLIYGASNRYTGVPDRFTGSGSATDFTLTISSVQAEDLADYHCGQSYSYPFTFGSGTKLEIK |
| 126 | 7C9 | CDR-L1 | KASENVNTYVS |
| 127 | 7C9 | CDR-L2 | GASNRYT |
| 128 | 7C9 | CDR-L3 | GQSYSYPFT |
| 129 | 7D9 | VH | QIQLKESGPGLVQPSQSLSITCTVSGFSLTSYGVQWVRQSPGKGLEWLGVIWSGGSTDYNAAFISRLSISKDNSKSQVFFKMNSLQADDTAIYYCARDITTIVEGFAYWAQGTLVTVSA |
| 130 | 7D9 | CDR-H1 | GFSLTSYGVQ |
| 131 | 7D9 | CDR-H2 | VIWSGGSTDYNAAFIS |
| 132 | 7D9 | CDR-H3 | ITTIVEGFAY |
| 133 | 7D9 | VL | NIVMTQSPKSMSMSVGERVTLSCKASENVGTYVSWYQQKPEQSPKLLIYGASNRYTGVPDRFTGSGSATDFTLTISSVQAEDLADYHCGQTYSYPFTFGSGTKLEIK |
| 134 | 7D9 | CDR-L1 | KASENVGTYVS |
| 135 | 7D9 | CDR-L2 | GASNRYT |
| 136 | 7D9 | CDR-L3 | GQTYSYPFT |
| 137 | 7F10 | VH | QVQLQQSGPGLVQPSQSLSITCTVSGFSLTSYGIHWVRQSPGKGLEWLGVIWSSGSTDYNAAFISRLSISKDNSKSQVFFKMNSLQSDDTAIHYCARDITTIAEGFAYWGQGTLVTVSA |
| 138 | 7F10 | CDR-H1 | GFSLTSYGIH |
| 139 | 7F10 | CDR-H2 | VIWSSGSTDYNAAFIS |
| 140 | 7F10 | CDR-H3 | ITTIAEGFAY |
| 141 | 7F10 | VL | NIVMTQSPKSMSMSVGERVTLSCKASENVGTYVSWYQQKPEQSPKLLIYGASNRYTGVPDRFTGSGSATDFTLTISSVQAEDLADYHCGQSYSYPFTFGSGTKLEIK |
| 142 | 7F10 | CDR-L1 | KASENVGTYVS |
| 143 | 7F10 | CDR-L2 | GASNRYT |
| 144 | 7F10 | CDR-L3 | GQSYSYPFT |

TABLE 4-continued

Variable Region Sequences for Mouse Antibodies

| SEQ ID NO: | Antibody Name | Protein Domain | Amino Acid Sequence |
|---|---|---|---|
| 145 | 7G9 | VH | QVQMQESGPGLVQPSQSLSITCTVSGFSLTSYGVQWVRQSPG KGLQWLGVIWSSGSTDYNAAVISRLSISKDTSKSQVFFKMNS LQPDDTAIYYCARDITTIVEGFAYWGQGTLVTVSS |
| 146 | 7G9 | CDR-H1 | GFSLTSYGVQ |
| 147 | 7G9 | CDR-H2 | VIWSSGSTDYNAAVIS |
| 148 | 7G9 | CDR-H3 | ITTIVEGFAY |
| 149 | 7G9 | VL | IIVMTQSPKSMSMSVGERVTLSCKASENVGTYVSWYQQKPEQ SPKLLIYGASNRYTGVPDRFTGSGSATDFTLTISSVQAEDLA DYHCGQSYSYPFTFGSGTKLEIK |
| 150 | 7G9 | CDR-L1 | KASENVGTYVS |
| 151 | 7G9 | CDR-L2 | GASNRYT |
| 152 | 7G9 | CDR-L3 | GQSYSYPFT |
| 153 | 9E7 | VH | QIQLQQSGPGLVQPSQSLSITCTVSGFSLTSYGIHWVRQSPG KGLEWLGVIWSSGSTDYNAAFISRLSISKDNSKSQVFFKMNS LQSDDTAIHYCARDITTIAEGFAYWGQGTLVTVSA |
| 154 | 9E7 | CDR-H1 | GFSLTSYGIH |
| 155 | 9E7 | CDR-H2 | VIWSSGSTDYNAAFIS |
| 156 | 9E7 | CDR-H3 | ITTIAEGFAY |
| 157 | 9E7 | VL | NIVMTQSPKSMSMSVGERVTLSCKASENVGTYVSWYQQKPEQ SPKLLIYGASNRYTGVPDRFTGSGSATDFTLTISSVQAEDLA DYHCGQSYSYPFTFGSGTKLEIK |
| 158 | 9E7 | CDR-L1 | KASENVGTYVS |
| 159 | 9E7 | CDR-L2 | GASNRYT |
| 160 | 9E7 | CDR-L3 | GQSYSYPFT |
| 161 | 9F10 | VH | QVQLKQSGPGLVQPSQSLSITCTVSGFSLTSYGIHWVRQSPG KGLEWLGVIWSSGSTDYNAAFISRLSISKDNSKSQVFFKMNS LQSDDTAIHYCARDITTIAEGFAYWGQGTLVTVSA |
| 162 | 9F10 | CDR-H1 | GFSLTSYGIH |
| 163 | 9F10 | CDR-H2 | VIWSSGSTDYNAAFIS |
| 164 | 9F10 | CDR-H3 | ITTIAEGFAY |
| 165 | 9F10 | VL | NIVMTQSPKSMSMSVGERVTLSCKASENVGTYVSWYQQKPEQ SPKLLIYGASNRYTGVPDRFTGSGSATDFTLTISSVQAEDLA DYHCGQSYSYPFTFGSGTKLEIK |
| 166 | 9F10 | CDR-L1 | KASENVGTYVS |
| 167 | 9F10 | CDR-L2 | GASNRYT |
| 168 | 9F10 | CDR-L3 | GQSYSYPFT |
| 169 | 9H12 | VH | QIQLQESGPGLVQPSQSLSITCTVSGFSLTSYGVQWVRQSPG KGLEWLGVIWSGGSTDYNAAFISRLSISKDNSKSQVFFKMNS LQADDTAIYYCARDITTIVEGFAHWGQGTLVTVSA |
| 170 | 9H12 | CDR-H1 | GFSLTSYGVQ |
| 171 | 9H12 | CDR-H2 | VIWSGGSTDYNAAFIS |
| 172 | 9H12 | CDR-H3 | ITTIVEGFAH |
| 173 | 9H12 | VL | NIVMTQSPKSMSMSVGERVTLSCKASEKVGTYVSWYQQKPEQ SPKLLIYGASNRYTGVPDRFTGSGSATDFTLTISSVQAEDLA DYHCGQSYSYPFTFGSGTKLEIK |

TABLE 4-continued

Variable Region Sequences for Mouse Antibodies

| SEQ ID NO: | Antibody Name | Protein Domain | Amino Acid Sequence |
|---|---|---|---|
| 174 | 9H12 | CDR-L1 | KASEKVGTYVS |
| 175 | 9H12 | CDR-L2 | GASNRYT |
| 176 | 9H12 | CDR-L3 | GQSYSYPFT |
| 177 | 9H7 | VH | QVQLQESGPELVKPGASVKLSCKASGYSFTDYTMHWVKQSPG QGLEWIGWIYPGSGNTMYNDKFKGEATMTADKSSSTTYMQLS SLTSEDSAVYFCARGGDSIITVFPFTYWGQGTLVTVSA |
| 178 | 9H7 | CDR-H1 | GYSFTDYTMH |
| 179 | 9H7 | CDR-H2 | WIYPGSGNTMYNDKFKGEATMTAD |
| 180 | 9H7 | CDR-H3 | GDSIITVFPFTY |
| 181 | 9H7 | VL | DIVMSQSPSSLAVSVGEKVTMSCKSSQSLLYSSNQKNYLAWY QQKPGQSPELLIYWASTRESGVPDRFTGSGSGTDFTLTISSV KAEDLAVYYCQQYYSYPPTFGAGTKLEIK |
| 182 | 9H7 | CDR-L1 | KSSQSLLYSSNQKNYLA |
| 183 | 9H7 | CDR-L2 | WASTRES |
| 184 | 9H7 | CDR-L3 | QQYYSYPPT |

Example 6: Characterization of Surrogate Mouse VTCN1 Antibodies

Binding to 293-VTCN1 Cells and MX-1 Cells by Flow Cytometry

Antibody concentration was determined by OCTET™ using protein G biosensor. 0.05 µg/ml, 0.1 µg/ml, 0.5 µg/ml, 1 µg/ml, 5 µg/ml, 10 µg/ml antibodies were incubated with live cells for 30 min. on ice, unbound antibodies were washed off, and a conjugated anti-mouse $2^{nd}$ antibody was added to the wells for 15 min. Cells were washed twice with flow buffer and analyzed using MACSQuant Analyzer 10 flow cytometer (Miltenyi Biotec, Bergisch Gladbach, Germany). Results from flow cytometry assays indicate that mouse anti-VTCN1 antibodies are capable of binding to 293-VTCN1 cells and MX-1 cells.

VTCN1 Antibodies Inhibit 293-VTCN1 Cell and SKBR3 Cell Growth in a Secondary ADC Assay 293-VTCN1 cells and SKBR3 cells were seeded at 3,000 cells/well on 96 well lysine coated flat clear bottom black polystyrene microplates (Corning Lifescience, Tewksbury, MA). Twenty-four hours later, medium was aspirated from the wells, and anti-VTCN1 antibody in complete DMEM was added to the wells. Within 5 minutes, 20 µL/well of secondary ADC (anti-mouse IgG-MMAE conjugate) or media alone were added onto the cell plates. The final concentration of VTCN1 antibodies range from 0.1 µg/ml to 1 µg/ml, $2^{nd}$ ADC concentration was 0.4 µg/ml for all wells. Plates were incubated for 72 hours at 37° C. At 72 hours, the CellTiter Glo reagent (Promega, Madison, WI) was thawed and equilibrated to room temperature as well as the plate for 10 min, 100 µL of prepared CellTiter Glo was added to each well, followed by a gentle shake with an orbital shaker. The plates were incubated for 30 minutes at room temperature and read with an EnSpire multimode plate luminometer (Perkin Elmer, Waltham, MA).

Figure 2:
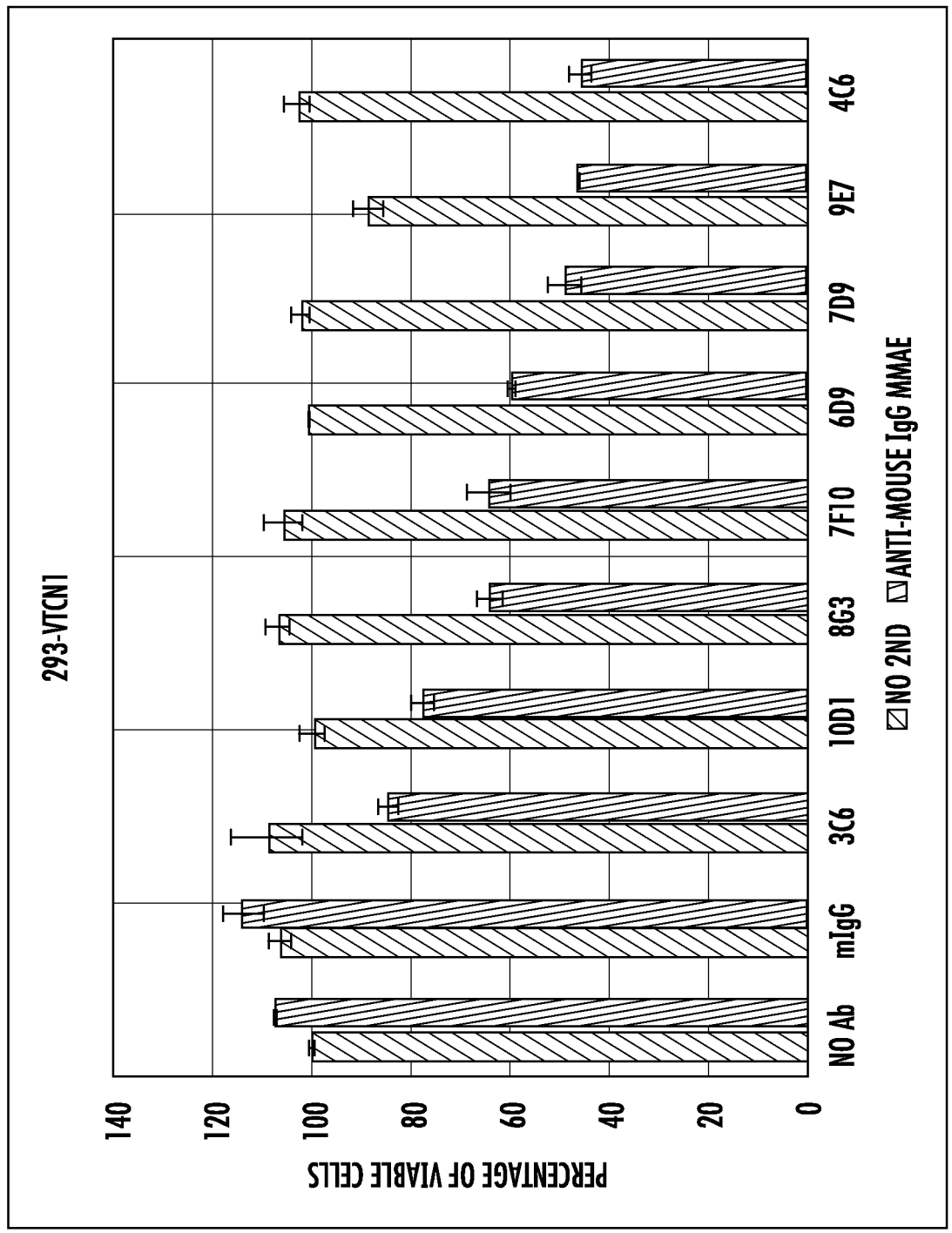
FIG. 2 shows VTCN1 antibodies inhibit 293-VTCN1 cell growth in secondary ADC assays. VTCN1 antibodies (0.5 µg/mL) and anti-mouse IgG MMAE (1 µg/mL) antibodies were added to 293-VTCN1 cells, the cells were incubated for 72 hours, and the cell viability was determined using CellTiter Glo™.

FIG. 2 shows that VTCN1 antibodies are cytotoxic as exhibited in a secondary cytotoxicity assay using 293-VTCN1 cells.

Example 7. Large Scale Production of VTCN1 Antibodies and Affinity Measurement

Selected VTCN1 antibodies were produced in 100 ml culture of CHO-Expi cells. The supernatant was purified on an AKTA pure system with a 5 mL MabSelect SuRe® column (GE Healthcare). Antibodies were eluted with 100 mM glycine, pH 3.5 and neutralized with 1 M Tris-Cl, pH 8.5. and dialyzed into 1xPBS. Antibody purity was assessed by SDS-PAGE and HPLC-SEC chromatography.

The affinity of antibodies to recombinant VTCN1 was determined on an OCTET™ Red (Pall, ForteBio) instrument. After loading reagents into a 96-well plate, the OCTET™ Red with Protein A-conjugated biosensors was programmed as follows: 30 seconds for baseline #1; 45 seconds to immobilize the antibody; 30 seconds for baseline #2; 300 seconds for association of antibody to recombinant VTCN1-his; and 300 seconds for dissociation of recombinant VTCN1-his from the antibody. Table 5 lists the affinity measured for selected antibodies.

TABLE 5

Affinity of selected VTCN1 antibodies against human VTCN1 protein by OCTET ™

| Sample | KD (human) | Kon (human) | Kdis (human) | KD (cyno) |
|---|---|---|---|---|
| 3D11 | 6 nM | | | 2 nM |
| 3G10 | 12 nM | $1.07 \times 10^6$ | $1.26 \times 10^{-2}$ | 14 nM |
| 4C6 | 14 nM | | | 16 nM |
| 5A12 | 4 nM | $3.93 \times 10^5$ | $1.64 \times 10^{-3}$ | 12 nM |
| 6D9 | 2 nM | $6.19 \times 10^5$ | $1.52 \times 10^{-3}$ | 7 nM |
| 6E2 | 8 nM | $9.41 \times 10^5$ | $7.46 \times 10^{-3}$ | 19 nM |
| 7F10 | 5 nM | $1.15 \times 10^6$ | $5.94 \times 10^{-3}$ | 12 nM |
| 10D1 | 4 nM | $9.83 \times 10^5$ | $4.04 \times 10^{-3}$ | 1 nM |

Figure 3A:
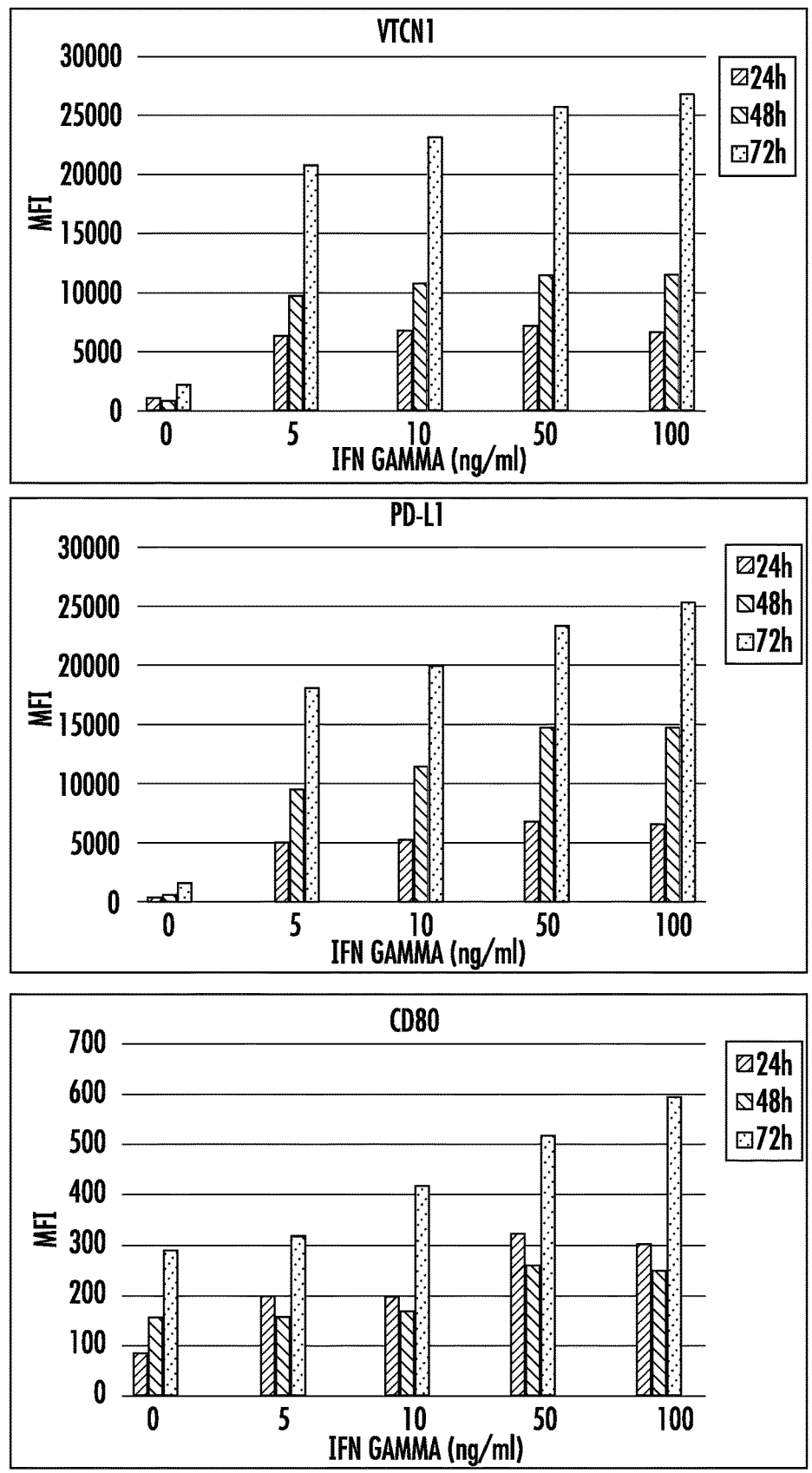
FIG. 3A and FIG. 3B show IFNγ treatment (FIG. 3A) and IL6 treatment (FIG. 3B) induces expression of VTCN1, PD-L1 and CD80 in human monocytes. IFNγ or IL-6 were added to human monocyte cultures to achieve final concentrations of 0.5-100 ng/ml. In instances, VTCN1, PD-L1, and CD80 expression was increased in a time-dependent manner.
Figure 3B:
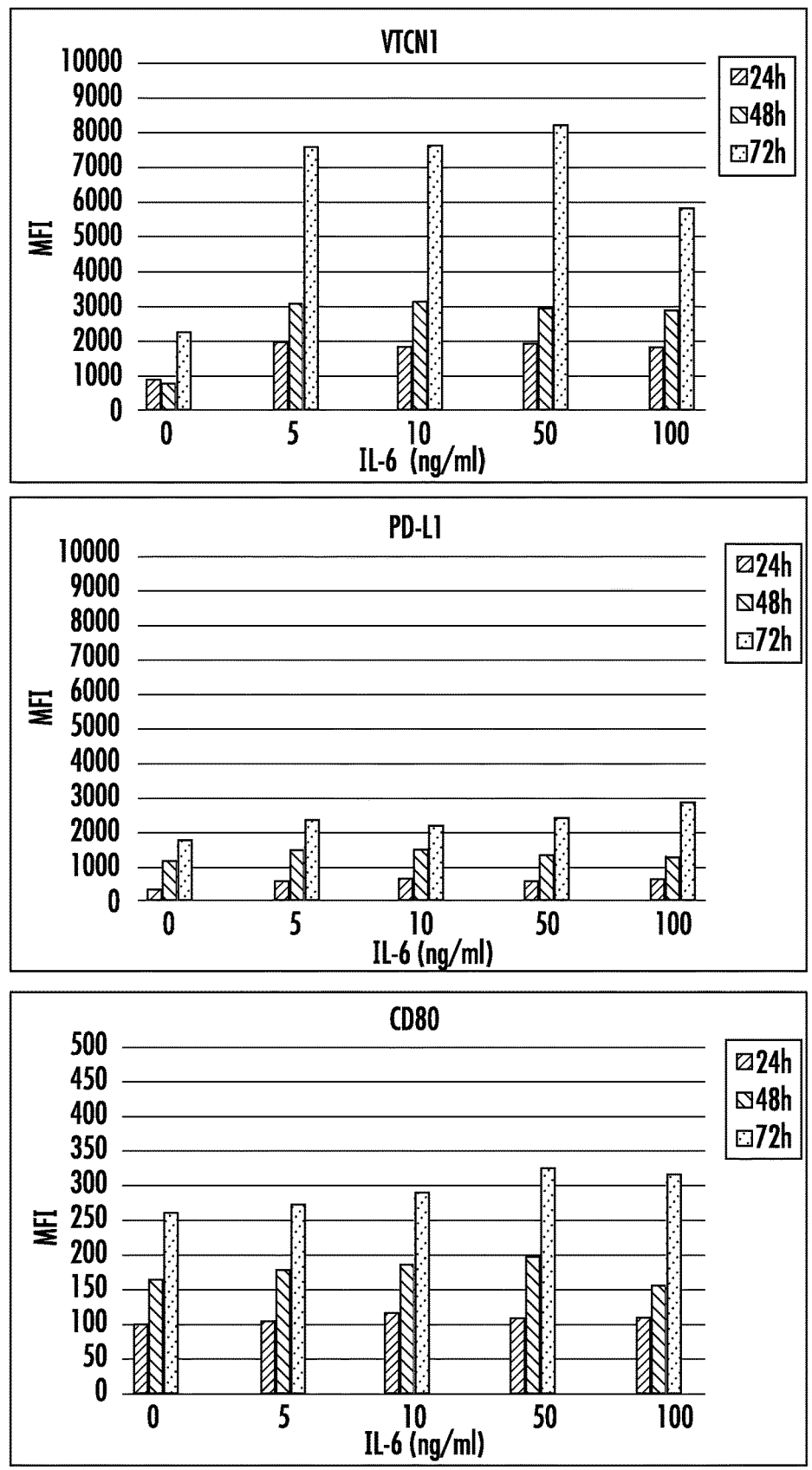

Example 8. Mouse VTCN1 Antibodies Increase T Cell Activity in a T Cell Monocyte MLR Assay IFNγ and IL6 Treatment Induces VTCN1 and PD-L1 Expression VTCN1 is expressed in monocytes and macrophages in a tumor microenviroment, the expression induced by cytokines in tumor microenviroment. VTCN1 positive macrophages inhibit T cell activation. Monocytes from healthy donors were treated with IFNγ and IL-6 to assess VTCN1 expression. Monocytes were enriched from fresh PBMC from healthy donor using a monocyte enrichment kit from Stemcell Technologies, and the purity of the obtained monocytes is greater than 95%. Monocytes were cultured in 24 well plate with different concentration of INFγ or LI-6 for 24, 48, or 73 hours, expression of VTCN1, PD-L1, and CD80 was assessed by flow cytometry. FIG. 3A shows that VTCN1 and PD-L1 expression was induced by IFNγ, and FIG. 3B shows that VTCN1 and PD-L1 expression was induced by IL6. CD80 was expressed at low level in monocytes, and is not very responsive to cytokine treatment.

Mouse VTCN1 Antibodies Increase IFNgamma Secretion by T Cells in T Cell Monocyte Coculture Experiment.

CD4+ T cells were enriched from fresh PBMC using a kit from Stemcell Technologies from healthy donors, autologous monocytes were enriched from the same fresh PBMC. CD4+ T cells and monocytes were co-cultured at 10:1 ratio (200,000 CD4+ T cells, and 20,000 monocytes), with 1 µg/ml CD3 antibody OKT3 in solution or coated on 96 well plate. Mouse IgG control or VTCN1 antibodies were added to triplicate wells at 20 µg/ml. Cells were incubated for 5 days in incubator. The medium was analyzed for IFNγ expression by ELISA using an ELISA kit from R&D system. The cells analyzed for activation by CD25 marker or CFSE dilution by flow cytometry. VTCN1-rabbit Fc staining in flow experiment was used to analyze VTCN1 receptor expression in T cells.

Figure 4A:
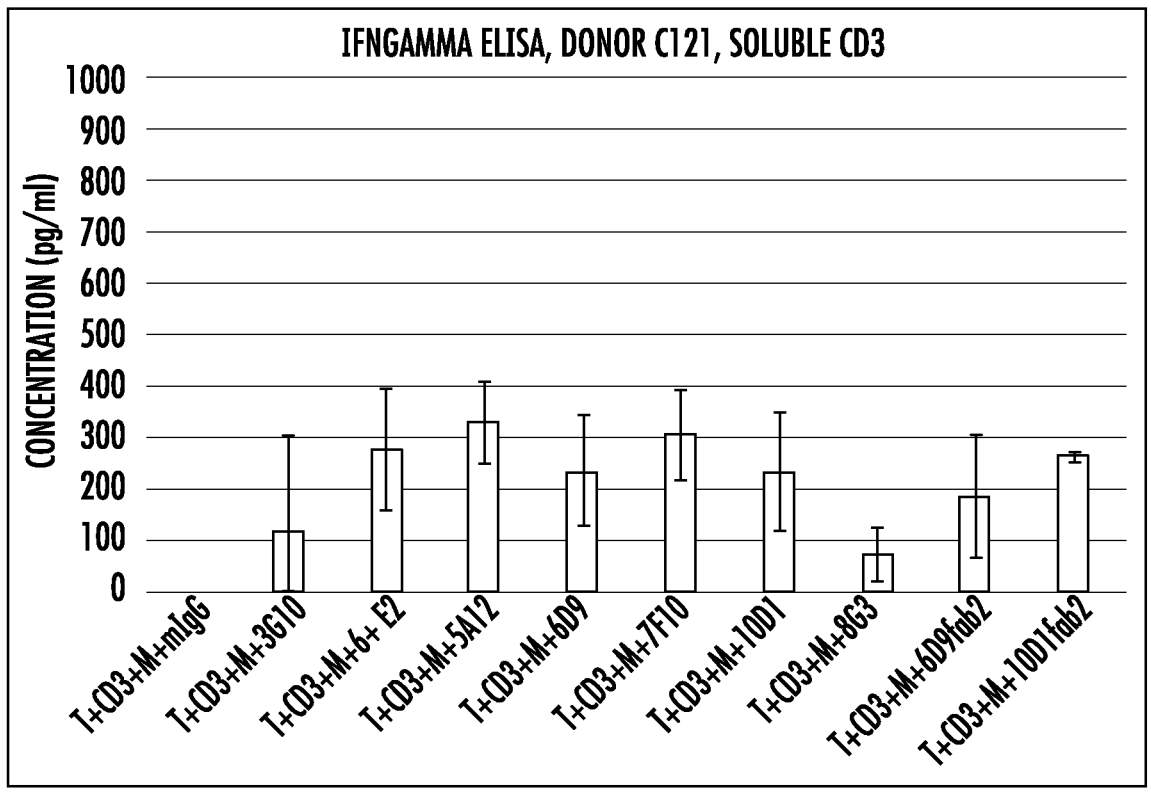
FIG. 4A and FIG. 4B show anti-VTCN1 antibodies increase IFNγ secretion when CD4+ T cells are co-cultured with autologous monocytes and the CD3 antibody OKT3 (1 µg/ml either added to culture medium (FIG. 4A) or coated on plate (FIG. 4B).
Figure 4B:
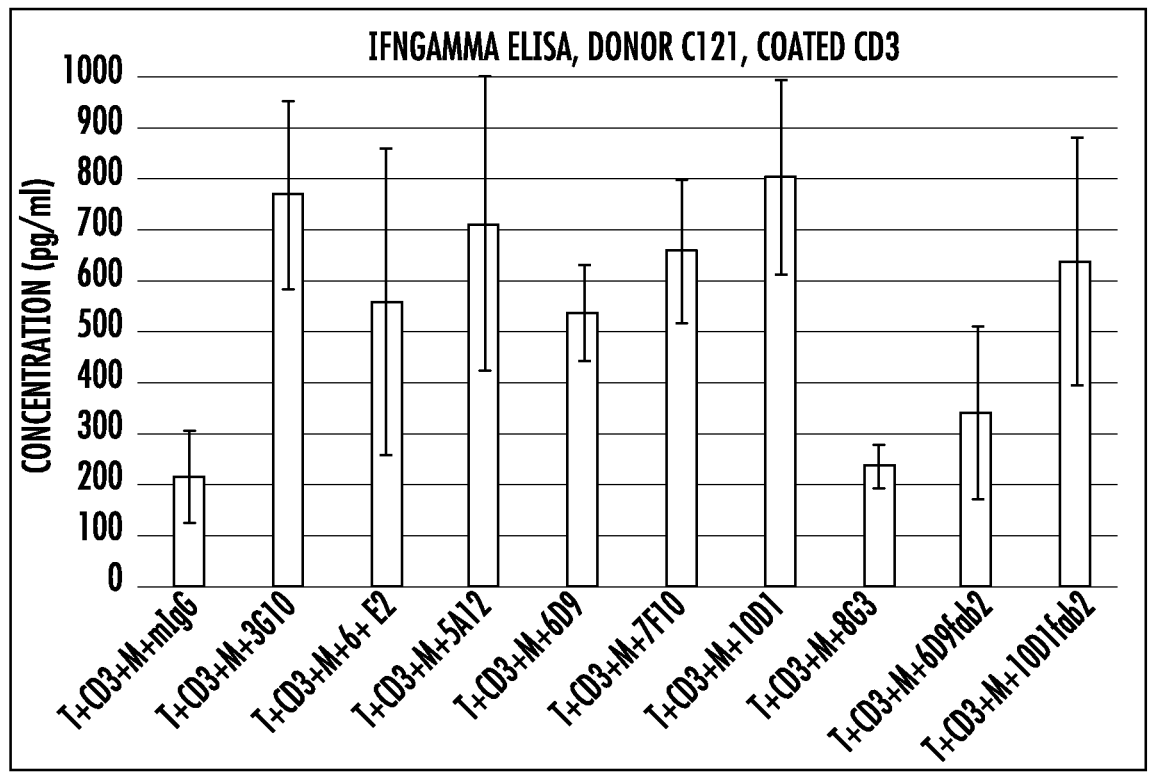

FIGS. 4A and 4B show that VTCN1 antibodies increase IFNγ secretion by CD4+ T cells when CD4+ T cells were co-cultured with autologous monocytes in the presence of low amount of CD3 antibody OKT3 (1 µg/ml coated on plate FIG. 4B or included in medium in solution FIG. 4A).

Example 9: Mouse VTCN1 Antibodies have ADCC Activity

Figure 5:
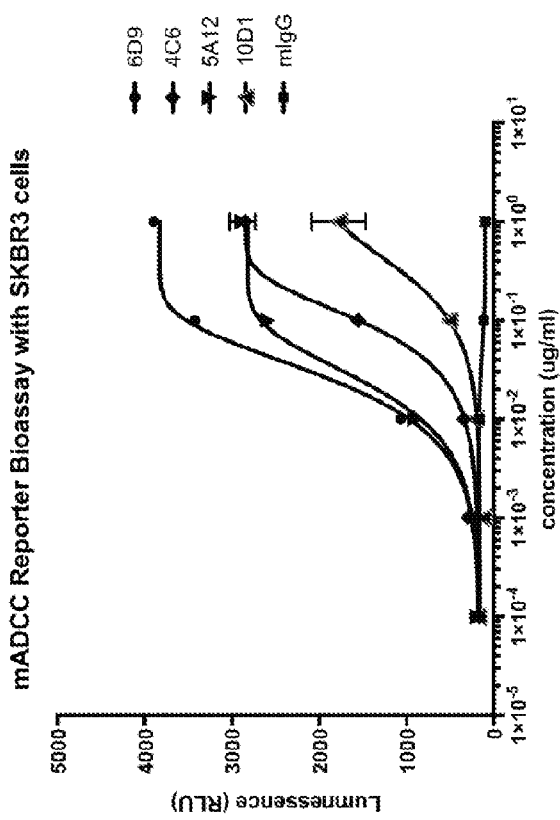
FIG. 5 shows anti-VTCN1 antibodies demonstrate ADCC activity in an ADCC reporter assay (SKBR3 cells are the target cells; Jurkat-mFcγR cells are the effector cells). The effector:target ratio is 8:1.
Figure 6A:
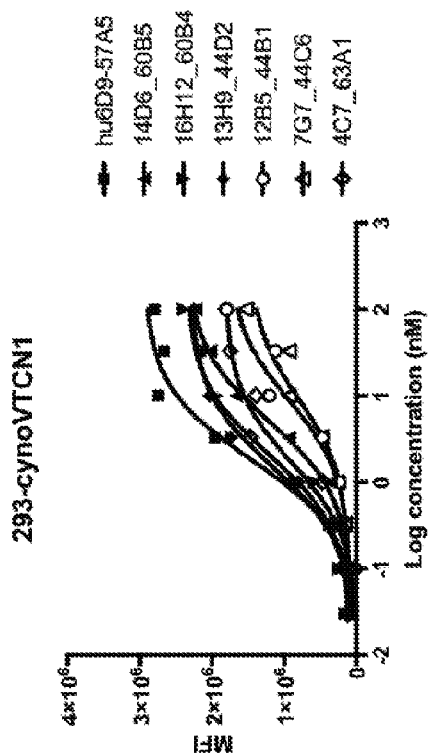
FIGS. 6A, 6B, 6C and FIG. 6D show anti-VTCN1 antibodies bind 293 cells expressing human, cynomolgus macaque, or mouse VTCN1 and wildtype SKBR3 cells naturally expressing VTCN1. Results shown are FACS analysis of serial diluted antibodies against 293-humanVTCN1 (FIG. 6A), 293-cynoVTCN1 (FIG. 6B), 293 mouseVTCN1 (FIG. 6C), and SKBR3 cells (FIG. 6D)
Figure 6C:
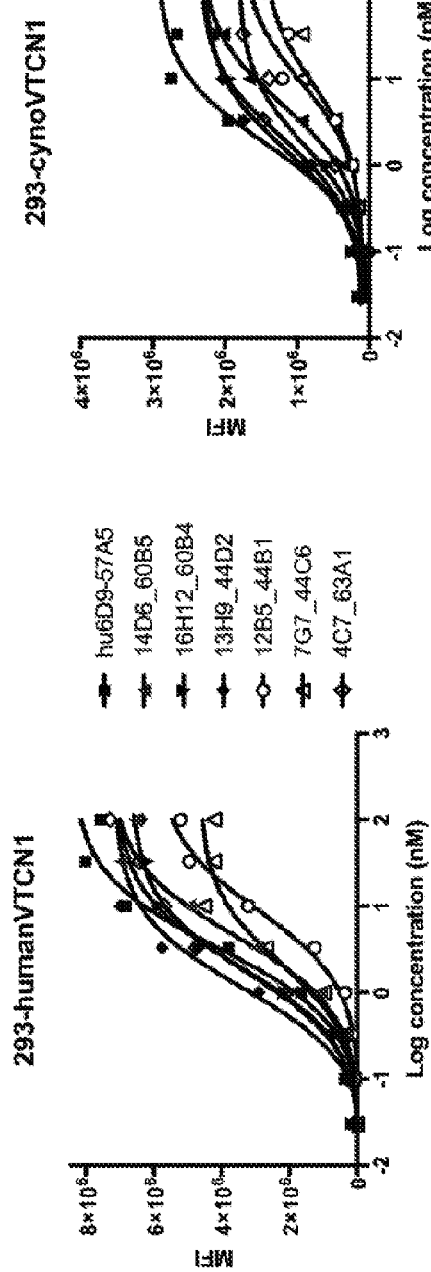
Figure 6B:
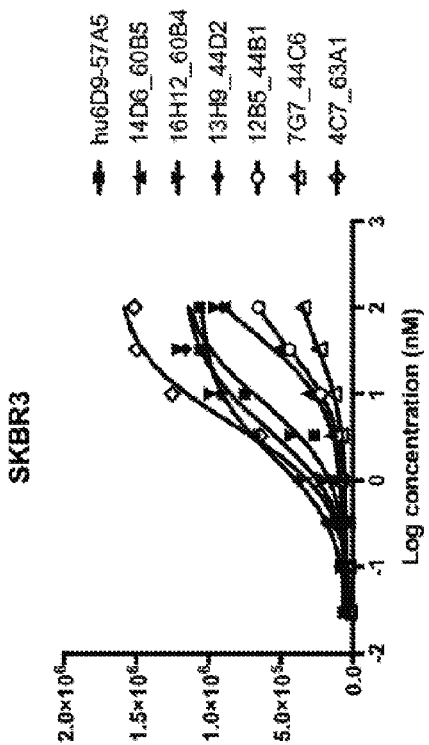
Figure 6D:
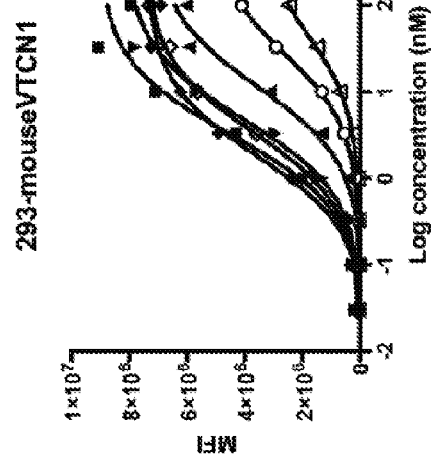

Mouse VTCN1 antibodies possess ADCC activity as shown in an ADCC reporter assay (Promega M1211). SKBR3 cells, which express the VTCN1 protein, were used as target cells in the assay. 5000 cells/well of SKBR3 were seeded in black 96 well plate the day before the assay was performed. To set up the assay, antibody serial dilutions were made ranging from 1 µg/ml to 0.1 ng/ml. Then 95 µl of culture medium was removed from each well of the SKBR3 cell plates, to which was added 25 µl of ADCC assay buffer (to each well), followed by the addition of 25 µl of diluted antibodies (to the assay wells). Subsequently, 25 µl of effector cells Jurkat-FcγR (effector:target ratio at 8:1) was added to the assay wells. The plates were incubated for 6 hours at 37° C. in a humidified $CO_2$ incubator. At the end of the incubation, 75 µl Bio-Glo Luciferase assay reagent was added to the assay wells, which were then incubated at room temperature for 30 min, after which the plates were analyzed in fluorescence plate reader. The absorbance curve was generated using GraphPad Prism software. The results in FIG. 5 show that VTCN1 antibodies tested possess ADCC activity.

Example 10: Humanization of Murine Antibody 6D9

The 6D9 murine antibody was humanized using complementarity determining region (CDR) grafting. Human frameworks for heavy and light chains were selected based on sequence and structure similarity with respect to functional human germline genes. In this regard, the structural similarity was evaluated by comparing the mouse canonical CDR structure to human candidates with the same canonical structures.

Specifically, the 6D9 antibody was humanized using a computer-aided CDR-grafting method and standard molecular engineering techniques to provide the human counterpart. The human framework regions of the variable regions were first sorted based on their highest sequence homology to the subject mouse framework sequence. And second, canonical residues known to be important for maintaining CDR structures were found to be the same or similar to the mouse donor sequence. Independently, IGHV3-66 and IGKV1-39 sequences were also used as a human acceptor framework based on previous stability properties of those frameworks. For the purposes of the humanization analysis, the assignment of amino acids to each of the CDR domains is in accordance with Kabat numbering.

For back mutation analysis in the framework region, a structural comparison between mouse and human homology models was analyzed. BioLuminate software was used to construct the homology models. The canonical residue positions, hydrophobic pockets in the proximity of heavy chain CDRs, and residues adjacent to the CDRs were examined. An emphasis was made to maintain the steric volume of the hydrophobic pockets between human candidates and mouse donor sequence as suggested by the homology models.

Molecular engineering procedures were conducted using recognized molecular biology techniques. Total mRNA was extracted from the hybridomas and amplified with appropriate oligonucleotide primers as set forth in Example 2.

From the nucleotide sequence information, data regarding V, D and J gene segments of the heavy and light chains of subject murine antibodies were obtained. Based on the sequence data new primer sets specific to the leader sequence of the IgVh and Vk light chains of the antibodies were designed for cloning of the recombinant monoclonal antibody. Subsequently, the V-D-J sequences were aligned with mouse IgG germ line sequences. The resulting genetic arrangements for each of the 6D9 humanized constructs are shown in Table 6 below. The process demonstrates that multiple framework changes in the heavy chain were required to maintain the favorable properties of the binding modulators. However, no framework modifications were needed for the light chain.

TABLE 6

Genetic arrangement of 6D9 humanized constructs

| Antibody Name | Human VH | Human JH | FW Changes | Human VK | Human JK | FW Changes |
|---|---|---|---|---|---|---|
| hu6D9_57A3 | IGHV3-33 | JH1 | A24V, V48L, A49G, F67L, R71K, L78V, L80F | IGKV1-39 | JK2 | none |
| hu6D9_57A4 | IGHV3-33 | JH1 | G9P, A24V, V48L, F67L, R71K, N76S, L78V, L80F | IGKV1-39 | JK2 | none |
| hu6D9_57A5 | IGHV3-33 | JH1 | A24V, V48L, F67L, R71K, L78V, L80F | IGKV1-39 | JK2 | none |
| hu6D9_66B1 | IGHV3-33 | JH1 | A24V, V48L, A49G, F67L, R71K, L78V, L80F | IGKV1-39 | JK2 | none |
| hu6D9_66C2 | IGHV3-66 | JH6 | A24V, V48L, S49G, F67L, R71K, L78V, L80F | IGKV1-39 | JK1 | G66R |

The humanized antibodies listed in Table 7, below, correspond to the annotated heavy and light chain sequences. The corresponding nucleic acid sequences of the heavy and light chain variable regions are set forth in Table 8.

TABLE 7

Anti-VTCN1 humanized antibody heavy and light chain variable region amino acid sequences

| SEQ ID NO: | Antibody Name | Protein Domain | Amino Acid Sequence |
|---|---|---|---|
| 220 | Hu6D9_57A3 | VH | QVQLVESGGGVVQPGRSLRLSCAVSGFSLTSYGVQWVRQAPGKGLEW LGVIWSSGSTDYNAAFLSRLTISKDNSKNTVYFQMNSLRAEDTAVYY CARDVTTIVEGFAHWGQGTLVTVSS |
| 221 | Hu6D9_57A3 | CDR-H1 | GFSLTSYGVQ |
| 222 | Hu6D9_57A3 | CDR-H2 | VIWSSGSTDYNAAFLS |
| 223 | Hu6D9_57A3 | CDR-H3 | DVTTIVEGFAH |
| 224 | Hu6D9_57A3 | VL | DIQMTQSPSSLSASVGDRVTITCKASEKVGTYVSWYQQKPGKAPKLL IYGASNRYTGVPSRFSGSGSGTDFTLTISSLQPEDFATYYCGQTYSY PFTFGQGTKLEIK |
| 225 | Hu6D9_57A3 | CDR-L1 | KASEKVGTYVS |
| 226 | Hu6D9_57A3 | CDR-L2 | GASNRYT |
| 227 | Hu6D9_57A3 | CDR-L3 | GQTYSYPFT |
| 228 | Hu6D9_57A4 | VH | QVQLVESGPGVVQPGRSLRLSCAVSGFSLTSYGVQWVRQAPGKGLEW LAVIWSSGSTDYNAAFLSRLTISKDNSKSTVYFQMNSLRAEDTAVYY CARDVTTIVEGFAHWGQGTLVTVSS |
| 229 | Hu6D9_57A4 | CDR-H1 | GFSLTSYGVQ |
| 230 | Hu6D9_57A4 | CDR-H2 | VIWSSGSTDYNAAFLS |
| 231 | Hu6D9_57A4 | CDR-H3 | DVTTIVEGFAH |
| 224 | Hu6D9_57A4 | VL | DIQMTQSPSSLSASVGDRVTITCKASEKVGTYVSWYQQKPGKAPKLL IYGASNRYTGVPSRFSGSGSGTDFTLTISSLQPEDFATYYCGQTYSY PFTFGQGTKLEIK |
| 225 | Hu6D9_57A4 | CDR-L1 | KASEKVGTYVS |
| 226 | Hu6D9_57A4 | CDR-L2 | GASNRYT |
| 227 | Hu6D9_57A4 | CDR-L3 | GQTYSYPFT |
| 232 | Hu6D9_57A5 | VH | QVQLVESGGGVVQPGRSLRLSCAVSGFSLTSYGVQWVRQAPGKGLEW LAVIWSSGSTDYNAAFLSRLTISKDNSKNTVYFQMNSLRAEDTAVYY CARDVTTIVEGFAHWGQGTLVTVSS |

TABLE 7-continued

Anti-VTCN1 humanized antibody heavy and light chain variable region amino acid sequences

| SEQ ID NO: | Antibody Name | Protein Domain | Amino Acid Sequence |
|---|---|---|---|
| 233 | Hu6D9_57A5 | CDR-H1 | GFSLTSYGVQ |
| 234 | Hu6D9_57A5 | CDR-H2 | VIWSSGSTDYNAAFLS |
| 235 | Hu6D9_57A5 | CDR-H3 | DVTTIVEGFAH |
| 224 | Hu6D9_57A5 | VL | DIQMTQSPSSLSASVGDRVTITCKASEKVGTYVSWYQQKPGKAPKLLIYGASNRYTGVPSRFSGSGSGTDFTLTISSLQPEDFATYYCGQTYSYPFTFGQGTKLEIK |
| 225 | Hu6D9_57A5 | CDR-L1 | KASEKVGTYVS |
| 226 | Hu6D9_57A5 | CDR-L2 | GASNRYT |
| 227 | Hu6D9_57A5 | CDR-L3 | GQTYSYPFT |
| 236 | Hu6D9_66B1 | VH | QVQLVESGGGVVQPGRSLRLSCAVSGFTFSSYGVQWVRQAPGKGLEWLGVIWSSGSTDYNAAFLSRLTISKDNSKNTVYFQMNSLRAEDTAVYYCARDVTTIVEGFAHWGQGTLVTVSS |
| 237 | Hu6D9_66B1 | CDR-H1 | GFTFSSYGVQ |
| 238 | Hu6D9_66B1 | CDR-H2 | VIWSSGSTDYNAAFLS |
| 239 | Hu6D9_66B1 | CDR-H3 | DVTTIVEGFAH |
| 224 | Hu6D9_66B1 | VL | DIQMTQSPSSLSASVGDRVTITCKASEKVGTYVSWYQQKPGKAPKLLIYGASNRYTGVPSRFSGSGSGTDFTLTISSLQPEDFATYYCGQTYSYPFTFGQGTKLEIK |
| 225 | Hu6D9_66B1 | CDR-L1 | KASEKVGTYVS |
| 226 | Hu6D9_66B1 | CDR-L2 | GASNRYT |
| 227 | Hu6D9_66B1 | CDR-L3 | GQTYSYPFT |
| 240 | Hu6D9_66C2 | VH | EVQLVESGGGLVQPGGSLRLSCAVSGFSLTSYGVQWVRQAPGKGLEWLGVIWSSGSTDYNAAFLSRLTISKDTSKNTVYFQMNSLRAEDTAVYYCARDVTTIVEGFAHWGQGTLVTVSS |
| 241 | Hu6D9_66C2 | CDR-H1 | GFSLTSYGVQ |
| 242 | Hu6D9_66C2 | CDR-H2 | VIWSSGSTDYNAAFLS |
| 243 | Hu6D9_66C2 | CDR-H3 | DVTTIVEGFAH |
| 244 | Hu6D9_66C2 | VL | DIQMTQSPSSLSASVGDRVTITCKASEKVGTYVSWYQQKPGKAPKLLIYGASNRYTGVPSRFSGSRSGTDFTLTISSLQPEDFATYYCGQTYSYPFTFGQGTKVEIK |
| 245 | Hu6D9_66C2 | CDR-L1 | KASEKVGTYVS |
| 246 | Hu6D9_66C2 | CDR-L2 | GASNRYT |
| 247 | Hu6D9_66C2 | CDR-L3 | GQTYSYPFT |

TABLE 8

Anti-VTCN1 humanized antibody heavy and light chain variable region nucleic acid sequences

| SEQ ID NO: | Antibody Name | Domain | DNA Sequence |
|---|---|---|---|
| 290 | Hu6D9_57A3 | VH | CAAGTTCAACTCGTGGAATCCGGTGGCGGGGTAGTACAACCTGGTCGCAGCCTCCGGCTTTCATGCGCTGTTAGTGGTTTCTCTCTCACATCTTACGGTGTGCAATGGGTACGGCAAGCCCCCGGCAAGGGTTTGGAATGGCTCGGAGTGATCTGGAGTAGCGGGTCTACCGACTATAACGCTGCGTTTCTTAGCAGGCTGACTATTTCTAAAGATAATTCCAAAAATACGGTTT |

TABLE 8-continued

Anti-VTCN1 humanized antibody heavy and light chain
variable region nucleic acid sequences

| SEQ ID NO: | Antibody Name | Domain | DNA Sequence |
|---|---|---|---|
| | | | ATTTCCAAATGAACTCCCTGCGGGCTGAAGACACTGCCGTTTATTAC<br>TGTGCTCGGGATGTTACAACGATTGTAGAAGGCTTCGCCCATTGGGG<br>CCAAGGGACATTGGTCACAGTATCCTCA |
| 291 | Hu6D9_57A3 | VL | GACATTCAGATGACCCAATCACCTAGTTCACTCTCAGCAAGTGTAGG<br>TGACAGAGTAACAATTACATGCAAGGCCAGCGAAAAAGTTGGCACCT<br>ACGTGAGTTGGTACCAGCAAAAACCGGGCAAAGCTCCGAAATTGCTT<br>ATTTACGGTGCTTCAAATCGCTATACTGGAGTGCCCAGTCGATTTAG<br>TGGGTCTGGCTCAGGTACCGACTTTACACTCACCATCTCTAGCCTGC<br>AGCCAGAGGACTTTGCGACGTATTATTGCGGCCAGACGTATAGTTAT<br>CCGTTCACCTTTGGACAAGGTACCAAGTTGGAAATAAAG |
| 292 | Hu6D9_57A4 | VH | CAAGTCCAGTTGGTTGAGAGCGGTCCTGGGGTCGTGCAGCCTGGGCG<br>GTCTCTGAGGCTGAGTTGTGCAGTGTCAGGTTTCAGCCTTACATCAT<br>ACGGGGTTCAATGGGTAAGGCAAGCACCTGGGAAAGGTCTGGAATGG<br>CTTGCGGTAATTTGGTCTAGCGGTAGCACTGACTACAATGCGGCGTT<br>TCTGAGTAGGCTCACGATTTCTAAAGACAATTCAAAAAGCACGGTTT<br>ATTTTCAAATGAACAGTCTTCGAGCAGAAGATACTGCTGTTTACTAT<br>TGTGCTCGCGACGTGACGACAATCGTGGAGGGATTCGCCCATTGGGG<br>TCAGGGCACCCTCGTTACTGTAAGTTCT |
| 291 | Hu6D9_57A4 | VL | GACATTCAGATGACCCAATCACCTAGTTCACTCTCAGCAAGTGTAGG<br>TGACAGAGTAACAATTACATGCAAGGCCAGCGAAAAAGTTGGCACCT<br>ACGTGAGTTGGTACCAGCAAAAACCGGGCAAAGCTCCGAAATTGCTT<br>ATTTACGGTGCTTCAAATCGCTATACTGGAGTGCCCAGTCGATTTAG<br>TGGGTCTGGCTCAGGTACCGACTTTACACTCACCATCTCTAGCCTGC<br>AGCCAGAGGACTTTGCGACGTATTATTGCGGCCAGACGTATAGTTAT<br>CCGTTCACCTTTGGACAAGGTACCAAGTTGGAAATAAAG |
| 293 | Hu6D9_57A5 | VH | CAGGTTCAACTTGTAGAGTCTGGTGGTGGAGTTGTGCAACCGGGTAG<br>GTCCCTCCGCCTCTCATGCGCAGTGTCTGGGTTCTCCTTGACTAGCT<br>ACGGGGTTCAGTGGGTCCGGCAAGCCCCAGGAAAGGGTCTTGAATGG<br>TTGGCAGTAATTTGGTCCAGCGGAAGTACCGATTATAACGCAGCCTT<br>CCTGTCCCGGTTGACCATAAGTAAGGATAATTCAAAAAACACCGTTT<br>ACTTTCAGATGAATAGTCTGCGAGCGGAGGACACAGCGGTTTACTAC<br>TGCGCTAGAGACGTTACCACCATTGTGGAAGGGTTTGCTCATTGGGG<br>TCAAGGGACACTTGTGACGGTTTCTAGC |
| 291 | Hu6D9_57A5 | VL | GACATTCAGATGACCCAATCACCTAGTTCACTCTCAGCAAGTGTAGG<br>TGACAGAGTAACAATTACATGCAAGGCCAGCGAAAAAGTTGGCACCT<br>ACGTGAGTTGGTACCAGCAAAAACCGGGCAAAGCTCCGAAATTGCTT<br>ATTTACGGTGCTTCAAATCGCTATACTGGAGTGCCCAGTCGATTTAG<br>TGGGTCTGGCTCAGGTACCGACTTTACACTCACCATCTCTAGCCTGC<br>AGCCAGAGGACTTTGCGACGTATTATTGCGGCCAGACGTATAGTTAT<br>CCGTTCACCTTTGGACAAGGTACCAAGTTGGAAATAAAG |
| 294 | Hu6D9_66B1 | VH | CAAGTTCAACTTGTTGAGTCAGGGGGAGGAGTTGTGCAACCGGGCCG<br>CTCCCTGCGACTTTCATGTGCAGTATCAGGCTTTACCTTTTCATCCT<br>ACGGGGTCCAATGGGTTAGGCAGGCTCAGGTAAAGGACTGGAATGG<br>CTTGGTGTAATATGGAGCAGCGGCAGTACGGATTACAATGCTGCATT<br>CTTGAGTCGGCTCACTATATCAAAGGACAACTCTAAGAATACCGTCT<br>ATTTTCAAATGAACTCACTGCGCGCCGAAGACACCGCAGTTTACTAT<br>TGCGCCCGAGATGTCACTACAATAGTGGAGGGTTTTGCACATTGGGG<br>CCAAGGAACCCTCGTAACTGTGTCCTCA |
| 291 | Hu6D9_66B1 | VL | GACATTCAGATGACCCAATCACCTAGTTCACTCTCAGCAAGTGTAGG<br>TGACAGAGTAACAATTACATGCAAGGCCAGCGAAAAAGTTGGCACCT<br>ACGTGAGTTGGTACCAGCAAAAACCGGGCAAAGCTCCGAAATTGCTT<br>ATTTACGGTGCTTCAAATCGCTATACTGGAGTGCCCAGTCGATTTAG<br>TGGGTCTGGCTCAGGTACCGACTTTACACTCACCATCTCTAGCCTGC<br>AGCCAGAGGACTTTGCGACGTATTATTGCGGCCAGACGTATAGTTAT<br>CCGTTCACCTTTGGACAAGGTACCAAGTTGGAAATAAAG |
| 295 | Hu6D9_66C2 | VH | GAGGTCAACTCGTGGAATCTGGAGGAGGTTTGGTTCAGCCAGGCGG<br>TTCTCTCCGACTGTCTTGCGCTGTAAGTGGATTAGTCTGACGTCCT<br>ATGGAGTACAGTGGGTGCGCCAAGCTCCTGGGAAGGGCTTGGAATGG<br>TTGGGGGTGATCTGGTCTTCCGGTTCTACAGATTACAATGCAGCATT<br>CCTCTCACGCCTGACTATAAGTAAAGATACTTCTAAAAATACCGTCT<br>ACTTTCAGATGAACAGTCTTAGGGCTGAGGATACTGCGGTCTACTAT<br>TGTGCGAGGGATGTCACGACGATTGTAGAAGGATTCGCTCACTGGGG<br>CCAGGGCACTTTGGTAACAGTCTCCTCA |
| 296 | Hu6D9_66C2 | VL | GACATTCAGATGACTCAATCTCCTTCATCCCTTAGCGCATCCGTAGG<br>AGATCGAGTGACCATAACATGCAAGGCCTCTGAGAAAGTAGGGACTT |

TABLE 8-continued

Anti-VTCN1 humanized antibody heavy and light chain
variable region nucleic acid sequences

| SEQ ID NO: | Antibody Name | Domain | DNA Sequence |
|---|---|---|---|
| | | | ACGTGAGCTGGTATCAGCAAAAGCCGGGGAAAGCACCGAAGTTGCTC<br>ATTTATGGGGCGTCTAATAGGTACACGGGAGTCCCGAGCAGATTTTC<br>CGGCTCTCGGAGTGGAACCGACTTTACCCTTACAATTAGTAGTCTCC<br>AACCTGAGGATTTTGCCACGTACTACTGTGGCCAGACTTACTCTTAT<br>CCATTTACATTCGGCCAAGGTACGAAGGTTGAAATTAAA |

Note that for some humanized light and heavy chain variable regions, conservative amino acid mutations were introduced in the CDRs to address stability concerns while maintaining antigen binding. In each case, the binding affinity of the antibodies with modified CDRs was found to be equivalent or within 2-fold of the chimeric antibody.

Table 9, below, shows affinity of humanized 6D9 antibodies against human VTCN1 protein as determined by OCTET™ binding.

TABLE 9

Affinity of humanized 6D9 antibodies against human VTCN1 protein by OCTET ™

| Clone | KD, nM | k(on) | K(off) |
|---|---|---|---|
| hu6D9_57A3 | 28 | 8.21E+04 | 2.27E-03 |
| hu6D9_57A4 | 36 | 6.21E+04 | 2.26E-03 |
| hu6D9_57A5 | 36 | 8.14E+04 | 2.89E-03 |
| hu6D9_66B1 | 27 | 1.20E+05 | 3.25E-03 |
| hu6D9_66C2 | 44 | 1.82E+05 | 7.94E-03 |

Example 11: Generation of Fully Human VTCN1 Antibodies Against Human VTCN1

In order to generate more fully human VTCN1 antibodies besides clone 7C8, a second hybridoma campaign using humanized mice H2L2 was performed. The mice were immunized with either human VTCN1-his recombinant protein, or 293 cells expressing the human VTCN1 gene. Hybridoma generation and screening were performed using the same procedure described in Example 5.

6 Clones: 4C7_63A1, 7G7_44C6, 13H9_44D2, 12B5_44B1, 14D6_60B5, and 16H12_60B4 were chosen for further characterization. Clones 4C7_63A1, 7G7_44C6, 13H9_44D2 were obtained from 293-VTCN1 immunization. Clones 12B5_44B1, 14D6_60B5, and 16H12_60B4 were obtained from VTCN1-his protein immunization.

Table 10, below, shows sequences of variable regions of the heavy chain and light chain from these human antibodies. The corresponding nucleic acid sequences of the heavy and light chain variable regions are set forth in Table 11.

TABLE 10

Anti-VTCN1 human antibody heavy and light chain
variable region amino acid sequences

| SEQ ID NO: | Antibody Name | Protein Domain | Amino Acid Sequence |
|---|---|---|---|
| 248 | 4C7_63A1 | VH | QVQLQESGPGLVKPSGTLSLTCAVSGGSISSSNWWSWVRQPPGKGLE<br>AIGEIYHSGNTNYNPSLKSRVTISVDKSKNQFSLKLSSVTAADTAIY<br>YCARDGYSSGWYWGYFDYWGQGTLVTVSS |
| 249 | 4C7_63A1 | CDR-H1 | GGSISSSNWWS |
| 250 | 4C7_63A1 | CDR-H2 | EIYHSGNTNYNPSLKS |
| 251 | 4C7_63A1 | CDR-H3 | DGYSSGWY |
| 252 | 4C7_63A1 | VL | EIVMTQSPATLSVSPGERATLSCRASQSVNSNLAWYQQKPGQAPWLL<br>IYGASTRATGIPARFSGSGSGTEFTLTISSLQSEDFAVYYCQQYNHW<br>PYTFGQGTKLEIK |
| 253 | 4C7_63A1 | CDR-L1 | RASQSVNSNLA |
| 254 | 4C7_63A1 | CDR-L2 | GASTRAT |
| 255 | 4C7_63A1 | CDR-L3 | QQYNHWPYT |
| 256 | 7G7_44C6 | VH | QVQLQESGPGLVKPSETLSLTCTVSGGSISHYYWSWIRQPPGKGLEW<br>IGYIYYSGPTNYNPSLKSRVTISVDTSKNQFSLKLSSVTAADTAVYY<br>CARTYYYGSGSFPDAFDIWGQGTMVTVSS |
| 257 | 7G7_44C6 | CDR-H1 | GGSISHYYWS |
| 258 | 7G7_44C6 | CDR-H2 | YIYYSGPTNYNPSLKS |
| 259 | 7G7_44C6 | CDR-H3 | TYYYGSGSFPDAFDI |

TABLE 10-continued

Anti-VTCN1 human antibody heavy and light chain variable region amino acid sequences

| SEQ ID NO: | Antibody Name | Protein Domain | Amino Acid Sequence |
|---|---|---|---|
| 260 | 7G7_44C6 | VL | KIVLTQSPATLSLSPGERATLSCRASQSVSSYLAWYQQTPGQAPRLLIYDASNRATGIPARFSVSGSGTDFTLTISSLEPEDFAVYYCQQRSSWPLTFGGGTKLEIK |
| 261 | 7G7_44C6 | CDR-L1 | RASQSVSSYLA |
| 262 | 7G7_44C6 | CDR-L2 | DASNRAT |
| 263 | 7G7_44C6 | CDR-L3 | QQRSSWPLT |
| 264 | 12B5_44B1 | VH | QVQLVQSGAEVKKPGSSMKVSCKASGDTFSSYAISWVRQAPGQGLEWMAGIIPVFGTAHNAQKFQGRVTITADKSTSTAYMELSSLRSEDTAVYYCTRGGPYFDYWGQGTLVTVSS |
| 265 | 12B5_44B1 | CDR-H1 | GDTFSSYAIS |
| 266 | 12B5_44B1 | CDR-H2 | GIIPVFGTAHNAQKFQG |
| 267 | 12B5_44B1 | CDR-H3 | GGPYFDY |
| 268 | 12B5_44B1 | VL | EIVMTQSPATLSVSPGERAALSCRASQSVSSNLAWYQQKPGQAPRLLIYGVSTRATGIPDRFNGSGSGTEFTLTISSLQSEDFGAYYCQQYKKWPFIFGPGTKLEIK |
| 269 | 12B5_44B1 | CDR-L1 | RASQSVSSNLA |
| 270 | 12B5_44B1 | CDR-L2 | GVSTRAT |
| 271 | 12B5_44B1 | CDR-L3 | QQYKKWPFI |
| 272 | 13H9_44D2 | VH | QVQLQESGPGLVKPSETLSLTCTVSGGSISSYYWSWIRQPPGKGLEWIGYIYYSGSTNNNPSLKSRVTISVDTSKNQFSLKLISVTAADTAVYYCARVYNNYDWGFDYWGQGTLVTVSS |
| 273 | 13H9_44D2 | CDR-H1 | GGSISSYYWS |
| 274 | 13H9_44D2 | CDR-H2 | YIYYSGSTNNNPSLKS |
| 275 | 13H9_44D2 | CDR-H3 | VYNNYDWGFDY |
| 276 | 13H9_44D2 | VL | EIVMTQSPATLSVSPGERATLSCRASQSVSSNLAWYQQKPGQAPRLLIYGASTRATGIPARFSGSGSGTEFTLTIRSLQSEDFAVYYCQQYHNWPLTFGGGTKLEIK |
| 269 | 13H9_44D2 | CDR-L1 | RASQSVSSNLA |
| 254 | 13H9_44D2 | CDR-L2 | GASTRAT |
| 277 | 13H9_44D2 | CDR-L3 | QQYHNWPLT |
| 278 | 14D6_60B5 | VH | QVQLVHSGAEVKRPGSSVKVSCKASGGTFSSYAISWVRQAPGQGLEWMGGIIPIFGIANYAQKFQGRVTIIADKSTRTAYMELSSLRSEDTAVYYCARGGPYFDYWGQGILVTVSS |
| 279 | 14D6_60B5 | CDR-H1 | GGTFSSYAIS |
| 280 | 14D6_60B5 | CDR-H2 | GIIPIFGIANYAQKFQG |
| 267 | 14D6_60B5 | CDR-H3 | GGPYFDY |
| 281 | 14D6_60B5 | VL | EIVMTQSPATLSVSPGERATLSCRASQSVSSNLAWYQQKPGQAPRLLIYGASTRATGIPARFSGSGSGTEFTLTISSLQSEDFAVYYCQQYNKWPFTFGPGTKVDIK |
| 269 | 14D6_60B5 | CDR-L1 | RASQSVSSNLA |
| 254 | 14D6_60B5 | CDR-L2 | GASTRAT |
| 282 | 14D6_60B5 | CDR-L3 | QQYNKWPFT |
| 283 | 16H12_60B4 | VH | QVQVVQSGAEVKKPGSSVKVSCKASGDTFSNYAISWVRQAPGQGLEWMGGIIPIFGITNYAQKFQGRVTIIADKSTRTAYMELSSLRSEDTAVYYCSRGGPYFDYWGQGILVTVSS |

TABLE 10-continued

Anti-VTCN1 human antibody heavy and light chain
variable region amino acid sequences

| SEQ ID NO: | Antibody Name | Protein Domain | Amino Acid Sequence |
|---|---|---|---|
| 284 | 16H12_60B4 | CDR-H1 | GDTFSNYAIS |
| 285 | 16H12_60B4 | CDR-H2 | GIIPIFGITNYAQKFQG |
| 267 | 16H12_60B4 | CDR-H3 | GGPYFDY |
| 286 | 16H12_60B4 | VL | EIVMTQSPATLSVSPGERATLSCRASQSVSSNLAWYQQKPGQAPRLLIYGASTRATGIPARFSGSGSGTEFTLTISSLQSEDFAVYYCQQYKKWPFTFGPGTKVDIK |
| 269 | 16H12_60B4 | CDR-L1 | RASQSVSSNLA |
| 254 | 16H12_60B4 | CDR-L2 | GASTRAT |
| 287 | 16H12_60B4 | CDR-L3 | QQYKKWPFT |

TABLE 11

Anti-VTCN1 human antibody heavy and light chain
variable region nucleic acid sequences

| SEQ ID NO: | Antibody Name | Domain | DNA Sequence |
|---|---|---|---|
| 297 | 4C7_63A1 | VH | CAGGTGCAGCTGCAGGAGTCGGGCCCAGGACTGGTGAAGCCTTCGGGGACCCTGTCCCTCACCTGCGCTGTCTCTGGTGGCTCCATCAGCAGTAGTAACTGGTGGAGTTGGGTCCGCCAGCCCCCAGGGAAGGGGCTGGAGGCCATTGGGGAAATCTATCATAGTGGAAACACCAACTACAACCCGTCCCTCAAGAGTCGAGTCACCATATCAGTAGACAAGTCCAAGAACCAGTTCTCCCTGAAGCTGAGCTCTGTGACCGCCGCGGACACGGCCATTTATTACTGTGCGAGAGATGGGTATAGCAGTGGCTGGTACTGGGGCTACTTTGACTACTGGGGCCAGGGAACCCTGGTCACCGTCTCCTCA |
| 298 | 4C7_63A1 | VL | GAAATAGTGATGACGCAGTCTCCAGCCACCCTGTCTGTGTCTCCAGGGGAAAGAGCCACCCTCTCCTGCAGGGCCAGTCAGAGTGTTAACAGCAACTTAGCCTGGTACCAGCAGAAACCTGGCCAGGCTCCCTGGCTCCTCATCTATGGTGCATCCACCAGGGCCACTGGTATCCCAGCCAGGTTCAGTGGCAGTGGGTCTGGGACAGAGTTCACTCTCACCATCAGCAGCCTGCAGTCTGAAGATTTTGCAGTTTATTACTGTCAGCAGTATAATCACTGGCCGTACACTTTTGGCCAGGGGACCAAGCTGGAGATCAAA |
| 299 | 7G7_44C6 | VH | CAGGTGCAGCTGCAGGAGTCGGGCCCCGGACTGGTGAAGCCTTCGGAGACCCTGTCCCTCACCTGCACTGTCTCTGGTGGCTCCATCAGTCATTACTACTGGAGCTGGATCCGGCAGCCCCCAGGGAAGGGACTGGAGTGGATTGGGTATATCTATTACAGTGGGCCCACCAACTACAACCCCTCCCTCAAGAGTCGAGTCACCATATCAGTAGACACGTCCAAGAACCAGTTCTCCCTGAAGCTGAGCTCTGTGACCGCTGCGGACACGGCCGTGTATTACTGTGCGAGGACGTATTACTATGGTTCGGGGAGTTTTCCCGATGCTTTTGATATCTGGGGCCAAGGGACAATGGTCACCGTCTCCTCA |
| 300 | 7G7_44C6 | VL | AAAATTGTGTTGACACAGTCTCCAGCCACCCTGTCTTTGTCTCCAGGTGAAAGAGCCACCCTCTCCTGCAGGGCCAGTCAGAGTGTTAGCAGCTACTTAGCCTGGTACCAACAGACACCTGGCCAGGCTCCCAGGCTCCTCATCTATGATGCATCCAACAGGGCCACTGGCATCCCAGCCAGGTTCAGTGTCAGTGGGTCTGGGACAGACTTCACTCTCACCATCAGCAGCCTAGAGCCTGAAGATTTTGCAGTTTATTACTGTCAGCAGCGTAGCAGCTGGCCTCTCACTTTCGGCGGAGGGACCAAGCTGGAGATCAAA |
| 301 | 12B5_44B1 | VH | CAGGTGCAGCTGGTGCAGTCTGGGGCTGAGGTGAAGAAGCCTGGGTCCTCAATGAAGGTCTCCTGCAAGGCTTCTGGAGACACCTTCAGCAGCTATGCTATCAGCTGGGTGCGACAGGCCCCTGGACAAGGGCTTGAGTGGATGGCAGGGATCATCCCTATCTTTGGTACAGCACACAACGCACAGAAGTTCCAGGGCAGAGTCACGATTAGCGCGGACAAATCCACGAGCACAGCCTACATGGAGCTGAGCAGCCTGAGATCTGAGGACACGGCCGTGTATTACTGTACGAGAGGGGGTCCTTACTTTGACTACTGGGGCCAGGGAACCCTGGTCACCGTCTCCTCA |
| 302 | 12B5_44B1 | VL | GAAATAGTGATGACGCAGTCTCCAGCCACCCTGTCTGTGTCTCCAGGGGAAAGAGCCGCCCTCTCCTGTAGGGCCAGTCAGAGTGTTAGCAGCAACTTAGCCTGGTACCAGCAGAAACCTGGCCAGGCTCCCAGGCTCCTCATCTATGGTGTTTCTACCAGGGCCACTGGTATCCCAGACAGGTTCAA |

TABLE 11-continued

Anti-VTCNI human antibody heavy and light chain
variable region nucleic acid sequences

| SEQ ID NO: | Antibody Name | Domain | DNA Sequence |
|---|---|---|---|
| | | | TGGCAGTGGGTCTGGGACAGAGTTCACTCTCACCATCAGCAGCCTGC<br>AGTCTGAAGATTTTGGAGCTTATTACTGTCAGCAGTATAAAAAGTGG<br>CCATTCATTTTCGGCCCTGGGACCAAGCTGGAGATCAAA |
| 303 | 13H9_44D2 | VH | CAGGTGCAGCTGCAGGAGTCGGGCCCAGGACTGGTGAAGCCTTCGGA<br>GACCCTGTCCCTCACCTGCACTGTCTCTGGTGGCTCCATCAGTAGTT<br>ACTACTGGAGCTGGATCCGGCAGCCCCCAGGGAAGGGACTGGAGTGG<br>ATTGGGTATATCTATTACAGTGGGAGTACCAATAACAACCCCTCCCT<br>CAAGAGTCGAGTCACCATATCAGTAGACACGTCCAAGAACCAGTTCT<br>CCCTGAAGCTGATCTCTGTGACCGCTGCGGACACGGCCGTATACTAC<br>TGTGCGAGGGTCTATAATAATTACGATTGGGGCTTTGACTACTGGGG<br>CCAGGGAACCCTGGTCACCGTCTCCTCA |
| 304 | 13H9_44D2 | VL | GAAATAGTAATGACGCAGTCTCCAGCCACCCTGTCTGTGTCTCCAGG<br>GGAGAGAGCCACCCTCTCCTGCAGGGCCAGTCAGAGTGTTAGCAGCA<br>ACTTAGCCTGGTACCAGCAGAAACCTGGTCAGGCTCCCAGACTCCTC<br>ATCTATGGTGCATCCACCAGGGCCACTGGTATCCCAGCCAGGTTCAG<br>TGGCAGTGGGTCTGGGACAGAGTTCACTCTCACCATCCGCAGCCTGC<br>AGTCTGAAGATTTTGCAGTTTATTACTGTCAGCAGTATCATAACTGG<br>CCTCTCACTTTCGGCGGAGGGACCAAGCTGGAGATCAAA |
| 305 | 14D6_60B5 | VH | CAGGTGCAGCTGGTTCATTCTGGGGCTGAGGTGAAGAGGCCTGGGTC<br>CTCGGTGAAGGTCTCCTGCAAGGCTTCTGGAGGCACCTTCAGCAGCT<br>ATGCTATCAGTTGGGTGCGACAGGCCCCTGGACAAGGGCTTGAGTGG<br>ATGGGAGGGATCATCCCTATCTTTGGTATAGCAAACTACGCACAGAA<br>GTTCCAGGGCAGAGTCACGATTATCGCGGACAAATCCACGAGGACAG<br>CCTACATGGAGCTGAGCAGCCTGAGATCTGAGGACACGGCCGTGTAT<br>TACTGTGCGAGAGGGGGTCCTTACTTTGACTACTGGGGCCAGGGAAT<br>CCTGGTCACCGTCTCCTCA |
| 306 | 14D6_60B5 | VL | GAAATAGTGATGACGCAGTCTCCAGCCACCCTGTCTGTGTCTCCAGG<br>GGAAAGAGCCACCCTCTCCTGCAGGGCCAGTCAGAGTGTTAGCAGCA<br>ACTTAGCCTGGTACCAGCAGAAACCTGGCCAGGCTCCCAGGCTCCTC<br>ATCTATGGTGCATCCACCAGGGCCACTGGTATCCCAGCCAGGTTCAG<br>TGGCAGTGGGTCTGGGACAGAGTTCACTCTCACCATCAGCAGCCTGC<br>AGTCTGAAGATTTTGCAGTTTATTACTGTCAGCAGTATAATAAGTGG<br>CCATTCACTTTCGGCCCTGGGACCAAAGTGGATATCAAA |
| 307 | 16H12_60B4 | VH | CAGGTGCAGGTGGTGCAGTCTGGGGCTGAGGTGAAGAAGCCTGGGTC<br>CTCGGTGAAGGTCTCCTGCAAGGCTTCTGGAGACACCTTCAGCAACT<br>ATGCTATCAGTTGGGTGCGACAGGCCCCTGGACAAGGACTTGAGTGG<br>ATGGGAGGGATCATCCCTATCTTTGGTATAACAAACTACGCACAAAA<br>GTTCCAGGGCAGAGTCACGATTATCGCGGACAAATCCACGAGGACAG<br>CCTACATGGAGCTGAGCAGCCTGAGATCTGAGGACACGGCCGTGTAT<br>TACTGTTCGAGAGGGGGTCCTTACTTTGACTACTGGGGCCAGGGAAT<br>CCTGGTCACCGTCTCCTCA |
| 308 | 16H12_60B4 | VL | GAAATAGTGATGACGCAGTCTCCAGCCACCCTGTCTGTGTCTCCAGG<br>GGAAAGAGCCACCCTCTCCTGCAGGGCCAGTCAGAGTGTGAGCAGCA<br>ACTTAGCCTGGTACCAGCAGAAACCTGGCCAGGCTCCCAGGCTCCTC<br>ATCTATGGTGCATCCACCAGGGCCACTGGTATCCCAGCCAGGTTCAG<br>TGGCAGTGGGTCTGGGACAGAGTTCACTCTCACCATCAGCAGCCTGC<br>AGTCTGAAGATTTTGCAGTTTATTACTGTCAGCAGTATAAAAAGTGG<br>CCATTCACTTTCGGCCCTGGGACCAAAGTGGATATCAAA |

Table 12, below, shows the affinity of these human antibodies against human, cynomolgus monkey, and mouse VTCN1 proteins determined by OCTET™.

TABLE 12

Affinity of human VTCN1 antibodies

| clone | Human | | | cynomolgus monkey | | | mouse | | |
|---|---|---|---|---|---|---|---|---|---|
| | KD, nM | k(on) | K(off) | KD, nM | k(on) | k(off) | KD, nM | k(on) | k(off) |
| 4C7_63A1 | 49 | 1.19E+05 | 5.81E−03 | 47 | 1.23E+05 | 5.80E−03 | 44 | 9.07E+04 | 4.01E−03 |
| 7G7_44C6 | 192 | 8.42E+05 | 1.62E−01 | 227 | 6.61E+05 | 1.50E−01 | >500 | n/a | n/a |
| 13H9_44D2 | 128 | 1.33E+06 | 1.71E−01 | 144 | 1.16E+06 | 1.67E−01 | 268 | 2.16E+06 | 5.79E−01 |
| 12B5_44B1 | 2 | 1.61E+05 | 3.54E−04 | 2 | 1.80E+05 | 3.74E−04 | 38 | 2.15E+05 | 8.11E−03 |
| 14D6_60B5 | 5 | 1.32E+05 | 6.29E−04 | 5 | 1.32E+05 | 6.91E−04 | 56 | 1.15E+05 | 6.47E−03 |
| 16H12_60B4 | 0.7 | 2.62E+05 | 1.95E−04 | 1 | 2.45E+05 | 2.40E−04 | 27 | 1.37E+05 | 3.76E−03 |

To assess if these human VTCN1 antibodies bind to same or different regions of VTCN1 protein, a cell-based competition binding FACS assay was performed. 293 cells expressing recombinant human VTCN1 were incubated with 10 ug/ml of murine VTCN1 antibody 6D9 for 40 minutes in 50 ul on ice, then human VTCN1 antibodies 4C7_63A1, 7G7_44C6, 13H9_44D2, 12B5_44B1, 14D6_60B5, and 16H12_60B4, at final concentration of 1 ug/ml was added to individual wells in 96 well plate, the binding was incubated for 40 min on ice, was then washed twice, and subsequently incubated with anti-human-Alexa 647 for 30 minutes on ice, and washed twice. The cells were then resuspend in FACS buffer with DAPI, and analyzed by flow cytometry.

The results show that 4C7_63A1, 7G7_44C6, and 13H9_44 D2 compete with 6D9 to bind to the same region of VTCN1 protein, but 12B5_44B1, 14D6_60B5, and 16H12_60B4 do not compete with 6D9, indicating that they bind to different regions on VTCN1 protein. It was also assessed whether these antibodies bind to IgV or IgC domain of VTCN1 protein, using 293-VTCN1-IgV domain expressing cells and 293-VTCN1-IgC domain expressing cells using FACS analysis, as in Example 3. The results show that all the antibodies tested bind to the IgV domain of VTCN1.

Flow cytometry analysis of a serial titration (0.03 nM-100 nM) of antibodies binding to 293-humanVTCN1, 293-cynoVTCN1, 293-mouseVTCN1, and human breast cancer cell line SKBR3 showed that these antibodies have good cell binding activity. Cells were incubated with antibodies for 30 minutes on ice, and then washed. Dye labeled secondary antibody was added at excess and incubated on ice for 20 minutes, and then washed. Fluorescence signal read from flow cytometer was plotted and EC50 was calculated with Prism™ software. FIG. 6A, FIG. 6B, FIG. 6C and FIG. 6D show the binding curve of human VTCN1 antibodies from flow cytometry analysis, and Table 13, below, contains a summary of cell binding EC50 of these antibodies.

TABLE 13 cell binding EC50 (nM) of human VTCNI antibodies by flow cytometry analysis

| | 4C7_63A1 | 7G7_44C6 | 13H9_44D2 | 12B5_44B1 | 14D6_60B5 | 16H12_60B4 |
|---|---|---|---|---|---|---|
| 293-huVTCNI | 2.1 | 2.2 | 1.2 | 9.0 | 4.6 | 1.7 |
| 293-cynoVTCNI | 1.7 | 9.2 | 1.5 | 9.0 | 5.1 | 2.1 |
| 293-muVTCNI | 3.5 | 45.0 | 1.8 | 28.5 | 11.4 | 4.8 |
| SKBR3 | 4.4 | 36.8 | 1.9 | 35.5 | 51.4 | 4.0 |

Figure 7:
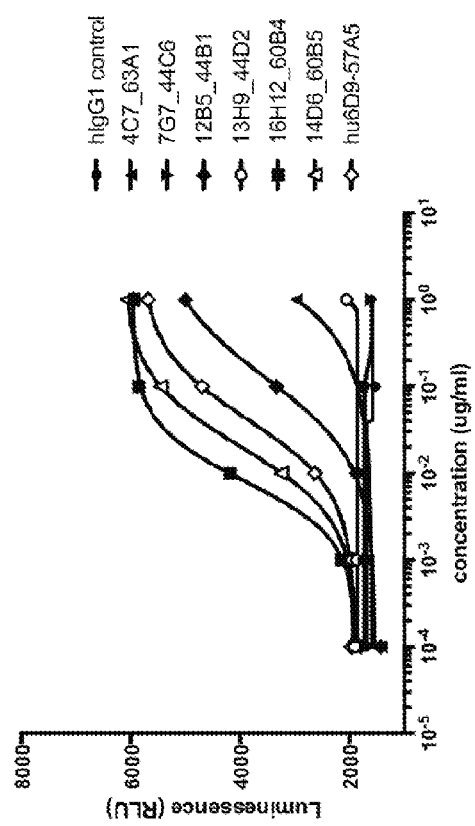
FIG. 7 shows human anti-VTCN1 antibodies have ADCC activity in an ADCC reporter assay. SKBR3 cells are the target cells and Jurkat-huFcγR cells are the effector cells. Effector and target ratio is 9:1.

Mouse VTCN1 antibodies possess ADCC activity as shown by ADCC reporter assay (Promega M1211), as described in Example 9. The results in FIG. 7 show that human VTCN1 antibodies also possess ADCC activity.

Example 12: Identification of Syngeneic Mouse Tumor Models Expressing VTCN1 for In Vivo Efficacy Studies of VTCN1 Antibodies The proteomics methods described for Example 1 for VTCN1 expression analysis were also used to evaluate syngeneic mouse cell lines and harvested xenograft tumors for VTCN1 expression. Mouse tumor cells lines were cultured to 70-80% confluency, harvested with trypsin, washed with cold PBS two times, and resuspended in PBS to achieve appropriate working concentrations. 0.1-1 million cells were injected subcutaneously into appropriate syngeneic mouse strains. Tumor growth was assessed every two days and when tumor reached 700-1000 mm$^3$, the mice were humanely euthanized, tumors harvested, flash frozen in liquid nitrogen and stored at –80° C. Separately, these same cell lines were grown in culture until plates were 70-80% confluent and then cells were harvested by mechanical scraping, and centrifuged to pellet the cells. The cells were washed two times with cold PBS and pelleted again by centrifugation. Cell pellets were stored at –80° C. until use. Both frozen tumor tissues and cell pellets were lysed in urea buffer to make cell lysate, and lysate was digested with trypsin to make peptides. Proteomic analysis was performed as described in Example 1.

Figure 8:
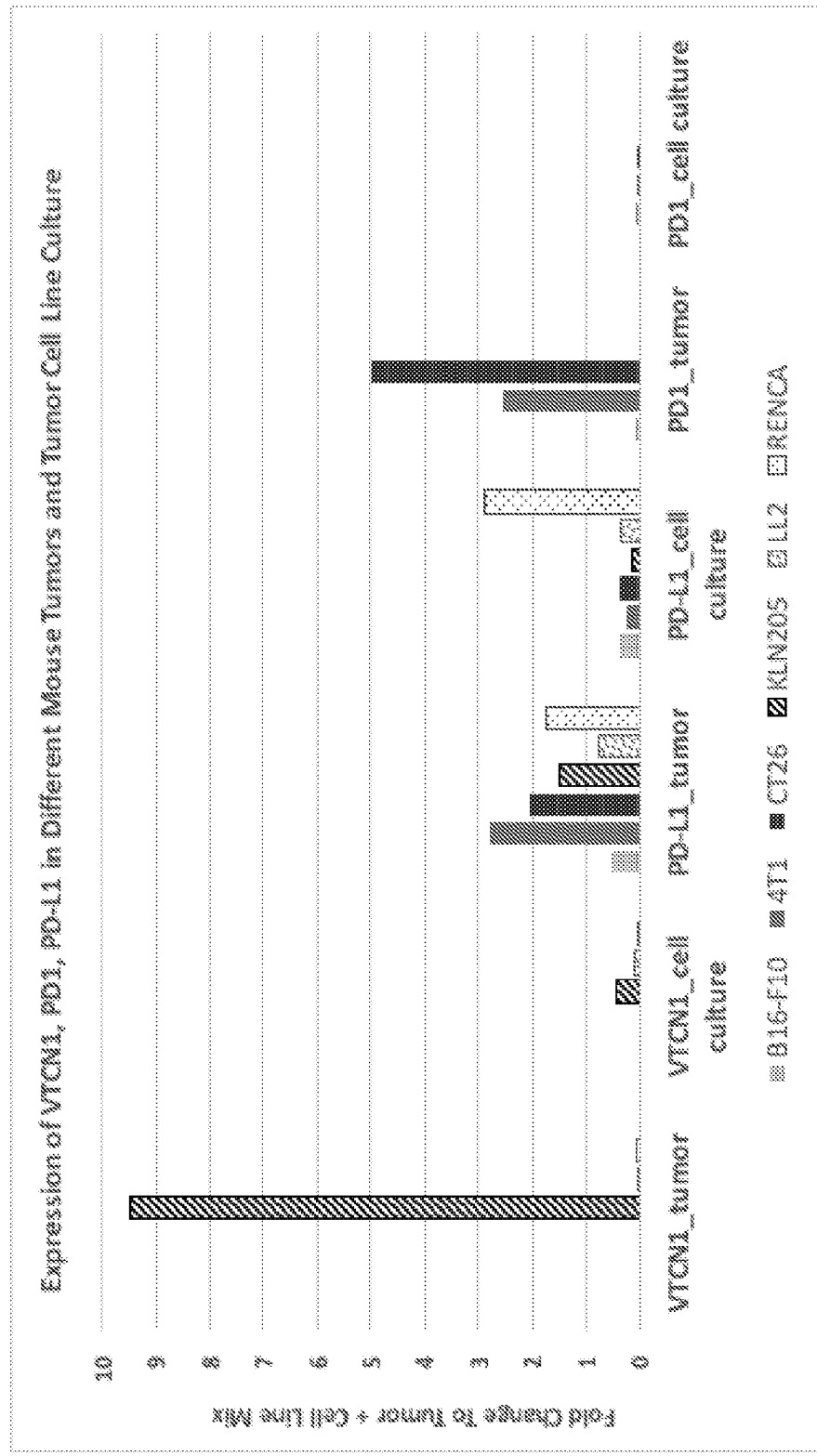
FIG. 8 shows VTCN1, PD-L1, and PD-1 expression in syngeneic cell lines. VTCN1 expression is markedly increased in KLN205 tumors harvested from implanted mice relative to the KLN205 cell line grown in 2-D culture. PD-L1 expression is increased in B16-F10, 4T1, CT26, KLN205, and LL2 tumors harvested from implanted mice relative to these cell lines grown in 2-D culture. PD-1 expression is increased in 4T1 and CT26 cell tumors harvested from implanted mice relative to these cell lines grown in 2-D culture. Expression is shown as fold change of peptide intensity by MS analysis from different tumor or cell cultures over peptide intensity from the mixture of all samples.
Figure 9A:
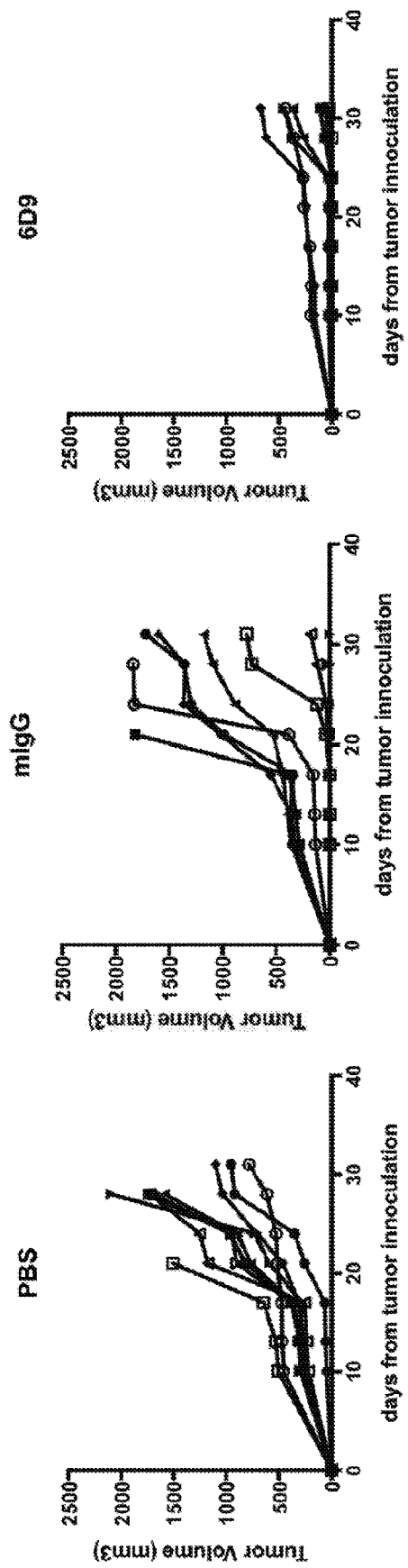
FIG. 9A and FIG. 9B show anti-VTCN1 antibody 6D9 inhibits KLN205 tumor growth.
Figure 9B:
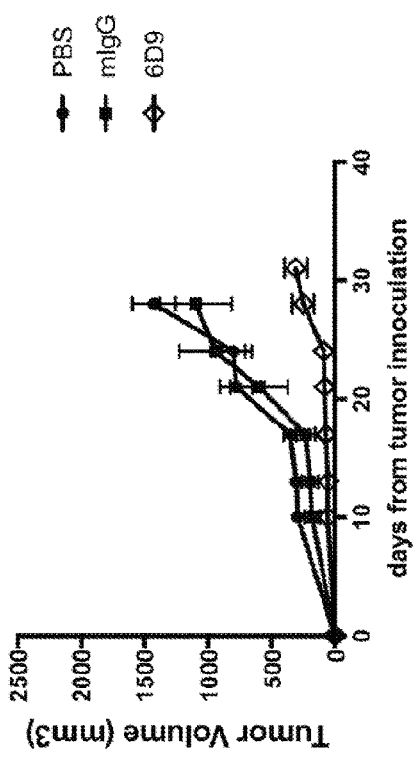

The results are shown in FIG. 8. These data demonstrate that VTCN1 expression is markedly increased in KLN205 tumors harvested from implanted mice relative to the KLN205 cell line grown in 2-D culture. Similarly, PD-L1 expression is increased in B16-F10, 4T1, CT26, KLN205, and LL2 tumors harvested from implanted mice relative to these cell lines grown in 2-D culture and finally, PD-1 expression is increased in 4T1 and CT26 cell tumors harvested from implanted mice relative to these cell lines grown in 2-D culture.

These are the first observations the inventors are aware of that VTCN1 is expressed in syngeneic mouse tumors, and illustrates the importance of evaluating protein expression in in vivo systems when 2D cultures might not be suitable. The identification of natural tumor models expressing VTCN1 enables the evaluation of anti-VTCN1 antibodies, and appropriate combinations of anti-VTCN1 antibodies and other anti-cancer agents, in models where carcinoma or sarcoma tumors are influenced by extracellular matrix components, immune effectors, vasculature and cytokines in a more "natural" state that mimics the human tumor setting.

Example 13: In Vivo Activity of Murine Anti-Human VTCN1 Antibody 6D9 in Mouse Tumor Model KLN205

The murine anti-human VTCN1 antibody 6D9 cross-reacts with mouse VTCN1 protein and allows for repeat dosing in syngeneic mouse models that have intact immune responses. The KLN205 cell line is a mouse lung squamous tumor model that grows in the syngeneic mouse strain DBA2.

For the tumor study, 6-8 week-old female DBA2 mice were implanted subcutaneously in the right flank with 2.5×10$^5$ mouse lung squamous carcinoma KLN205 cells in 50% matrigel on day 0. Mice were treated with PBS as a vehicle control, a mouse IgG isotype control (10 mg/kg), or anti-VTCN1 6D9 antibody (10 mg/kg) on days 3, 6, 10, 13, 15, 17, 20, and 22 following tumor implantation by intraperitoneal (i.p.) injection. Tumors were measured using an electronic caliper twice a week and tumor volume was calculated using the formula 0.52*length*width*width. Mouse body weight was also measured and recorded. Mice were humanely euthanized when the tumors reached 1500 mm$^3$ or animals showed greater than 15% weight loss. As shown in FIG. 9A and FIG. 9B, 6D9 treatment inhibits primary tumor growth of KLN205 tumors in DBA2 mice.

Example 14: In Vivo Activity of 6D9 in Combination with PD-1 or CTLA-4 Antibodies in the KLN205 Model 6-8 week-old female DBA2 mice were implanted subcutaneously in the right flank with 2.5×10$^5$ mouse lung squamous carcinoma cell KLN205 cells in 50% matrigel on day 0. Tumors were measured on day 7 and mice are randomized to 7 treatment groups. The average size was 50 mm$^3$. The treatment groups were: PBS vehicle control, mIgG2a isotype control, 6D9, anti-mouse PD1 antibody RMP1-14, 6D9+RMP1-14, anti-mouse CTLA-4 antibody 9D9, and 6D9+9D9. The mice were treated on days 8, 11, 13, 15, 18, 20, 22, and 25. All antibodies were 10 mg/kg by i.p.

Figure 10:
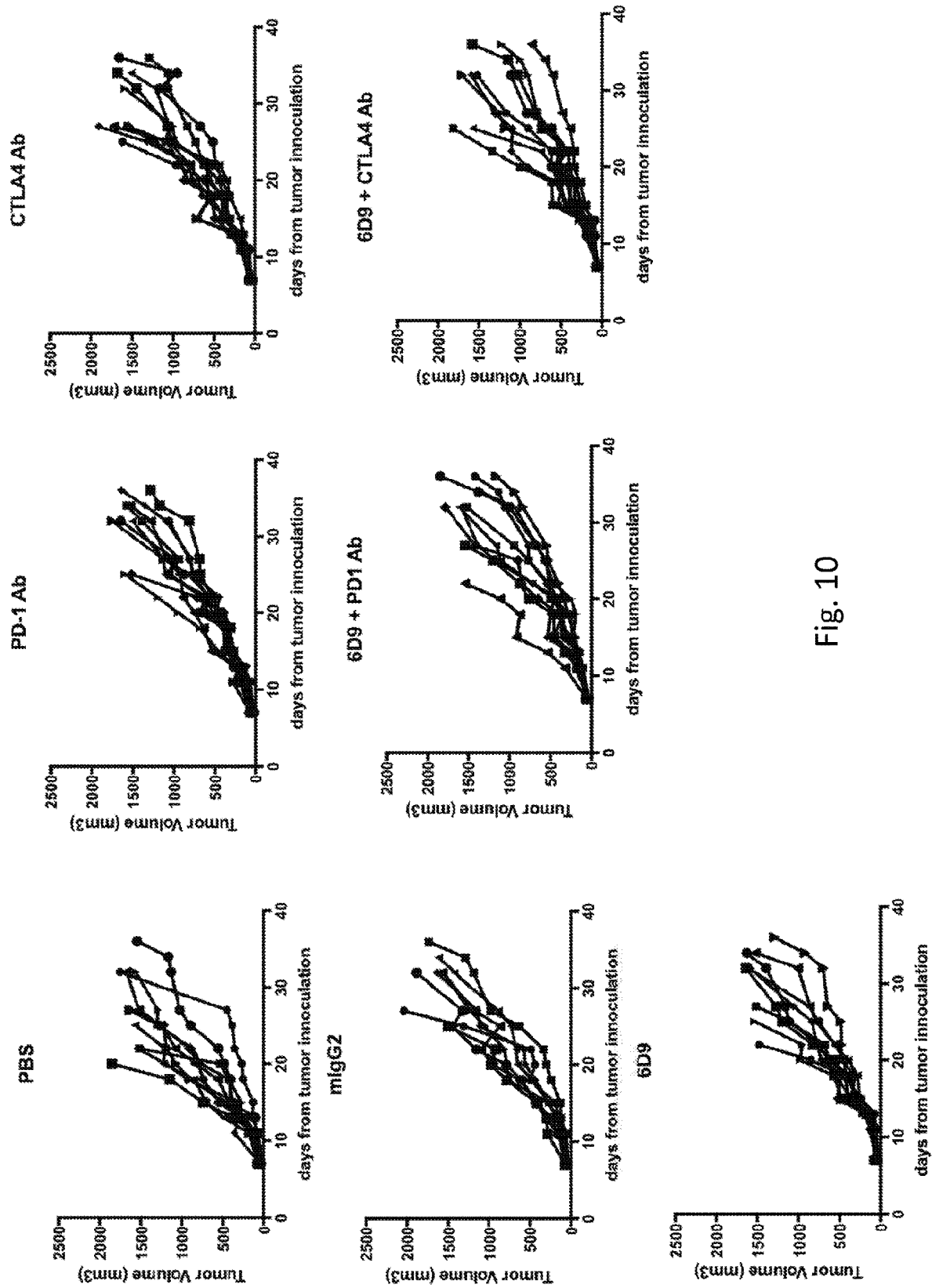
FIG. 10 shows KLN205 tumor response to 6D9 murine VTCN1 antibody and murine PD-1 antibody (RMP1-41), murine CTLA-4 antibody (9D9), 6D9 and PD-1 antibody combination, and 6D9 and CTLA-4 antibody combination. Tumor Volume over time in individual mice in each treatment group is shown.

The results are shown in FIG. 10. With established tumors, 6D9 delayed tumor growth, especially at early stage of tumor treatment. PD1 antibody and CTLA-4 antibody also slightly delayed tumor growth. Combination treatment showed a better effect than single antibody treatment. At the end of the study on day 36, 0 mice survived from the PBS and mIgG control groups; one mouse survived from the 6D9, PD-1 antibody, and CTLA-4 antibody treatment groups; and two mice survived from the combination treatment groups.

Example 15: In Vivo Study of 6D9-mIgG1 vs. 6D9-mIgG2a in the KLN205 Model

The mouse IgG2a is analogous to a human IgG1 while the mouse IgG1 is analogous to a human IgG4 and has little, if any, effector function (e.g., lacks antibody dependent cytotoxicity effector function). In order to assess if ADCC function is necessary for the in vivo anti-tumor activity of anti-VTCN1 antibodies, the 6D9 antibody was converted from a mouse IgG2a to a mouse IgG1. OCTET™ analysis demonstrated that 6D9-mIgG2a and 6D9-mIgG1 antibodies have similar affinity against human VTCN1 protein. If not otherwise specified, 6D9 antibody represents 6D9-mIgG2a.

Figure 11A:
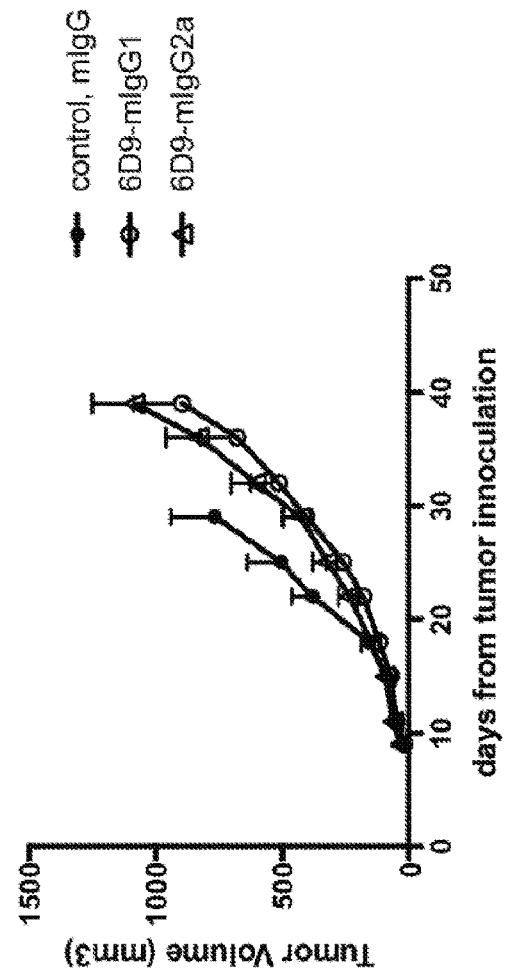
FIG. 11A and FIG. 11B show the anti-VTCN1 antibody 6D9 inhibits primary tumor growth and prolongs the median time to endpoint irrespective of isotype (murine IgG1 or murine IgG2a).
Figure 11B:
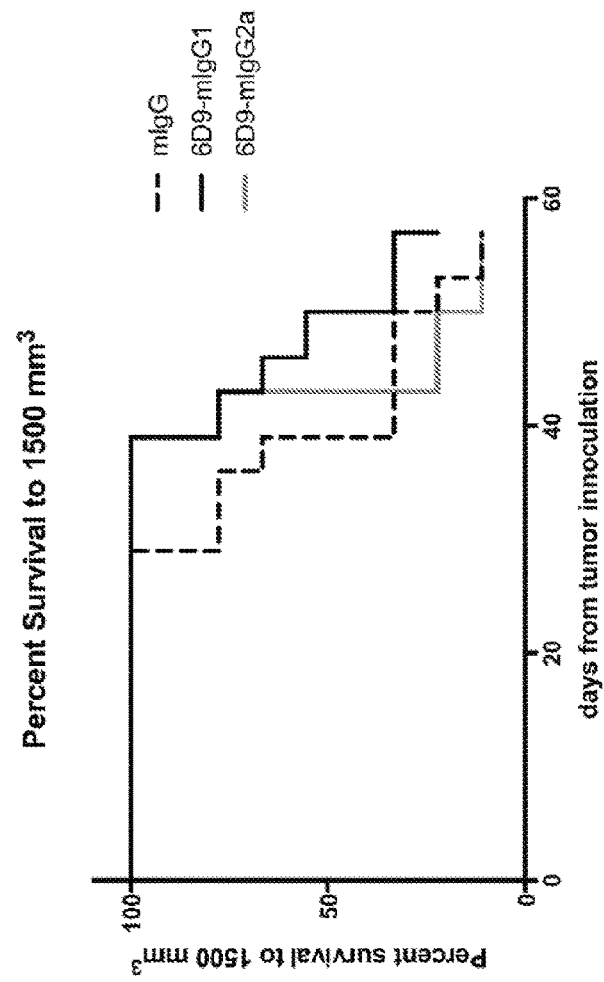

To test the activity of the 6D9 and 6D9-mIgG1 antibodies, 6-8 weeks old female DBA2 mice were implanted subcutaneously in the right flank with 0.2 million KLN205 cells in PBS on day 0. Mice were randomized on day 9 into 3 treatment groups, mIgG1 control, 6D9-mIgG1, 6D9-mIgG2a. Mice were treated on days 9, 11, 15, 18, and 22 by i.p. with 200 ug antibodies (10 mg/kg). The results are shown in FIG. 11A and FIG. 11B. Both 6D9-mIgG1 and 6D9-mIgG2a inhibit primary tumor growth. However, 6D9-mIgG1 treatment prolonged mouse survival while 6D9-mIgG2a did not. Results obtained from this study demonstrate that ADCC activity is not necessary for anti-VTCN1 antibodies to inhibit tumor growth and that an anti-VTCN1 antibody comprised of an isotype lacking effector function (e.g., mouse IgG1 or human IgG4) may be more efficacious.

Example 16: In Vivo Study of 6D9 and Gemcitabine Combination in 4T1 Mouse Tumor Model Current immune check-point inhibitor therapy only works in a subset of patients and it has been hypothesized that negative regulatory effector cells such as myeloid derived suppressor cells (MDSCs) and regulatory T cells (Tregs) might contribute to the lack of efficacy noted in the majority of patients. Therapeutic agents that inhibit MDSCs and/or T regulatory cell activity or reduce their cell numbers in combination with immune check-point inhibitors (ICI) might overcome this resistance and improve clinical outcomes. The murine triple negative breast cancer model 4T1 is high in MDSCs and typically does not respond to immune check-point inhibition. Here, it is explored if the combination of the anti-VTCN1 antibody 6D9 and the chemotherapy drug gemcitabine, known for its effects on both MDSCs and Tregs (decreasing population of MDSCs and Tregs) can inhibitor tumor growth in a 4T1 model.

Figure 12A:
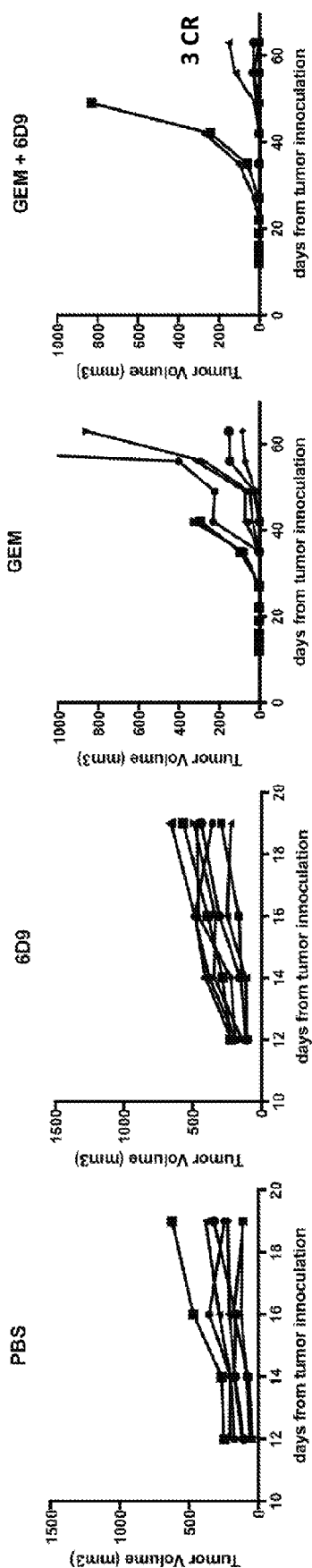
FIGS. 12A and 12B show 4T1 tumor response to murine VTCN1 antibody 6D9, gemcitabine, and 6D9 and gemcitabine combination.

6-8 week-old Balb/C mice were injected with 0.1 million of 4T1 cells in the mammary fat pad. On day 5, mice were randomized to 4 treatment groups, PBS, 6D9 (10 mg/kg), Gemcitabine (75 mg/kg), and 6D9 (10 mg/kg) plus gemcitabine (75 mg/kg). All treatments were by intraperitoneal injection and mice received a total of 5 treatments on days 5, 8, 12, 14, and 16. The results are shown in FIG. 12A. 6D9 alone did not show any effect in 4T1 tumor growth. Gemcitabine treatment totally inhibited tumor growth at the early stage of the study with tumor regrowth after 30 days. The combination of 6D9 and gemcitabine treatment also inhibited tumor growth with some tumor regrowth after 30 days, but at a slower rate compared to the gemcitabine alone group. By the end of the study on day 65, three mice receiving the combination were tumor-free (complete response; CR) while none of the mice in the gemcitabine alone group were tumor-free.

Figure 12B:
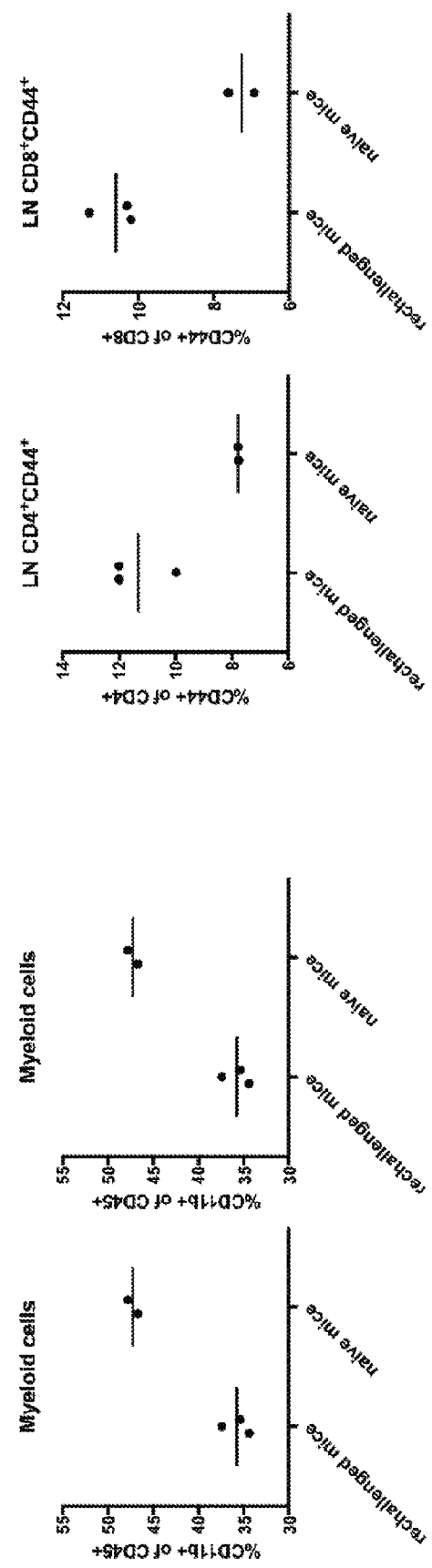

Three tumor free mice from 6D9 and gemcitabine combination group were rechallenged with 0.1 million 4T1 cells on day 65, two naïve mice were also injected with the same number of 4T1 tumor cells. The tumors and lymph nodes were harvested from these mice, and cells were dissociated and subjected to immune cell profiling by flow cytometry analysis. The results are shown in FIG. 12B. A striking reduction in myeloid derived suppressor cells (MDSC; CD11b+Ly6G+Ly6C+) was observed in the tumors that grew in the rechallenged mice compared to the naïve controls. Conversely, the rechallenged mice presented with a significantly higher percentage of effector-memory CD4+CD44+ and CD8+CD44+ T cells infiltrating the tumor and in draining lymph nodes.

These data indicate that anti-VTCN1 antibody in combination with gemcitabine can inhibit primary tumor growth and prolong survival and supports the use of anti-VTCN1 antibodies in combination with therapeutic agents that negatively impact MDSC or T regulatory cell number or activity.

Example 17: In Vivo Efficacy of 6D9 in Hepa 1-6 Tumor Model

Figure 13:
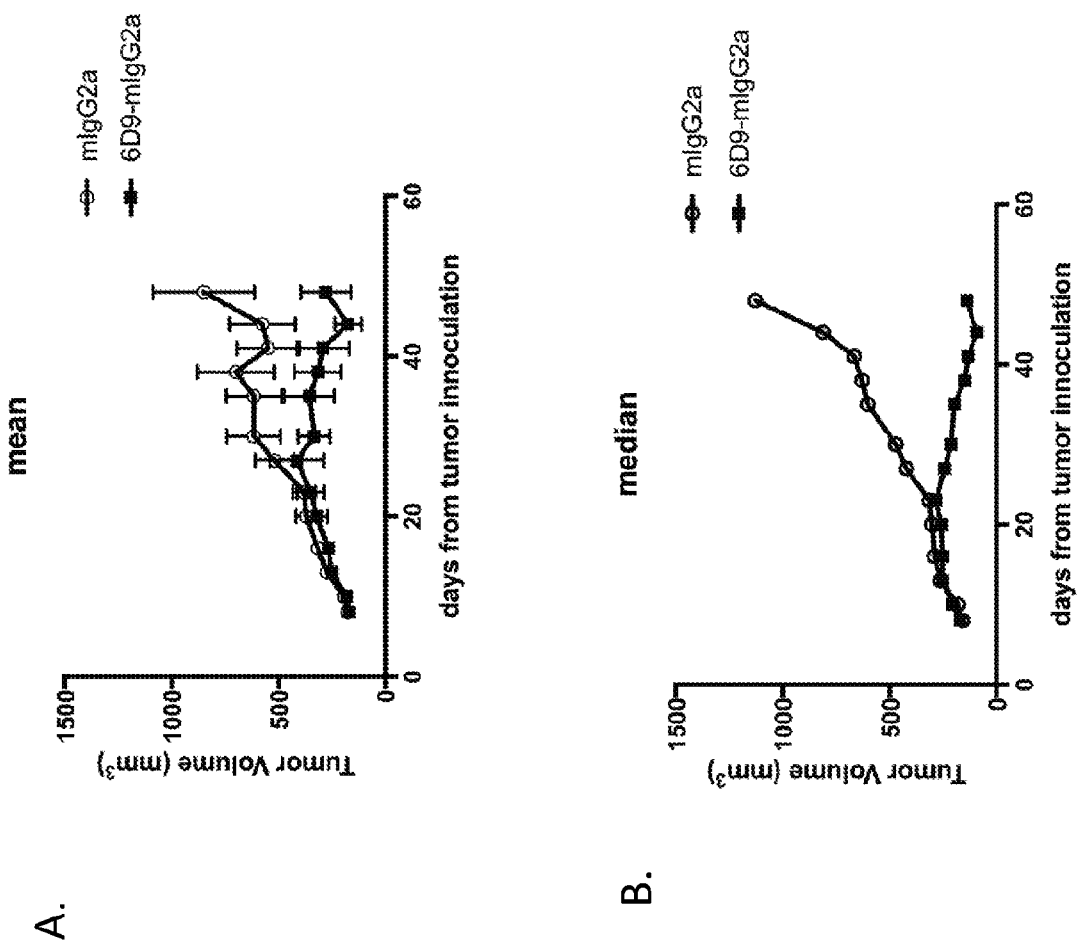
FIG. 13A and FIG. 13B show the anti-VTCN1 antibody 6D9 inhibits primary tumor growth in Hepa1-6 tumor-bearing mice.

The same proteomics and immunohistochemistry analysis used in Example 1 and Example 12 were also used to analyze tumors harvested from mice subcutaneously injected with Hepa 1-6 mouse hepatoma cells, and these tumors were fount to express VTCN1. To test the efficacy of anti-VTCN1 antibodies in this alternate syngeneic tumor model, 6-8 week old C57BL/6 female mice were injected with 2.5 million Hepa1-6 cells in matrigel. On day 8 after tumor cell implantation, when tumors were 100-200 mm3, tumor-bearing mice were randomized to two treatment groups and received either the isotype control, mIgG2a or the anti-VTCN1 antibody 6D9. Treatment was started on day 8 with mice receiving 10 mg/kg of antibody by ip. injection. Mice were treated at this dose level and route twice a week for a total of 7 doses. Tumor volume and body weight were recorded twice a week. The results are shown in FIG. 13. FIG. 13A shows mean tumor volume+SEM in the mIgG2a isotype control group vs the anti-VTCN1 6D9 treatment group. FIG. 13B shows median tumor volume from the mIgG2a isotype control group vs the anti-VTCN1 6D9 treatment group. The data demonstrate that 6D9 treatment inhibits tumor growth of Hepa1-6 tumors in DBA2 mice.

Sequence Summary

| SEQ ID NO: | Description |
| --- | --- |
| 1 | 1F8 VH amino acid sequence |
| 2 | 1F8 VH CDR1 amino acid sequence |
| 3 | 1F8 VH CDR2 amino acid sequence |
| 4 | 1F8 VH CDR3 amino acid sequence |
| 5 | 1F8 VL amino acid sequence |
| 6 | 1F8 VL CDR1 amino acid sequence |
| 7 | 1F8 VL CDR2 amino acid sequence |
| 8 | 1F8 VL CDR3 amino acid sequence |
| 9 | 3C6 VH amino acid sequence |
| 10 | 3C6 VH CDR1 amino acid sequence |
| 11 | 3C6 VH CDR2 amino acid sequence |
| 12 | 3C6 VH CDR3 amino acid sequence |
| 13 | 3C6 VL amino acid sequence |
| 14 | 3C6 VL CDR1 amino acid sequence |
| 15 | 3C6 VL CDR2 amino acid sequence |
| 16 | 3C6 VL CDR3 amino acid sequence |
| 17 | 3G10 VH amino acid sequence |
| 18 | 3G10 VH CDR1 amino acid sequence |
| 19 | 3G10 VH CDR2 amino acid sequence |
| 20 | 3G10 VH CDR3 amino acid sequence |
| 21 | 3G10 VL amino acid sequence |
| 22 | 3G10 VL CDR1 amino acid sequence |
| 23 | 3G10 VL CDR2 amino acid sequence |
| 24 | 3G10 VL CDR3 amino acid sequence |
| 25 | 4B9 VH amino acid sequence |
| 26 | 4B9 VH CDR1 amino acid sequence |
| 27 | 4B9 VH CDR2 amino acid sequence |
| 28 | 4B9 VH CDR3 amino acid sequence |
| 29 | 4B9 VL amino acid sequence |
| 30 | 4B9 VL CDR1 amino acid sequence |
| 31 | 4B9 VL CDR2 amino acid sequence |
| 32 | 4B9 VL CDR3 amino acid sequence |
| 33 | 6E2 VH amino acid sequence |
| 34 | 6E2 VH CDR1 amino acid sequence |
| 35 | 6E2 VH CDR2 amino acid sequence |
| 36 | 6E2 VH CDR3 amino acid sequence |
| 37 | 6E2 VL amino acid sequence |
| 38 | 6E2 VL CDR1 amino acid sequence |
| 39 | 6E2 VL CDR2 amino acid sequence |
| 40 | 6E2 VL CDR3 amino acid sequence |
| 41 | 7E12 VH amino acid sequence |
| 42 | 7E12 VH CDR1 amino acid sequence |
| 43 | 7E12 VH CDR2 amino acid sequence |
| 44 | 7E12 VH CDR3 amino acid sequence |
| 45 | 7E12 VL amino acid sequence |
| 46 | 7E12 VL CDR1 amino acid sequence |
| 47 | 7E12 VL CDR2 amino acid sequence |
| 48 | 7E12 VL CDR3 amino acid sequence |
| 49 | 8G3 VH amino acid sequence |
| 50 | 8G3 VH CDR1 amino acid sequence |
| 51 | 8G3 VH CDR2 amino acid sequence |
| 52 | 8G3 VH CDR3 amino acid sequence |

| SEQ ID NO: | Description |
|---|---|
| 53 | 8G3 VL amino acid sequence |
| 54 | 8G3 VL CDR1 amino acid sequence |
| 55 | 8G3 VL CDR2 amino acid sequence |
| 56 | 8G3 VL CDR3 amino acid sequence |
| 57 | 10D1 VH amino acid sequence |
| 58 | 10D1 VH CDR1 amino acid sequence |
| 59 | 10D1 VH CDR2 amino acid sequence |
| 60 | 10D1 VH CDR3 amino acid sequence |
| 61 | 10D1 VL amino acid sequence |
| 62 | 10D1 VL CDR1 amino acid sequence |
| 63 | 10D1 VL CDR2 amino acid sequence |
| 64 | 10D1 VL CDR3 amino acid sequence |
| 65 | 1A2 VH amino acid sequence |
| 66 | 1A2 VH CDR1 amino acid sequence |
| 67 | 1A2 VH CDR2 amino acid sequence |
| 68 | 1A2 VH CDR3 amino acid sequence |
| 69 | 1A2 VL amino acid sequence |
| 70 | 1A2 VL CDR1 amino acid sequence |
| 71 | 1A2 VL CDR2 amino acid sequence |
| 72 | 1A2 VL CDR3 amino acid sequence |
| 73 | 1C3 VH amino acid sequence |
| 74 | 1C3 VH CDR1 amino acid sequence |
| 75 | 1C3 VH CDR2 amino acid sequence |
| 76 | 1C3 VH CDR3 amino acid sequence |
| 77 | 1C3 VL amino acid sequence |
| 78 | 1C3 VL CDR1 amino acid sequence |
| 79 | 1C3 VL CDR2 amino acid sequence |
| 80 | 1C3 VL CDR3 amino acid sequence |
| 81 | 2C2 VH amino acid sequence |
| 82 | 2C2 VH CDR1 amino acid sequence |
| 83 | 2C2 VH CDR2 amino acid sequence |
| 84 | 2C2 VH CDR3 amino acid sequence |
| 85 | 2C2 VL amino acid sequence |
| 86 | 2C2 VL CDR1 amino acid sequence |
| 87 | 2C2 VL CDR2 amino acid sequence |
| 88 | 2C2 VL CDR3 amino acid sequence |
| 89 | 3D11 VH amino acid sequence |
| 90 | 3D11 VH CDR1 amino acid sequence |
| 91 | 3D11 VH CDR2 amino acid sequence |
| 92 | 3D11 VH CDR3 amino acid sequence |
| 93 | 3D11 VL amino acid sequence |
| 94 | 3D11 VL CDR1 amino acid sequence |
| 95 | 3D11 VL CDR2 amino acid sequence |
| 96 | 3D11 VL CDR3 amino acid sequence |
| 97 | 4C6 VH amino acid sequence |
| 98 | 4C6 VH CDR1 amino acid sequence |
| 99 | 4C6 VH CDR2 amino acid sequence |
| 100 | 4C6 VH CDR3 amino acid sequence |
| 101 | 4C6 VL amino acid sequence |
| 102 | 4C6 VL CDR1 amino acid sequence |
| 103 | 4C6 VL CDR2 amino acid sequence |
| 104 | 4C6 VL CDR3 amino acid sequence |
| 105 | 5A12 VH amino acid sequence |
| 106 | 5A12 VH CDR1 amino acid sequence |
| 107 | 5A12 VH CDR2 amino acid sequence |
| 108 | 5A12 VH CDR3 amino acid sequence |
| 109 | 5A12 VL amino acid sequence |
| 110 | 5A12 VL CDR1 amino acid sequence |
| 111 | 5A12 VL CDR2 amino acid sequence |
| 112 | 5A12 VL CDR3 amino acid sequence |
| 113 | 6D9 VH amino acid sequence |
| 114 | 6D9 VH CDR1 amino acid sequence |
| 115 | 6D9 VH CDR2 amino acid sequence |
| 116 | 6D9 VH CDR3 amino acid sequence |
| 117 | 6D9 VL amino acid sequence |
| 118 | 6D9 VL CDR1 amino acid sequence |
| 119 | 6D9 VL CDR2 amino acid sequence |
| 120 | 6D9 VL CDR3 amino acid sequence |
| 121 | 7C9 VH amino acid sequence |
| 122 | 7C9 VH CDR1 amino acid sequence |
| 123 | 7C9 VH CDR2 amino acid sequence |
| 124 | 7C9 VH CDR3 amino acid sequence |
| 125 | 7C9 VL amino acid sequence |
| 126 | 7C9 VL CDR1 amino acid sequence |
| 127 | 7C9 VL CDR2 amino acid sequence |
| 128 | 7C9 VL CDR3 amino acid sequence |
| 129 | 7D9 VH amino acid sequence |
| 130 | 7D9 VH CDR1 amino acid sequence |
| 131 | 7D9 VH CDR2 amino acid sequence |
| 132 | 7D9 VH CDR3 amino acid sequence |
| 133 | 7D9 VL amino acid sequence |
| 134 | 7D9 VL CDR1 amino acid sequence |
| 135 | 7D9 VL CDR2 amino acid sequence |
| 136 | 7D9 VL CDR3 amino acid sequence |
| 137 | 7F10 VH amino acid sequence |
| 138 | 7F10 VH CDR1 amino acid sequence |
| 139 | 7F10 VH CDR2 amino acid sequence |
| 140 | 7F10 VH CDR3 amino acid sequence |
| 141 | 7F10 VL amino acid sequence |
| 142 | 7F10 VL CDR1 amino acid sequence |
| 143 | 7F10 VL CDR2 amino acid sequence |
| 144 | 7F10 VL CDR3 amino acid sequence |
| 145 | 7G9 VH amino acid sequence |
| 146 | 7G9 VH CDR1 amino acid sequence |
| 147 | 7G9 VH CDR2 amino acid sequence |
| 148 | 7G9 VH CDR3 amino acid sequence |
| 149 | 7G9 VL amino acid sequence |
| 150 | 7G9 VL CDR1 amino acid sequence |
| 151 | 7G9 VL CDR2 amino acid sequence |
| 152 | 7G9 VL CDR3 amino acid sequence |
| 153 | 9E7 VH amino acid sequence |
| 154 | 9E7 VH CDR1 amino acid sequence |
| 155 | 9E7 VH CDR2 amino acid sequence |
| 156 | 9E7 VH CDR3 amino acid sequence |
| 157 | 9E7 VL amino acid sequence |
| 158 | 9E7 VL CDR1 amino acid sequence |
| 159 | 9E7 VL CDR2 amino acid sequence |
| 160 | 9E7 VL CDR3 amino acid sequence |
| 161 | 9F10 VH amino acid sequence |
| 162 | 9F10 VH CDR1 amino acid sequence |
| 163 | 9F10 VH CDR2 amino acid sequence |
| 164 | 9F10 VH CDR3 amino acid sequence |
| 165 | 9F10 VL amino acid sequence |
| 166 | 9F10 VL CDR1 amino acid sequence |
| 167 | 9F10 VL CDR2 amino acid sequence |
| 168 | 9F10 VL CDR3 amino acid sequence |
| 169 | 9H12 VH amino acid sequence |
| 170 | 9H12 VH CDR1 amino acid sequence |
| 171 | 9H12 VH CDR2 amino acid sequence |
| 172 | 9H12 VH CDR3 amino acid sequence |
| 173 | 9H12 VL amino acid sequence |
| 174 | 9H12 VL CDR1 amino acid sequence |
| 175 | 9H12 VL CDR2 amino acid sequence |
| 176 | 9H12 VL CDR3 amino acid sequence |
| 177 | 9H7 VH amino acid sequence |
| 178 | 9H7 VH CDR1 amino acid sequence |
| 179 | 9H7 VH CDR2 amino acid sequence |
| 180 | 9H7 VH CDR3 amino acid sequence |
| 181 | 9H7 VL amino acid sequence |
| 182 | 9H7 VL CDR1 amino acid sequence |
| 183 | 9H7 VL CDR2 amino acid sequence |
| 184 | 9H7 VL CDR3 amino acid sequence |
| 185 | VTCN1 (wt) amino acid sequence |
| 186 | IGHV4 leader (primer sequence) |
| 187 | IGHV2 leader (primer sequence) |
| 188 | IGHV2-26 leader (primer sequence) |
| 189 | IGHV6 leader (primer sequence) |
| 190 | IGHV1 leader (primer sequence) |
| 191 | IGHV1-58 leader (primer sequence) |
| 192 | IGHV1-24 leader (primer sequence) |
| 193 | IGHV1-69/1-46/7-4-1 leader (primer sequence) |
| 194 | IGHV3 leader (primer sequence) |
| 195 | IGHV3-53/3-49 leader (primer sequence) |
| 196 | IGHV3-21 leader (primer sequence) |
| 197 | IGHV3-48/3-7 leader (primer sequence) |
| 198 | IGHV5 leader (primer sequence) |
| 199 | IgkV1a leader (primer sequence) |
| 200 | IgkV1b leader (primer sequence) |
| 201 | IgkV3 leader (primer sequence) |
| 202 | IgkV3-20 leader (primer sequence) |
| 203 | IgkV4 leader (primer sequence) |
| 204 | IgkV5 leader (primer sequence) |

| SEQ ID NO: | Description |
|---|---|
| 205 | IgkV2 leader (primer sequence) |
| 206 | Kappa FW4 (primer sequence) |
| 207 | Kappa FW4 (primer sequence) |
| 208 | Heavy FW4 (primer sequence) |
| 209 | VL-FOR L1 (primer sequence) |
| 210 | VL-FOR L2 (primer sequence) |
| 211 | VL-REV L (primer sequence) |
| 212 | 7C8 VH amino acid sequence |
| 213 | 7C8 VH CDR1 amino acid sequence |
| 214 | 7C8 VH CDR2 amino acid sequence |
| 215 | 7C8 VH CDR3 amino acid sequence |
| 216 | 7C8 VL amino acid sequence |
| 217 | 7C8 VL CDR1 amino acid sequence |
| 218 | 7C8 VL CDR2 amino acid sequence |
| 219 | 7C8 VL CDR3 amino acid sequence |
| 220 | Hu6D9_57A3 VH amino acid sequence |
| 221 | Hu6D9_57A3 VH CDR1 amino acid sequence |
| 222 | Hu6D9_57A3 VH CDR2 amino acid sequence |
| 223 | Hu6D9_57A3 VH CDR3 amino acid sequence |
| 224 | Hu6D9_57A3, Hu6D9_57A4, Hu6D9_57A5, Hu6D9_66B1 VL amino acid sequence |
| 225 | Hu6D9_57A3, Hu6D9_57A4, Hu6D9_57A5, Hu6D9_66B1 VL CDR1 amino acid sequence |
| 226 | Hu6D9_57A3, Hu6D9_57A4, Hu6D9_57A5, Hu6D9_66B1 VL CDR2 amino acid sequence |
| 227 | Hu6D9_57A3, Hu6D9_57A4, Hu6D9_57A5, Hu6D9_66B1 VL CDR3 amino acid sequence |
| 228 | Hu6D9_57A4 VH amino acid sequence |
| 229 | Hu6D9_57A4 VH CDR1 amino acid sequence |
| 230 | Hu6D9_57A4 VH CDR2 amino acid sequence |
| 231 | Hu6D9_57A4 VH CDR3 amino acid sequence |
| 232 | Hu6D9_57A5 VH amino acid sequence |
| 233 | Hu6D9_57A5 VH CDR1 amino acid sequence |
| 234 | Hu6D9_57A5 VH CDR2 amino acid sequence |
| 235 | Hu6D9_57A5 VH CDR3 amino acid sequence |
| 236 | Hu6D9_66B1 VH amino acid sequence |
| 237 | Hu6D9_66B1 VH CDR1 amino acid sequence |
| 238 | Hu6D9_66B1 VH CDR2 amino acid sequence |
| 239 | Hu6D9_66B1 VH CDR3 amino acid sequence |
| 240 | Hu6D9_66C2 VH amino acid sequence |
| 241 | Hu6D9_66C2 VH CDR1 amino acid sequence |
| 242 | Hu6D9_66C2 VH CDR2 amino acid sequence |
| 243 | Hu6D9_66C2 VH CDR3 amino acid sequence |
| 244 | Hu6D9_66C2 VL amino acid sequence |
| 245 | Hu6D9_66C2 VL CDR1 amino acid sequence |
| 246 | Hu6D9_66C2 VL CDR2 amino acid sequence |
| 247 | Hu6D9_66C2 VL CDR3 amino acid sequence |
| 248 | 4C7_63A1 VH amino acid sequence |
| 249 | 4C7_63A1 VH CDR1 amino acid sequence |
| 250 | 4C7_63A1 VH CDR2 amino acid sequence |
| 251 | 4C7_63A1 VH CDR3 amino acid sequence |
| 252 | 4C7_63A1 VL amino acid sequence |
| 253 | 4C7_63A1 VL CDR1 amino acid sequence |
| 254 | 4C7_63A1, 13H9_44D2, 14D6_60B5, 16H12_60B4 VL CDR2 amino acid sequence |
| 255 | 4C7_63A1 VL CDR3 amino acid sequence |
| 256 | 7G7_44C6 VH amino acid sequence |
| 257 | 7G7_44C6 VH CDR1 amino acid sequence |
| 258 | 7G7_44C6 VH CDR2 amino acid sequence |
| 259 | 7G7_44C6 VH CDR3 amino acid sequence |
| 260 | 7G7_44C6 VL amino acid sequence |
| 261 | 7G7_44C6 VL CDR1 amino acid sequence |
| 262 | 7G7_44C6 VL CDR2 amino acid sequence |
| 263 | 7G7_44C6 VL CDR3 amino acid sequence |
| 264 | 12B5_44B1 VH amino acid sequence |
| 265 | 12B5_44B1 VH CDR1 amino acid sequence |
| 266 | 12B5_44B1 VH CDR2 amino acid sequence |
| 267 | 12B5_44B1, 14D6_60B5, 16H12_60B4 VH CDR3 amino acid sequence |
| 268 | 12B5_44B1 VL amino acid sequence |
| 269 | 12B5_44B1, 13H9_44D2, 14D6_60B5, 16H12_60B4 VL CDR1 amino acid sequence |
| 270 | 12B5_44B1 VL CDR2 amino acid sequence |
| 271 | 12B5_44B1 VL CDR3 amino acid sequence |
| 272 | 13H9_44D2 VH amino acid sequence |
| 273 | 13H9_44D2 VH CDR1 amino acid sequence |
| 274 | 13H9_44D2 VH CDR2 amino acid sequence |
| 275 | 13H9_44D2 VH CDR3 amino acid sequence |
| 276 | 13H9_44D2 VL amino acid sequence |
| 277 | 13H9_44D2 VL CDR3 amino acid sequence |
| 278 | 14D6_60B5 VH amino acid sequence |
| 279 | 14D6_60B5 VH CDR1 amino acid sequence |
| 280 | 14D6_60B5 VH CDR2 amino acid sequence |
| 281 | 14D6_60B5 VL amino acid sequence |
| 282 | 14D6_60B5 VL CDR3 amino acid sequence |
| 283 | 16H12_60B4 VH amino acid sequence |
| 284 | 16H12_60B4 VH CDR1 amino acid sequence |
| 285 | 16H12_60B4 VH CDR2 amino acid sequence |
| 286 | 16H12_60B4 VL amino acid sequence |
| 287 | 16H12_60B4 VL CDR3 amino acid sequence |
| 288 | 7C8 VH nucleic acid sequence |
| 289 | 7C8 VL nucleic acid sequence |
| 290 | Hu6D9_57A3 VH nucleic acid sequence |
| 291 | Hu6D9_57A3, Hu6D9_57A4, Hu6D9_57A5, Hu6D9_66B1 VL nucleic acid sequence |
| 292 | Hu6D9_57A4 VH nucleic acid sequence |
| 293 | Hu6D9_57A5 VH nucleic acid sequence |
| 294 | Hu6D9_66B1 VH nucleic acid sequence |
| 295 | Hu6D9_66C2 VH nucleic acid sequence |
| 296 | Hu6D9_66C2 VL nucleic acid sequence |
| 297 | 4C7_63A1 VH nucleic acid sequence |
| 298 | 4C7_63A1 VL nucleic acid sequence |
| 299 | 7G7_44C6 VH nucleic acid sequence |
| 300 | 7G7_44C6 VL nucleic acid sequence |
| 301 | 12B5_44B1 VH nucleic acid sequence |
| 302 | 12B5_44B1 VL nucleic acid sequence |
| 303 | 13H9_44D2 VH nucleic acid sequence |
| 304 | 13H9_44D2 VL nucleic acid sequence |
| 305 | 14D6_60B5 VH nucleic acid sequence |
| 306 | 14D6_60B5 VL nucleic acid sequence |
| 307 | 16H12_60B4 VH nucleic acid sequence |
| 308 | 16H12_60B4 VL nucleic acid sequence |

INCORPORATION BY REFERENCE

The contents of all references, patents, pending patent applications and published patents, and Accession Numbers, and Sequence Listing cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An anti-VTCN1 antibody, or antigen-binding portion thereof, comprising
a heavy chain variable region comprising a CDR3 domain comprising the amino acid sequence of SEQ ID NO: 239, a CDR2 domain comprising the amino acid sequence of SEQ ID NO: 238, and a CDR1 domain comprising the amino acid sequence of SEQ ID NO: 237, and a light chain variable region comprising a CDR3 domain comprising the amino acid sequence of SEQ ID NO: 227, a CDR2 domain comprising the amino acid sequence of SEQ ID NO: 226, and a CDR1 domain comprising the amino acid sequence of SEQ ID NO: 225;
a heavy chain variable region comprising a CDR3 domain comprising the amino acid sequence of SEQ ID NO: 251, a CDR2 domain comprising the amino acid sequence of SEQ ID NO: 250, and a CDR1 domain comprising the amino acid sequence of SEQ ID NO: 249, and a light chain variable region comprising a CDR3 domain comprising the amino acid sequence of SEQ ID NO: 255, a CDR2 domain comprising the amino acid sequence of SEQ ID NO: 254, and a CDR1 domain comprising the amino acid sequence of SEQ ID NO: 253;
a heavy chain variable region comprising a CDR3 domain comprising the amino acid sequence of SEQ ID NO: 267, a CDR2 domain comprising the amino acid sequence of SEQ ID NO: 266, and a CDR1 domain comprising the amino acid sequence of SEQ ID NO: 265, and a light chain variable region comprising a CDR3 domain comprising the amino acid sequence of SEQ ID NO: 271, a CDR2 domain comprising the amino acid sequence of SEQ ID NO: 270, and a CDR1 domain comprising the amino acid sequence of SEQ ID NO: 269;
a heavy chain variable region comprising a CDR3 domain comprising the amino acid sequence of SEQ ID NO: 267, a CDR2 domain comprising the amino acid sequence of SEQ ID NO: 285, and a CDR1 domain comprising the amino acid sequence of SEQ ID NO: 284, and a light chain variable region comprising a CDR3 domain comprising the amino acid sequence of SEQ ID NO: 287, a CDR2 domain comprising the amino acid sequence of SEQ ID NO: 254, and a CDR1 domain comprising the amino acid sequence of SEQ ID NO: 269;
a heavy chain variable region comprising a CDR3 domain comprising the amino acid sequence of SEQ ID NO: 267, a CDR2 domain comprising the amino acid sequence of SEQ ID NO: 280, and a CDR1 domain comprising the amino acid sequence of SEQ ID NO: 279, and a light chain variable region comprising a CDR3 domain comprising the amino acid sequence of SEQ ID NO: 282, a CDR2 domain comprising the amino acid sequence of SEQ ID NO: 254, and a CDR1 domain comprising the amino acid sequence of SEQ ID NO: 269; or
a heavy chain variable region comprising a CDR3 domain comprising the amino acid sequence of SEQ ID NO: 215, a CDR2 domain comprising the amino acid sequence of SEQ ID NO: 214, and a CDR1 domain comprising the amino acid sequence of SEQ ID NO: 213, and a light chain variable region comprising a CDR3 domain comprising the amino acid sequence of SEQ ID NO: 219, a CDR2 domain comprising the amino acid sequence of SEQ ID NO: 218, and a CDR1 domain comprising the amino acid sequence of SEQ ID NO: 217.

2. The antibody, or antigen-binding portion thereof, of claim 1, wherein the antibody, or antigen-binding portion thereof, is a human or humanized antibody.

3. The antibody, or antigen-binding portion thereof, of claim 1, wherein the antibody, or antigen-binding portion thereof, is an IgG1 or IgG4 isotype.

4. The antibody, or antigen-binding portion thereof, of claim 1, wherein the antibody, or antigen-binding portion thereof, is multispecific.

5. The antibody, or antigen-binding portion thereof, of claim 1, wherein the antibody, or antigen-binding portion thereof, is bispecific.

6. An isolated nucleic acid encoding an antibody, or antigen-binding portion thereof, of claim 1.

7. A pharmaceutical composition comprising the antibody, or antigen-binding portion thereof, of claim 1 and a pharmaceutically acceptable carrier.

8. A method for reducing or ameliorating one or more symptoms of cancer, comprising administering a therapeutically effective amount of the antibody or antigen-binding portion thereof of claim 1, to a subject in need thereof.

9. The method of claim 8, wherein the cancer is selected from the groups consisting of triple negative breast cancer (TNBC), renal cancer, ovarian cancer, NSCLC, endometrial cancer, and liver cancer.

10. A method for inhibiting or decreasing solid tumor growth in a subject having a solid tumor, said method comprising administering an effective amount of an anti-VTCN1 antibody, or antigen-binding portion thereof, of claim 1, to the subject having the solid tumor, such that the solid tumor growth is inhibited or decreased.

11. The method of claim 10, wherein the tumor is selected from the groups consisting of triple negative breast cancer (TNBC), renal cancer, and ovarian cancer.

12. The method of claim 10, wherein the antibody or antigen-binding portion thereof, is administered in combination with an additional agent or an additional therapy.

13. The method of claim 12, wherein the additional agent or additional therapy is an immune checkpoint inhibitor, an antibody, radiation, one or more chemotherapeutic agent, an inhibitor of activity or cell number of myeloid derived suppressor cells (MDSCs), a DNA alkylator, a PARP inhibitor, IL-6, interferon-gamma (IFN-γ), an agent which is capable of decreasing T regulatory cells and/or increasing effector T cell:T regulatory cell ratio, gemcitabine, or a combination thereof.

14. An anti-VTCN1 antibody, or antigen-binding portion thereof, comprising
   a heavy chain variable domain comprising an amino acid sequence set forth in SEQ ID NO: 236 and a light chain variable domain comprising an amino acid sequence set forth in SEQ ID NO: 224;
   a heavy chain variable domain comprising an amino acid sequence set forth in SEQ ID NO: 248 and a light chain variable domain comprising an amino acid sequence set forth in SEQ ID NO: 252;
   a heavy chain variable domain comprising an amino acid sequence set forth in SEQ ID NO: 264 and a light chain variable domain comprising an amino acid sequence set forth in SEQ ID NO: 268;
   a heavy chain variable domain comprising an amino acid sequence set forth in SEQ ID NO: 283 and a light chain variable domain comprising an amino acid sequence set forth in SEQ ID NO: 286;
   a heavy chain variable domain comprising an amino acid sequence set forth in SEQ ID NO: 278 and a light chain variable domain comprising an amino acid sequence set forth in SEQ ID NO: 281; or
   a heavy chain variable domain comprising an amino acid sequence set forth in SEQ ID NO: 212 and a light chain variable domain comprising an amino acid sequence set forth in SEQ ID NO: 216.

* * * * *